US009580707B2

(12) United States Patent
Cunningham et al.

(10) Patent No.: US 9,580,707 B2
(45) Date of Patent: Feb. 28, 2017

(54) PEPTIDE ANTIMICROBIALS

(75) Inventors: Philip R. Cunningham, Troy, MI (US); Wes Colangelo, West Bloomfield, MI (US)

(73) Assignee: Wayne State University, Detroit, MI (US)

( * ) Notice: Subject to any disclaimer, the term of this patent is extended or adjusted under 35 U.S.C. 154(b) by 481 days.

(21) Appl. No.: 13/635,296

(22) PCT Filed: Mar. 16, 2011

(86) PCT No.: PCT/US2011/028733
§ 371 (c)(1),
(2), (4) Date: Mar. 1, 2013

(87) PCT Pub. No.: WO2011/116138
PCT Pub. Date: Sep. 22, 2011

(65) Prior Publication Data

US 2013/0150260 A1 Jun. 13, 2013

Related U.S. Application Data

(60) Provisional application No. 61/314,269, filed on Mar. 16, 2010.

(51) Int. Cl.

| | |
|---|---|
| ***C40B 30/04*** | (2006.01) |
| ***C12N 15/10*** | (2006.01) |
| ***C07K 7/08*** | (2006.01) |
| ***C12N 15/63*** | (2006.01) |
| ***C12Q 1/18*** | (2006.01) |

(52) U.S. Cl.
CPC ............ *C12N 15/1086* (2013.01); *C07K 7/08* (2013.01); *C12N 15/1034* (2013.01); *C12N 15/1079* (2013.01); *C12N 15/635* (2013.01); *C12Q 1/18* (2013.01); *C07K 2319/60* (2013.01); *C07K 2319/61* (2013.01); *C40B 30/04* (2013.01)

(58) Field of Classification Search
None
See application file for complete search history.

(56) References Cited

U.S. PATENT DOCUMENTS

2009/0137481 A1 5/2009 Hogenhaug et al.

FOREIGN PATENT DOCUMENTS

| | | |
|---|---|---|
| WO | 0073433 | 12/2000 |
| WO | WO2011116138 | 9/2011 |

OTHER PUBLICATIONS

Krumpe at al, BMC Biotechnology, 2007, 7:65, pp. 1-8.*
Paul et al, FEMS Microbiology Letters, 176, 1999, p. 45-50.*
(Continued)

*Primary Examiner* — Christian Boesen
(74) *Attorney, Agent, or Firm* — Lee & Hayes, PLLC; C. Rachal Winger

(57) ABSTRACT

Provided are methods and compositions for in vivo display and screening of peptides for antimicrobial activity. The methods can include expressing a random peptide library in a microbial cell culture and identifying clones in which microbial cell growth or survival is affected by the peptide expressed by that clone. Also provided are peptide antimicrobials identified using these methods and compositions.

9 Claims, 151 Drawing Sheets

(56) References Cited

OTHER PUBLICATIONS

Choi, et al., "Design and Screening of in vivo Expressed Antimicrobial Peptide Library," *Biotechnology Letters* 24:251-256, 2002.
Giuliani, et al., "Antimicrobial Peptides: An Overview of a Promising Class of Therapeutics", Central European Journal of Biology, 2007, vol. 2 (1), pp. 1-33.
Palzkill, et al., "Selection of Functional Signal Peptide Cleavage Sites from a Library of Random Sequences", Journal of Bacteriology, Feb. 1994, vol. 176, No. 3, pp. 563-568.
Pini, et al., "Antimicrobial Activity of Novel Dendrimeric Peptides Obtained by Phage Display Selection and Rational Modification", Antimicrobial Agents and Chemotherapy, Jul. 2005, vol. 49, No. 7, pp. 2665-2672.
Search Report dated Jan. 6, 2012 in PCT Application No. PCT/US2011/28733.
Tanaka, et al., "Novel Method for Selection of Antimicrobial Peptides from a Phage Display Library by Use of Bacterial Magnetic Particles", Applied & Environmental Mircrobiology, Dec. 2008, vol. 74, No. 24, pp. 7600-7606.

* cited by examiner

FIGURE 2

| Clone | Phenotype | Peptide | | | | | | | | | | | | Growth Curve | SEQ ID NO: |
|---|---|---|---|---|---|---|---|---|---|---|---|---|---|---|---|
| PL012 | Weakly Inhibitory < 0.7 | G | I | G | A | I | V | G | V | L | I | L | G | GCI | 7 |
| PL014 | Static | W | T | V | R | V | D | V | I | E | S | R | W | GCII | 8 |
| PL021 | Weakly Inhibitory < 0.7 | A | L | L | V | A | M | W | A | G | V | A | G | GCII | 9 |
| PL023 | Weakly Inhibitory > 0.7 | V | C | E | C | G | P | R | V | T | L | T | Q | GCIII | 10 |
| PL027 | Weakly Inhibitory > 0.7 | L | T | T | I | C | R | W | M | R | R | R | D | GCIII | 11 |
| PL029 | Lytic | M | T | K | M | F | R | R | W | R | T | N | K | GCIII | 12 |
| PL030 | Lytic | L | G | W | L | R | G | K | A | L | G | R | G | GCIII | 13 |
| PL034 | Lytic | F | A | A | V | V | R | W | V | R | G | R | A | GCIII | 14 |
| PL032 | Weakly Inhibitory < 0.7 | F | K | W | V | L | A | R | L | T | Q | S | S | PL032 | 15 |
| PL035 | Lytic | Y | G | K | A | R | R | W | L | G | R | W | T | GCIV | 16 |
| PL037 | Static/Cidal | F | R | W | L | Y | R | L | F | M | F | R | L | GCIV | 17 |
| PL038 | Lytic | I | S | W | L | G | G | L | L | G | R | R | E | GCIV | 18 |
| PL039 | Weakly Inhibitory < 0.7 | C | E | S | G | K | S | Y | R | I | G | K | W | GCIV | 19 |
| PL045 | Static/Cidal | C | I | L | V | V | L | V | H | L | F | V | A | GCIV | 20 |
| PL047 | Lytic | I | R | A | F | R | S | F | T | Q | L | L | C | GCIV | 21 |
| PL048 | Static/Cidal | V | T | L | G | L | V | M | L | A | V | S | L | GCIV | 22 |
| PL049 | Lytic | W | R | Y | L | L | G | R | G | K | R | R | K | GCIV | 23 |
| PL054 | Lytic | W | G | S | L | M | L | K | W | R | R | T | R | GCV | 24 |
| PL055 | Lytic | I | K | W | I | R | S | L | L | V | R | G | R | GCVI | 25 |
| PL060 | Static/Cidal | L | S | W | V | W | R | Q | L | G | G | A | W | GCVI | 26 |
| PL061 | Lytic | I | K | W | I | R | S | L | L | V | R | G | R | GCVI | 27 |
| PL062 | Lytic | F | A | R | L | H | K | W | F | Q | R | R | K | PL062 | 28 |
| PL063 | Lytic | I | K | L | L | R | I | L | S | Q | K | W | R | GCVI | 29 |
| PL064 | Lytic | W | V | W | L | S | R | W | L | R | R | G | W | GCVI | 30 |
| PL065 | Lytic | L | K | G | L | K | R | W | W | R | P | E | H | GCVI | 31 |
| PL066 | Lytic | W | K | W | L | Q | S | L | W | G | C | E | V | PL066 | 32 |
| PL068 | Lytic | W | K | W | L | Q | S | L | W | G | C | E | V | GCVI | 33 |
| PL069 | Static/Cidal | F | F | C | L | W | V | L | Y | L | G | T | P | GCVI | 34 |
| PL072 | Lytic | W | R | G | V | R | K | V | W | R | R | M | R | GCVI | 35 |
| PL073 | Static/Cidal | N | V | R | I | I | V | D | M | T | I | S | A | GCVI | 36 |
| PL088 | Static/Cidal | I | I | V | L | V | F | V | T | Y | L | T | A | GC1 | 37 |
| PL092 | Lytic | Y | C | W | L | R | E | K | L | G | G | G | Q | GC1 | 38 |
| PL093 | Lytic | Y | C | W | L | R | E | K | L | G | G | G | Q | GC1 | 39 |
| PL094 | Lytic | Y | C | W | L | R | E | K | L | G | G | G | Q | GC1 | 40 |
| PL095 | Lytic | W | Q | L | V | R | R | L | L | G | Q | L | G | GC1 | 41 |
| PL097 | Lytic | W | V | T | A | R | D | W | V | K | S | W | W | GC2 | 42 |
| PL098 | Lytic | W | R | R | W | K | M | R | G | R | A | R | V | GC2 | 43 |
| PL101 | Static/Cidal | I | L | Y | L | C | V | L | S | V | S | R | N | GC2 | 44 |
| PL104 | Lytic | M | G | M | L | R | W | L | F | S | F | W | R | GC2 | 45 |
| PL111 | Lytic | L | S | R | A | K | A | L | L | K | R | A | K | GC2 | 46 |
| PL112 | Static/Cidal | G | L | W | G | K | W | E | P | G | G | Q | G | GC3 | 47 |
| PL113 | Lytic | C | R | Y | L | R | L | L | W | S | N | I | R | GC3 | 48 |
| PL114 | Non-Inhibitory | Q | A | E | S | S | M | I | A | P | S | Q | C | GC3 | 49 |
| PL115 | Weakly Inhibitory < 0.7 | V | L | S | A | N | I | W | A | G | M | R | F | GC3 | 50 |
| PL116 | Weakly Inhibitory > 0.7 | I | V | I | C | C | V | G | V | L | T | H | P | GC3 | 51 |
| PL117 | Static/Cidal | V | I | G | T | V | M | C | T | L | T | W | G | GC3 | 52 |
| PL118 | Lytic | Y | R | R | V | G | G | W | L | R | R | V | L | GC3 | 53 |
| PL119 | Static/Cidal | T | S | D | L | E | T | Q | S | G | G | R | L | GC3 | 54 |
| PL120 | Static/Cidal | I | V | T | T | N | H | V | L | V | C | T | Y | GC3 | 55 |
| PL121 | Static/Cidal | D | G | M | F | R | M | T | L | L | T | S | W | GC3 | 56 |
| PL122 | Lytic | V | N | W | W | R | R | C | W | K | Q | W | H | GC3 | 57 |
| PL123 | Lytic | W | T | W | I | K | R | V | L | Q | E | M | G | GC3 | 58 |
| PL124 | Static/Cidal | L | L | V | S | L | P | V | L | L | S | C | G | GC3 | 59 |
| PL125 | Static/Cidal | L | N | W | L | R | G | W | T | G | L | V | G | GC3 | 60 |
| PL126 | Static/Cidal | W | T | R | F | M | R | A | L | G | F | T | Q | GC3 | 61 |
| PL127 | Weakly Inhibitory > 0.7 | Y | C | P | G | P | S | V | E | I | R | R | C | GC3 | 62 |
| PL128 | Weakly Inhibitory < 0.7 | L | Y | A | F | G | T | C | E | F | S | V | M | GC3 | 63 |
| PL129 | Weakly Inhibitory < 0.7 | Y | Y | T | F | I | L | P | L | S | L | S | C | GC4 | 64 |
| PL130 | Weakly Inhibitory > 0.7 | M | E | R | V | R | K | W | F | N | E | G | R | GC4 | 65 |
| PL131 | Lytic | Y | S | A | I | K | R | R | L | L | Q | G | R | GC4 | 66 |
| PL132 | Static/Cidal | I | T | F | W | S | F | V | F | T | M | R | W | GC4 | 67 |
| PL136 | Weakly Inhibitory > 0.7 | F | Q | L | E | F | S | V | A | V | G | A | V | GC4 | 68 |
| PL137 | Lytic | L | S | L | A | I | E | F | S | L | S | V | Q | GC4 | 69 |
| PL138 | Lytic | W | R | W | V | S | R | K | W | Q | T | R | G | GC4 | 70 |
| PL139 | Lytic | M | A | W | L | A | Q | W | W | G | A | R | R | GC4 | 71 |
| PL140 | Lytic | V | N | A | W | R | K | L | A | Q | I | W | R | GC4 | 72 |
| PL141 | Weakly Inhibitory < 0.7 | Y | C | A | H | L | S | C | T | V | C | V | Y | GC4 | 73 |
| PL142 | Lytic | I | G | L | L | K | R | L | V | T | T | R | S | GC4 | 74 |
| PL144 | Lytic | W | D | R | V | I | K | W | L | R | C | G | K | GC4 | 75 |
| PL145 | Lytic | G | R | L | V | A | R | V | W | R | K | W | K | GC4 | 76 |

| Static/Cidal | Clone | Peptide | | | | | | | | | | | | SEQ I NO: |
|---|---|---|---|---|---|---|---|---|---|---|---|---|---|---|
| | PL014 | W | T | V | R | V | D | V | I | E | S | R | W | 8 |
| | PL037 | F | R | W | L | Y | R | L | F | M | F | R | L | 17 |
| | PL045 | C | I | L | V | V | L | V | H | L | F | V | A | 20 |
| | PL048 | V | T | L | G | L | V | M | L | A | V | S | L | 22 |
| | PL060 | L | S | W | V | W | R | Q | L | G | G | A | W | 26 |
| | PL069 | F | F | C | L | W | V | L | Y | L | G | T | P | 34 |
| | PL073 | N | V | R | I | I | V | D | M | T | I | S | A | 36 |
| | PL088 | I | I | V | L | V | F | V | T | Y | L | T | A | 37 |
| | PL101 | I | L | Y | L | C | V | L | S | V | S | R | N | 44 |
| | PL112 | G | L | W | G | K | W | E | P | G | G | Q | G | 47 |
| | PL117 | V | I | G | T | V | M | C | T | L | T | W | G | 52 |
| | PL119 | T | S | D | L | E | T | Q | S | G | G | R | L | 54 |
| | PL120 | I | V | T | T | N | H | V | L | V | C | T | Y | 55 |
| | PL121 | D | G | M | F | R | M | T | L | L | T | S | W | 56 |
| | PL124 | L | L | V | S | L | P | V | L | L | S | C | G | 59 |
| | PL126 | W | T | R | F | M | R | A | L | G | F | T | Q | 61 |
| | PL125 | L | N | W | L | R | G | W | T | G | L | V | G | 60 |
| | PL132 | I | T | F | W | S | F | V | F | T | M | R | W | 67 |

FIGURE 3B

| | | | | | | | | | | | | | | SEQ ID NO: |
|---|---|---|---|---|---|---|---|---|---|---|---|---|---|---|
| Weakly Inhibitory < 0.7 | PL012 | G | I | G | A | I | V | G | V | L | I | L | G | 7 |
| | PL021 | A | L | L | V | A | M | W | A | G | V | A | G | 9 |
| | PL032 | F | K | W | V | L | A | R | L | T | Q | S | S | 15 |
| | PL039 | C | E | S | G | K | S | Y | R | I | G | K | W | 19 |
| | PL115 | V | L | S | A | N | I | W | A | G | M | R | F | 50 |
| | PL128 | L | Y | A | F | G | T | C | E | F | S | V | M | 63 |
| | PL129 | Y | Y | T | F | I | L | P | L | S | L | S | C | 64 |
| | PL141 | Y | C | A | H | L | S | C | T | V | C | V | Y | 73 |

FIGURE 3C

| | | | | | | | | | | | | | | SEQ ID NO: |
|---|---|---|---|---|---|---|---|---|---|---|---|---|---|---|
| Weakly Inhibitory > 0.7 | PL023 | V | C | E | C | G | P | R | V | T | L | T | Q | 10 |
| | PL027 | L | T | T | I | C | R | W | M | R | R | R | D | 11 |
| | PL116 | I | V | I | C | C | V | G | V | L | T | H | P | 51 |
| | PL127 | Y | C | P | G | P | S | V | E | I | R | R | C | 62 |
| | PL130 | M | E | R | V | R | K | W | F | N | E | G | R | 65 |
| | PL136 | F | Q | L | E | F | S | V | A | V | G | A | V | 68 |

FIGURE 3D

| | | | | | | | | | | | | | | SEQ ID NO: |
|---|---|---|---|---|---|---|---|---|---|---|---|---|---|---|
| Non-Inhibitory | PL062c | F | Y | L | N | I | C | A | C | W | P | S | N | 77 |
| | PL066c | W | P | R | G | R | Q | E | L | A | G | R | E | 78 |

FIGURE 3E

| | | | | | | | | | | | | | | SEQ ID NO. |
|---|---|---|---|---|---|---|---|---|---|---|---|---|---|---|
| Lytic | PL029 | M | T | K | M | F | R | R | W | R | T | N | K | 12 |
| | PL030 | L | G | W | L | R | G | K | A | L | G | R | G | 13 |
| | PL034 | F | A | A | V | V | R | W | V | R | G | R | A | 14 |
| | PL035 | Y | G | K | A | R | R | W | L | G | R | W | T | 16 |
| | PL038 | I | S | W | L | G | G | L | L | G | R | R | E | 18 |
| | PL047 | I | R | A | F | R | S | F | T | Q | L | L | C | 21 |
| | PL049 | W | R | Y | L | L | G | R | G | K | R | R | K | 23 |
| | PL054 | W | G | S | L | M | L | K | W | R | R | T | R | 24 |
| | PL055 | I | K | W | I | R | S | L | L | V | R | G | R | 25 |
| | PL061 | I | K | W | I | R | S | L | L | V | R | G | R | 27 |
| | PL062 | F | A | R | L | H | K | W | F | Q | R | R | K | 28 |
| | PL063 | I | K | L | L | R | I | L | S | Q | K | W | R | 29 |
| | PL064 | W | V | W | S | R | W | L | R | R | G | W | | 30 |
| | PL065 | L | K | G | L | K | R | W | W | R | P | E | H | 31 |
| | PL066 | W | K | W | L | Q | S | L | W | G | C | E | V | 32 |
| | PL068 | W | K | W | L | Q | S | L | W | G | C | E | V | 33 |
| | PL072 | W | R | G | V | R | K | V | W | R | R | M | R | 35 |
| | PL092 | Y | C | W | L | R | E | K | L | G | G | G | Q | 38 |
| | PL093 | Y | C | W | L | R | E | K | L | G | G | G | Q | 39 |
| | PL094 | Y | C | W | L | R | E | K | L | G | G | G | Q | 40 |
| | PL095 | W | Q | L | V | R | R | L | L | G | Q | L | G | 41 |
| | PL097 | W | V | T | A | R | D | W | V | K | S | W | W | 42 |
| | PL098 | W | R | R | W | K | M | R | G | R | A | R | V | 43 |
| | PL104 | M | G | M | L | R | W | L | F | S | F | W | R | 45 |
| | PL111 | L | S | R | A | K | A | L | L | K | R | A | K | 46 |
| | PL113 | C | R | Y | L | R | L | L | W | S | N | I | R | 48 |
| | PL118 | Y | R | R | V | G | G | W | L | R | R | V | L | 53 |
| | PL122 | V | N | W | W | R | R | C | W | K | Q | W | H | 57 |
| | PL123 | W | T | W | I | K | R | V | L | Q | E | M | G | 58 |
| | PL126 | W | T | R | F | M | R | A | L | G | F | T | Q | 61 |
| | PL131 | Y | S | A | I | K | R | R | L | L | Q | G | R | 66 |
| | PL137 | L | S | L | A | I | E | F | S | L | S | V | Q | 69 |
| | PL138 | W | R | W | V | S | R | K | W | Q | T | R | G | 70 |
| | PL139 | M | A | W | L | A | Q | W | W | G | A | R | R | 71 |
| | PL140 | V | N | A | W | R | K | L | A | Q | I | W | R | 72 |
| | PL142 | I | G | L | L | K | R | L | V | T | T | R | S | 74 |
| | PL144 | W | D | R | V | I | K | W | L | R | C | G | K | 75 |
| | PL145 | G | R | L | V | A | R | V | W | R | K | W | K | 76 |

| Reoccuring Lytic residues |
|---|
| Arginine |
| Tryptophan |
| Lysine |
| Leucine |

FIGURE 7-1

ACTTTTCATACTCCCGCCATTCAGAGAAGAAACCAATTGTCCATATTGCATC
AGACATTGCCGTCACTGCGTCTTTTACTGGCTCTTCTCGCTAACCAAACCGG
TAACCCCGCTTATTAAAAGCATTCTGTAACAAAGCGGGACCAAAGCCATGAC
AAAAACGCGTAACAAAAGTGTCTATAATCACGGCAGAAAAGTCCACATTGAT
TATTTGCACGGCGTCACACTTTGCTATGCCATAGCATTTTTATCCATAAGATT
AGCGGATCCTACCTGACGCTTTTTATCGCAACTCTCTACTGTTTCTCCATGC
GGCCGCGAAATAATTTTGTTTAACTTTAAGAAGGAGATATACATATGAAACAA
AGCACTATTGCACTGGCACTCTTACCGTTACTGTACACCCCTGTGACAAAAG
CCGAAGGCGGCGGCGCCCGGACACCAGAAATGCCTGTTCTGGAAAACCGG
GCTGCTCAGGGCGATATTACTGCACCCGGCGGTGCTCGCCGTTTAACGGG
TGATCAGACTGCCGCTCTGCGTGATTCTCTTAGCGATAAACCTGCAAAAAT
ATTATTTTGCTGATTGGCGATGGGATGGGGGACTCGGAAATTACTGCCGCA
CGTAATTATGCCGAAGGTGCGGGCGGCTTTTTTAAAGGTATAGATGCCTTAC
CGCTTACCGGGCAATACACTCACTATGCGCTGAATAAAAAAACCGGCAAAC
CGGACTACGTCACCGACTCGGCTGCATCAGCAACCGCCTGGTCAACCGGT
GTCAAAACCTATAACGGCGCGCTGGGCGTCGATATTCACGAAAAAGATCAC
CCAACGATTCTGGAAATGGCAAAAGCCGCAGGTCTGGCGACCGGTAACGTT
TCTACCGCAGAGTTGCAGGATGCCACGCCCGCTGCGCTGGTGGCACATGT
GACCTCGCGCAAATGCTACGGTCCGAGCGCGACCAGTGAAAAATGTCCGG
GTAACGCTCTGGAAAAAGGCGGAAAAGGATCGATTACCGAACAGCTGCTTA
ACGCTCGTGCCGACGTTACGCTTGGCGGCGGCGCAAAAACCTTTGCTGAAA
CGGCAACCGCTGGTGAATGGCAGGGAAAAACGCTGCGTGAACAGGCACAG
GCGCGTGGTTATCAGTTGGTGAGCGATGCTGCCTCACTGAATTCGGTGACG
GAAGCGAATCAGCAAAAACCCCTGCTTGGCCTGTTTGCTGACGGCAATATG
CCAGTGCGCTGGCTAGGACCGAAAGCAACGTACCATGGCAATATCGATAAG
CCCGCAGTCACCTGTACGCCAAATCCGCAACGTAATGACAGTGTACCAACC
CTGGCGCAGATGACCGACAAAGCCATTGAATTGTTGAGTAAAAATGAGAAA
GGCTTTTTCCTGCAAGTTGAAGGTGCGTCAATCGATAAACAGGATCATGCTG
CGAATCCTTGTGGGCAAATTGGCGAGACGGTCGATCTCGATGAAGCCGTAC
AACGGGCGCTGGAATTCGCTAAAAAGGAGGGTAACACGCTGGTCATAGTCA
CCGCTGATCACGCCCACGCCAGCCAGATTGTTGCGCCGGATACCAAAGCT
CCGGGCCTCACCCAGGCGCTAAATACCAAAGATGGCGCAGTGATGGTGAT
GAGTTACGGGAACTCCGAAGAGGATTCACAAGAACATACCGGCAGTCAGTT
GCGTATTGCGGCGTATGGCCCGCATGCCGCCAATGTTGTTGGACTGACCGA
CCAGACCGATCTCTTCTACACCATGAAAGCCGCTCTGGGGCTGAAACATCA
TCATCATCATCATTAACTGTTATCTAGAATAAAACGAAAGGCTCAGTCGAAA
GACTGGGCCTTTCGTTTTATCTGTTGTTTGTCGGTGAACGCTCTCCTGAGTA
GGACAAATCCGCCGGGAGCGGATTTGAACGTTGCGAAGCAACGGCCCGGA
GGGTGGCGGGCAGGACGCCCGCCATAAACTGCCAGGCATCAAATTAAGCA
GAAGGCCATCCTGACGGATGGCCTTTTTGAATTCACTGGCCGTCGTTTTACA
ACGTCGTGACTGGGAAAACCCTGGCGTTACCCAACTTAATCGCCTTGCAGC
ACATCCCCCTTTCGCCAGACTCACCAGTCACAGAAAAGCATCTTACGGATG

Figure 7-2

GCATGACAGTAAGAGAATTATGCAGTGCTGCCATAACCATGAGTGATAACAC
TGCGGCCAACTTACTTCTGACAACGATCGGAGGACCGAAGGAGCTAACCGC
TTTTTTGCACAACATGGGGGATCATGTAACTCGCCTTGATCGTTGGGAACCG
GAGCTGAATGAAGCCATACCAAACGACGAGCGTGACACCACGATGCCTGCA
GCAATGGCAACAACGTTGCGCAAACTATTAACTGGCGAACTACTTACTCTAG
CTTCCCGGCAACAATTAATAGACTGGATGGAGGCGGATAAAGTTGCAGGAC
CACTTCTGCGCTCGGCCCTTCCGGCTGGCTGGTTTATTGCTGATAAATCTG
GAGCCGGTGAGCGTGGGTCTCGCGGTATCATTGCAGCACTGGGGCCAGAT
GGTAAGCCCTCCCGTATCGTAGTTATCTACACGACGGGGAGTCAGGCAACT
ATGGATGAACGAAATAGACAGATCGCTGAGATAGGTGCCTCACTGATTAAG
CATTGGTAACTGTCAGACCAAGTTTACTCATATATACTTTAGATTGATTTAAA
ACTTCATTTTTAATTTAAAAGGATCTAGGTGAAGATCCTTTTTGATAATCTCAT
GACCAAAATCCCTTAACGTGAGTTTTCGTTCCACTGAGCGTCAGACCCCTTA
ATAAGATGATCTTCTTGAGATCGTTTTGGTCTGCGCGTAATCTCTTGCTCTG
AAAACGAAAAAACCGCCTTGCAGGGCGGTTTTTCGAAGGTTCTCTGAGCTA
CCAACTCTTTGAACCGAGGTAACTGGCTTGGAGGAGCGCAGTCACCAAAAC
TTGTCCTTTCAGTTTAGCCTTAACCGGCGCATGACTTCAAGACTAACTCCTC
TAAATCAATTACCAGTGGCTGCTGCCAGTGGTGCTTTTGCATGTCTTTCCGG
GTTGGACTCAAGACGATAGTTACCGGATAAGGCGCAGCGGTCGGACTGAA
CGGGGGGTTCGTGCATACAGTCCAGCTTGGAGCGAACTGCCTACCCGGAA
CTGAGTGTCAGGCGTGGAATGAGACAAACGCGGCCATAACAGCGGAATGA
CACCGGTAAACCGAAAGGCAGGAACAGGAGAGCGCACGAGGGAGCCGCC
AGGGGGAAACGCCTGGTATCTTTATAGTCCTGTCGGGTTTCGCCACCACTG
ATTTGAGCGTCAGATTTCGTGATGCTTGTCAGGGGGGCGGAGCCTATGGAA
AAACGGCTTTGCCGCGGCCCTCTCACTTCCCTGTTAAGTATCTTCCTGGCAT
CTTCCAGGAAATCTCCGCCCCGTTCGTAAGCCATTTCCGCTCGCCGCAGTC
GAACGACCGAGCGTAGCGAGTCAGTGAGCGAGGAAGCGGAATATATCCTG
TATCACATATTCTGCTGACGCACCGGTGCAGCCTTTTTTCTCCTGCCACATG
AAGCACTTCACTGACACCCTCATCAGTGCCAACATAGTAAGCCAGTATACAC
TCCGCTAGCGCTGAGGTCTGCCTCGTGAAGAAGGTGTTGCTGACTCATACC
AGGCCTGAATCGCCCCATCATCCAGCCAGAAAGTGAGGGAGCCACGGTTG
ATGAGAGCTTTGTTGTAGGTGGACCAGTTGGTGATTTTGAACTTTTGCTTTG
CCACGGAACGGTCTGCGTTGTCGGGAAGATGCGTGATCTGATCCTTCAACT
CAGCAAAAGTTCGATTTATTCAACAAAGCCACGTTGTGTCTCAAAATCTCTG
ATGTTACATTGCACAAGATAAAAATATATCATCATGAACAATAAAACTGTCTG
CTTACATAAACAGTAATACAAGGGGTGTTATGAGCCATATTCAACGGGAAAC
GTCTTGCTCGAGGCCGCGATTAAATTCCAACATGGATGCTGATTTATATGGG
TATAAATGGGCTCGCGATAATGTCGGGCAATCAGGTGCGACAATCTATCGA
TTGTATGGGAAGCCCGATGCGCCAGAGTTGTTTCTGAAACATGGCAAAGGT
AGCGTTGCCAATGATGTTACAGATGAGATGGTCAGACTAAACTGGCTGACG
GAATTTATGCCTCTTCCGACCATCAAGCATTTTATCCGTACTCCTGATGATG
CATGGTTACTCACCACTGCGATCCCCGGGAAAACAGCATTCCAGGTATTAG
AAGAATATCCTGATTCAGGTGAAAATATTGCTGATGCGCTGGCAGTGTTCCT
GCGCCGGTTGCATTCGATTCCTGTTTGTAATTGTCCTTTTAACAGCGATCGC
GTATTTCGTCTCGCTCAGGCGCAATCACGAATGAATAACGGTTTGGTTGATG
CGAGTGATTTTGATGACGAGCGTAATGGCTGGCCTGTTGAACAAGTCTGGA

Figure 7-3

AAGAAATGCATAAACTTTTGCCATTCTCACCGGATTCAGTCGTCACTCATGG
TGATTTCTCACTTGATAACCTTATTTTTGACGAGGGGAAATTAATAGGTTGTA
TTGATGTTGGACGAGTCGGAATCGCAGACCGATACCAGGATCTTGCCATCC
TATGGAACTGCCTCGGTGAGTTTTCTCCTTCATTACAGAAACGGCTTTTTCA
AAAATATGGTATTGATAATCCTGATATGAATAAATTGCAGTTTCATTTGATGC
TCGATGAGTTTTTCTAATCAGAATTGGTTAATTGGTTGTAACACTGGCAGAG
CATTACGCTGACTTGACGGGACGGCGGCTTTGTTGAATAAATCGAACTTTTG
CTGAGTTGAAGGATCAGATCACGCATCTTCCCGACAACGCAGACCGTTCCG
TGGCAAAGCAAAAGTTCAAAATCACTAGTCGACCATGGTACCATCGATGCAT
AATGTGCCTGTCAAATGGACGAAGCAGGGATTCTGCAAACCCTATGCTACT
CCGTCAAGCCGTCAATTGTCTGATTCGTTACCAATTATGACAACTTGACGGC
TACATCATTCACTTTTTCTTCACAACCGGCACGGAACTCGCTCGGGCTGGCC
CCGGTGCATTTTTTAAATACCCGCGAGAAATAGAGTTGATCGTCAAAACCAA
CATTGCGACCGACGGTGGCGATAGGCATCCGGGTGGTGCTCAAAAGCAGC
TTCGCCTGGCTGATACGTTGGTCCTCGCGCCAGCTTAAGACGCTAATCCCT
AACTGCTGGCGGAAAAGATGTGACAGACGCGACGGCGACAAGCAAACATG
CTGTGCGACGCTGGCGATATCAAAATTGCTGTCTGCCAGGTGATCGCTGAT
GTACTGACAAGCCTCGCGTACCCGATTATCCATCGGTGGATGGAGCGACTC
GTTAATCGCTTCCATGCGCCGCAGTAACAATTGCTCAAGCAGATTTATCGCC
AGCAGCTCCGAATAGCGCCCTTCCCCTTGCCCGGCGTTAATGATTTGCCCA
AACAGGTCGCTGAAATGCGGCTGGTGCGCTTCATCCGGGCGAAAGAACCC
CGTATTGGCAAATATTGACGGCCAGTTAAGCCATTCATGCCAGTAGGCGCG
CGGACGAAAGTAAACCCACTGGTGATACCATTCGCGAGCCTCCGGATGACG
ACCGTAGTGATGAATCTCTCCTGGCGGGAACAGCAAAATATCACCCGGTCG
GCAAACAAATTCTCGTCCCTGATTTTTCACCACCCCCTGACCGCGAATGGTG
AGATTGAGAATATAACCTTTCATTCCCAGCGGTCGGTCGATAAAAAAATCGA
GATAACCGTTGGCCTCAATCGGCGTTAAACCCGCCACCAGATGGGCATTAA
ACGAGTATCCCGGCAGCAGGGGATCATTTTGCGCTTCAGCCAT (SEQ ID NO:1)

Figure 13
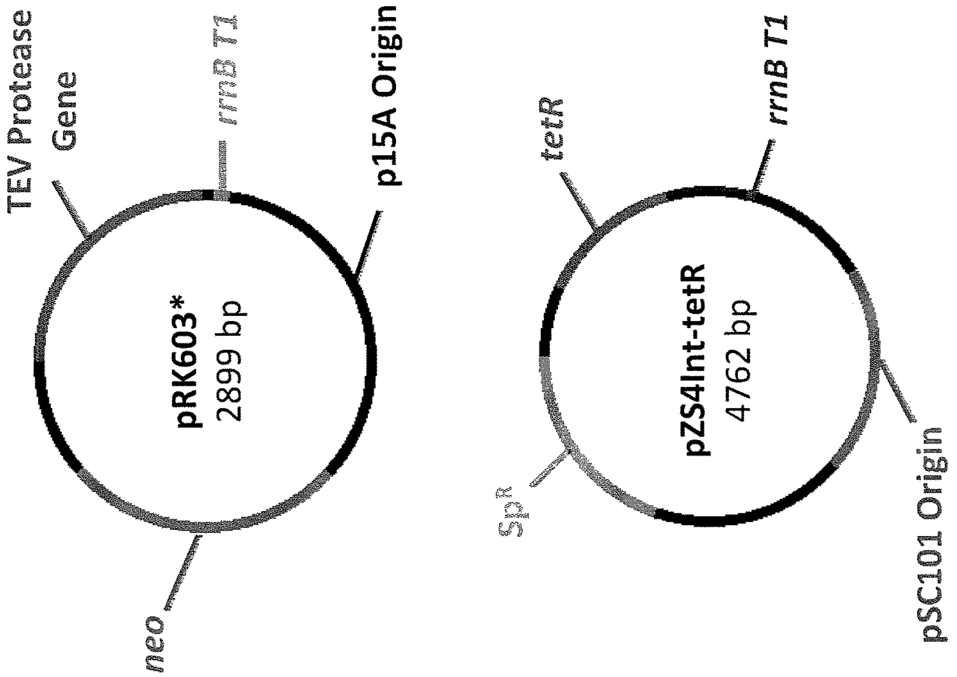
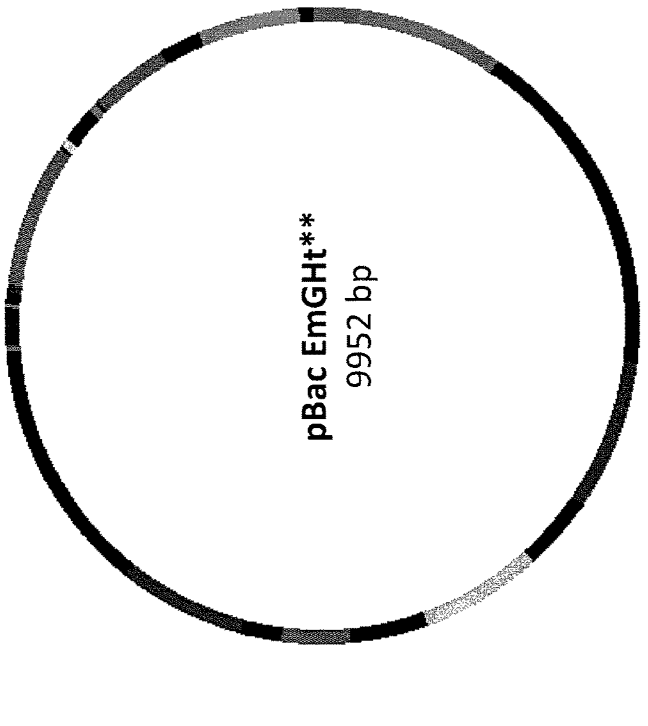
* Kapust RB et al. Protein Expr Purif. 2000 Jul . 19(2):312-8.
** Figure 14

Figure 15

| Element | Location (bp) |
|---|---|
| $p_{BAD}$ | 1-28 |
| $(His)_6$ tag | 95-112 |
| TEV Protease Recognition Sequence | 152-172 |
| DNK $(NNK)_{11}$ Random Sequence | 173-208 |
| Linker Peptide | 209-223 |
| *emgfp* | 224-943 |
| *rrnB T1* | 961-1004 |
| *rrnB T2* | 1136-1165 |
| *loxP* | 1188-1231 |
| *cos* | 1244-1644 |
| *parC* | 1861-2376 |
| *parB* | 2449-3421 |
| *parA* | 3421-4587 |
| *repE* | 5174-5930 |
| *oriV* | 6313-6930 |
| *redF* | 7325-7672 |
| *cat* | 7979-8538 |
| *araC* | 8799-9677 |
| *pC* | 9828-9854 |

Figure 16-1 pBac EmGHt Sequence

```
   1 GACGCTTTTT ATCGCAACTC TCTACTGTTT CTCCATGCGG CCGCGAAATA
  51 ATTTTGTTTA ACTTTAAGAA GGAGATATAC ATATGCGGGG TTCTCATCAT
 101 CATCATCATC ATGGTATGGC TAGCATGACT GGTGGACAGC AAATGGGTCG
 151 GGAAAACCTG TACTTCCAGG GCDNKNNKNN KNNKNNKNNK NNKNNKNNKN
 201 NKNNKNNKGA AGGCGGCGGC GCCATGGTGA GCAAGGGCGA GGAGCTGTTC
 251 ACCGGGGTGG TGCCCATCCT GGTCGAGCTG GACGGCGACG TAAACGGCCA
 301 CAAGTTCAGC GTGTCCGGCG AGGGCGAGGG CGATGCCACC TACGGCAAGC
 351 TGACCCTGAA GTTCATCTGC ACCACCGGCA AGCTGCCCGT GCCCTGGCCC
 401 ACCCTCGTGA CCACCTTGAC CTACGGCGTG CAGTGCTTCG CCCGCTACCC
 451 CGACCACATG AAGCAGCACG ACTTCTTCAA GTCCGCCATG CCCGAAGGCT
 501 ACGTCCAGGA GCGCACCATC TTCTTCAAGG ACGACGGCAA CTACAAGACC
 551 CGCGCCGAGG TGAAGTTCGA GGGCGACACC CTGGTGAACC GCATCGAGCT
 601 GAAGGGCATC GACTTCAAGG AGGACGGCAA CATCCTGGGG CACAAGCTGG
 651 AGTACAACTA CAACAGCCAC AAGGTCTATA TCACCGCCGA CAAGCAGAAG
 701 AACGGCATCA AGGTGAACTT CAAGACCCGC CACAACATCG AGGACGGCAG
 751 CGTGCAGCTC GCCGACCACT ACCAGCAGAA CACCCCCATC GGCGACGGCC
 801 CCGTGCTGCT GCCCGACAAC CACTACCTGA GCACCCAGTC CGCCCTGAGC
 851 AAAGACCCCA ACGAGAAGCG CGATCACATG GTCCTGCTGG AGTTCGTGAC
 901 CGCCGCCGGG ATCACTCTCG GCATGGACGA GCTGTACAAG TAACTCGAGA
 951 AGCTTCTAGA ATAAAACGAA AGGCTCAGTC GAAAGACTGG GCCTTTCGTT
1001 TTATCTGTTG TTTGTCGGTG AACGCTCTCC TGAGTAGGAC AAATCCGCCG
1051 GGAGCGGATT TGAACGTTGC GAAGCAACGG CCCGGAGGGT GGCGGGCAGG
1101 ACGCCCGCCA TAAACTGCCA GGCATCAAAT TAAGCAGAAG GCCATCCTGA
1151 CGGATGGCCT TTTTGAATTC ATGCCGTAAT AGGCCGCATC GAATATAACT
1201 TCGTATAATG TATGCTATAC GAAGTTATTA GCGATGAGCT CGGACTTCCA
1251 TTGTTCATTC CACGGACAAA AACAGAGAAA GGAAACGACA GAGGCCAAAA
1301 AGCTCGCTTT CAGCACCTGT CGTTTCCTTT CTTTTCAGAG GGTATTTTAA
1351 ATAAAAACAT TAAGTTATGA CGAAGAAGAA CGGAAACGCC TTAAACCGGA
1401 AAATTTTCAT AAATAGCGAA AACCCGCGAG GTCGCCGCCC CGTAACCTGT
1451 CGGATCACCG GAAAGGACCC GTAAAGTGAT AATGATTATC ATCTACATAT
1501 CACAACGTGC GTGGAGGCCA TCAAACCACG TCAAATAATC AATTATGACG
1551 CAGGTATCGT ATTAATTGAT CTGCATCAAC TTAACGTAAA AACAACTTCA
1601 GACAATACAA ATCAGCGACA CTGAATACGG GGCAACCTCA TGTCCGAGCT
1651 CGCGAGCTCG TCGACAGCGA CACACTTGCA TCGGATGCAG CCCGGTTAAC
1701 GTGCCGGCAC GGCCTGGGTA ACCAGGTATT TTGTCCACAT AACCGTGCGC
1751 AAAATGTTGT GGATAAGCAG GACACAGCAG CAATCCACAG CAGGCATACA
1801 ACCGCACACC GAGGTTACTC CGTTCTACAG GTTACGACGA CATGTCAATA
1851 CTTGCCCTTG ACAGGCATTG ATGGAATCGT AGTCTCACGC TGATAGTCTG
1901 ATCGACAATA CAAGTGGGAC CGTGGTCCCA GACCGATAAT CAGACCGACA
1951 ACACGAGTGG GATCGTGGTC CCAGACTAAT AATCAGACCG ACGATACGAG
2001 TGGGACCGTG GTCCCAGACT AATAATCAGA CCGACGATAC GAGTGGGACC
2051 GTGGTTCCAG ACTAATAATC AGACCGACGA TACGAGTGGG ACCGTGGTCC
2101 CAGACTAATA ATCAGACCGA CGATACGAGT GGGACCATGG TCCCAGACTA
2151 ATAATCAGAC CGACGATACG AGTGGGACCG TGGTCCCAGT CTGATTATCA
2201 GACCGACGAT ACGAGTGGGA CCGTGGTCCC AGACTAATAA TCAGACCGAC
2251 GATACGAGTG GGACCGTGGT CCCAGACTAA TAATCAGACC GACGATACGA
2301 GTGGGACCGT GGTCCCAGTC TGATTATCAG ACCGACGATA CAAGTGGAAC
2351 AGTGGGCCCA GAGAGAATAT TCAGGCCAGT TATGCTTTCT GGCCTGTAAC
2401 AAAGGACATT AAGTAAAGAC AGATAAACGT AGACTAAAAC GTGGTCGCAT
2451 CAGGGTGCTG GCTTTTCAAG TTCCTTAAGA ATGGCCTCAA TTTTCTCTAT
2501 ACACTCAGTT GGAACACGAG ACCTGTCCAG GTTAAGCACC ATTTTATCGC
2551 CCTTATACAA TACTGTCGCT CCAGGAGCAA ACTGATGTCG TGAGCTTAAA
2601 CTAGTTCTTG ATGCAGATGA CGTTTTAAGC ACAGAAGTTA AAAGAGTGAT
2651 AACTTCTTCA GCTTCAAATA TCACCCCAGC TTTTTTCTGC TCATGAAGGT
2701 TAGATGCCTG CTGCTTAAGT AATTCCTCTT TATCTGTAAA GGCTTTTTGA
2751 AGTGCATCAC CTGACCGGGC AGATAGTTCA CCGGGGTGAG AAAAAAGAGC
2801 AACAACTGAT TTAGGCAATT TGGCGGTGTT GATACAGCGG GTAATAATCT
2851 TACGTGAAAT ATTTTCCGCA TCAGCCAGCG CAGAAATATT TCCAGCAAAT
2901 TCATTCTGCA ATCGGCTTGC ATAACGCTGA CCACGTTCAT AAGCACTTGT
2951 TGGGCGATAA TCGTTACCCA ATCTGGATAA TGCAGCCATC TGCTCATCAT
3001 CCAGCTCGCC AACCAGAACA CGATAATCAC TTTCGGTAAG TGCAGCAGCT
3051 TTACGACGGC GACTCCCATC GGCAATTTCT ATGACACCAG ATACTCTTCG
3101 ACCGAACGCC GGTGTCTGTT GACCAGTCAG TAGAAAAGAA GGGATGAGAT
3151 CATCCAGTGC GTCCTCAGTA AGCAGCTCCT GGTCACGTTC ATTACCTGAC
3201 CATACCCGAG AGGTCTTCTC AACACTATCA CCCCGGAGCA CTTCAAGAGT
3251 AAACTTCACA TCCCGACCAC ATACAGGCAA AGTAATGGCA TTACCGCGAG
```

Figure 16-2

3301 CCATTACTCC TACGCGCGCA ATTAACGAAT CCACCATCGG GGCAGCTGGT
3351 GTCGATAACG AAGTATCTTC AACCGGTTGA GTATTGAGCG TATGTTTTGG
3401 AATAACAGGC GCACGCTTCA TTATCTAATC TCCCAGCGTG GTTTAATCAG
3451 ACGATCGAAA ATTTCATTGC AGACAGGTTC CCAAATAGAA AGAGCATTTC
3501 TCCAGGCACC AGTTGAAGAG CGTTGATCAA TGGCCTGTTC AAAAACAGTT
3551 CTCATCCGGA TCTGACCTTT ACCAACTTCA TCCGTTTCAC GTACAACATT
3601 TTTTAGAACC ATGCTTCCCC AGGCATCCCG AATTTGCTCC TCCATCCACG
3651 GGGACTGAGA GCCATTGCTA TTGCTGTATT TGGTAAGCAA AATACGTACA
3701 TCAGGCTCGA ACCCTTTAAG ATCAACGTTC TTGAGCAGAT CACGAAGCAT
3751 ATCGAAAAAC TGCAGTGCGG AGGTGTAGTC AAACAACTCA GCAGGCGTGG
3801 GAACAATCAG CACATCAGCA GCACATACGA CATTAATCGT GCCGATACCC
3851 AGGTTAGGCG CGCTGTCAAT AACTATGACA TCATAGTCAT GAGCAACAGT
3901 TTCAATGGCC AGTCGGAGCA TCAGGTGTGG ATCGGTGGGC AGTTTACCTT
3951 CATCAAATTT GCCCATTAAC TCAGTTTCAA TACGGTGCAG AGCCAGACAG
4001 GAAGGAATAA TGTCAAGCCC CGGCCAGCAA GTGGGCTTTA TTGCATAAGT
4051 GACATCGTCC TTTTCCCCAA GATAGAAAGG CAGGAGAGTG TCTTCTGCAT
4101 GAATATGAAG ATCTGGTACC CATCCGTGAT ACATTGAGGC TGTTCCCTGG
4151 GGGTCGTTAC CTTCCACGAG CAAAACACGT AGCCCCTTCA GAGCCAGATC
4201 CTGAGCAAGA TGAACAGAAA CTGAGGTTTT GTAAACGCCA CCTTTATGGG
4251 CAGCAACCCC GATCACCGGT GGAAATACGT CTTCAGCACG TCGCAATCGC
4301 GTACCAAACA CATCACGCAT ATGATTAATT TGTTCAATTG TATAACCAAC
4351 ACGTTGCTCA ACCCGTCCTC GAATTTCCAT ATCCGGGTGC GGTAGTCGCC
4401 CTGCTTTCTC GGCATCTCTG ATAGCCTGAG AAGAAACCCC AACTAAATCC
4451 GCTGCTTCAC CTATTCTCCA GCGCCGGGTT ATTTTCCTCG CTTCCGGGCT
4501 GTCATCATTA AACTGTGCAA TGGCGATAGC CTTCGTCATT TCATGACCAG
4551 CGTTTATGCA CTGGTTAAGT GTTTCCATGA GTTTCATTCT GAACATCCTT
4601 TAATCATTGC TTTGCGTTTT TTTATTAAAT CTTGCAATTT ACTGCAAAGC
4651 AACAACAAAA TCGCAAAGTC ATCAAAAAAC CGCAAAGTTG TTTAAAATAA
4701 GAGCAACACT ACAAAAGGAG ATAAGAAGAG CACATACCTC AGTCACTTAT
4751 TATCACTAGC GCTCGCCGCA GCCGTGTAAC CGAGCATAGC GAGCGAACTG
4801 GCGAGGAAGC AAAGAAGAAC TGTTCTGTCA GATAGCTCTT ACGCTCAGCG
4851 CAAGAAGAAA TATCCACCGT GGGAAAAACT CCAGGTAGAG GTACACACGC
4901 GGATAGCCAA TTCAGAGTAA TAAACTGTGA TAATCAACCC TCATCAATGA
4951 TGACGAACTA ACCCCCGATA TCAGGTCACA TGACGAAGGG AAAGAGAAGG
5001 AAATCAACTG TGACAAACTG CCCTCAAATT TGGCTTCCTT AAAAATTACA
5051 GTTCAAAAAG TATGAGAAAA TCCATGCAGG CTGAAGGAAA CAGCAAAACT
5101 GTGACAAATT ACCCTCAGTA GGTCAGAACA AATGTGACGA ACCACCCTCA
5151 AATCTGTGAC AGATAACCCT CAGACTATCC TGTCGTCATG GAAGTGATAT
5201 CGCGGAAGGA AAATACGATA TGAGTCGTCT GGCGGCCTTT CTTTTTCTCA
5251 ATGTATGAGA GGCGCATTGG AGTTCTGCTG TTGATCTCAT TAACACAGAC
5301 CTGCAGGAAG CGGCGGCGGA AGTCAGGCAT ACGCTGGTAA CTTTGAGGCA
5351 GCTGGTAACG CTCTATGATC CAGTCGATTT TCAGAGAGAC GATGCCTGAG
5401 CCATCCGGCT TACGATACTG ACACAGGGAT TCGTATAAAC GCATGGCATA
5451 CGGATTGGTG ATTTCTTTTG TTTCACTAAG CCGAAACTGC GTAAACCGGT
5501 TCTGTAACCC GATAAAGAAG GGAATGAGAT ATGGGTTGAT ATGTACGCTG
5551 TAAAGCCCTC TGGATGGACT GTGCGCACGT TTGATAAACC AAGGAAAAGA
5601 TTCATAGCCT TTTTCATCGC CGGCATCCTC TTCAGGGCGA TAAAAAACCA
5651 CTTCCTTCCC CGCGAAACTC TTCAATGCCT GCCGTATATC CTTACTGGCT
5701 TCCGCAGAGG TCAATCCGAA TATTTCAGCA TATTTAGCAA CATGGATCTC
5751 GCAGATACCG TCATGTTCCT GTAGGGTGCC ATCAGATTTT CTGATCTGGT
5801 CAACGAACAG ATACAGCATA CGTTTTTGAT CCCGGGAGAG ACTATATGCC
5851 GCCTCAGTGA GGTCGTTTGA CTGGACGATT CGCGGGCTAT TTTTACGTTT
5901 CTTGTGATTG ATAACCGCTG TTTCCGCCAT GACAGATCCA TGTGAAGTGT
5951 GACAAGTTTT TAGATTGTCA CACTAAATAA AAAAGAGTCA ATAAGCAGGG
6001 ATAACTTTGT GAAAAAACAG CTTCTTCTGA GGGCAATTTG TCACAGGGTT
6051 AAGGGCAATT TGTCACAGAC AGGACTGTCA TTTGAGGGTG ATTTGTCACA
6101 CTGAAAGGGC AATTTGTCAC AACACCTTCT CTAGAACCAG CATGGATAAA
6151 GGCCTACAAG GCGCTCTAAA AAAGAAGATC TAAAAACTAT AAAAAAAATA
6201 ATTATAAAAA TATCCCCGTG GATAAGTGGA TAACCCCAAG GGAAGTTTTT
6251 TCAGGCATCG TGTGTAAGCA GAATATATAA GTGCTGTTCC CTGGTGCTTC
6301 CTCGCTCACT CGACCGGGAG GGTTCGAGAA GGGGGGGCAC CCCCCTTCGG
6351 CGTGCGCGGT CACGCGCACA GGGCGCAGCC CTGGTTAAAA ACAAGGTTTA
6401 TAAATATTGG TTTAAAAGCA GGTTAAAAGA CAGGTTAGCG GTGGCCGAAA
6451 AACGGGCGGA AACCCTTGCA AATGCTGGAT TTTCTGCCTG TGGACAGCCC
6501 CTCAAATGTC AATAGGTGCG CCCCTCATCT GTCAGCACTC TGCCCCTCAA
6551 GTGTCAAGGA TCGCGCCCCT CATCTGTCAG TAGTCGCGCC CCTCAAGTGT
6601 CAATACCGCA GGGCACTTAT CCCCAGGCTT GTCCACATCA TCTGTGGGAA
6651 ACTCGCGTAA AATCAGGCGT TTTCGCCGAT TTGCGAGGCT GGCCAGCTCC
6701 ACGTCGCCGG CCGAAATCGA GCCTGCCCCT CATCTGTCAA CGCCGCGCCG
6751 GGTGAGTCGG CCCCTCAAGT GTCAACGTCC GCCCCTCATC TGTCAGTGAG
6801 GGCCAAGTTT TCCGCGAGGT ATCCACAACG CCGGCGGCCG GCCGCGGTGT
6851 CTCGCACACG GCTTCGACGG CGTTTCTGGC GCGTTTGCAG GGCCATAGAC

Figure 16-3

```
6901 GGCCGCCAGC CCAGCGGCGA GGGCAACCAG CTCGAGGGCT TCGCCCTGTC
6951 GCTCGACTGC GGCGAGCACT ACTGGCTGTA AAAGGACAGA CCACATCATG
7001 GTTCTGTGTT CATTAGGTTG TTCTGTCCAT TGCTGACATA ATCCGCTCCA
7051 CTTCAACGTA ACACCGCACG AAGATTTCTA TTGTTCCTGA AGGCATATTC
7101 AAATCGTTTT CGTTACCGCT TGCAGGCATC ATGACAGAAC ACTACTTCCT
7151 ATAAACGCTA CACAGGCTCC TGAGATTAAT AATGCGGATC TCTACGATAA
7201 TGGGAGATTT TCCCGACTGT TTCGTTCGCT TCTCAGTGGA TAACAGCCAG
7251 CTTCTCTGTT TAACAGACAA AAACAGCATA TCCACTCAGT TCCACATTTC
7301 CATATAAAGG CCAAGGCATT TATTCTCAGG ATAATTGTTT CAGCATCGCA
7351 ACCGCATCAG ACTCCGGCAT CGCAAACTGC ACCCGGTGCC GGGCAGCCAC
7401 ATCCAGCGCA AAAACCTTCG TGTAGACTTC CGTTGAACTG ATGGACTTAT
7451 GTCCCATCAG GCTTTGCAGA ACTTTCAGCG GTATACCGGC ATACAGCATG
7501 TGCATCGCAT AGGAATGGCG GAACGTATGT GGTGTGACCG GAACAGAGAA
7551 CGTCACACCG TCAGCAGCAG CGGCGGCAAC CGCCTCCCCA ATCCAGGTCC
7601 TGACCGTTCT GTCCGTCACT TCCCAGATCC GCGCTTTCTC TGTCCTTCCT
7651 GTGCGACGGT TACGCCGCTC CATGAGCTTA TCGCGAATAA ATACCTGTGA
7701 CGGAAGATCA CTTCGCAGAA TAAATAAATC CTGGTGTCCC TGTTGATACC
7751 GGGAAGCCCT GGGCCAACTT TTGGCGAAAA TGAGACGTTG ATCGGCACGT
7801 AAGAGGTTCC AACTTTCACC ATAATGAAAT AAGATCACTA CCGGGCGTAT
7851 TTTTTGAGTT ATCGAGATTT TCAGGAGCTA AGGAAGCTAA AATGGAGAAA
7901 AAAATCACTG GATATACCAC CGTTGATATA TCCCAATGGC ATCGTAAAGA
7951 ACATTTTGAG GCATTTCAGT CAGTTGCTCA ATGTACCTAT AACCAGACCG
8001 TTCAGCTGGA TATTACGGCC TTTTTAAAGA CCGTAAAGAA AAATAAGCAC
8051 AAGTTTTATC CGGCCTTTAT TCACATTCTT GCCCGCCTGA TGAATGCTCA
8101 TCCGGAATTT CGTATGGCAA TGAAAGACGG TGAGCTGGTG ATATGGGATA
8151 GTGTTCACCC TTGTTACACC GTTTTCCATG AGCAAACTGA AACGTTTTCA
8201 TCGCTCTGGA GTGAATACCA CGACGATTTC CGGCAGTTTC TACACATATA
8251 TTCGCAAGAT GTGGCGTGTT ACGGTGAAAA CCTGGCCTAT TTCCCTAAAG
8301 GGTTTATTGA GAATATGTTT TTCGTCTCAG CCAATCCCTG GGTGAGTTTC
8351 ACCAGTTTTG ATTTAAACGT GGCCAATATG GACAACTTCT TCGCCCCCGT
8401 TTTCACCATG GGCAAATATT ATACGCAAGG CGACAAGGTG CTGATGCCGC
8451 TGGCGATTCA GGTTCATCAT GCCGTTTGTG ATGGCTTCCA TGTCGGCAGA
8501 ATGCTTAATG AATTACAACA GTACTGCGAT GAGTGGCAGG GCGGGGCGTA
8551 ATTTTTTTAA GGCAGTTATT GGTGCCCTTA AACGCCTGGT TGCTACGCCT
8601 GAATAAGTGA TAATAAGCGG ATGAATGGCA GAAATTCGAT GATAAGCTGT
8651 CAAACATGAG AATTGGTCGA CGGCCCGGGC GGCCATCGAA GCCTATAGGT
8701 ACCATCGATG CATAATGTGC CTGTCAAATG GACGAAGCAG GGATTCTGCA
8751 AACCCTATGC TACTCCGTCA AGCCGTCAAT TGTCTGATTC GTTACCAATT
8801 ATGACAACTT GACGGCTACA TCATTCACTT TTTCTTCACA ACCGGCACGG
8851 AACTCGCTCG GGCTGGCCCC GGTGCATTTT TTAAATACCC GCGAGAAATA
8901 GAGTTGATCG TCAAAACCAA CATTGCGACC GACGGTGGCG ATAGGCATCC
8951 GGGTGGTGCT CAAAAGCAGC TTCGCCTGGC TGATACGTTG GTCCTCGCGC
9001 CAGCTTAAGA CGCTAATCCC TAACTGCTGG CGGAAAAGAT GTGACAGACG
9051 CGACGGCGAC AAGCAAACAT GCTGTGCGAC GCTGGCGATA TCAAAATTGC
9101 TGTCTGCCAG GTGATCGCTG ATGTACTGAC AAGCCTCGCG TACCCGATTA
9151 TCCATCGGTG GATGGAGCGA CTCGTTAATC GCTTCCATGC GCCGCAGTAA
9201 CAATTGCTCA AGCAGATTTA TCGCCAGCAG CTCCGAATAG CGCCCTTCCC
9251 CTTGCCCGGC GTTAATGATT TGCCCAAACA GGTCGCTGAA ATGCGGCTGG
9301 TGCGCTTCAT CCGGGCGAAA GAACCCCGTA TTGGCAAATA TTGACGGCCA
9351 GTTAAGCCAT TCATGCCAGT AGGCGCGCGG ACGAAAGTAA ACCCACTGGT
9401 GATACCATTC GCGAGCCTCC GGATGACGAC CGTAGTGATG AATCTCTCCT
9451 GGCGGGAACA GCAAAATATC ACCCGGTCGG CAAACAAATT CTCGTCCCTG
9501 ATTTTTCACC ACCCCCTGAC CGCGAATGGT GAGATTGAGA ATATAACCTT
9551 TCATTCCCAG CGGTCGGTCG ATAAAAAAAT CGAGATAACC GTTGGCCTCA
9601 ATCGGCGTTA AACCCGCCAC CAGATGGGCA TTAAACGAGT ATCCCGGCAG
9651 CAGGGGATCA TTTTGCGCTT CAGCCATACT TTTCATACTC CCGCCATTCA
9701 GAGAAGAAAC CAATTGTCCA TATTGCATCA GACATTGCCG TCACTGCGTC
9751 TTTTACTGGC TCTTCTCGCT AACCAAACCG GTAACCCCGC TTATTAAAAG
9801 CATTCTGTAA CAAAGCGGGA CCAAAGCCAT GACAAAAACG CGTAACAAAA
9851 GTGTCTATAA TCACGGCAGA AAAGTCCACA TTGATTATTT GCACGGCGTC
9901 ACACTTTGCT ATGCCATAGC ATTTTTATCC ATAAGATTAG CGGATCCTAC CT
```

(SEQ ID NO. 4)

* Based on Epicentre's CopyControl™ pCC1BAC™ Vector

Figure 18

| Element | Location (bp) |
|---|---|
| *$p_{BAD}$* | 1-28 |
| $(His)_6$ tag | 95-112 |
| *emgfp* | 203-919 |
| Linker Peptide | 920-931 |
| $(NNK)_{12}$ Random Sequence | 932-967 |
| *rrnB T1* | 988-1031 |
| *rrnB T2* | 1163-1192 |
| *loxP* | 1215-1258 |
| *cos* | 1271-1671 |
| *parC* | 1886-2403 |
| *parB* | 2476-3448 |
| *parA* | 3448-4614 |
| *repE* | 5201-5957 |
| *oriV* | 6340-6957 |
| *redF* | 7352-7699 |
| *cat* | 7906-8565 |
| *araC* | 8826-9704 |
| *pC* | 9855-9881 |

Figure 19-1 pBac EmGH Sequence

```
   1 GACGCTTTTT ATCGCAACTC TCTACTGTTT CTCCATGCGG CCGCGAAATA
  51 ATTTTGTTTA ACTTTAAGAA GGAGATATAC ATATGCGGGG TTCTCATCAT
 101 CATCATCATC ATGGTATGGC TAGCATGACT GGTGGACAGC AAATGGGTCG
 151 GGATCTGTAC GACGATGACG ATAAGGATCG ATGGGGATCC GAATTCGCCA
 201 CCATGGTGAG CAAGGGCGAG GAGCTGTTCA CCGGGGTGGT GCCCATCCTG
 251 GTCGAGCTGG ACGGCGACGT AAACGGCCAC AAGTTCAGCG TGTCCGGCGA
 301 GGGCGAGGGC GATGCCACCT ACGGCAAGCT GACCCTGAAG TTCATCTGCA
 351 CCACCGGCAA GCTGCCCGTG CCCTGGCCCA CCCTCGTGAC CACCTTGACC
 401 TACGGCGTGC AGTGCTTCGC CCGCTACCCC GACCACATGA AGCAGCACGA
 451 CTTCTTCAAG TCCGCCATGC CCGAAGGCTA CGTCCAGGAG CGCACCATCT
 501 TCTTCAAGGA CGACGGCAAC TACAAGACCC GCGCCGAGGT GAAGTTCGAG
 551 GGCGACACCC TGGTGAACCG CATCGAGCTG AAGGGCATCG ACTTCAAGGA
 601 GGACGGCAAC ATCCTGGGGC ACAAGCTGGA GTACAACTAC AACAGCCACA
 651 AGGTCTATAT CACCGCCGAC AAGCAGAAGA ACGGCATCAA GGTGAACTTC
 701 AAGACCCGCC ACAACATCGA GGACGGCAGC GTGCAGCTCG CCGACCACTA
 751 CCAGCAGAAC ACCCCCATCG GCGACGGCCC CGTGCTGCTG CCCGACAACC
 801 ACTACCTGAG CACCCAGTCC GCCCTGAGCA AAGACCCCAA CGAGAAGCGC
 851 GATCACATGG TCCTGCTGGA GTTCGTGACC GCCGCCGGGA TCACTCTCGG
 901 CATGGACGAG CTGTACAAGG GCGGCGGCGA ANNKNNKNNK NNKNNKNNKN
 951 NKNNKNNKNN KNNKNNKTAA CTCGAGAAGC TTCTAGAATA AAACGAAAGG
1001 CTCAGTCGAA AGACTGGGCC TTTCGTTTTA TCTGTTGTTT GTCGGTGAAC
1051 GCTCTCCTGA GTAGGACAAA TCCGCCGGGA GCGGATTTGA ACGTTGCGAA
1101 GCAACGGCCC GGAGGGTGGC GGGCAGGACG CCCGCCATAA ACTGCCAGGC
1151 ATCAAATTAA GCAGAAGGCC ATCCTGACGG ATGGCCTTTT TGAATTCATG
1201 CCGTAATAGG CCGCATCGAA TATAACTTCG TATAATGTAT GCTATACGAA
1251 GTTATTAGCG ATGAGCTCGG ACTTCCATTG TTCATTCCAC GGACAAAAAC
1301 AGAGAAAGGA AACGACAGAG GCCAAAAAGC TCGCTTTCAG CACCTGTCGT
1351 TTCCTTTCTT TTCAGAGGGT ATTTTAAATA AAAACATTAA GTTATGACGA
1401 AGAAGAACGG AAACGCCTTA AACCGGAAAA TTTTCATAAA TAGCGAAAAC
1451 CCGCGAGGTC GCCGCCCCGT AACCTGTCGG ATCACCGGAA AGGACCCGTA
1501 AAGTGATAAT GATTATCATC TACATATCAC AACGTGCGTG GAGGCCATCA
1551 AACCACGTCA AATAATCAAT TATGACGCAG GTATCGTATT AATTGATCTG
1601 CATCAACTTA ACGTAAAAAC AACTTCAGAC AATACAAATC AGCGACACTG
1651 AATACGGGGC AACCTCATGT CCGAGCTCGC GAGCTCGTCG ACAGCGACAC
1701 ACTTGCATCG GATGCAGCCC GGTTAACGTG CCGGCACGGC CTGGGTAACC
1751 AGGTATTTTG TCCACATAAC CGTGCGCAAA ATGTTGTGGA TAAGCAGGAC
1801 ACAGCAGCAA TCCACAGCAG GCATACAACC GCACACCGAG GTTACTCCGT
1851 TCTACAGGTT ACGACGACAT GTCAATACTT GCCCTTGACA GGCATTGATG
1901 GAATCGTAGT CTCACGCTGA TAGTCTGATC GACAATACAA GTGGGACCGT
1951 GGTCCCAGAC CGATAATCAG ACCGACAACA CGAGTGGGAT CGTGGTCCCA
2001 GACTAATAAT CAGACCGACG ATACGAGTGG GACCGTGGTC CCAGACTAAT
2051 AATCAGACCG ACGATACGAG TGGGACCGTG GTTCCAGACT AATAATCAGA
2101 CCGACGATAC GAGTGGGACC GTGGTCCCAG ACTAATAATC AGACCGACGA
2151 TACGAGTGGG ACCATGGTCC CAGACTAATA ATCAGACCGA CGATACGAGT
2201 GGGACCGTGG TCCCAGTCTG ATTATCAGAC CGACGATACG AGTGGGACCG
2251 TGGTCCCAGA CTAATAATCA GACCGACGAT ACGAGTGGGA CCGTGGTCCC
2301 AGACTAATAA TCAGACCGAC GATACGAGTG GGACCGTGGT CCCAGTCTGA
2351 TTATCAGACC GACGATACAA GTGGAACAGT GGGCCCAGAG AGAATATTCA
2401 GGCCAGTTAT GCTTTCTGGC CTGTAACAAA GGACATTAAG TAAAGACAGA
2451 TAAACGTAGA CTAAAACGTG GTCGCATCAG GGTGCTGGCT TTTCAAGTTC
2501 CTTAAGAATG GCCTCAATTT TCTCTATACA CTCAGTTGGA ACACGAGACC
2551 TGTCCAGGTT AAGCACCATT TTATCGCCCT TATACAATAC TGTCGCTCCA
2601 GGAGCAAACT GATGTCGTGA GCTTAAACTA GTTCTTGATG CAGATGACGT
2651 TTTAAGCACA GAAGTTAAAA GAGTGATAAC TTCTTCAGCT TCAAATATCA
2701 CCCCAGCTTT TTTCTGCTCA TGAAGGTTAG ATGCCTGCTG CTTAAGTAAT
2751 TCCTCTTTAT CTGTAAAGGC TTTTTGAAGT GCATCACCTG ACCGGGCAGA
2801 TAGTTCACCG GGGTGAGAAA AAAGAGCAAC AACTGATTTA GGCAATTTGG
2851 CGGTGTTGAT ACAGCGGGTA ATAATCTTAC GTGAAATATT TTCCGCATCA
2901 GCCAGCGCAG AAATATTTCC AGCAAATTCA TTCTGCAATC GGCTTGCATA
2951 ACGCTGACCA CGTTCATAAG CACTTGTTGG GCGATAATCG TTACCCAATC
3001 TGGATAATGC AGCCATCTGC TCATCATCCA GCTCGCCAAC CAGAACACGA
3051 TAATCACTTT CGGTAAGTGC AGCAGCTTTA CGACGGCGAC TCCCATCGGC
3101 AATTTCTATG ACACCAGATA CTCTTCGACC GAACGCCGGT GTCTGTTGAC
3151 CAGTCAGTAG AAAAGAAGGG ATGAGATCAT CCAGTGCGTC CTCAGTAAGC
3201 AGCTCCTGGT CACGTTCATT ACCTGACCAT ACCCGAGAGG TCTTCTCAAC
3251 ACTATCACCC CGGAGCACTT CAAGAGTAAA CTTCACATCC CGACCACATA
```

Figure 19-2

```
3301 CAGGCAAAGT AATGGCATTA CCGCGAGCCA TTACTCCTAC GCGCGCAATT
3351 AACGAATCCA CCATCGGGGC AGCTGGTGTC GATAACGAAG TATCTTCAAC
3401 CGGTTGAGTA TTGAGCGTAT GTTTTGGAAT AACAGGCGCA CGCTTCATTA
3451 TCTAATCTCC CAGCGTGGTT TAATCAGACG ATCGAAAATT TCATTGCAGA
3501 CAGGTTCCCA AATAGAAAGA GCATTTCTCC AGGCACCAGT TGAAGAGCGT
3551 TGATCAATGG CCTGTTCAAA AACAGTTCTC ATCCGGATCT GACCTTTACC
3601 AACTTCATCC GTTTCACGTA CAACATTTTT TAGAACCATG CTTCCCCAGG
3651 CATCCCGAAT TTGCTCCTCC ATCCACGGGG ACTGAGAGCC ATTGCTATTG
3701 CTGTATTTGG TAAGCAAAAT ACGTACATCA GGCTCGAACC CTTTAAGATC
3751 AACGTTCTTG AGCAGATCAC GAAGCATATC GAAAAACTGC AGTGCGGAGG
3801 TGTAGTCAAA CAACTCAGCA GGCGTGGGAA CAATCAGCAC ATCAGCAGCA
3851 CATACGACAT TAATCGTGCC GATACCCAGG TTAGGCGCGC TGTCAATAAC
3901 TATGACATCA TAGTCATGAG CAACAGTTTC AATGGCCAGT CGGAGCATCA
3951 GGTGTGGATC GGTGGGCAGT TTACCTTCAT CAAATTTGCC CATTAACTCA
4001 GTTTCAATAC GGTGCAGAGC CAGACAGGAA GGAATAATGT CAAGCCCCGG
4051 CCAGCAAGTG GGCTTTATTG CATAAGTGAC ATCGTCCTTT TCCCCAAGAT
4101 AGAAAGGCAG GAGAGTGTCT TCTGCATGAA TATGAAGATC TGGTACCCAT
4151 CCGTGATACA TTGAGGCTGT TCCCTGGGGG TCGTTACCTT CCACGAGCAA
4201 AACACGTAGC CCCTTCAGAG CCAGATCCTG AGCAAGATGA ACAGAAACTG
4251 AGGTTTTGTA AACGCCACCT TTATGGGCAG CAACCCCGAT CACCGGTGGA
4301 AATACGTCTT CAGCACGTCG CAATCGCGTA CCAAACACAT CACGCATATG
4351 ATTAATTTGT TCAATTGTAT AACCAACACG TTGCTCAACC CGTCCTCGAA
4401 TTTCCATATC CGGGTGCGGT AGTCGCCCTG CTTTCTCGGC ATCTCTGATA
4451 GCCTGAGAAG AAACCCCAAC TAAATCCGCT GCTTCACCTA TTCTCCAGCG
4501 CCGGGTTATT TTCCTCGCTT CCGGGCTGTC ATCATTAAAC TGTGCAATGG
4551 CGATAGCCTT CGTCATTTCA TGACCAGCGT TTATGCACTG GTTAAGTGTT
4601 TCCATGAGTT TCATTCTGAA CATCCTTTAA TCATTGCTTT GCGTTTTTTT
4651 ATTAAATCTT GCAATTTACT GCAAAGCAAC AACAAAATCG CAAAGTCATC
4701 AAAAAACCGC AAAGTTGTTT AAAATAAGAG CAACACTACA AAAGGAGATA
4751 AGAAGAGCAC ATACCTCAGT CACTTATTAT CACTAGCGCT CGCCGCAGCC
4801 GTGTAACCGA GCATAGCGAG CGAACTGGCG AGGAAGCAAA GAAGAACTGT
4851 TCTGTCAGAT AGCTCTTACG CTCAGCGCAA GAAGAAATAT CCACCGTGGG
4901 AAAAACTCCA GGTAGAGGTA CACACGCGGA TAGCCAATTC AGAGTAATAA
4951 ACTGTGATAA TCAACCCTCA TCAATGATGA CGAACTAACC CCCGATATCA
5001 GGTCACATGA CGAAGGGAAA GAGAAGGAAA TCAACTGTGA CAAACTGCCC
5051 TCAAATTTGG CTTCCTTAAA AATTACAGTT CAAAAAGTAT GAGAAAATCC
5101 ATGCAGGCTG AAGGAAACAG CAAAACTGTG ACAAATTACC CTCAGTAGGT
5151 CAGAACAAAT GTGACGAACC ACCCTCAAAT CTGTGACAGA TAACCCTCAG
5201 ACTATCCTGT CGTCATGGAA GTGATATCGC GGAAGGAAAA TACGATATGA
5251 GTCGTCTGGC GGCCTTTCTT TTTCTCAATG TATGAGAGGC GCATTGGAGT
5301 TCTGCTGTTG ATCTCATTAA CACAGACCTG CAGGAAGCGG CGGCGGAAGT
5351 CAGGCATACG CTGGTAACTT TGAGGCAGCT GGTAACGCTC TATGATCCAG
5401 TCGATTTTCA GAGAGACGAT GCCTGAGCCA TCCGGCTTAC GATACTGACA
5451 CAGGGATTCG TATAAACGCA TGGCATACGG ATTGGTGATT TCTTTTGTTT
5501 CACTAAGCCG AAACTGCGTA AACCGGTTCT GTAACCCGAT AAAGAAGGGA
5551 ATGAGATATG GGTTGATATG TACGCTGTAA AGCCCTCTGG ATGGACTGTG
5601 CGCACGTTTG ATAAACCAAG GAAAAGATTC ATAGCCTTTT TCATCGCCGG
5651 CATCCTCTTC AGGGCGATAA AAAACCACTT CCTTCCCCGC GAAACTCTTC
5701 AATGCCTGCC GTATATCCTT ACTGGCTTCC GCAGAGGTCA ATCCGAATAT
5751 TTCAGCATAT TTAGCAACAT GGATCTCGCA GATACCGTCA TGTTCCTGTA
5801 GGGTGCCATC AGATTTTCTG ATCTGGTCAA CGAACAGATA CAGCATACGT
5851 TTTTGATCCC GGGAGAGACT ATATGCCGCC TCAGTGAGGT CGTTTGACTG
5901 GACGATTCGC GGGCTATTTT TACGTTTCTT GTGATTGATA ACCGCTGTTT
5951 CCGCCATGAC AGATCCATGT GAAGTGTGAC AAGTTTTTAG ATTGTCACAC
6001 TAAATAAAAA AGAGTCAATA AGCAGGGATA ACTTTGTGAA AAAACAGCTT
6051 CTTCTGAGGG CAATTTGTCA CAGGGTTAAG GGCAATTTGT CACAGACAGG
6101 ACTGTCATTT GAGGGTGATT TGTCACACTG AAAGGGCAAT TTGTCACAAC
6151 ACCTTCTCTA GAACCAGCAT GGATAAAGGC CTACAAGGCG CTCTAAAAAA
6201 GAAGATCTAA AAACTATAAA AAAAATAATT ATAAAAATAT CCCCGTGGAT
6251 AAGTGGATAA CCCCAAGGGA AGTTTTTTCA GGCATCGTGT GTAAGCAGAA
6301 TATATAAGTG CTGTTCCCTG GTGCTTCCTC GCTCACTCGA CCGGGAGGGT
6351 TCGAGAAGGG GGGGCACCCC CCTTCGGCGT GCGCGGTCAC GCGCACAGGG
6401 CGCAGCCCTG GTTAAAAACA AGGTTTATAA ATATTGGTTT AAAAGCAGGT
6451 TAAAAGACAG GTTAGCGGTG GCCGAAAAAC GGGCGGAAAC CCTTGCAAAT
6501 GCTGGATTTT CTGCCTGTGG ACAGCCCCTC AAATGTCAAT AGGTGCGCCC
6551 CTCATCTGTC AGCACTCTGC CCCTCAAGTG TCAAGGATCG CGCCCCTCAT
6601 CTGTCAGTAG TCGCGCCCCT CAAGTGTCAA TACCGCAGGG CACTTATCCC
6651 CAGGCTTGTC CACATCATCT GTGGGAAACT CGCGTAAAAT CAGGCGTTTT
6701 CGCCGATTTG CGAGGCTGGC CAGCTCCACG TCGCCGGCCG AAATCGAGCC
6751 TGCCCCTCAT CTGTCAACGC CGCGCCGGGT GAGTCGGCCC CTCAAGTGTC
6801 AACGTCCGCC CCTCATCTGT CAGTGAGGGC CAAGTTTTCC GCGAGGTATC
6851 CACAACGCCG GCGGCCGGCC GCGGTGTCTC GCACACGGCT TCGACGGCGT
```

Figure 19-3

```
6901 TTCTGGCGCG TTTGCAGGGC CATAGACGGC CGCCAGCCCA GCGGCGAGGG
6951 CAACCAGCTC GAGGGCTTCG CCCTGTCGCT CGACTGCGGC GAGCACTACT
7001 GGCTGTAAAA GGACAGACCA CATCATGGTT CTGTGTTCAT TAGGTTGTTC
7051 TGTCCATTGC TGACATAATC CGCTCCACTT CAACGTAACA CCGCACGAAG
7101 ATTTCTATTG TTCCTGAAGG CATATTCAAA TCGTTTTCGT TACCGCTTGC
7151 AGGCATCATG ACAGAACACT ACTTCCTATA AACGCTACAC AGGCTCCTGA
7201 GATTAATAAT GCGGATCTCT ACGATAATGG GAGATTTTCC CGACTGTTTC
7251 GTTCGCTTCT CAGTGGATAA CAGCCAGCTT CTCTGTTTAA CAGACAAAAA
7301 CAGCATATCC ACTCAGTTCC ACATTTCCAT ATAAAGGCCA AGGCATTTAT
7351 TCTCAGGATA ATTGTTTCAG CATCGCAACC GCATCAGACT CCGGCATCGC
7401 AAACTGCACC CGGTGCCGGG CAGCCACATC CAGCGCAAAA ACCTTCGTGT
7451 AGACTTCCGT TGAACTGATG GACTTATGTC CCATCAGGCT TTGCAGAACT
7501 TTCAGCGGTA TACCGGCATA CAGCATGTGC ATCGCATAGG AATGGCGGAA
7551 CGTATGTGGT GTGACCGGAA CAGAGAACGT CACACCGTCA GCAGCAGCGG
7601 CGGCAACCGC CTCCCCAATC CAGGTCCTGA CCGTTCTGTC CGTCACTTCC
7651 CAGATCCGCG CTTTCTCTGT CCTTCCTGTG CGACGGTTAC GCCGCTCCAT
7701 GAGCTTATCG CGAATAAATA CCTGTGACGG AAGATCACTT CGCAGAATAA
7751 ATAAATCCTG GTGTCCCTGT TGATACCGGG AAGCCCTGGG CCAACTTTTG
7801 GCGAAAATGA GACGTTGATC GGCACGTAAG AGGTTCCAAC TTTCACCATA
7851 ATGAAATAAG ATCACTACCG GGCGTATTTT TTGAGTTATC GAGATTTTCA
7901 GGAGCTAAGG AAGCTAAAAT GGAGAAAAAA ATCACTGGAT ATACCACCGT
7951 TGATATATCC CAATGGCATC GTAAAGAACA TTTTGAGGCA TTTCAGTCAG
8001 TTGCTCAATG TACCTATAAC CAGACCGTTC AGCTGGATAT TACGGCCTTT
8051 TTAAAGACCG TAAAGAAAAA TAAGCACAAG TTTTATCCGG CCTTTATTCA
8101 CATTCTTGCC CGCCTGATGA ATGCTCATCC GGAATTTCGT ATGGCAATGA
8151 AAGACGGTGA GCTGGTGATA TGGGATAGTG TTCACCCTTG TTACACCGTT
8201 TTCCATGAGC AAACTGAAAC GTTTTCATCG CTCTGGAGTG AATACCACGA
8251 CGATTTCCGG CAGTTTCTAC ACATATATTC GCAAGATGTG GCGTGTTACG
8301 GTGAAAACCT GGCCTATTTC CCTAAAGGGT TTATTGAGAA TATGTTTTTC
8351 GTCTCAGCCA ATCCCTGGGT GAGTTTCACC AGTTTTGATT TAAACGTGGC
8401 CAATATGGAC AACTTCTTCG CCCCCGTTTT CACCATGGGC AAATATTATA
8451 CGCAAGGCGA CAAGGTGCTG ATGCCGCTGG CGATTCAGGT TCATCATGCC
8501 GTTTGTGATG GCTTCCATGT CGGCAGAATG CTTAATGAAT TACAACAGTA
8551 CTGCGATGAG TGGCAGGGCG GGGCGTAATT TTTTTAAGGC AGTTATTGGT
8601 GCCCTTAAAC GCCTGGTTGC TACGCCTGAA TAAGTGATAA TAAGCGGATG
8651 AATGGCAGAA ATTCGATGAT AAGCTGTCAA ACATGAGAAT TGGTCGACGG
8701 CCCGGGCGGC CATCGAAGCC TATAGGTACC ATCGATGCAT AATGTGCCTG
8751 TCAAATGGAC GAAGCAGGGA TTCTGCAAAC CCTATGCTAC TCCGTCAAGC
8801 CGTCAATTGT CTGATTCGTT ACCAATTATG ACAACTTGAC GGCTACATCA
8851 TTCACTTTTT CTTCACAACC GGCACGGAAC TCGCTCGGGC TGGCCCCGGT
8901 GCATTTTTTA AATACCCGCG AGAAATAGAG TTGATCGTCA AAACCAACAT
8951 TGCGACCGAC GGTGGCGATA GGCATCCGGG TGGTGCTCAA AAGCAGCTTC
9001 GCCTGGCTGA TACGTTGGTC CTCGCGCCAG CTTAAGACGC TAATCCCTAA
9051 CTGCTGGCGG AAAAGATGTG ACAGACGCGA CGGCGACAAG CAAACATGCT
9101 GTGCGACGCT GGCGATATCA AAATTGCTGT CTGCCAGGTG ATCGCTGATG
9151 TACTGACAAG CCTCGCGTAC CCGATTATCC ATCGGTGGAT GGAGCGACTC
9201 GTTAATCGCT TCCATGCGCC GCAGTAACAA TTGCTCAAGC AGATTTATCG
9251 CCAGCAGCTC CGAATAGCGC CCTTCCCCTT GCCCGGCGTT AATGATTTGC
9301 CCAAACAGGT CGCTGAAATG CGGCTGGTGC GCTTCATCCG GGCGAAAGAA
9351 CCCCGTATTG GCAAATATTG ACGGCCAGTT AAGCCATTCA TGCCAGTAGG
9401 CGCGCGGACG AAAGTAAACC CACTGGTGAT ACCATTCGCG AGCCTCCGGA
9451 TGACGACCGT AGTGATGAAT CTCTCCTGGC GGGAACAGCA AAATATCACC
9501 CGGTCGGCAA ACAAATTCTC GTCCCTGATT TTTCACCACC CCCTGACCGC
9551 GAATGGTGAG ATTGAGAATA TAACCTTTCA TTCCCAGCGG TCGGTCGATA
9601 AAAAAATCGA GATAACCGTT GGCCTCAATC GGCGTTAAAC CCGCCACCAG
9651 ATGGGCATTA AACGAGTATC CCGGCAGCAG GGGATCATTT TGCGCTTCAG
9701 CCATACTTTT CATACTCCCG CCATTCAGAG AAGAAACCAA TTGTCCATAT
9751 TGCATCAGAC ATTGCCGTCA CTGCGTCTTT TACTGGCTCT TCTCGCTAAC
9801 CAAACCGGTA ACCCCGCTTA TTAAAAGCAT TCTGTAACAA AGCGGGACCA
9851 AAGCCATGAC AAAAACGCGT AACAAAAGTG TCTATAATCA CGGCAGAAAA
9901 GTCCACATTG ATTATTTGCA CGGCGTCACA CTTTGCTATG CCATAGCATT
9951 TTTATCCATA AGATTAGCGG ATCCTACCT
```

(SEQ ID NO:5)

Figure 21 Further Characterization and Optimization of Bacteriolytic Peptides

Figure 24

| Element | Location (bp) |
|---|---|
| $p_{BAD}$ | 1-28 |
| PhoA Leader Peptide | 83-145 |
| DNK $(NNK)_{11}$ Random Sequence | 146-181 |
| Linker Peptide | 182-196 |
| *phoA* | 197-1546 |
| $(His)_6$ tag | 1547-1564 |
| *rrnB T1* | 1580-1623 |
| *rrnB T2* | 1755-1784 |
| pACYC Replication Origin | 2599-3144 |
| *neo* | 3738-4553 |
| *araC* | 4826-5704 |
| *pC* | 5855-5881 |

Figure 25-1 pKan PhoA Sequence

```
   1 GACGCTTTTT ATCGCAACTC TCTACTGTTT CTCCATGCGG CCGCGAAATA
  51 ATTTTGTTTA ACTTTAAGAA GGAGATATAC ATATGAAACA AAGCACTATT
 101 GCACTGGCAC TCTTACCGTT ACTGTACACC CCTGTGACAA AAGCCDNKNN
 151 KNNKNNKNNK NNKNNKNNKN NKNNKNNKNN KGAAGGCGGC GGCGCCCGGA
 201 CACCAGAAAT GCCTGTTCTG GAAAACCGGG CTGCTCAGGG CGATATTACT
 251 GCACCCGGCG GTGCTCGCCG TTTAACGGGT GATCAGACTG CCGCTCTGCG
 301 TGATTCTCTT AGCGATAAAC CTGCAAAAAA TATTATTTTG CTGATTGGCG
 351 ATGGGATGGG GGACTCGGAA ATTACTGCCG CACGTAATTA TGCCGAAGGT
 401 GCGGGCGGCT TTTTTAAAGG TATAGATGCC TTACCGCTTA CCGGGCAATA
 451 CACTCACTAT GCGCTGAATA AAAAAACCGG CAAACCGGAC TACGTCACCG
 501 ACTCGGCTGC ATCAGCAACC GCCTGGTCAA CCGGTGTCAA AACCTATAAC
 551 GGCGCGCTGG GCGTCGATAT TCACGAAAAA GATCACCCAA CGATTCTGGA
 601 AATGGCAAAA GCCGCAGGTC TGGCGACCGG TAACGTTTCT ACCGCAGAGT
 651 TGCAGGATGC CACGCCCGCT GCGCTGGTGG CACATGTGAC CTCGCGCAAA
 701 TGCTACGGTC CGAGCGCGAC CAGTGAAAAA TGTCCGGGTA ACGCTCTGGA
 751 AAAAGGCGGA AAAGGATCGA TTACCGAACA GCTGCTTAAC GCTCGTGCCG
 801 ACGTTACGCT TGGCGGCGGC GCAAAAACCT TTGCTGAAAC GGCAACCGCT
 851 GGTGAATGGC AGGGAAAAAC GCTGCGTGAA CAGGCACAGG CGCGTGGTTA
 901 TCAGTTGGTG AGCGATGCTG CCTCACTGAA TTCGGTGACG GAAGCGAATC
 951 AGCAAAAACC CCTGCTTGGC CTGTTTGCTG ACGGCAATAT GCCAGTGCGC
1001 TGGCTAGGAC CGAAAGCAAC GTACCATGGC AATATCGATA AGCCCGCAGT
1051 CACCTGTACG CCAAATCCGC AACGTAATGA CAGTGTACCA ACCCTGGCGC
1101 AGATGACCGA CAAAGCCATT GAATTGTTGA GTAAAAATGA GAAAGGCTTT
1151 TTCCTGCAAG TTGAAGGTGC GTCAATCGAT AAACAGGATC ATGCTGCGAA
1201 TCCTTGTGGG CAAATTGGCG AGACGGTCGA TCTCGATGAA GCCGTACAAC
1251 GGGCGCTGGA ATTCGCTAAA AAGGAGGGTA ACACGCTGGT CATAGTCACC
1301 GCTGATCACG CCCACGCCAG CCAGATTGTT GCGCCGGATA CCAAAGCTCC
1351 GGGCCTCACC CAGGCGCTAA ATACCAAAGA TGGCGCAGTG ATGGTGATGA
1401 GTTACGGGAA CTCCGAAGAG GATTCACAAG AACATACCGG CAGTCAGTTG
1451 CGTATTGCGG CGTATGGCCC GCATGCCGCC AATGTTGTTG GACTGACCGA
1501 CCAGACCGAT CTCTTCTACA CCATGAAAGC CGCTCTGGGG CTGAAACATC
1551 ATCATCATCA TCATTAACTG TTATCTAGAA TAAAACGAAA GGCTCAGTCG
1601 AAAGACTGGG CCTTTCGTTT TATCTGTTGT TTGTCGGTGA ACGCTCTCCT
1651 GAGTAGGACA AATCCGCCGG GAGCGGATTT GAACGTTGCG AAGCAACGGC
1701 CCGGAGGGTG GCGGGCAGGA CGCCCGCCAT AAACTGCCAG GCATCAAATT
1751 AAGCAGAAGG CCATCCTGAC GGATGGCCTT TTTGAATTCA CTGGCCGTCG
1801 TTTTACAACG TCGTGACTGG GAAAACCCTG GCGTTACCCA ACTTAATCGC
1851 CTTGCAGCAC ATCCCCCTTT CGCCAGACTC ACCAGTCACA GAAAAGCATC
1901 TTACGGATGG CATGACAGTA AGAGAATTAT GCAGTGCTGC CATAACCATG
1951 AGTGATAACA CTGCGGCCAA CTTACTTCTG ACAACGATCG GAGGACCGAA
2001 GGAGCTAACC GCTTTTTTGC ACAACATGGG GGATCATGTA ACTCGCCTTG
2051 ATCGTTGGGA ACCGGAGCTG AATGAAGCCA TACCAAACGA CGAGCGTGAC
2101 ACCACGATGC CTGCAGCAAT GGCAACAACG TTGCGCAAAC TATTAACTGG
2151 CGAACTACTT ACTCTAGCTT CCCGGCAACA ATTAATAGAC TGGATGGAGG
2201 CGGATAAAGT TGCAGGACCA CTTCTGCGCT CGGCCCTTCC GGCTGGCTGG
2251 TTTATTGCTG ATAAATCTGG AGCCGGTGAG CGTGGGTCTC GCGGTATCAT
2301 TGCAGCACTG GGGCCAGATG GTAAGCCCTC CCGTATCGTA GTTATCTACA
2351 CGACGGGGAG TCAGGCAACT ATGGATGAAC GAAATAGACA GATCGCTGAG
2401 ATAGGTGCCT CACTGATTAA GCATTGGTAA CTGTCAGACC AAGTTTACTC
2451 ATATATACTT TAGATTGATT TAAAACTTCA TTTTTAATTT AAAAGGATCT
2501 AGGTGAAGAT CCTTTTTGAT AATCTCATGA CCAAAATCCC TTAACGTGAG
2551 TTTTCGTTCC ACTGAGCGTC AGACCCCTTA ATAAGATGAT CTTCTTGAGA
2601 TCGTTTTGGT CTGCGCGTAA TCTCTTGCTC TGAAAACGAA AAAACCGCCT
2651 TGCAGGGCGG TTTTTCGAAG GTTCTCTGAG CTACCAACTC TTTGAACCGA
2701 GGTAACTGGC TTGGAGGAGC GCAGTCACCA AAACTTGTCC TTTCAGTTTA
2751 GCCTTAACCG GCGCATGACT TCAAGACTAA CTCCTCTAAA TCAATTACCA
2801 GTGGCTGCTG CCAGTGGTGC TTTTGCATGT CTTTCCGGGT TGGACTCAAG
2851 ACGATAGTTA CCGGATAAGG CGCAGCGGTC GGACTGAACG GGGGGTTCGT
2901 GCATACAGTC CAGCTTGGAG CGAACTGCCT ACCCGGAACT GAGTGTCAGG
2951 CGTGGAATGA GACAAACGCG GCCATAACAG CGGAATGACA CCGGTAAACC
3001 GAAAGGCAGG AACAGGAGAG CGCACGAGGG AGCCGCCAGG GGGAAACGCC
3051 TGGTATCTTT ATAGTCCTGT CGGGTTTCGC CACCACTGAT TTGAGCGTCA
3101 GATTTCGTGA TGCTTGTCAG GGGGGCGGAG CCTATGGAAA AACGGCTTTG
3151 CCGCGGCCCT CTCACTTCCC TGTTAAGTAT CTTCCTGGCA TCTTCCAGGA
3201 AATCTCCGCC CCGTTCGTAA GCCATTTCCG CTCGCCGCAG TCGAACGACC
3251 GAGCGTAGCG AGTCAGTGAG CGAGGAAGCG GAATATATCC TGTATCACAT
```

Figure 25-2

```
3301 ATTCTGCTGA CGCACCGGTG CAGCCTTTTT TCTCCTGCCA CATGAAGCAC
3351 TTCACTGACA CCCTCATCAG TGCCAACATA GTAAGCCAGT ATACACTCCG
3401 CTAGCGCTGA GGTCTGCCTC GTGAAGAAGG TGTTGCTGAC TCATACCAGG
3451 CCTGAATCGC CCCATCATCC AGCCAGAAAG TGAGGGAGCC ACGGTTGATG
3501 AGAGCTTTGT TGTAGGTGGA CCAGTTGGTG ATTTTGAACT TTTGCTTTGC
3551 CACGGAACGG TCTGCGTTGT CGGGAAGATG CGTGATCTGA TCCTTCAACT
3601 CAGCAAAAGT TCGATTTATT CAACAAAGCC ACGTTGTGTC TCAAAATCTC
3651 TGATGTTACA TTGCACAAGA TAAAAATATA TCATCATGAA CAATAAAACT
3701 GTCTGCTTAC ATAAACAGTA ATACAAGGGG TGTTATGAGC CATATTCAAC
3751 GGGAAACGTC TTGCTCGAGG CCGCGATTAA ATTCCAACAT GGATGCTGAT
3801 TTATATGGGT ATAAATGGGC TCGCGATAAT GTCGGGCAAT CAGGTGCGAC
3851 AATCTATCGA TTGTATGGGA AGCCCGATGC GCCAGAGTTG TTTCTGAAAC
3901 ATGGCAAAGG TAGCGTTGCC AATGATGTTA CAGATGAGAT GGTCAGACTA
3951 AACTGGCTGA CGGAATTTAT GCCTCTTCCG ACCATCAAGC ATTTTATCCG
4001 TACTCCTGAT GATGCATGGT TACTCACCAC TGCGATCCCC GGGAAAACAG
4051 CATTCCAGGT ATTAGAAGAA TATCCTGATT CAGGTGAAAA TATTGCTGAT
4101 GCGCTGGCAG TGTTCCTGCG CCGGTTGCAT TCGATTCCTG TTTGTAATTG
4151 TCCTTTTAAC AGCGATCGCG TATTTCGTCT CGCTCAGGCG CAATCACGAA
4201 TGAATAACGG TTTGGTTGAT GCGAGTGATT TTGATGACGA GCGTAATGGC
4251 TGGCCTGTTG AACAAGTCTG GAAAGAAATG CATAAACTTT TGCCATTCTC
4301 ACCGGATTCA GTCGTCACTC ATGGTGATTT CTCACTTGAT AACCTTATTT
4351 TTGACGAGGG GAAATTAATA GGTTGTATTG ATGTTGGACG AGTCGGAATC
4401 GCAGACCGAT ACCAGGATCT TGCCATCCTA TGGAACTGCC TCGGTGAGTT
4451 TTCTCCTTCA TTACAGAAAC GGCTTTTTCA AAAATATGGT ATTGATAATC
4501 CTGATATGAA TAAATTGCAG TTTCATTTGA TGCTCGATGA GTTTTTCTAA
4551 TCAGAATTGG TTAATTGGTT GTAACACTGG CAGAGCATTA CGCTGACTTG
4601 ACGGGACGGC GGCTTTGTTG AATAAATCGA ACTTTTGCTG AGTTGAAGGA
4651 TCAGATCACG CATCTTCCCG ACAACGCAGA CCGTTCCGTG GCAAAGCAAA
4701 AGTTCAAAAT CACTAGTCGA CCATGGTACC ATCGATGCAT AATGTGCCTG
4751 TCAAATGGAC GAAGCAGGGA TTCTGCAAAC CCTATGCTAC TCCGTCAAGC
4801 CGTCAATTGT CTGATTCGTT ACCAATTATG ACAACTTGAC GGCTACATCA
4851 TTCACTTTTT CTTCACAACC GGCACGGAAC TCGCTCGGGC TGGCCCCGGT
4901 GCATTTTTTA AATACCCGCG AGAAATAGAG TTGATCGTCA AAACCAACAT
4951 TGCGACCGAC GGTGGCGATA GGCATCCGGG TGGTGCTCAA AAGCAGCTTC
5001 GCCTGGCTGA TACGTTGGTC CTCGCGCCAG CTTAAGACGC TAATCCCTAA
5051 CTGCTGGCGG AAAAGATGTG ACAGACGCGA CGGCGACAAG CAAACATGCT
5101 GTGCGACGCT GGCGATATCA AAATTGCTGT CTGCCAGGTG ATCGCTGATG
5151 TACTGACAAG CCTCGCGTAC CCGATTATCC ATCGGTGGAT GGAGCGACTC
5201 GTTAATCGCT TCCATGCGCC GCAGTAACAA TTGCTCAAGC AGATTTATCG
5251 CCAGCAGCTC CGAATAGCGC CCTTCCCCTT GCCCGGCGTT AATGATTTGC
5301 CCAAACAGGT CGCTGAAATG CGGCTGGTGC GCTTCATCCG GGCGAAAGAA
5351 CCCCGTATTG GCAAATATTG ACGGCCAGTT AAGCCATTCA TGCCAGTAGG
5401 CGCGCGGACG AAAGTAAACC CACTGGTGAT ACCATTCGCG AGCCTCCGGA
5451 TGACGACCGT AGTGATGAAT CTCTCCTGGC GGGAACAGCA AAATATCACC
5501 CGGTCGGCAA ACAAATTCTC GTCCCTGATT TTTCACCACC CCCTGACCGC
5551 GAATGGTGAG ATTGAGAATA TAACCTTTCA TTCCCAGCGG TCGGTCGATA
5601 AAAAAATCGA GATAACCGTT GGCCTCAATC GGCGTTAAAC CCGCCACCAG
5651 ATGGGCATTA AACGAGTATC CCGGCAGCAG GGGATCATTT TGCGCTTCAG
5701 CCATACTTTT CATACTCCCG CCATTCAGAG AAGAAACCAA TTGTCCATAT
5751 TGCATCAGAC ATTGCCGTCA CTGCGTCTTT TACTGGCTCT TCTCGCTAAC
5801 CAAACCGGTA ACCCCGCTTA TTAAAAGCAT TCTGTAACAA AGCGGGACCA
5851 AAGCCATGAC AAAAACGCGT AACAAAAGTG TCTATAATCA CGGCAGAAAA
5901 GTCCACATTG ATTATTTGCA CGGCGTCACA CTTTGCTATG CCATAGCATT
5951 TTTATCCATA AGATTAGCGG ATCCTACCT
```

(SEQ ID NO:6)

Figure 27

All Peptides Isolated from the Cytoplasmic N-terminal Bacteriostatic/Bactericidal Screen

| Clone | Lethality | | *E. coli* MIC (μM) | Peptide Sequence | | | | | | | | | | | | SEQ ID NO: |
|---|---|---|---|---|---|---|---|---|---|---|---|---|---|---|---|---|
| | Peptide-EmGFP | Free Peptide | | | | | | | | | | | | | | |
| NC010 | ++++ | | | W | W | I | V | P | L | L | L | P | V | L | L | 79 |
| NC052 | ++++ | | | M | R | V | T | L | L | C | V | M | I | L | F | 80 |
| NC055 | ++++ | | | A | M | S | L | A | C | W | L | L | F | F | P | 81 |

Lethality Key

| Symbol | Strength* |
|---|---|
| ++++ | ≥ 0.7 |
| +++ | 0.7 > OD ≥ 6 |
| ++ | 0.6 > OD ≥ 5 |

* The difference in optical density between the induced and uninduced growth curves at stationary phase.

Figure 28-1

Growth Rate Reducing Peptides Isolated from Cytoplasmic Bacteriostatic/Bactericidal Screen

| Clone | Lethality | | E. coli MIC (µM) | Peptide Sequence | | | | | | | | | | | | SEQ ID NO: |
|---|---|---|---|---|---|---|---|---|---|---|---|---|---|---|---|---|
| | EmGFP-Peptide | Free Peptide | | | | | | | | | | | | | | |
| CC006 | + | | | A | L | L | R | S | V | F | W | F | C | C | L | 82 |
| CC009 | + | | | V | M | W | L | N | V | C | N | L | V | S | A | 83 |
| CC012 | ++ | | | F | A | N | Y | L | G | V | R | Q | T | L | P | 84 |
| CC013 | ++ | | | W | L | F | C | W | W | F | C | F | F | M | T | 85 |
| CC015 | ++ | | | L | L | Y | A | L | F | V | S | C | L | P | F | 86 |
| CC021 | + | | | G | S | G | H | Y | T | L | V | R | T | P | P | 87 |
| CC023 | + | | | M | L | S | L | I | V | M | Q | F | I | Q | L | 88 |
| CC042 | ++ | | | C | M | R | M | C | E | E | V | G | V | S | D | 89 |
| CC053 | ++ | | | G | A | R | R | F | L | Y | P | M | G | F | G | 90 |
| CC058 | + | | | F | V | D | K | C | L | L | F | V | Y | S | L | 91 |
| CC069 | + | | | L | L | M | W | A | C | A | T | V | F | M | G | 92 |
| CC077 | + | | | S | V | S | G | V | W | G | F | G | H | V | L | 93 |
| CC084 | ++ | | | W | L | F | V | L | V | S | G | V | F | T | L | 94 |
| CC086 | + | | | I | L | I | G | L | L | F | M | M | M | D | A | 95 |
| CC090 | ++ | | | W | L | I | Y | L | L | I | T | S | F | Q | L | 96 |
| CC100 | ++ | | | W | V | W | A | N | M | M | N | W | C | A | C | 97 |
| CC106 | ++ | | | F | M | N | Y | V | V | K | F | F | C | M | Q | 98 |
| CC112 | ++ | | | I | L | L | S | V | P | W | A | L | F | L | T | 99 |
| CC128 | ++ | | | N | F | V | N | R | G | S | W | L | M | T | R | 100 |

Figure 28-2

Lethality Key

| Symbol | Stationary phase optical density |
|---|---|
| ++ | ≤ 0.7 |
| + | > 0.7 |

Figure 29-1

Bacteriostatic/Bactericidal Peptides Isolated from the Cytoplasmic Bacteriostatic/Bactericidal Screen

| Clone | Lethality | | *E. coli* MIC (µM) | Peptide Sequence | | | | | | | | | | | | SEQ ID NO: |
|---|---|---|---|---|---|---|---|---|---|---|---|---|---|---|---|---|
| | EmGFP-Peptide | Free Peptide | | | | | | | | | | | | | | |
| CL011 | +++ | | | W | V | Y | L | L | L | S | C | T | G | W | F | 101 |
| CL015 | + | | | R | S | A | I | Q | E | V | N | L | M | V | G | 102 |
| CC001 | ++++ | | | A | Q | H | D | Q | R | G | L | V | Y | V | R | 103 |
| CC026 | ++ | | | A | I | L | T | I | L | L | G | L | G | L | L | 104 |
| CC046 | ++ | ++ | | L | F | L | T | F | L | V | S | F | A | W | N | 105 |
| CC057 | +++ | | | M | F | S | C | L | L | Q | V | L | C | V | V | 106 |
| CC066 | +++ | | | F | S | S | Q | N | D | Y | P | S | R | P | P | 107 |
| CC078 | ++ | | | G | L | A | R | G | P | P | G | G | W | R | G | 108 |
| CC080 | +++ | | | F | Y | M | I | P | E | N | F | W | V | D | W | 109 |
| CC096 | +++ | | | W | L | A | R | V | D | Y | L | Y | T | V | S | 110 |
| CC098 | ++ | | > 250 | Q | Y | G | W | K | Q | E | Y | G | R | H | G | 111 |
| CC102 | ++ | | | Q | V | L | S | F | L | V | S | W | L | A | Q | 112 |
| CC114 | ++ | | | V | D | L | C | W | L | R | S | E | R | R | V | 113 |
| CC122 | ++ | | | L | D | F | W | F | A | P | G | L | D | P | P | 114 |
| CC127 | ++ | | | S | W | L | L | F | F | F | I | S | S | S | R | 115 |
| CC129 | ++ | | | S | S | S | S | S | S | S | S | S | S | S | S | 116 |
| CL001K | +++ | | | D | T | K | S | A | L | V | V | A | L | I | H | 117 |
| CL006K | +++ | | | R | V | L | D | L | V | P | Y | A | P | D | A | 118 |
| CC009K | +++ | | | L | A | F | F | F | F | I | S | A | S | L | G | 119 |

Figure 29-2

Lethality Key

| Symbol | Strength* |
|---|---|
| ++++ | $\geq$ 0.7 |
| +++ | 0.7 > OD $\geq$ 6 |
| ++ | 0.6 > OD $\geq$ 5 |

* The difference in optical density between the induced and uninduced growth curves at stationary phase.

Figure 30-1

| Bacteriolytic Peptides Isolated from Periplasmic Bacteriolytic Screen | | | | | | | | | | | | | | | | |
|---|---|---|---|---|---|---|---|---|---|---|---|---|---|---|---|---|
| Clone | Lethality | | *E. coli* MIC (μM) | Peptide Sequence | | | | | | | | | | | | |
| | Peptide-PhoA | Free Peptide | | | | | | | | | | | | | | SEQ ID NO: |
| PL029 | +++ | | | M | T | K | M | F | R | R | W | R | T | N | K | 120 |
| PL030 | ++ | | | L | G | W | L | R | G | K | A | L | G | R | G | 121 |
| PL034 | +++ | | | F | A | A | V | V | R | W | V | R | G | R | A | 122 |
| PL035 | ++ | | | Y | G | K | A | R | R | W | L | G | R | W | T | 123 |
| PL038 | + | | | I | S | W | L | G | G | L | L | G | R | R | E | 124 |
| PL047 | + | | | I | R | A | F | R | S | F | T | Q | L | L | C | 125 |
| PL049 | +++ | | | W | R | Y | L | L | G | R | G | K | R | R | K | 126 |
| PL054 | +++ | | | W | G | S | L | M | L | K | W | R | R | T | R | 127 |
| PL055 | ++ | | | I | K | W | I | R | S | L | L | V | R | G | R | 128 |
| PL062 | ++++ | | | F | A | R | L | H | K | W | F | Q | R | R | K | 129 |
| PL063 | + | | | I | K | L | L | R | I | L | S | Q | K | W | R | 130 |
| PL064 | ++ | | | W | V | W | L | S | R | W | L | R | R | G | W | 131 |
| PL065 | ++ | | | L | K | G | L | K | R | W | W | R | P | E | H | 132 |
| PL066 | ++ | | | W | K | W | L | Q | S | L | W | G | C | E | V | 133 |
| PL072 | ++ | | | W | R | G | V | R | K | V | W | R | R | M | R | 134 |
| PL092 | + | | | Y | C | W | L | R | E | K | L | G | G | G | Q | 135 |
| PL095 | ++ | | | W | Q | L | V | R | R | L | L | G | Q | L | G | 136 |
| PL097 | + | | | W | V | T | A | R | D | W | V | K | S | W | W | 137 |
| PL098 | +++ | | | W | R | R | W | K | M | R | G | R | A | R | V | 138 |
| PL104 | + | | | M | G | M | L | R | W | L | F | S | F | W | R | 139 |
| PL111 | + | | | L | S | R | A | K | A | L | L | K | R | A | K | 140 |
| PL113 | ++ | | | C | R | Y | L | R | L | L | W | S | N | I | R | 141 |
| PL118 | ++ | | | Y | R | R | V | G | G | W | L | R | R | V | L | 142 |
| PL122 | +++ | | | V | N | W | W | R | R | C | W | K | Q | W | H | 143 |

Figure 30-2

| | | | | | | | | | | | | | | | | |
|---|---|---|---|---|---|---|---|---|---|---|---|---|---|---|---|---|
| PL123 | ++ | | | W | T | W | I | K | R | V | L | Q | E | M | G | 144 |
| PL126 | + | - | | W | T | R | F | M | R | A | L | G | F | T | Q | 145 |
| PL131 | + | | | Y | S | A | I | K | R | R | L | L | Q | G | R | 146 |
| PL137 | ++++ | | | L | S | L | A | I | E | F | S | L | S | V | Q | 147 |
| PL138 | + | | | W | R | W | V | S | R | K | W | Q | T | R | G | 148 |
| PL139 | +++ | | | M | A | W | L | A | Q | W | W | G | A | R | R | 149 |
| PL140 | + | | | V | N | A | W | R | K | L | A | Q | I | W | R | 150 |
| PL142 | + | | | I | G | L | L | K | R | L | V | T | T | R | S | 151 |
| PL144 | +++ | | | W | D | R | V | I | K | W | L | R | C | G | K | 152 |
| PL145 | + | | | G | R | L | V | A | R | V | W | R | K | W | K | 153 |
| PL146 | ++ | | | M | R | F | L | R | R | L | W | W | R | A | R | 154 |
| PL149 | + | | | W | T | W | I | K | R | V | L | Q | E | M | G | 155 |
| PL166 | +++ | | | A | G | I | I | K | R | W | L | F | R | H | T | 156 |
| PL177 | +++ | | | W | G | Y | L | I | R | A | I | R | R | R | V | 157 |
| PL184 | ++ | | | V | A | A | V | Q | R | W | C | R | K | W | Q | 158 |
| PL189 | + | | | W | E | W | M | R | R | A | A | G | A | R | R | 159 |
| PL200 | ++ | | | W | R | W | L | R | R | R | Q | G | P | G | R | 160 |
| PL202 | ++ | | | W | A | R | V | K | R | G | W | Q | K | K | A | 161 |
| PL208 | +++ | | | F | Q | L | L | L | S | W | A | R | K | C | K | 162 |
| PL211 | + | | | I | S | L | W | R | S | V | A | Q | R | W | G | 163 |
| PL212 | +++ | | | G | R | W | L | R | N | R | W | A | G | W | R | 164 |
| PL213 | ++ | | | W | Q | L | V | T | R | L | L | R | R | Q | G | 165 |
| PL214 | + | | | S | A | M | L | K | R | W | W | Q | G | T | G | 166 |
| PL215 | + | | | Y | R | A | L | R | A | W | L | W | A | P | R | 167 |
| PL225 | +++ | | | A | E | R | S | R | A | W | L | R | R | I | T | 168 |
| PL226 | ++ | | | M | R | V | I | R | R | L | V | R | W | P | R | 169 |
| PL239 | + | | | W | S | R | V | V | R | G | F | A | A | A | R | 170 |
| PL240 | ++ | | | W | A | L | L | R | R | M | W | R | D | G | K | 171 |
| PL248 | +++ | | | F | C | R | L | R | S | W | W | R | S | W | Q | 172 |
| PL251 | ++++ | | | G | D | R | V | A | A | A | P | G | A | L | L | 173 |
| PL260 | ++ | | | V | G | R | V | R | K | A | W | R | R | V | R | 174 |
| PL261 | + | | | M | R | R | L | K | A | L | W | A | G | K | E | 175 |

Figure 30-3

| | | | | | | | | | | | | | | | | |
|---|---|---|---|---|---|---|---|---|---|---|---|---|---|---|---|---|
| PL268 | ++ | | | L | E | F | T | A | R | L | F | R | R | R | S | 176 |
| PL274 | +++ | | | S | V | C | E | W | S | W | R | M | A | V | W | 177 |
| PL275 | ++ | | | V | R | R | F | K | R | A | V | F | R | R | S | 178 |
| PL291 | ++ | | | I | C | L | M | R | R | L | T | R | R | L | T | 179 |
| PL293 | ++ | | | A | A | W | L | G | G | W | W | R | G | R | G | 180 |
| PL294 | ++ | | | L | S | W | L | R | R | R | S | R | E | L | G | 181 |
| PL297 | ++ | | | L | T | W | I | R | N | W | V | G | D | R | S | 182 |
| PL299 | +++ | | | L | R | L | L | G | T | V | C | R | K | W | R | 183 |
| PL308 | ++ | | | W | R | W | L | R | D | G | V | A | R | A | L | 184 |
| PL309 | +++ | | | Y | A | W | W | R | R | F | C | G | R | S | E | 185 |
| PL311 | +++ | | | W | A | R | I | R | A | W | W | W | R | V | K | 186 |
| PL312 | ++ | | | W | G | W | F | K | R | W | G | V | R | G | A | 187 |
| PL325 | ++ | | | W | A | Q | I | R | G | R | L | G | R | N | M | 188 |
| PL344 | ++++ | | | L | H | N | L | W | G | W | F | I | R | R | F | 189 |
| PL350 | +++ | | | W | G | W | V | R | K | L | M | R | M | R | S | 190 |
| PL353 | ++++ | | | I | R | W | C | V | S | R | C | I | S | L | W | 191 |
| PL358 | ++ | | | Y | A | W | C | R | A | K | V | R | R | A | L | 192 |
| PL361 | ++ | | | V | S | W | I | R | R | Q | W | K | A | T | I | 193 |
| PL376 | ++ | | | W | G | A | F | G | R | A | W | R | R | Y | R | 194 |
| PL380 | +++ | | | L | R | R | A | R | A | W | M | K | G | R | R | 195 |
| PL403 | ++ | | | A | Q | L | L | R | R | F | R | T | R | G | R | 196 |
| PL406 | ++ | | | W | T | F | L | K | K | L | A | S | S | K | A | 197 |
| PL421 | ++ | | | A | G | A | V | R | R | L | W | R | S | W | R | 198 |
| PL431 | ++ | | | V | Q | W | L | R | R | L | G | G | S | G | V | 199 |
| PL443 | + | | | F | S | F | F | R | R | K | S | I | R | L | R | 200 |
| PL444 | ++++ | - | 250 | A | A | W | L | A | R | R | W | R | A | W | V | 201 |
| PL459 | +++ | | | F | E | V | F | W | S | I | T | Y | I | Y | A | 202 |
| PL460 | + | | | F | N | I | I | R | C | W | W | K | G | T | R | 203 |
| PL461 | +++ | | | W | R | W | V | A | R | R | T | R | G | K | K | 204 |
| PL466 | ++ | | | L | S | F | F | A | R | K | K | R | V | R | Q | 205 |
| PL468 | + | | | K | A | W | A | G | R | W | W | K | K | W | S | 206 |
| PL471 | + | | | W | N | V | L | K | K | Y | L | W | L | T | E | 207 |

Figure 30-4

| | | | | | | | | | | | | | | | | |
|---|---|---|---|---|---|---|---|---|---|---|---|---|---|---|---|---|
| PL472 | ++ | | | W | R | R | L | T | G | R | R | R | G | S | G | 208 |
| PL473 | +++ | | | L | S | W | M | K | A | R | W | A | G | C | G | 209 |
| PL481 | ++ | | | W | K | G | L | V | R | L | L | K | A | A | V | 210 |
| PL491 | ++ | | | L | K | A | V | A | K | L | A | Q | W | V | R | 211 |
| PL497 | + | | | F | R | R | I | W | T | V | L | F | G | R | A | 212 |
| PL500 | +++ | | | W | R | A | L | T | R | R | V | R | L | W | R | 213 |

Figure 30-5

Lethality Key

| Symbol | Time elapsed before lysis | Rate of lysis |
|---|---|---|
| ++++ | $\leq$ 30 mins | All |
| +++ | 30 mins > t $\geq$ 1 hr | All |
| ++ | $\geq$ 1 hr | Fast |
| + | $\geq$ 1 hr | Slow |

Figure 31-1

Bacteriostatic/Bactericidal Peptides Isolated from Periplasmic Bacteriolytic Screen

| Clone | Lethality | | *E. coli* MIC (μM) | Peptide Sequence | | | | | | | | | | | | SEQ ID NO: |
|---|---|---|---|---|---|---|---|---|---|---|---|---|---|---|---|---|
| | Peptide-PhoA | Free Peptide | | | | | | | | | | | | | | |
| PL014 | ++++ | | | W | T | V | R | V | D | V | I | E | S | R | W | 214 |
| PL037 | ++ | | | F | R | W | L | Y | R | L | F | M | F | R | L | 215 |
| PL045 | ++++ | | | C | I | L | V | V | L | V | H | L | F | V | A | 216 |
| PL048 | ++++ | | | V | T | L | G | L | V | M | L | A | V | S | L | 217 |
| PL060 | ++ | | | L | S | W | V | W | R | Q | L | G | G | A | W | 218 |
| PL069 | ++++ | | | F | F | C | L | W | V | L | Y | L | G | T | P | 219 |
| PL073 | ++ | | | N | V | R | I | I | V | D | M | T | I | S | A | 220 |
| PL088 | ++++ | | | I | I | V | L | V | F | V | T | Y | L | T | A | 221 |
| PL089 | ++++ | | | F | V | I | A | S | F | V | W | V | I | L | V | 222 |
| PL101 | ++++ | | | I | L | Y | L | C | V | L | S | V | S | R | N | 223 |
| PL112 | ++++ | | | G | L | W | G | K | W | E | P | G | G | Q | G | 224 |
| PL117 | +++ | | | V | I | G | T | V | M | C | T | L | T | W | G | 225 |
| PL119 | +++ | | | T | S | D | L | E | T | Q | S | G | G | R | L | 226 |
| PL121 | +++ | | | D | G | M | F | R | M | T | L | L | T | S | W | 227 |
| PL125 | ++ | | | L | N | W | L | R | G | W | T | G | L | V | G | 228 |
| PL126 | ++ | | | W | T | R | F | M | R | A | L | G | F | T | Q | 229 |
| PL132 | ++ | | | I | T | F | W | S | F | V | F | T | M | R | W | 230 |
| PL148 | ++++ | | | G | F | W | V | Y | G | G | V | G | W | Y | A | 231 |
| PL151 | + | | | I | C | W | L | K | D | F | Y | G | R | L | Q | 232 |
| PL164 | +++ | | | C | T | F | V | S | I | H | Y | G | C | E | C | 233 |
| PL165 | ++++ | | | L | I | V | C | C | L | V | V | V | W | G | E | 234 |
| PL176 | ++ | | | W | H | T | L | T | K | L | L | G | R | K | D | 235 |
| PL181 | ++++ | | | W | G | V | S | V | Q | V | P | W | A | G | V | 236 |
| PL187 | ++++ | | | G | A | R | W | V | A | E | G | W | S | E | R | 237 |

Figure 31-2

| | | | | | | | | | | | | | | | | |
|---|---|---|---|---|---|---|---|---|---|---|---|---|---|---|---|---|
| PL188 | ++++ | | | V | N | T | C | Q | V | T | V | A | S | A | H | 238 |
| PL218 | ++++ | | | F | L | L | S | I | I | Y | L | W | S | W | G | 239 |
| PL233 | ++++ | | | S | D | T | L | E | L | L | G | C | V | N | W | 240 |
| PL235 | ++++ | | | A | I | V | V | Y | L | A | L | F | N | Y | G | 241 |
| PL242 | +++ | | | V | S | E | V | S | V | I | S | P | W | G | C | 242 |
| PL246 | ++++ | | | D | I | S | L | S | A | V | M | V | Y | V | N | 243 |
| PL247 | ++++ | | | I | A | Y | M | V | L | V | A | V | V | A | G | 244 |
| PL250 | +++ | | | L | K | G | L | W | G | W | W | I | G | R | S | 245 |
| PL254 | ++++ | | | I | I | H | S | Y | N | F | V | S | I | C | K | 246 |
| PL276 | ++++ | | | S | D | T | L | E | A | V | G | C | V | N | W | 247 |
| PL280 | +++ | | | M | V | V | A | M | V | G | V | W | W | G | G | 248 |
| PL281 | +++ | | | W | I | I | S | M | S | A | L | A | W | G | C | 249 |
| PL360 | ++++ | | | G | S | W | Q | A | H | T | E | S | P | R | E | 250 |
| PL365 | ++++ | | | G | S | H | F | Y | L | H | I | H | V | D | W | 251 |
| PL408 | ++++ | | | V | L | Y | I | T | V | L | V | G | L | V | V | 252 |
| PL436 | ++ | | | V | S | I | M | I | F | I | T | G | V | Y | W | 253 |
| PL449 | ++++ | | | I | M | W | S | L | L | V | T | A | N | Y | P | 254 |
| PL467 | ++ | | | I | R | M | L | G | R | V | R | T | W | W | R | 255 |
| PL477 | +++ | | | Y | L | T | C | L | C | M | F | L | A | G | P | 256 |
| PL482 | ++ | | | W | E | L | H | A | Y | A | M | C | W | S | M | 257 |

Figure 31-3

Lethality Key

| Symbol | Strength* |
| --- | --- |
| ++++ | ≥ 0.7 |
| +++ | 0.7 > OD ≥ 6 |
| ++ | 0.6 > OD ≥ 5 |
| + | < 0.5 |

* The difference in optical density between the induced and uninduced growth curves at stationary phase.

Figure 32-1

Growth Rate Reducing Peptides Isolated from Periplasmic Bacteriolytic Screen

| Clone | Lethality | | *E. coli* MIC (μM) | Peptide Sequence | | | | | | | | | | | | SEQ ID NO: |
|---|---|---|---|---|---|---|---|---|---|---|---|---|---|---|---|---|
| | Peptide-PhoA | Free Peptide | | | | | | | | | | | | | | |
| PL012 | ++ | | | G | I | G | A | I | V | G | V | L | I | L | G | 258 |
| PL021 | ++ | | | A | L | L | V | A | M | W | A | G | V | A | G | 259 |
| PL023 | + | | | V | C | E | C | G | P | R | V | T | L | T | Q | 260 |
| PL027 | + | | | L | T | T | I | C | R | W | M | R | R | R | D | 261 |
| PL032 | ++ | | | F | K | W | V | L | A | R | L | T | Q | S | S | 262 |
| PL039 | ++ | | | C | E | S | G | K | S | Y | R | I | G | K | W | 263 |
| PL115 | ++ | | | V | L | S | A | N | I | W | A | G | M | R | F | 264 |
| PL116 | + | | | I | V | I | C | C | V | G | V | L | T | H | P | 265 |
| PL120 | ++ | | | I | V | T | T | N | H | V | L | V | C | T | Y | 266 |
| PL124 | ++ | | | L | L | V | S | L | P | V | L | L | S | C | G | 267 |
| PL127 | + | | | Y | C | P | G | P | S | V | E | I | R | R | C | 268 |
| PL128 | ++ | | | L | Y | A | F | G | T | C | E | F | S | V | M | 269 |
| PL129 | ++ | | | Y | Y | T | F | I | L | P | L | S | L | S | C | 270 |
| PL130 | + | | | M | E | R | V | R | K | W | F | N | E | G | R | 271 |
| PL136 | + | | | F | Q | L | E | F | S | V | A | V | G | A | V | 272 |
| PL141 | ++ | | | Y | C | A | H | L | S | C | T | V | C | V | Y | 273 |
| PL147 | ++ | | | F | F | G | Y | T | E | A | L | V | V | T | V | 274 |
| PL150 | + | | | C | I | D | C | A | P | R | I | C | C | S | L | 275 |
| PL154 | ++ | | | T | E | H | S | R | V | A | V | R | S | A | R | 276 |
| PL169 | ++ | | | I | F | S | C | W | V | G | W | V | V | L | T | 277 |
| PL170 | + | | | V | E | P | V | L | F | I | G | A | C | A | C | 278 |
| PL178 | + | | | W | V | C | E | V | K | Q | S | V | W | L | A | 279 |
| PL179 | + | | | N | I | H | L | C | T | T | N | W | H | W | V | 280 |
| PL182 | ++ | | | G | D | L | N | L | P | H | F | Q | Y | A | M | 281 |

Figure 32-2

| | | | | | | | | | | | | | | | | |
|---|---|---|---|---|---|---|---|---|---|---|---|---|---|---|---|---|
| PL192 | ++ | | | V | V | T | A | V | L | A | L | W | G | S | G | 282 |
| PL195 | ++ | | | V | V | N | Y | Q | E | L | A | V | V | V | G | 283 |
| PL204 | ++ | | | C | V | S | Y | D | Y | L | A | I | V | R | F | 284 |
| PL223 | + | | | | | | | | | | | | | | | |
| PL229 | ++ | | | S | M | A | A | A | F | F | W | C | M | A | Y | 285 |
| PL249 | ++ | | | D | A | M | N | F | W | A | V | R | F | S | V | 286 |
| PL253 | ++ | | | I | L | Q | E | D | V | F | M | L | L | M | N | 287 |
| PL254 | ++ | | | | | | | | | | | | | | | |
| PL257 | + | | | L | V | V | Q | N | M | A | V | H | L | V | Q | 288 |
| PL270 | + | | | F | V | L | P | S | V | F | V | C | M | L | V | 289 |
| PL288 | + | | | D | H | L | N | A | C | L | N | M | Q | W | A | 290 |
| PL332 | + | | | V | S | C | V | L | D | V | H | L | L | W | V | 291 |
| PL381 | + | | | V | F | A | F | V | V | G | A | L | T | D | Y | 292 |
| PL388 | + | | | C | Q | C | T | V | T | S | C | H | V | R | W | 293 |
| PL426 | ++ | | | V | V | L | N | T | V | T | I | T | A | S | M | 294 |
| PL456 | + | | | E | Y | H | L | F | I | G | A | V | E | V | R | 295 |
| PL494 | + | | | E | Y | H | L | F | I | G | A | V | E | V | R | 296 |

Figure 32-3

Lethality Key

| Symbol | Stationary phase optical density |
|---|---|
| ++ | $\leq$ 0.7 |
| + | > 0.7 |

Figure 33-1

Bacteriostatic/Bactericidal Peptides Isolated from Periplasmic Bacteriostatic/Bactericidal Screen

| Clone | Lethality | | *E. coli* MIC (µM) | Peptide Sequence | | | | | | | | | | | | SEQ ID NO: |
|---|---|---|---|---|---|---|---|---|---|---|---|---|---|---|---|---|
| | Peptide-PhoA | Free Peptide | | | | | | | | | | | | | | |
| PC001 | + | | | L | V | V | V | V | R | E | A | I | A | L | W | 297 |
| PC006 | ++ | | | C | H | G | A | L | C | W | R | G | Q | P | I | 298 |
| PC013 | ++ | | | V | S | F | S | L | V | A | S | L | L | Y | A | 299 |
| PC024 | +++ | | | A | P | P | P | P | P | P | P | W | P | P | P | 300 |
| PC025 | +++ | | | V | S | W | A | L | L | G | M | V | L | I | A | 301 |
| PC034 | + | | | I | L | L | Y | L | V | R | A | V | L | N | V | 302 |
| PC035 | ++ | | | F | L | F | L | I | S | H | F | W | C | S | A | 303 |
| PC036 | ++++ | | | R | R | K | G | E | E | A | H | T | R | Q | G | 304 |
| PC042 | ++++ | | | L | G | A | W | G | L | G | L | W | L | M | V | 305 |

Figure 33-2

| Lethality Key | |
|---|---|
| Symbol | Strength* |
| ++++ | $\geq$ 0.7 |
| +++ | 0.7 > OD $\geq$ 6 |
| ++ | 0.6 > OD $\geq$ 5 |
| + | < 0.5 |

* The difference in optical density between the induced and uninduced growth curves at stationary phase.

Figure 34-1

Bacteriolytic Peptides Isolated from Periplasmic Bacteriostatic/Bactericidal Screen

| Clone | Lethality | | *E. coli* MIC (μM) | Peptide Sequence | | | | | | | | | | | | SEQ ID NO: |
|---|---|---|---|---|---|---|---|---|---|---|---|---|---|---|---|---|
| | Peptide-PhoA | Free Peptide | | | | | | | | | | | | | | |
| PC016 | + | | | Y | N | F | I | K | R | R | L | C | L | I | K | 306 |

Growth Rate Reducing Peptides Isolated from Periplasmic Bacteriostatic/Bactericidal Screen

| Clone | Lethality | | *E. coli* MIC (μM) | Peptide Sequence | | | | | | | | | | | | SEQ ID NO: |
|---|---|---|---|---|---|---|---|---|---|---|---|---|---|---|---|---|
| | Peptide-PhoA | Free Peptide | | | | | | | | | | | | | | |
| PC022 | + | | | I | I | M | S | A | L | W | V | P | L | G | W | 307 |
| PC030 | ++ | | | A | V | S | T | Q | V | V | V | N | F | E | A | 308 |
| PC041 | ++ | | | I | L | I | A | F | G | Y | V | V | C | A | T | 309 |

Figure 34-2

| Lethality Key | | |
|---|---|---|
| Symbol | Time elapsed before lysis | Rate of lysis |
| ++++ | ≤ 30 mins | All |
| +++ | 30 mins > t ≥ 1 hr | All |
| ++ | ≥ 1 hr | Fast |
| + | ≥ 1 hr | Slow |

| Lethality Key | |
|---|---|
| Symbol | Stationary phase optical density |
| ++ | ≤ 0.7 |
| + | > 0.7 |

Figure 35-1

Consensus Peptides based on Bacteriolytic Peptide Residue Distribution

| Clone | Lethality | | *E. coli* MIC (µM) | Peptide Sequence | | | | | | | | | | | | SEQ ID NO: |
|---|---|---|---|---|---|---|---|---|---|---|---|---|---|---|---|---|
| | Peptide-PhoA | Free Peptide | | | | | | | | | | | | | | |
| EO1 | ++++ | ++++* | 15.6 | F | A | W | L | W | S | W | W | R | A | R | R | 310 |
| EO2 | +++ | | | F | A | R | L | R | R | W | W | R | R | W | R | 311 |
| RR1 | +++ | | | W | R | W | L | A | R | R | W | R | R | W | R | 312 |
| RR2 | +++ | | | W | A | R | L | A | R | W | W | R | R | A | R | 313 |
| GD1 | + | | | W | R | W | L | R | R | W | W | R | R | A | R | 314 |
| GD2 | + | | | A | A | R | L | R | R | L | W | R | A | A | R | 315 |

* The free peptide of EO1 is lethal in the periplasm but not in the cytoplasm (see Figure 54)

Figure 35-2

Lethality Key

Bacteriolytic (EO1, EO2, RR1, RR2)

| Symbol | Time elapsed before lysis | Rate of lysis |
|---|---|---|
| ++++ | $\leq$ 30 mins | All |
| +++ | 30 mins > t $\geq$ 1 hr | All |
| ++ | $\geq$ 1 hr | Fast |
| + | $\geq$ 1 hr | Slow |

Growth Rate Reducing (GD1, GD2)

| Symbol | Stationary phase optical |
|---|---|
| ++ | $\leq$ 0.7 |
| + | > 0.7 |

Figure 36

Bacteriostatic/Bactericidal Peptides from Early Onset Degenerate Peptide Screen

| Clone | Lethality | Peptide Sequence | | | | | | | | | | | | SEQ ID NO: |
|---|---|---|---|---|---|---|---|---|---|---|---|---|---|---|
| EOD001 | +++ | I | K | L | L | A | R | W | W | R | R | P | Y | 316 |
| EOD007 | + | F | R | L | L | M | R | R | W | R | R | Y | V | 317 |
| EOD022 | +++ | I | K | L | L | A | R | W | W | R | R | P | Y | 318 |
| EOD032 | + | F | W | R | L | L | R | R | W | R | G | S | G | 319 |
| EOD061 | +++ | M | M | R | L | L | R | R | W | R | R | P | A | 320 |
| EOD098 | + | M | T | W | L | D | R | W | W | R | G | R | T | 321 |
| EOD107 | ++ | F | V | R | L | R | R | W | W | R | R | H | N | 322 |
| EOD122 | + | I | S | L | L | D | S | W | W | R | G | S | R | 323 |

Lethality Key

| Symbol | Strength* |
|---|---|
| ++++ | ≥ 0.7 |
| +++ | 0.7 > OD ≥ 6 |
| ++ | 0.6 > OD ≥ 4 |
| + | < 0.4 |

* The difference in optical density between the induced and uninduced growth curves at stationary phase.

Weakly Inhibitory Peptides from Early Onset Degenerate Peptide Screen

| Clone | Lethality | Peptide Sequence | | | | | | | | | | | | SEQ ID NO: |
|---|---|---|---|---|---|---|---|---|---|---|---|---|---|---|
| EOD003 | + | I | D | W | L | P | R | W | W | R | R | G | W | 324 |
| EOD025 | + | F | R | L | L | M | R | R | W | R | R | Y | V | 325 |
| EOD042 | + | M | N | L | L | V | R | R | W | R | G | N | S | 326 |
| EOD093 | + | F | T | W | L | A | S | R | W | R | G | Q | L | 327 |

Lethality Key

| Symbol | Stationary phase optical density |
|---|---|
| ++ | ≤ 0.7 |
| + | > 0.7 |

Figure 37-1

Bacteriolytic Peptides from Early Onset Degenerate Peptide Screen

| Clone | Lethality | Peptide Sequence | | | | | | | | | | | | SEQ ID NO: |
|---|---|---|---|---|---|---|---|---|---|---|---|---|---|---|
| EOD004 | ++ | L | N | L | L | K | R | W | W | R | R | P | N | 328 |
| EOD006 | +++ | I | K | L | L | A | R | W | W | R | R | P | Y | 329 |
| EOD008 | ++++ | L | V | W | L | L | R | W | W | R | R | Y | Y | 330 |
| EOD010 | +++ | F | W | L | L | A | R | W | W | R | R | C | L | 331 |
| EOD012 | + | M | R | R | L | R | S | R | W | R | R | G | S | 332 |
| EOD013 | +++ | L | N | L | L | K | R | W | W | R | R | P | N | 333 |
| EOD016 | +++ | L | R | R | L | S | S | W | W | R | G | W | S | 334 |
| EOD017 | ++ | I | D | L | L | C | R | W | W | R | G | W | T | 335 |
| EOD018 | ++++ | M | N | L | L | W | S | W | W | R | R | V | T | 336 |
| EOD019 | ++ | I | A | R | L | R | S | W | W | R | G | S | L | 337 |
| EOD020 | +++ | L | L | W | L | R | R | R | W | R | R | A | V | 338 |
| EOD021 | ++ | F | R | L | L | K | S | W | W | R | G | R | S | 339 |
| EOD023 | +++ | M | E | L | L | G | R | W | W | R | G | H | K | 340 |
| EOD024 | + | I | I | L | L | R | R | W | W | R | R | S | S | 341 |
| EOD027 | + | I | L | L | L | M | S | W | W | R | G | L | F | 342 |
| EOD028 | ++++ | F | I | W | L | C | S | W | W | R | R | V | R | 343 |
| EOD029 | ++ | F | I | W | L | N | R | W | W | R | R | T | H | 344 |
| EOD030 | ++++ | I | A | W | L | F | S | W | W | R | G | Y | T | 345 |
| EOD035 | + | F | R | L | L | D | R | W | W | R | R | M | S | 346 |
| EOD037 | ++++ | I | R | W | L | A | R | R | W | R | R | T | F | 347 |
| EOD038 | +++ | F | K | L | L | V | S | W | W | R | G | H | G | 348 |
| EOD039 | +++ | I | R | L | L | T | S | W | W | R | R | G | Q | 349 |
| EOD040 | +++ | L | S | W | L | R | R | R | W | R | R | W | P | 350 |
| EOD041 | ++ | I | R | L | L | T | S | W | W | R | R | G | Q | 351 |

Figure 37-2

| | | | | | | | | | | | | | | |
|---|---|---|---|---|---|---|---|---|---|---|---|---|---|---|
| EOD043 | +++ | I | H | W | L | R | S | R | W | R | R | D | E | 352 |
| EOD044 | +++ | L | Q | L | L | K | S | W | W | R | R | I | Q | 353 |
| EOD045 | +++ | F | I | W | L | L | R | W | W | R | G | S | L | 354 |
| EOD046 | +++ | L | S | W | L | R | R | R | W | R | R | W | P | 355 |
| EOD047 | +++ | F | A | W | L | H | R | W | W | R | G | V | T | 356 |
| EOD048 | ++++ | M | C | W | L | A | R | R | W | R | R | D | Q | 357 |
| EOD049 | + | I | H | L | L | T | R | W | W | R | G | S | T | 358 |
| EOD052 | +++ | L | R | W | L | C | S | W | W | R | R | T | I | 359 |
| EOD053 | ++++ | L | M | R | L | L | R | W | W | R | G | T | S | 360 |
| EOD056 | ++++ | F | K | L | L | F | R | W | W | R | R | R | L | 361 |
| EOD057 | ++++ | F | S | L | L | V | R | W | W | R | R | Q | T | 362 |
| EOD058 | + | I | R | L | L | R | R | W | W | R | R | V | E | 363 |
| EOD059 | +++ | F | R | L | L | S | R | W | W | R | R | L | K | 364 |
| EOD060 | ++++ | I | Q | L | L | L | S | W | W | R | R | T | L | 365 |
| EOD062 | ++ | I | S | R | L | R | S | R | W | R | R | A | S | 366 |
| EOD064 | ++ | M | E | L | L | S | R | R | W | R | R | S | R | 367 |
| EOD065 | ++++ | F | D | W | L | C | R | R | W | R | G | V | K | 368 |
| EOD070 | ++++ | I | T | W | L | L | S | R | W | R | R | I | Q | 369 |
| EOD071 | +++ | F | L | W | L | S | R | R | W | R | R | S | E | 370 |
| EOD073 | +++ | F | H | L | L | Q | S | W | W | R | R | H | L | 371 |
| EOD075 | +++ | I | Y | L | L | F | S | W | W | R | R | C | L | 372 |
| EOD076 | ++++ | M | T | L | L | H | R | W | W | R | G | K | T | 373 |
| EOD077 | +++ | I | R | L | L | T | S | W | W | R | R | P | R | 374 |
| EOD078 | ++++ | I | K | W | L | M | R | W | W | R | G | S | D | 375 |
| EOD082 | +++ | I | G | L | L | R | R | W | W | R | G | P | G | 376 |
| EOD083 | +++ | I | S | W | L | K | R | W | W | R | R | I | N | 377 |
| EOD089 | ++++ | I | I | W | L | M | S | R | W | R | R | L | K | 378 |
| EOD091 | +++ | I | N | W | L | L | S | W | W | R | G | T | S | 379 |
| EOD094 | +++ | F | R | W | L | L | S | W | W | R | G | R | G | 380 |
| EOD099 | +++ | I | N | W | L | L | S | W | W | R | G | T | S | 381 |
| EOD103 | +++ | M | F | L | L | K | R | W | W | R | R | W | L | 382 |
| EOD106 | ++++ | L | C | W | L | T | S | W | W | R | R | H | L | 383 |

Figure 37-3

| | | | | | | | | | | | | | | |
|---|---|---|---|---|---|---|---|---|---|---|---|---|---|---|
| EOD110 | +++ | M | V | R | L | R | R | W | W | R | R | T | L | 384 |
| EOD112 | +++ | I | N | L | L | R | R | R | W | R | R | D | R | 385 |
| EOD113 | +++ | F | S | L | L | R | R | W | W | R | G | D | D | 386 |
| EOD116 | ++++ | F | S | L | L | S | R | W | W | R | G | R | L | 387 |
| EOD121 | ++++ | F | H | W | L | V | R | W | W | R | G | H | S | 388 |
| EOD123 | +++ | I | A | L | L | L | S | R | W | R | R | R | G | 389 |
| EOD126 | ++++ | I | A | L | L | L | S | R | W | R | R | R | G | 390 |
| EOD128 | ++++ | F | H | W | L | A | S | R | W | R | R | S | Y | 391 |
| EOD133 | +++ | I | A | L | L | R | R | W | W | R | G | S | R | 392 |
| EOD136 | ++++ | I | Q | R | L | M | S | W | W | R | G | L | T | 393 |

Figure 37-4

Lethality Key

| Symbol | Time elapsed before lysis | Rate of lysis |
|---|---|---|
| ++++ | $\leq$ 30 mins | All |
| +++ | 30 mins > t $\geq$ 1 hr | All |
| ++ | $\geq$ 1 hr | Fast |
| + | $\geq$ 1 hr | Slow |

Figure 38-1

Non-Inhibitory Peptides from Early Onset Degenerate Peptide Screen

| Clone | Peptide Sequence | | | | | | | | | | | SEQ ID NO: |
|---|---|---|---|---|---|---|---|---|---|---|---|---|
| EOD002 | I | Q | L | L | G | R | R | W | R | R | I | P | 394 |
| EOD005 | I | C | L | L | Q | R | R | W | R | R | M | H | 395 |
| EOD009 | M | N | L | L | E | R | R | W | R | R | W | W | 396 |
| EOD011 | M | N | L | L | E | R | R | W | R | R | W | N | 397 |
| EOD014 | I | A | L | L | A | S | R | W | R | R | R | P | 398 |
| EOD015 | L | P | R | L | L | S | R | W | R | R | R | P | 399 |
| EOD026 | F | A | R | L | T | R | R | W | R | R | T | S | 400 |
| EOD031 | F | T | L | L | L | S | W | W | R | G | Y | H | 401 |
| EOD036 | F | T | L | L | I | S | R | W | R | R | H | V | 402 |
| EOD051 | I | G | R | L | R | S | R | W | R | G | Y | S | 403 |
| EOD054 | I | L | L | L | I | S | R | W | R | G | V | L | 404 |
| EOD055 | L | D | W | L | P | R | R | W | R | R | R | A | 405 |
| EOD063 | F | V | L | L | A | S | R | W | R | R | L | R | 406 |
| EOD067 | M | M | L | L | R | S | R | W | R | R | T | Q | 407 |
| EOD069 | M | D | R | L | S | R | R | W | R | G | L | K | 408 |
| EOD079 | M | V | L | L | K | R | R | W | R | G | A | R | 409 |
| EOD081 | F | D | L | L | A | R | R | W | R | R | P | V | 410 |
| EOD084 | F | M | R | L | P | R | W | W | R | R | M | Q | 411 |
| EOD085 | I | T | L | L | C | S | R | W | R | R | T | L | 412 |
| EOD086 | M | R | L | L | L | S | R | W | R | R | S | P | 413 |
| EOD087 | I | S | L | L | C | S | R | W | R | R | C | T | 414 |
| EOD088 | M | W | L | L | V | R | R | W | R | G | L | S | 415 |
| EOD090 | F | C | W | L | V | S | W | W | R | G | S | D | 416 |
| EOD097 | I | F | L | L | S | R | W | W | R | R | N | E | 417 |
| EOD100 | I | G | L | L | H | S | W | W | R | G | F | A | 418 |
| EOD101 | M | H | L | L | L | S | W | W | R | G | T | V | 419 |
| EOD102 | F | T | W | L | A | S | R | W | R | G | Q | L | 420 |
| EOD104 | L | W | R | L | G | S | W | W | R | G | S | P | 421 |
| EOD109 | M | R | R | L | G | R | R | W | R | R | P | R | 422 |
| EOD111 | I | L | L | L | N | S | W | W | R | G | H | C | 423 |
| EOD114 | M | V | L | L | W | R | R | W | R | G | L | L | 424 |
| EOD115 | I | L | L | L | V | R | R | W | R | R | T | N | 425 |
| EOD117 | M | S | L | L | P | S | R | W | R | R | R | P | 426 |
| EOD119 | I | Y | L | L | S | R | R | W | R | R | S | D | 427 |
| EOD120 | F | W | L | L | W | S | R | W | R | R | K | L | 428 |

Figure 38-2

| | | | | | | | | | | | | | |
|---|---|---|---|---|---|---|---|---|---|---|---|---|---|
| EOD125 | F | Y | L | L | R | R | R | W | R | R | P | S | 429 |
| EOD127 | F | H | L | L | Y | R | R | W | R | R | L | C | 430 |
| EOD129 | L | P | R | L | L | S | R | W | R | R | E | L | 431 |
| EOD130 | I | L | W | L | H | S | R | W | R | R | E | Q | 432 |
| EOD131 | I | H | L | L | V | S | W | W | R | G | T | S | 433 |
| EOD134 | I | S | L | L | A | S | R | W | R | G | S | R | 434 |
| EOD135 | F | M | L | L | H | R | R | W | R | G | L | T | 435 |
| EOD137 | F | H | L | L | H | S | R | W | R | R | S | A | 436 |

Figure 39

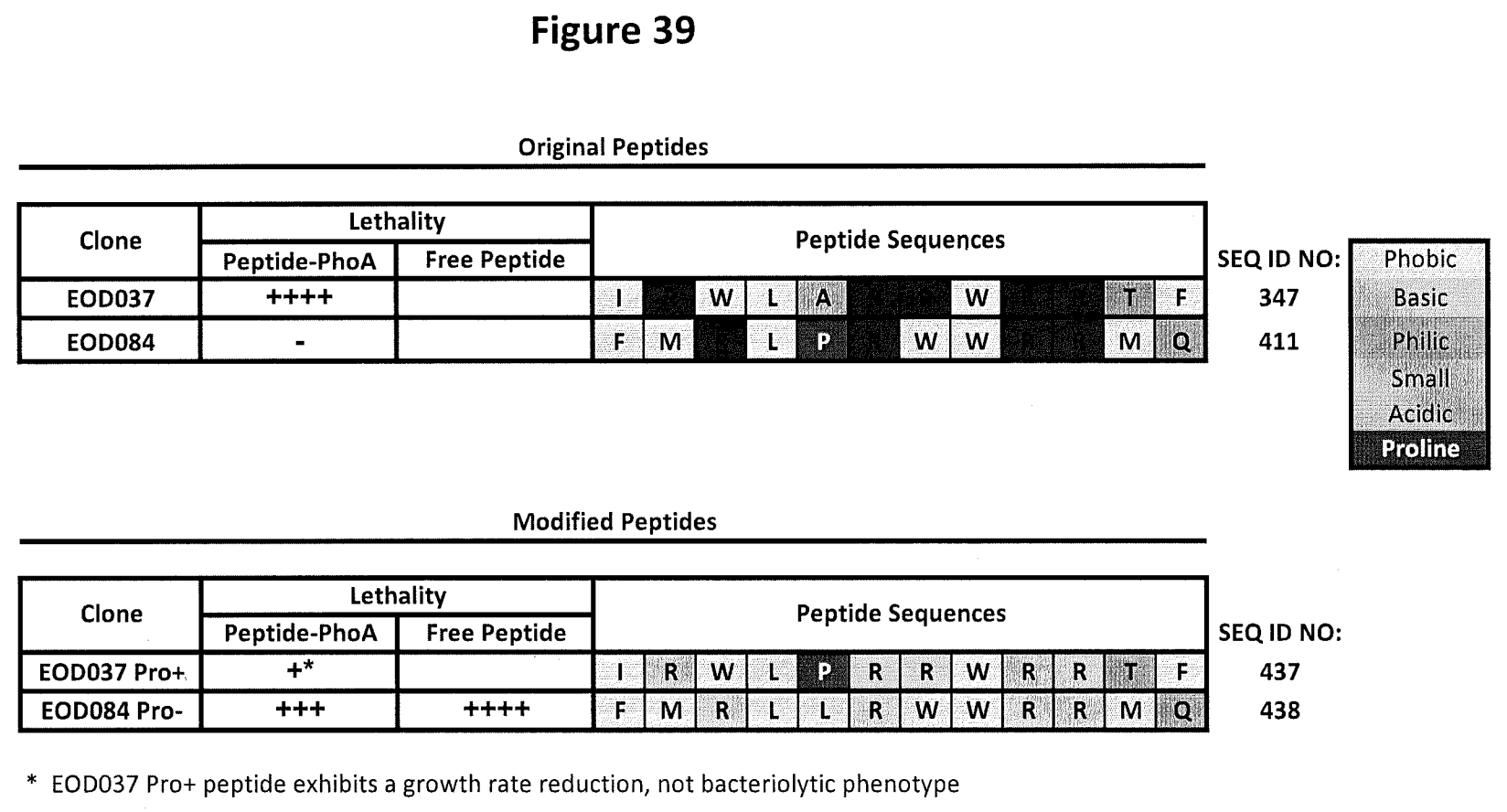

Original Peptides

| Clone | Lethality | | Peptide Sequences | | | | | | | | | | | | SEQ ID NO: |
|---|---|---|---|---|---|---|---|---|---|---|---|---|---|---|---|
| | Peptide-PhoA | Free Peptide | | | | | | | | | | | | | |
| EOD037 | ++++ | | I | [illegible] | W | L | A | [illegible] | [illegible] | W | [illegible] | [illegible] | T | F | 347 |
| EOD084 | - | | F | M | [illegible] | L | P | [illegible] | W | W | [illegible] | [illegible] | M | Q | 411 |

| |
|---|
| Phobic |
| Basic |
| Philic |
| Small |
| Acidic |
| **Proline** |

Modified Peptides

| Clone | Lethality | | Peptide Sequences | | | | | | | | | | | | SEQ ID NO: |
|---|---|---|---|---|---|---|---|---|---|---|---|---|---|---|---|
| | Peptide-PhoA | Free Peptide | | | | | | | | | | | | | |
| EOD037 Pro+ | +* | | I | R | W | L | P | R | R | W | R | R | T | F | 437 |
| EOD084 Pro- | +++ | ++++ | F | M | R | L | L | R | W | W | R | R | M | Q | 438 |

* EOD037 Pro+ peptide exhibits a growth rate reduction, not bacteriolytic phenotype

Figure 40

EO1 peptide MIC analysis

| Species | MIC (μm) |
|---|---|
| E. coli W3110 | 31.3 |
| E. coli SM101 | 15.6 |
| Pseudomonas aeruginosa | 7.8 |
| Enterococcu. faecalis | 15.6 |
| Staphylococcus aureus | 7.8 |
| Bacillus subtilis | 7.8 |

Figure 41-1

| Alanine Scan Peptides based on the EO1 Peptide | | | | | | | | | | | | | | | | |
|---|---|---|---|---|---|---|---|---|---|---|---|---|---|---|---|---|
| Clone | Lethality | | *E. coli* MIC (μM) | Peptide Sequence | | | | | | | | | | | | SEQ ID NO: |
| | Peptide-PhoA | Free Peptide | | | | | | | | | | | | | | |
| EO1 A1 | ++++ | | | A | A | W | L | W | S | W | W | R | A | R | R | 439 |
| EO1 A3 | ++++ | | | F | A | A | L | W | S | W | W | R | A | R | R | 440 |
| EO1 A4 | +* | | | F | A | W | A | W | S | W | W | R | A | R | R | 441 |
| EO1 A5 | ++++ | | | F | A | W | L | A | S | W | W | R | A | R | R | 442 |
| EO1 A6 | ++++ | | | F | A | W | L | W | A | W | W | R | A | R | R | 443 |
| EO1 A7 | ++++ | | | F | A | W | L | W | S | A | W | R | A | R | R | 444 |
| EO1 A8 | ++++ | | | F | A | W | L | W | S | W | A | R | A | R | R | 445 |
| EO1 A9 | ++++ | | | F | A | W | L | W | S | W | W | A | A | R | R | 446 |
| EO1 A11 | ++++ | | | F | A | W | L | W | S | W | W | R | A | A | R | 447 |
| EO1 A12 | ++++ | | | F | A | W | L | W | S | W | W | R | A | R | A | 448 |

* EO1 A4 peptide exhibits a weak growth rate reducing phenotype

Figure 41-2

Lethality Key

Bacteriolytic

| Symbol | Time elapsed before lysis | Rate of lysis |
|---|---|---|
| ++++ | $\leq$ 30 mins | All |
| +++ | 30 mins > t $\geq$ 1 hr | All |
| ++ | $\geq$ 1 hr | Fast |
| + | $\geq$ 1 hr | Slow |

Figure 42-1

| Site-directed Mutants of the EO1 Peptide | | | | | | | | | | | | | | | | |
|---|---|---|---|---|---|---|---|---|---|---|---|---|---|---|---|---|
| Clone | Lethality | | *E. coli* MIC (μM) | Peptide Sequence | | | | | | | | | | | | |
| | Peptide-PhoA | Free Peptide | | | | | | | | | | | | | | SEQ ID NO: |
| EO1I | ++++ | | | F | A | W | I | W | S | W | W | R | A | R | R | 449 |
| EO1V | ++++ | | | F | A | W | V | W | S | W | W | R | A | R | R | 450 |
| EO1F | - | | | F | A | W | F | W | S | W | W | R | A | R | R | 451 |
| EO1Y | - | | | F | A | W | Y | W | S | W | W | R | A | R | R | 452 |
| EO1N | - | | | F | A | W | N | W | S | W | W | R | A | R | R | 453 |
| EO1D | - | | | F | A | W | D | W | S | W | W | R | A | R | R | 454 |
| EO1K | - | | | F | A | W | K | W | S | W | W | R | A | R | R | 455 |
| EO1 1 | ++* | | | A | A | W | I | W | S | W | A | R | A | R | R | 456 |
| EO1 2 | - | | | | A | W | V | W | S | W | W | R | A | R | R | 457 |
| EO1 3 | - | | | S | A | W | F | W | S | W | A | R | A | R | R | 458 |
| EO1 4 | - | | | S | A | W | Y | W | S | W | S | R | A | R | R | 459 |
| EO1 5 | ++++** | | | F | A | W | N | W | S | W | W | R | A | R | E | 460 |
| EO1 6 | ++*** | | | F | A | W | D | W | S | W | W | R | E | R | E | 461 |

Figure 42-2

Lethality Key

Bacteriolytic (EO1I, EO1V, EO15)

| Symbol | Time elapsed before lysis | Rate of lysis |
|---|---|---|
| ++++ | ≤ 30 mins | All |
| +++ | 30 mins > t ≥ 1 hr | All |
| ++ | ≥ 1 hr | Fast |
| + | ≥ 1 hr | Slow |

Bacteriostatic/Bactericidal (EO1 1)

| Symbol | Strength* |
|---|---|
| ++++ | ≥ 0.7 |
| +++ | 0.7 > OD ≥ 6 |
| ++ | 0.6 > OD ≥ 5 |
| + | < 0.5 |

* The difference in optical density between the induced and uninduced growth curves at stationary phase.

Growth Rate Reducing (EO1 6)

| Symbol | Stationary phase optical density |
|---|---|
| ++ | ≤ 0.7 |
| + | > 0.7 |

Figure 59A

Distribution of Amino Acids in All Bacteriolytic Peptides from the Periplasmic-Bacteriolytic Peptide Screen

| Amino Acid | | Position | | | | | | | | | | | |
|---|---|---|---|---|---|---|---|---|---|---|---|---|---|
| Group | Residue | 1* | 2 | 3 | 4 | 5 | 6 | 7 | 8 | 9 | 10 | 11 | 12 |
| Basic | Lys | 0 | 6 | 2 | 0 | 15 | 9 | 6 | 0 | 6 | 6 | 3 | 9 |
| | His | 0 | 0 | 0 | 0 | 1 | 0 | 0 | 0 | 0 | 0 | 1 | 2 |
| | Arg | 0 | 21 | 17 | 0 | 38 | 39 | 12 | 3 | 31 | 29 | 18 | 25 |
| Acidic | Asp | 0 | 1 | 0 | 0 | 0 | 2 | 0 | 0 | 0 | 2 | 0 | 0 |
| | Glu | 0 | 4 | 0 | 1 | 0 | 2 | 0 | 0 | 0 | 2 | 2 | 4 |
| Hydrophobic | Pro | 0 | 0 | 0 | 0 | 0 | 0 | 0 | 0 | 0 | 2 | 2 | 0 |
| | Val | 6 | 3 | 3 | 15 | 3 | 0 | 6 | 9 | 2 | 0 | 6 | 6 |
| | Cys | 1 | 3 | 1 | 1 | 0 | 0 | 1 | 3 | 0 | 2 | 2 | 1 |
| | Leu | 11 | 0 | 12 | 36 | 2 | 2 | 22 | 20 | 3 | 3 | 5 | 3 |
| | Ile | 7 | 0 | 1 | 9 | 3 | 1 | 1 | 1 | 1 | 2 | 2 | 0 |
| | Met | 6 | 0 | 2 | 4 | 2 | 1 | 1 | 2 | 1 | 1 | 2 | 1 |
| | Phe | 7 | 0 | 4 | 7 | 1 | 0 | 4 | 4 | 3 | 2 | 0 | 0 |
| | Tyr | 7 | 0 | 3 | 0 | 0 | 0 | 1 | 0 | 1 | 0 | 2 | 0 |
| | Trp | 30 | 0 | 24 | 5 | 3 | 1 | 22 | 24 | 4 | 2 | 15 | 3 |
| Small | Gly | 2 | 12 | 3 | 0 | 5 | 7 | 3 | 4 | 13 | 11 | 10 | 11 |
| | Ala | 6 | 13 | 10 | 5 | 5 | 8 | 6 | 7 | 5 | 8 | 6 | 6 |
| Hydrophilic | Ser | 2 | 9 | 1 | 1 | 2 | 8 | 0 | 4 | 3 | 6 | 2 | 5 |
| | Thr | 0 | 5 | 1 | 1 | 3 | 2 | 0 | 3 | 2 | 3 | 4 | 4 |
| | Asn | 0 | 3 | 0 | 0 | 0 | 2 | 0 | 0 | 0 | 1 | 2 | 0 |
| | Gln | 0 | 5 | 1 | 0 | 2 | 1 | 0 | 1 | 10 | 3 | 1 | 5 |

Figure 59B

| Amino Acid Group | Position | | | | | | | | | | | |
|---|---|---|---|---|---|---|---|---|---|---|---|---|
| | 1* | 2 | 3 | 4 | 5 | 6 | 7 | 8 | 9 | 10 | 11 | 12 |
| Basic | 0 | 27 | 19 | 0 | 54 | 48 | 18 | 3 | 37 | 35 | 22 | 36 |
| Acidic | 0 | 5 | 0 | 1 | 0 | 4 | 0 | 0 | 0 | 4 | 2 | 4 |
| Hydrophobic | 75 | 6 | 50 | 77 | 14 | 5 | 58 | 63 | 15 | 14 | 36 | 14 |
| Small | 8 | 25 | 13 | 5 | 10 | 15 | 9 | 11 | 18 | 19 | 16 | 17 |
| Hydrophilic | 2 | 22 | 3 | 2 | 7 | 13 | 0 | 8 | 15 | 13 | 9 | 14 |

* 1st position is based on DNA sequence of DNK, remaining positions are based on NNK.

Figure 59C

| Group Key | | | | |
|---|---|---|---|---|
| **Basic** | **Acidic** | **Hydrophobic** | **Small** | **Hydrophilic** |
| Lys | Asp | Pro | Gly | Ser |
| His | Glu | Val | Ala | Thr |
| Arg | | Cys | | Asn |
| | | Leu | | Gln |
| | | Ile | | |
| | | Met | | |
| | | Phe | | |
| | | Tyr | | |
| | | Trp | | |

Figure 59D

Chi Test Data

| By Amino Acid | | | By Group | |
|---|---|---|---|---|
| Position | Chi | | Position | Chi |
| 1 | 3.7E-04 | | 1 | 6.5E-20 |
| 2 | 5.5E-09 | | 2 | 1.1E-11 |
| 3 | 1.3E-36 | | 3 | 3.2E-06 |
| 4 | 3.1E-30 | | 4 | 1.7E-18 |
| 5 | 4.3E-33 | | 5 | 7.8E-32 |
| 6 | 8.2E-27 | | 6 | 2.8E-25 |
| 7 | 1.2E-34 | | 7 | 5.2E-09 |
| 8 | 2.3E-37 | | 8 | 3.9E-09 |
| 9 | 1.9E-16 | | 9 | 1.9E-13 |
| 10 | 6.1E-11 | | 10 | 8.2E-12 |
| 11 | 9.2E-12 | | 11 | 1.5E-03 |
| 12 | 3.9E-10 | | 12 | 8.9E-12 |

Figure 59E

Binomial Distribution of Amino Acid Groups by Position in Bacteriolytic

| Position | Group | N | P | X | P value |
|---|---|---|---|---|---|
| 1 | Basic | 85 | 0.083 | 0 | 6.14E-04 |
| | Acidic | 85 | 0.083 | 0 | 6.14E-04 |
| | Phobic | 85 | 0.333 | 75 | 8.92E-26 |
| | Small | 85 | 0.167 | 8 | 2.29E-02 |
| | Philic | 85 | 0.333 | 2 | 9.61E-13 |
| 2 | Basic | 85 | 0.156 | 27 | 9.89E-05 |
| | Acidic | 85 | 0.063 | 5 | 1.79E-01 |
| | Phobic | 85 | 0.375 | 6 | 9.11E-11 |
| | Small | 85 | 0.125 | 25 | 1.92E-05 |
| | Philic | 85 | 0.281 | 22 | 8.84E-02 |
| 3 | Basic | 85 | 0.156 | 19 | 2.76E-02 |
| | Acidic | 85 | 0.063 | 0 | 4.15E-03 |
| | Phobic | 85 | 0.375 | 50 | 3.23E-05 |
| | Small | 85 | 0.125 | 13 | 8.97E-02 |
| | Philic | 85 | 0.281 | 3 | 3.81E-09 |
| 4 | Basic | 85 | 0.156 | 0 | 5.35E-07 |
| | Acidic | 85 | 0.063 | 1 | 2.35E-02 |
| | Phobic | 85 | 0.375 | 77 | 1.78E-24 |
| | Small | 85 | 0.125 | 5 | 2.30E-02 |
| | Philic | 85 | 0.281 | 2 | 3.52E-10 |
| 5 | Basic | 85 | 0.156 | 54 | 2.24E-23 |
| | Acidic | 85 | 0.063 | 0 | 4.15E-03 |
| | Phobic | 85 | 0.375 | 14 | 1.33E-05 |
| | Small | 85 | 0.125 | 10 | 1.30E-01 |
| | Philic | 85 | 0.281 | 7 | 4.47E-06 |
| 6 | Basic | 85 | 0.156 | 48 | 6.17E-18 |
| | Acidic | 85 | 0.063 | 4 | 1.66E-01 |
| | Phobic | 85 | 0.375 | 5 | 1.14E-11 |
| | Small | 85 | 0.125 | 15 | 4.46E-02 |
| | Philic | 85 | 0.281 | 13 | 2.40E-03 |

| Position | Group | N | P | X | P value |
|---|---|---|---|---|---|
| 7 | Basic | 85 | 0.156 | 18 | 4.23E-02 |
| | Acidic | 85 | 0.063 | 0 | 4.15E-03 |
| | Phobic | 85 | 0.375 | 58 | 6.67E-09 |
| | Small | 85 | 0.125 | 9 | 1.20E-01 |
| | Philic | 85 | 0.281 | 0 | 6.44E-13 |
| 8 | Basic | 85 | 0.156 | 3 | 3.35E-04 |
| | Acidic | 85 | 0.063 | 0 | 4.15E-03 |
| | Phobic | 85 | 0.375 | 63 | 5.96E-12 |
| | Small | 85 | 0.125 | 11 | 1.27E-01 |
| | Philic | 85 | 0.281 | 8 | 1.70E-05 |
| 9 | Basic | 85 | 0.156 | 37 | 7.03E-10 |
| | Acidic | 85 | 0.063 | 0 | 4.15E-03 |
| | Phobic | 85 | 0.375 | 15 | 3.78E-05 |
| | Small | 85 | 0.125 | 18 | 8.72E-03 |
| | Philic | 85 | 0.281 | 15 | 8.95E-03 |
| 10 | Basic | 85 | 0.156 | 35 | 1.11E-08 |
| | Acidic | 85 | 0.063 | 4 | 1.66E-01 |
| | Phobic | 85 | 0.375 | 14 | 1.33E-05 |
| | Small | 85 | 0.125 | 19 | 4.39E-03 |
| | Philic | 85 | 0.281 | 13 | 2.40E-03 |
| 11 | Basic | 85 | 0.156 | 22 | 5.22E-03 |
| | Acidic | 85 | 0.063 | 2 | 6.58E-02 |
| | Phobic | 85 | 0.375 | 36 | 5.73E-02 |
| | Small | 85 | 0.125 | 16 | 2.79E-02 |
| | Philic | 85 | 0.281 | 9 | 5.71E-05 |
| 12 | Basic | 85 | 0.156 | 36 | 2.87E-09 |
| | Acidic | 85 | 0.063 | 4 | 1.66E-01 |
| | Phobic | 85 | 0.375 | 14 | 1.33E-05 |
| | Small | 85 | 0.125 | 17 | 1.62E-02 |
| | Philic | 85 | 0.281 | 14 | 4.83E-03 |

Figure 59F

Binomial Distribution of Amino Acids by Position in Bacteriolytic Peptides

| Position | Residue | N | P | X | P value |
|---|---|---|---|---|---|
| 1 | K | 85 | 0.042 | 0 | 2.68E-02 |
| | H | 85 | 0.000 | 0 | 1.00E+00 |
| | R | 85 | 0.042 | 0 | 2.68E-02 |
| | D | 85 | 0.042 | 0 | 2.68E-02 |
| | E | 85 | 0.042 | 0 | 2.68E-02 |
| | P | 85 | 0.000 | 0 | 1.00E+00 |
| | V | 85 | 0.083 | 6 | 1.52E-01 |
| | C | 85 | 0.042 | 1 | 9.92E-02 |
| | L | 85 | 0.042 | 11 | 6.01E-04 |
| | I | 85 | 0.042 | 7 | 3.89E-02 |
| | M | 85 | 0.042 | 6 | 7.93E-02 |
| | F | 85 | 0.042 | 7 | 3.89E-02 |
| | Y | 85 | 0.042 | 7 | 3.89E-02 |
| | W | 85 | 0.042 | 30 | 3.16E-20 |
| | G | 85 | 0.083 | 2 | 1.81E-02 |
| | A | 85 | 0.083 | 6 | 1.52E-01 |
| | S | 85 | 0.125 | 2 | 8.57E-04 |
| | T | 85 | 0.083 | 0 | 6.14E-04 |
| | N | 85 | 0.042 | 0 | 2.68E-02 |
| | Q | 85 | 0.042 | 0 | 2.68E-02 |
| 2 | K | 85 | 0.031 | 6 | 3.32E-02 |
| | H | 85 | 0.031 | 0 | 6.73E-02 |
| | R | 85 | 0.094 | 21 | 2.06E-05 |
| | D | 85 | 0.031 | 1 | 1.85E-01 |
| | E | 85 | 0.031 | 4 | 1.48E-01 |
| | P | 85 | 0.063 | 0 | 4.15E-03 |
| | V | 85 | 0.063 | 3 | 1.21E-01 |
| | C | 85 | 0.031 | 3 | 2.23E-01 |
| | L | 85 | 0.094 | 0 | 2.32E-04 |
| | I | 85 | 0.031 | 0 | 6.73E-02 |
| | M | 85 | 0.031 | 0 | 6.73E-02 |
| | F | 85 | 0.031 | 0 | 6.73E-02 |
| | Y | 85 | 0.031 | 0 | 6.73E-02 |
| | W | 85 | 0.031 | 0 | 6.73E-02 |
| | G | 85 | 0.063 | 12 | 4.20E-03 |
| | A | 85 | 0.063 | 13 | 1.57E-03 |
| | S | 85 | 0.094 | 9 | 1.30E-01 |
| | T | 85 | 0.063 | 5 | 1.79E-01 |
| | N | 85 | 0.031 | 3 | 2.23E-01 |
| | Q | 85 | 0.063 | 5 | 1.79E-01 |

| Position | Residue | N | P | X | P value |
|---|---|---|---|---|---|
| 3 | K | 85 | 0.031 | 2 | 2.50E-01 |
| | H | 85 | 0.031 | 0 | 6.73E-02 |
| | R | 85 | 0.094 | 17 | 1.32E-03 |
| | D | 85 | 0.031 | 0 | 6.73E-02 |
| | E | 85 | 0.031 | 0 | 6.73E-02 |
| | P | 85 | 0.063 | 0 | 4.15E-03 |
| | V | 85 | 0.063 | 3 | 1.21E-01 |
| | C | 85 | 0.031 | 1 | 1.85E-01 |
| | L | 85 | 0.094 | 12 | 4.59E-02 |
| | I | 85 | 0.031 | 1 | 1.85E-01 |
| | M | 85 | 0.031 | 2 | 2.50E-01 |
| | F | 85 | 0.031 | 4 | 1.48E-01 |
| | Y | 85 | 0.031 | 3 | 2.23E-01 |
| | W | 85 | 0.031 | 24 | 9.70E-17 |
| | G | 85 | 0.063 | 3 | 1.21E-01 |
| | A | 85 | 0.063 | 10 | 2.25E-02 |
| | S | 85 | 0.094 | 1 | 2.04E-03 |
| | T | 85 | 0.063 | 1 | 2.35E-02 |
| | N | 85 | 0.031 | 0 | 6.73E-02 |
| | Q | 85 | 0.063 | 1 | 2.35E-02 |
| 4 | K | 85 | 0.031 | 0 | 6.73E-02 |
| | H | 85 | 0.031 | 0 | 6.73E-02 |
| | R | 85 | 0.094 | 0 | 2.32E-04 |
| | D | 85 | 0.031 | 0 | 6.73E-02 |
| | E | 85 | 0.031 | 1 | 1.85E-01 |
| | P | 85 | 0.063 | 0 | 4.15E-03 |
| | V | 85 | 0.063 | 15 | 1.70E-04 |
| | C | 85 | 0.031 | 1 | 1.85E-01 |
| | L | 85 | 0.094 | 36 | 9.80E-16 |
| | I | 85 | 0.031 | 9 | 1.05E-03 |
| | M | 85 | 0.031 | 4 | 1.48E-01 |
| | F | 85 | 0.031 | 7 | 1.21E-02 |
| | Y | 85 | 0.031 | 0 | 6.73E-02 |
| | W | 85 | 0.031 | 5 | 7.71E-02 |
| | G | 85 | 0.063 | 0 | 4.15E-03 |
| | A | 85 | 0.063 | 5 | 1.79E-01 |
| | S | 85 | 0.094 | 1 | 2.04E-03 |
| | T | 85 | 0.063 | 1 | 2.35E-02 |
| | N | 85 | 0.031 | 0 | 6.73E-02 |
| | Q | 85 | 0.063 | 0 | 4.15E-03 |

Figure 59G

| Position | Residue | N | P | X | P value | Position | Residue | N | P | X | P value |
|---|---|---|---|---|---|---|---|---|---|---|---|
| 5 | K | 85 | 0.031 | 15 | 5.16E-08 | 7 | K | 85 | 0.031 | 6 | 3.32E-02 |
| | H | 85 | 0.031 | 1 | 1.85E-01 | | H | 85 | 0.031 | 0 | 6.73E-02 |
| | R | 85 | 0.094 | 38 | 1.75E-17 | | R | 85 | 0.094 | 12 | 4.59E-02 |
| | D | 85 | 0.031 | 0 | 6.73E-02 | | D | 85 | 0.031 | 0 | 6.73E-02 |
| | E | 85 | 0.031 | 0 | 6.73E-02 | | E | 85 | 0.031 | 0 | 6.73E-02 |
| | P | 85 | 0.063 | 0 | 4.15E-03 | | P | 85 | 0.063 | 0 | 4.15E-03 |
| | V | 85 | 0.063 | 3 | 1.21E-01 | | V | 85 | 0.063 | 6 | 1.59E-01 |
| | C | 85 | 0.031 | 0 | 6.73E-02 | | C | 85 | 0.031 | 1 | 1.85E-01 |
| | L | 85 | 0.094 | 2 | 8.88E-03 | | L | 85 | 0.094 | 22 | 6.19E-06 |
| | I | 85 | 0.031 | 3 | 2.23E-01 | | I | 85 | 0.031 | 1 | 1.85E-01 |
| | M | 85 | 0.031 | 2 | 2.50E-01 | | M | 85 | 0.031 | 1 | 1.85E-01 |
| | F | 85 | 0.031 | 1 | 1.85E-01 | | F | 85 | 0.031 | 4 | 1.48E-01 |
| | Y | 85 | 0.031 | 0 | 6.73E-02 | | Y | 85 | 0.031 | 1 | 1.85E-01 |
| | W | 85 | 0.031 | 3 | 2.23E-01 | | W | 85 | 0.031 | 22 | 1.32E-14 |
| | G | 85 | 0.063 | 5 | 1.79E-01 | | G | 85 | 0.063 | 3 | 1.21E-01 |
| | A | 85 | 0.063 | 5 | 1.79E-01 | | A | 85 | 0.063 | 6 | 1.59E-01 |
| | S | 85 | 0.094 | 2 | 8.88E-03 | | S | 85 | 0.094 | 0 | 2.32E-04 |
| | T | 85 | 0.063 | 3 | 1.21E-01 | | T | 85 | 0.063 | 0 | 4.15E-03 |
| | N | 85 | 0.031 | 0 | 6.73E-02 | | N | 85 | 0.031 | 0 | 6.73E-02 |
| | Q | 85 | 0.063 | 2 | 6.58E-02 | | Q | 85 | 0.063 | 0 | 4.15E-03 |
| 6 | K | 85 | 0.031 | 9 | 1.05E-03 | 8 | K | 85 | 0.031 | 0 | 6.73E-02 |
| | H | 85 | 0.031 | 0 | 6.73E-02 | | H | 85 | 0.031 | 0 | 6.73E-02 |
| | R | 85 | 0.094 | 39 | 2.19E-18 | | R | 85 | 0.094 | 3 | 2.54E-02 |
| | D | 85 | 0.031 | 2 | 2.50E-01 | | D | 85 | 0.031 | 0 | 6.73E-02 |
| | E | 85 | 0.031 | 2 | 2.50E-01 | | E | 85 | 0.031 | 0 | 6.73E-02 |
| | P | 85 | 0.063 | 0 | 4.15E-03 | | P | 85 | 0.063 | 0 | 4.15E-03 |
| | V | 85 | 0.063 | 0 | 4.15E-03 | | V | 85 | 0.063 | 9 | 4.44E-02 |
| | C | 85 | 0.031 | 0 | 6.73E-02 | | C | 85 | 0.031 | 3 | 2.23E-01 |
| | L | 85 | 0.094 | 2 | 8.88E-03 | | L | 85 | 0.094 | 20 | 6.43E-05 |
| | I | 85 | 0.031 | 1 | 1.85E-01 | | I | 85 | 0.031 | 1 | 1.85E-01 |
| | M | 85 | 0.031 | 1 | 1.85E-01 | | M | 85 | 0.031 | 2 | 2.50E-01 |
| | F | 85 | 0.031 | 0 | 6.73E-02 | | F | 85 | 0.031 | 4 | 1.48E-01 |
| | Y | 85 | 0.031 | 0 | 6.73E-02 | | Y | 85 | 0.031 | 0 | 6.73E-02 |
| | W | 85 | 0.031 | 1 | 1.85E-01 | | W | 85 | 0.031 | 24 | 9.70E-17 |
| | G | 85 | 0.063 | 7 | 1.20E-01 | | G | 85 | 0.063 | 4 | 1.66E-01 |
| | A | 85 | 0.063 | 8 | 7.78E-02 | | A | 85 | 0.063 | 7 | 1.20E-01 |
| | S | 85 | 0.094 | 8 | 1.47E-01 | | S | 85 | 0.094 | 4 | 5.39E-02 |
| | T | 85 | 0.063 | 2 | 6.58E-02 | | T | 85 | 0.063 | 3 | 1.21E-01 |
| | N | 85 | 0.031 | 2 | 2.50E-01 | | N | 85 | 0.031 | 0 | 6.73E-02 |
| | Q | 85 | 0.063 | 1 | 2.35E-02 | | Q | 85 | 0.063 | 1 | 2.35E-02 |

Figure 59H

| Position | Residue | N | P | X | P value | Position | Residue | N | P | X | P value |
|---|---|---|---|---|---|---|---|---|---|---|---|
| 9 | K | 85 | 0.031 | 6 | 3.32E-02 | 11 | K | 85 | 0.031 | 3 | 2.23E-01 |
| | H | 85 | 0.031 | 0 | 6.73E-02 | | H | 85 | 0.031 | 1 | 1.85E-01 |
| | R | 85 | 0.094 | 31 | 9.86E-12 | | R | 85 | 0.094 | 18 | 5.16E-04 |
| | D | 85 | 0.031 | 0 | 6.73E-02 | | D | 85 | 0.031 | 0 | 6.73E-02 |
| | E | 85 | 0.031 | 0 | 6.73E-02 | | E | 85 | 0.031 | 2 | 2.50E-01 |
| | P | 85 | 0.063 | 0 | 4.15E-03 | | P | 85 | 0.063 | 2 | 6.58E-02 |
| | V | 85 | 0.063 | 2 | 6.58E-02 | | V | 85 | 0.063 | 6 | 1.59E-01 |
| | C | 85 | 0.031 | 0 | 6.73E-02 | | C | 85 | 0.031 | 2 | 2.50E-01 |
| | L | 85 | 0.094 | 3 | 2.54E-02 | | L | 85 | 0.094 | 5 | 9.03E-02 |
| | I | 85 | 0.031 | 1 | 1.85E-01 | | I | 85 | 0.031 | 2 | 2.50E-01 |
| | M | 85 | 0.031 | 1 | 1.85E-01 | | M | 85 | 0.031 | 2 | 2.50E-01 |
| | F | 85 | 0.031 | 3 | 2.23E-01 | | F | 85 | 0.031 | 0 | 6.73E-02 |
| | Y | 85 | 0.031 | 1 | 1.85E-01 | | Y | 85 | 0.031 | 2 | 2.50E-01 |
| | W | 85 | 0.031 | 4 | 1.48E-01 | | W | 85 | 0.031 | 15 | 5.16E-08 |
| | G | 85 | 0.063 | 13 | 1.57E-03 | | G | 85 | 0.063 | 10 | 2.25E-02 |
| | A | 85 | 0.063 | 5 | 1.79E-01 | | A | 85 | 0.063 | 6 | 1.59E-01 |
| | S | 85 | 0.094 | 3 | 2.54E-02 | | S | 85 | 0.094 | 2 | 8.88E-03 |
| | T | 85 | 0.063 | 2 | 6.58E-02 | | T | 85 | 0.063 | 4 | 1.66E-01 |
| | N | 85 | 0.031 | 0 | 6.73E-02 | | N | 85 | 0.031 | 2 | 2.50E-01 |
| | Q | 85 | 0.063 | 10 | 2.25E-02 | | Q | 85 | 0.063 | 1 | 2.35E-02 |
| 10 | K | 85 | 0.031 | 6 | 3.32E-02 | 12 | K | 85 | 0.031 | 9 | 1.05E-03 |
| | H | 85 | 0.031 | 0 | 6.73E-02 | | H | 85 | 0.031 | 2 | 2.50E-01 |
| | R | 85 | 0.094 | 29 | 2.78E-10 | | R | 85 | 0.094 | 25 | 1.18E-07 |
| | D | 85 | 0.031 | 2 | 2.50E-01 | | D | 85 | 0.031 | 0 | 6.73E-02 |
| | E | 85 | 0.031 | 2 | 2.50E-01 | | E | 85 | 0.031 | 4 | 1.48E-01 |
| | P | 85 | 0.063 | 2 | 6.58E-02 | | P | 85 | 0.063 | 0 | 4.15E-03 |
| | V | 85 | 0.063 | 0 | 4.15E-03 | | V | 85 | 0.063 | 6 | 1.59E-01 |
| | C | 85 | 0.031 | 2 | 2.50E-01 | | C | 85 | 0.031 | 1 | 1.85E-01 |
| | L | 85 | 0.094 | 3 | 2.54E-02 | | L | 85 | 0.094 | 3 | 2.54E-02 |
| | I | 85 | 0.031 | 2 | 2.50E-01 | | I | 85 | 0.031 | 0 | 6.73E-02 |
| | M | 85 | 0.031 | 1 | 1.85E-01 | | M | 85 | 0.031 | 1 | 1.85E-01 |
| | F | 85 | 0.031 | 2 | 2.50E-01 | | F | 85 | 0.031 | 0 | 6.73E-02 |
| | Y | 85 | 0.031 | 0 | 6.73E-02 | | Y | 85 | 0.031 | 0 | 6.73E-02 |
| | W | 85 | 0.031 | 2 | 2.50E-01 | | W | 85 | 0.031 | 3 | 2.23E-01 |
| | G | 85 | 0.063 | 11 | 1.02E-02 | | G | 85 | 0.063 | 11 | 1.02E-02 |
| | A | 85 | 0.063 | 8 | 7.78E-02 | | A | 85 | 0.063 | 6 | 1.59E-01 |
| | S | 85 | 0.094 | 6 | 1.25E-01 | | S | 85 | 0.094 | 5 | 9.03E-02 |
| | T | 85 | 0.063 | 3 | 1.21E-01 | | T | 85 | 0.063 | 4 | 1.66E-01 |
| | N | 85 | 0.031 | 1 | 1.85E-01 | | N | 85 | 0.031 | 0 | 6.73E-02 |
| | Q | 85 | 0.063 | 3 | 1.21E-01 | | Q | 85 | 0.063 | 5 | 1.79E-01 |

PEPTIDE ANTIMICROBIALS

CROSS REFERENCES TO RELATED APPLICATIONS

This application is a national phase application of International Patent Application No. PCT/US2011/028733 filed on Mar. 16, 2011, which claims priority to and the benefit of U.S. Provisional Patent Application No. 61/314,269, filed on Mar. 16, 2010, the entire contents of each of which are incorporated by reference herein.

STATEMENT OF GOVERNMENT INTEREST

The invention encompassed by this disclosure was made in part using funds from NIH grant U01AI061192. The government therefore has certain rights in the invention.

FIELD OF THE DISCLOSURE

The present disclosure provides methods of identifying effective antimicrobials and antimicrobials identified using these methods, as well as associated nucleic acid sequences, plasmids and methods of treatment.

BACKGROUND OF THE DISCLOSURE

The search for new antimicrobials is a critical process as many species of bacteria are becoming resistant to multiple antibiotics.

Currently, the most active approach to finding new antimicrobials is the chemical modification of existing antibiotics, many of which are produced by bacteria or fungi. A significant drawback to this approach is that natural antibiotics and resistance to natural antibiotics coevolved, in part to protect the producing organisms.

Some peptide antimicrobials have been identified using standard antimicrobial screening technologies or by generating peptide libraries and screening for peptides that bind to a specific target. Examples of peptide screening technologies are phage display and ribosome display.

While these techniques can be effective at identifying antimicrobial peptides, there are drawbacks associated with their use. For example, the methods often use in vitro screening methods to identify antimicrobials that bind to known targets. This strategy does not identify antimicrobials that are effective based on interaction with an unknown or unchosen target. Moreover, in vitro screening assumes that a target's structure and its interaction with the peptide will be the same in vitro as in vivo. In many cases, however, there are significant differences between in vitro and in vivo conditions. Accordingly, there is room for improvement in techniques and methods used to identify new antimicrobial compounds.

SUMMARY OF THE DISCLOSURE

The present disclosure provides methods of identifying effective peptide antimicrobials that address many drawbacks associated with previously-practiced methods. For example, in the methods disclosed herein, there is no target bias. Thus, any peptide that inhibits bacterial growth for any reason may be identified without prior knowledge of the target. In addition, screens are performed in vivo, so the inhibitory peptides that are identified are active under physiological conditions, providing greater assurance that peptides isolated using this technology will be effective within their target cells. Moreover, expression of the peptides occurs within the cell. Accordingly, peptides do not need to cross the outer membrane to reach their targets during the initial screen.

Peptides identified using these methods are also encompassed within the scope of the present disclosure. Additionally, peptides that share common structural features that produce antimicrobial activity with the particularly identified peptides disclosed herein are described.

Thus, in one aspect, a method is provided for identifying an effective peptide antimicrobial. The method can include the steps of controllably expressing a random peptide library in a microbial host cell within a culture, wherein random peptides are encoded by plasmids comprising a nucleic acid sequence which is under the control of an inducible promoter; and identifying clones in which microbial cell growth or survival is affected by the peptide expressed by that clone.

Various embodiments of the method can include one or more of the following steps or features.

In some embodiments, the method includes growing a microbial cell culture in the absence of an inducer of the inducible promoter before or after the controllable expression.

In some embodiments, the method includes growing the microbial cell culture in the presence of a transcriptional repressor.

In some embodiments, the method includes adding an inducer of the inducible promoter.

In some embodiments, the method includes transforming microbial cells with the plasmids.

In some embodiments, the method includes contacting host cells with an agent (e.g., ampicillin) that negatively selects against replicating cells.

In some embodiments, the method includes identifying the peptide sequence of a clone in which cell growth or survival is affected.

In some embodiments, the method includes constructing the plasmid.

In some embodiments, the nucleic acid sequence of the plasmid includes a $NNK_n$ sequence, wherein NNK is a nucleotide triplet that encodes a random amino acid, wherein:

N is A, T, C or G;

K is T or G; and n is 2-50;

wherein, optionally, n=12 (SEQ ID NO:462).

In some embodiments, the nucleic acid sequence of the plasmid includes a $DNK(NNK)_n$ sequence, wherein DNK and NNK are nucleotide triplets that encode a random amino acid, wherein:

N is A, T, C or G;

K is T or G; and

D is A, T, or G; and n is 1-49;

wherein, optionally, n=11 (SEQ ID NO:463).

In some embodiments, the plasmid encodes a leader peptide.

In some embodiments, the plasmid encodes a leader peptide that targets the random peptides to the periplasm.

In some embodiments, the plasmid encodes an alkaline phosphatase leader peptide.

In some embodiments, the inducible promoter is an arabinose inducible promoter ($P_{BAD}$).

In some embodiments, the nucleic acid sequence encodes a carrier protein.

In some embodiments, the carrier protein is alkaline phosphatase, and the C terminus of the random peptide is fused to the N terminus of the alkaline phosphatase protein.

In some embodiments, the carrier protein is alkaline phosphatase, and the N terminus of the random peptide is fused to the C terminus of the alkaline phosphatase protein In some embodiments, the carrier protein is emerald green fluorescent protein, and the C terminus of the random peptide is fused to the N terminus of the emerald green fluorescent protein.

In some embodiments, the carrier protein is emerald green fluorescent protein, and the N terminus of the random peptide is fused to the C terminus of the emerald green protein.

In some embodiments, the host cell is a bacterium (e.g., *E. coli*).

In another aspect, antimicrobial peptides are provided. The antimicrobial peptides can have the consensus sequence Xaa1 Xaa2 Xaa3 Xaa4 Xaa5 Xaa6 Xaa7 Xaa8 Xaa9 Xaa10 Xaa11 Xaa12 (SEQ ID NO:465); wherein Xaa1 is a hydrophobic amino acid (in one embodiment, tryptophan);

Xaa2, is a basic or small amino acid (in one embodiment, selected from glycine or alanine) or a basic amino acid (in one embodiment, arginine);

Xaa3 is a hydrophobic amino acid (in one embodiment, tryptophan) or a basic amino acid (in one embodiment, arginine);

Xaa4 is a hydrophobic amino acid (in one embodiment, leucine);

Xaa5 is a basic amino acid (in one embodiment, arginine or lysine);

Xaa6 is a basic amino acid (in one embodiment, arginine) or a small amino acid (in one embodiment, alanine or glycine);

Xaa7 is a hydrophobic amino acid (in one embodiment, selected from leucine or tryptophan) or a basic amino acid;

Xaa8 is a hydrophobic amino acid (in one embodiment, tryptophan or leucine) or a small amino acid (in one embodiment, alanine or glycine);

Xaa9 is a basic amino acid (in one embodiment, arginine) or a small amino acid (in one embodiment, glycine);

Xaa10 is a basic amino acid (in one embodiment, arginine) or a small amino acid (in one embodiment, glycine or alanine);

Xaa11 is tryptophan or arginine;

Xaa12 is a basic amino acid (in one embodiment, arginine) or a small amino acid (in one embodiment, glycine).

In another aspect, antimicrobial peptides are provided which include the amino acid sequence of any one of SEQ ID NOS:7-461, or a sequence 85% homologous thereto (e.g., at least 85% homologous, at least 90% homologous, at least 95% homologous).

In some embodiments, the antimicrobial peptide has an amino acid sequence which is at least 85% homologous to the amino acid sequence: FAWLWSWWRARR (SEQ ID NO:310).

In some embodiments, the antimicrobial peptide has an amino acid sequence which is at least 85% homologous to the amino acid sequence: FMRLLRWWRRMQ (SEQ ID NO:438).

In some embodiments, the antimicrobial peptide has an amino acid sequence which is at least 85% homologous to the amino acid sequence: IRWLARRWRRTF (SEQ ID NO:347).

In another aspect, artificial nucleic acid sequences are provided that encode a peptide having the amino acid sequence of any one of SEQ ID NOS:7-461.

In another aspect, expression vectors (e.g., plasmids) are provided that encode a nucleic acid sequence of a peptide having the amino acid sequence of any one of SEQ ID NOS:7-461.

In another aspect, a vector is provided having a DNA sequence encoding an inducible promoter and a $(NNK)_n$ sequence of DNA, where NNK is a nucleotide triplet that encodes a random amino acid, and where N is A, T, C or G, K is T or G, and n is 2-50.

In another aspect, a vector is provided having a DNA sequence encoding an inducible promoter and a DNK $(NNK)_n$ sequence of DNA, where NNK is a nucleotide triplet that encodes a random amino acid, wherein N is A, T, C or G, K is T or G, D is A, T, or G; and n is 1-49.

BRIEF DESCRIPTION OF THE DRAWINGS

The figures are not necessarily to scale, emphasis instead generally being placed upon illustrative principles. The figures are to be considered illustrative in all aspects and are not intended to limit the invention, the scope of which is defined only by the claims.

FIG. 2 is a table showing the clone, phenotype, peptide, and growth curve.

FIGS. 3A-E show the peptide sequences of clones according to phenotype: A. static/cidal; B. weakly inhibitory<0.7; C. weakly inhibitory>0.7; D. non-inhibitory; and E. lytic.

FIG. 7 shows the sequence of a pKan phoA plasmid.

FIG. 13 shows plasmid constructs for expressing N-terminal fusion proteins in the cytoplasm.

FIG. 15 shows the location of various elements of a plasmid for expressing N-terminal fusion proteins in the cytoplasm.

FIG. 16 shows the sequence of a pBac-EmGHt construct.

FIG. 18 shows the location of various elements of a plasmid for expressing C-terminal fusion proteins.

FIG. 19 shows the sequence of a pBac-EmGH construct.

FIG. 24 shows the location of various elements of a plasmid for expressing N-terminal fusion proteins in the periplasm.

FIG. 25 shows the sequence of a pKan-PhoA construct.

FIG. 27 shows peptide antimicrobials isolated using a cytoplasmic N-terminal bacteriostatic and bactericidal screen.

FIG. 28 shows growth rate reducing peptide antimicrobials isolated using a C-terminal constructs in a bacteriostatic and bactericidal screen.

FIG. 29 shows bacteriostatic and bactericidal peptide antimicrobials identified using C-terminal constructs in a bacteriostatic and bactericidal screen.

FIG. 30 shows bacteriolytic peptide antimicrobials isolated from a periplasmic bacteriolytic screen.

FIG. 31 shows bacteriostatic and bactericidal peptide antimicrobials isolated from a periplasmic bacteriolytic screen.

FIG. 32 shows growth rate reducing peptide antimicrobials isolated from a periplasmic bacteriolytic screen.

FIG. 33 shows bacteriostatic and bactericidal peptide antimicrobials isolated from a periplasmic bacteriostatic and bactericidal screen.

FIG. 34 shows bacteriolytic and growth rate reducing peptide antimicrobials isolated from a periplasmic bacteriostatic and bactericidal screen.

FIG. 35 shows consensus peptides based on bacteriolytic peptide residue distribution.

FIG. 36 shows bacteriostatic and bactericidal peptides isolated from an early onset degenerate peptide screen.

FIG. 37 shows bacteriolytic peptides isolated from an early onset degenerate peptide screen.

FIG. 38 shows non-inhibitory peptides isolated from an early onset degenerate peptide screen.

FIG. 39 shows select peptides with and without proline mutation.

FIG. 40 shows minimum inhibitory concentration of EO1 for various bacterial species.

FIG. 41 shows Alanine scan peptides based on EO1.

FIG. 42 shows EO1 site-directed mutations.

FIGS. 59A-H show statistical analyses of the amino acids located at each position of bacteriolytic peptide antimicrobials from the periplasmic screen.

DEFINITIONS

Peptide refers to a polymer comprising less than 50 amino acids and, in particular embodiments, less than 20 amino acids.

Antimicrobial refers to the biological activity of the peptides disclosed herein, including the ability to inhibit microbial growth by lysing (e.g., bacteriolytic), killing without lysing (e.g., bactericidal), and inhibiting (e.g., bacteriostatic) or reducing (e.g., weakly inhibitory or growth rate reducing) the ability of microbes to reproduce.

A bacteriolytic peptide refers to a peptide that causes the host cell to lyse or break open, releasing its inter-cellular components into the growth medium.

A bacteriostatic peptide refers to a peptide that causes the host cell to enter a state of dormancy.

A bactericidal peptide refers to a peptide that causes the irreversible death of the host cell without lysing it.

Growth rate reducing, or weakly inhibitory, peptides refer to a peptide that slows but does completely inhibit reproduction of the host cell.

DETAILED DESCRIPTION

This disclosure relates, in part, to the development of high-throughput methods for creating, screening, and isolating effective peptide antimicrobials using an in vivo display (IVD) system. Using these methods, peptide antimicrobial libraries can be transformed into, propagated, expressed, and screened in vivo under physiologic conditions in a host cell culture. Moreover, the methods disclosed herein also permit identification of toxic peptide antimicrobials that would go undetected using other screening methods due to their toxicity.

The IVD systems disclosed herein are advantageous for a number of reasons. For example, there is no target bias.

Thus, any peptide that inhibits bacterial growth for any reason may be identified without prior knowledge of the target. In addition, screens are performed in vivo, so the inhibitory peptides identified using IVD are active under physiological conditions, providing greater assurance that peptides isolated using this technology will be effective under therapeutic conditions. Moreover, expression of the peptides occurs within the cell. Accordingly, peptides do not need to cross the outer membrane to reach their targets during initial rounds of screening.

Figure 10:
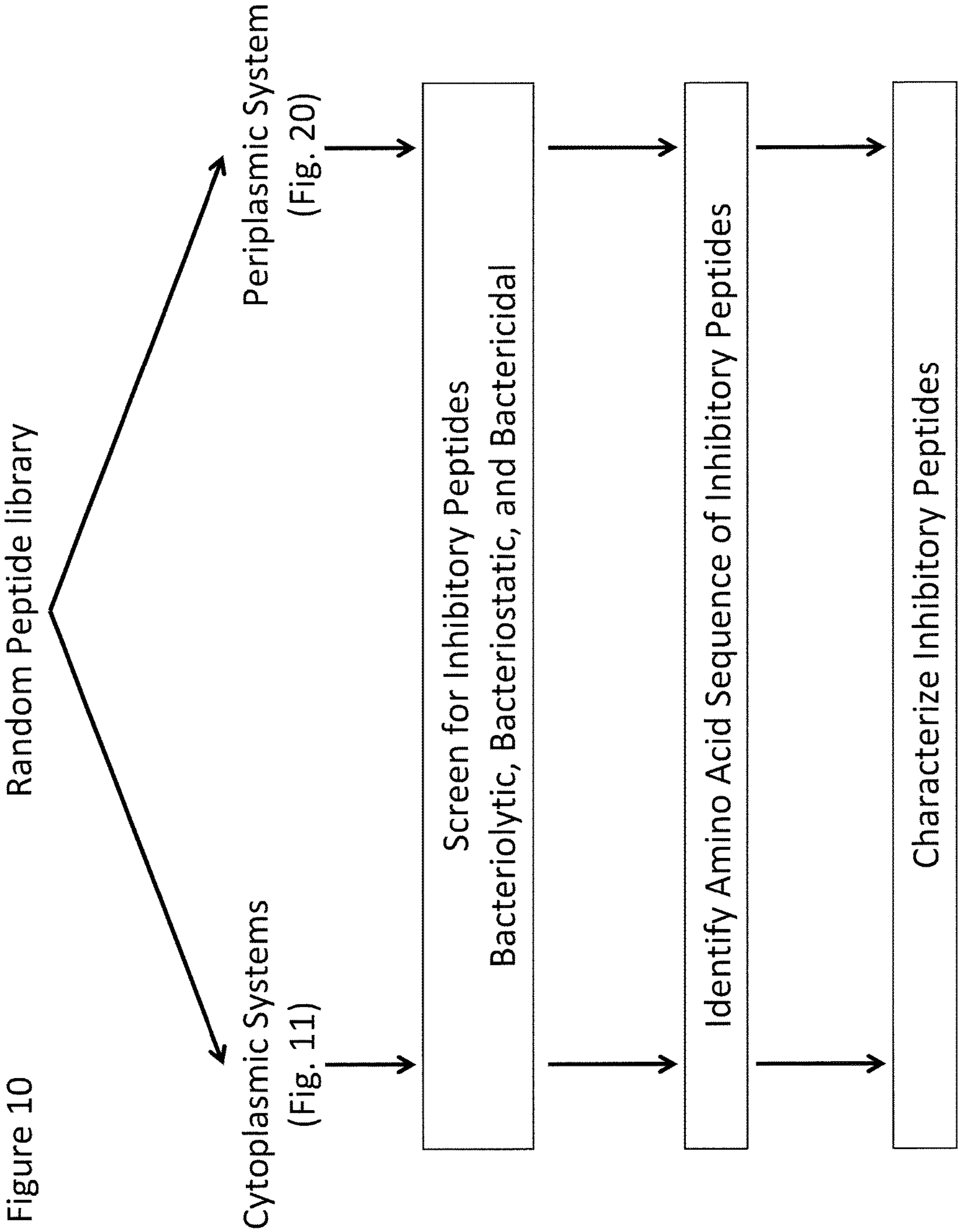
FIG. 10 is an overview of an in vivo display (IVD) system for screening and identifying peptide antimicrobials.

As shown in FIG. 10, peptide antimicrobials can be expressed in host cells. Host cell cultures are then screened to identify proteins that have a deleterious effect on the cells in which they are expressed. The screens are designed to identify peptides that cause the cells to lyse (e.g., bacteriolytic), kill the cell without lysing it (e.g., bactericidal/bacteriostatic) or reduce the ability of the cells to grow and reproduce (growth rate reducing). Plasmids encoding each of these types of peptides can then be isolated and cloned and the amino acid sequence of each of the inhibitory peptides can be determined by sequencing the peptide encoding portion of each plasmid.

Antimicrobial peptides can be characterized using a variety of in vivo and in vitro assays and this information can be used to rationally design additional peptide antimicrobials. Further optimization can involve changing the amino acid sequence and using peptidomimetic and medicinal chemistry to increase the antimicrobial activity, permeability, bioavailability, etc. of the peptide leads isolated with IVD. In addition, peptide antimicrobials can be externally introduced as free peptides to a microbial cell to test efficacy when the peptides originate from outside the microbial cell, such as would be the case during treatment of an infection.

Bacterial cells are relatively simple compared to eukaryotes and are generally divided into two distinct groups, the Gram positives and the Gram negatives. Gram positive bacteria have a thick cell wall composed of peptidoglycan and a plasma membrane that encloses the cytoplasm. Gram negative bacteria have a thinner layer of peptidoglycan and a plasma membrane that does not fully enclose the cytoplasm. In Gram negative bacteria, however, there is an additional outer membrane and the space between the plasma membrane and the outer membrane is called the periplasm or periplasmic space. This difference in the envelopes of Gram positive and Gram negative bacteria affects the flow of materials into and out of the cell, including antibiotics. Generally, it is more difficult for foreign compounds to enter the cytoplasm of Gram negative bacteria because of the two membranes and the periplasm. The periplasm, however, houses several essential enzymes and is the site of a number of critical microbial processes including those involved in generation of the proton motive force for energy transduction in Gram negatives and is therefore a suitable drug target for developing antimicrobials for the treatment of Gram negative infections.

IVD was developed to identify peptides that inhibit critical processes in the cytoplasm and/or the periplasm and can therefore be used directly as antimicrobials or to design antimicrobials for the treatment of diseases with, for example, Gram-positive and/or Gram-negative etiologies.

Using these methods, numerous peptide antimicrobials were isolated, sequenced, and characterized, as discussed in more detail herein. These peptide antimicrobials demonstrated various antimicrobial activities, including bacteriolytic, bacteriostatic, bactericidal, and growth rate reducing activities. In addition, analysis of peptides identified as having antimicrobial activities revealed features (e.g., a consensus sequence; alpha helices) common among bacteriolytic peptides. Using this information, additional peptide antimicrobials were identified using rational design and using degenerate peptides.

In various embodiments, plasmid vectors can be designed for expressing peptide antimicrobials in host cells. These plasmids can encode one or more of the following features, in no particular order: an inducible promoter, a leader peptide, a putative or potential peptide antimicrobial, a carrier and/or reporter protein, a linker amino acid or linker sequence, a protease recognition sequence, and an isolation tag.

In some embodiments, the plasmid encodes a peptide antimicrobial. The peptide antimicrobial can be encoded by a random sequence, a degenerate sequence, or a rationally designed sequence. During initial screening stages, vast numbers of random and/or degenerate peptide antimicrobials can be expressed as a peptide library.

According to various embodiments, a peptide antimicrobial library can be encoded by a random nucleic acid sequence. Accordingly, in some embodiments, the peptide library can be composed of about 12 amino acids encoded by a randomized sequence of DNA. However, it will be appreciated that any other peptide lengths can be used in accordance with this disclosure, such as, for example, peptide antimicrobials having 2 to 50 amino acids, and any length therebetween. For example, the peptide antimicrobial can be 2, 3, 4, 5, 6, 7, 8, 9, 10, 11, 12, 13, 14, 15, 16, 17, 18, 19, 20, 21, 22, 23, 24, 25, 30, 35, 40, 45, or 50 amino acids long. In embodiments were a 12-mer is used, the random amino acid sequence can be generated using the polymerase chain reaction in which one primer can contain the sequence (NNK)12. As will be appreciated, the NNK sequence (or DNK(NNK) sequence, as discussed below) can be lengthened or shortened depending on the desired number of amino acids. Use of the NNK sequence allows incorporation of all amino acids but eliminates stop codons, except for UAG. To avoid having a peptide sequence terminated by a UAG stop codon, the random peptide libraries can be expressed in host cells that can read-through UAG stop codons, such as *E. coli* strains that are supE44.

In some embodiments, a DNK(NNK)11 sequence can be used in plasmid constructs that include a proteolytic cleavage site adjacent the N terminus of the peptide antimicrobial. The DNK codon, where D is A, T, or G, prevents placement of a proline in the first amino acid position of the peptide antimicrobial, as proline can interfere with proper proteolytic cleavage. Examples of proteolytic cleavage sites include, for example, expression products having a leader peptide cleavage site or a TEV protease cleavage site.

Degenerate nucleic acid sequences also can be used to generate random peptides having conserved features. In some embodiments, the degenerate sequence is WTBNNKYKGCTGNNKAGNYGGTGGCGTSGTN NKNNK-3' (SEQ ID NO:464), using standard IUPAC nomenclature for DNA nucleotides.

In some embodiments, peptide antimicrobials can be expressed under the transcriptional regulation of an inducible promoter, thereby allowing peptide expression to be turned on and off. Using an inducible promoter allows transformed host cell cultures to propagate in the absence of peptide antimicrobials. Then, at a desired time, peptide expression can be induced to initiate the screening process. An inducible promoter reduces the likelihood that highly toxic peptide antimicrobials will prematurely kill their host cell, which would result in elimination of valuable peptides from a screen. Non-limiting examples of inducible promoters include, but are not limited to, those induced by the presence of a small molecule (e.g., arabinose ($P_{BAD}$), IPTG, galactose, tetracycline, abscisic acid), by metals or metal ions (e.g., copper, zinc, cadmium, nickel), and by environmental factors (e.g., heat, cold, stress). The arabinose inducible promoter is particularly advantageous because the promoter has multiple levels of control. For example, in the absence of arabinose, downstream sequences typically show minimal expression. Adding a catabolite, such as glucose, can further silence expression and permit propagation of plasmids encoding highly toxic peptide antimicrobials (e.g., EO1).

In various embodiments, premature peptide expression also can be minimized by using a low copy number plasmid. Suitable low copy number plasmids include, for example, pCC1BAC™ (Epicentre; Madison, Wis.). In addition, a low copy number plasmid can be transformed into a host cell strain (e.g., EPI300™ and EPI301™; Epicentre; Madison, Wis.) that, upon induction, increases plasmid copy numbers, which results in greater peptide expression. Beneficially, and in some embodiments, the gene that regulates plasmid copy number can be under the control of the same inducible promoter that controls peptide antimicrobial expression. Thus, a low copy number plasmid can be used in combination with an inducible promoter to tightly regulate expression of peptide antimicrobials using a single inducer, both to inhibit premature expression and to boost expression upon induction.

In some embodiments, plasmid vectors can encode, and expression products include, a suitable leader peptide or signal sequence for targeting peptide antimicrobials. For example, a leader peptide can be used to target peptide antimicrobials to the periplasm. In some embodiments, an alkaline phosphatase leader peptide can be inserted 5' to a peptide antimicrobial, which would result in the peptide being transported into the periplasmic space. The PhoA leader peptide would be cleaved following translocation to the periplasm, leaving the peptide antimicrobial exposed at the N-terminus.

In some embodiments, peptide antimicrobials can be expressed as fusion proteins—with or without a linker peptide—with a carrier and/or reporter protein (or peptide). Carrier and/or reporter proteins can serve several purposes, including improved stability by protecting against premature peptide degradation by intracellular machinery. In addition, carrier and/or reporter proteins can act as indicators of peptide expression and/or localization. For periplasmic IVD, the carrier and/or reporter can be a protein that is active in the periplasmic space (e.g., PhoA). For cytoplasmic IVD, the carrier and/or reporter can be a protein that resides and/or is active in the cytoplasm (e.g., emerald green fluorescent protein (EmGFP)). Moreover, expression of the peptide fusions may be monitored following induction where reporter proteins are used. For example, EmGFP is fluorescent and may be monitored in growing cultures by measuring fluorescence, and 5-Bromo-4-chloro-3-indoxylphosphate (X-Phos) is a colorimetric substrate for PhoA that may be added to growth media to follow alkaline phosphatase activity in host cells.

As stated, in some embodiments, peptide antimicrobials can be fused to a carrier and/or reporter protein using a linker. The linker can be, for example, a peptide linker of any suitable length, such as, for example, between 1 and 20 amino acids, and any length therebetween.

In some embodiments, peptide antimicrobials can be fused—directly, or indirectly via a linker—to the N terminus or the C terminus of a carrier and/or reporter.

In various embodiments, plasmid vectors can encode, and expression products can include, elements or tags to facilitate isolation of the expressed peptides and/or peptide-target complexes. Non-limiting examples of tags include polyhistidine (His)6, chitin binding protein (CBP), maltose binding protein (MBP), glutathione-S-transferase (GST), FLAG, myc, and hemagglutinin (HA).

In some embodiments, peptide antimicrobials can be expressed in host cells as free peptides. In some embodiments, free peptide antimicrobials destined for the cytoplasm can be expressed without a leader peptide and without a carrier and/or reporter. In some embodiments, peptide antimicrobials can be expressed as a fusion with a carrier and/or reporter, which fusion incorporates a proteolytic site (e.g., a TEV protease recognition sequence) between the peptide antimicrobial and the carrier and/or reporter. In the presence of a suitable protease (e.g., TEV protease), the peptide antimicrobial is cleaved from the carrier and/or reporter protein, resulting in a free peptide antimicrobial. In yet other embodiments, a peptide antimicrobial can be expressed with a leader peptide that directs the peptide antimicrobial to the periplasm. Upon transportation to the periplasm, the leader peptide is removed, for example, when it crosses the membrane into the periplasm, resulting in a free peptide antimicrobial in the periplasm.

As stated previously, the IVD systems disclosed herein are advantageous for a number of reasons including that there is no target bias and that screens are performed in vivo. Because expression of the peptides occurs within the cell, peptides do not need to cross the outer membrane to reach their targets during the initial screen.

In some embodiments, peptides can be expressed using a plasmid, pKan phoA, that expresses Alkaline phosphatase (PhoA) under the control of an inducible promoter. PhoA is a natural *E. coli* protein that, due to its leader peptide, is translocated into the periplasm. PhoA is active after it has been transported across the membrane into the periplasm, and therefore can be used as a reporter of successful transport to the periplasm. The fact that PhoA can only fold correctly and function only if it is translocated to the periplasm makes it both a suitable vehicle and reporter for the periplasmic screens disclosed herein. A stretch of DNA encoding a random peptide can be inserted 3' to the DNA sequence encoding the leader peptide and 5' or 3' to the PhoA gene. For example, in various embodiments, the random peptide sequence is (NNK)12, where N represents any nucleotide and K represents either guanine or thymine. NNK is a nucleotide triplet that encodes a random amino acid while reducing the probability of coding for a stop codon.

In addition to the periplasmic IVD system described above, a cytoplasmic expression system is also provided in which the peptide fusion construct is expressed and resides in the cytoplasm. In some embodiments, peptides can be expressed using a plasmid, pBAC-EmGH or pBAC-EmGHt, that expresses the Emerald Green Fluorescent protein (EmGFP) under the control of an inducible promoter. GFP is not a natural *E. coli* protein. It is fluorescent, highly stable, and localized to the cytoplasm in *E. coli* and therefore can be used as a reporter of successful cytoplasmic expression. A stretch of DNA encoding a random peptide can be inserted 3' or 5' to the EmGFP gene. For example, in various embodiments, the random peptide sequence is (NNK)12, where N represents any nucleotide and K represents either guanine or thymine. NNK is a nucleotide triplet that encodes a random amino acid while reducing the probability of coding for a stop codon.

There are at least three avenues for finding new antimicrobial leads: the peptide itself, a peptidomimetic, or a small molecule retaining the active chemical groups of the peptide.

In certain embodiments, a library of 12-mer random peptide sequences is displayed between the leader sequence and the N-terminus of alkaline phosphatase (PhoA) containing a histidine tag at the C-terminus. The display protein serves as a reporter for expression and translocation to the periplasm and facilitates purification of peptide-target complexes. The PhoA leader peptide is cleaved following translocation to the periplasm leaving the random peptide library exposed at the N-terminus. In one set of experiments, a library of 30 million clones was constructed and transformed into the phoA strain, DH5α. A high-throughput screen for inhibitory peptides yielded 28 peptides of varying phenotypes. Both bacteriostatic and bacteriolytic peptides were identified using these described embodiments.

Identification of peptide leads is the first step in the process of developing new antimicrobials. The screening methods disclosed herein are designed to provide many new hits. Approximation of a phage display screen against the entire genome, RNome, and proteome of *E. coli* within an in vivo environment, is underway. This screen will not only elucidate novel leads for antibiotics, but also targets that can be used in other subsequent in vitro screens. mRNA or phage display will then permit the screening of much more complex peptide libraries. The results will also give insight into the microbiology of *E. coli.*

In some embodiments, peptide antimicrobials are administered to microbial cells, as opposed to being expressed in vivo, to confirm their antimicrobial effects when not produced within the cell. A minimum inhibitory concentration (MIC) for a peptide antimicrobial can be determined and, if desired, compared against other known antimicrobial agents and antibiotics.

Peptide antimicrobials disclosed herein can be synthesized using methods well known in the art. For example, peptides can be synthesized chemically, such as by Fmoc or t-Boc synthesis. Peptides also can be synthesized biologically by generating a nucleic acid that encodes the peptide of interest. A nucleic acid encoding a particular peptide can be constructed based on the amino acid sequence of the peptide. This nucleic acid can be incorporated (e.g., ligated) into a plasmid or other vector for transforming and expressing in a host cell. The host cell can be prokaryotic (e.g., *E. coli*) or eukaryotic (e.g., chinese hamster ovary). Alternatively, a cell-free system can be used.

In various embodiments, the peptide antimicrobials disclosed herein (e.g., SEQ ID NOS:7-461) and their encoding nucleic acids are artificially made and therefore they are not naturally occurring.

Peptide antimicrobials can be isolated from other biologic compounds. In addition, peptide antimicrobials can be substantially free of impurities. Substantially free of impurities means at least 80% free, at least 85% free, at least 90% free, at least 95% free, at least 99% or 100% free of impurities.

These peptide antimicrobials are useful to treat microbial infections alone or in combination with other antimicrobial agents, such as, for example, other peptide antimicrobials and/or antibiotics.

In accordance with various embodiments, a protocol for high-throughput bacteriolytic peptide screening can include one or more of the following steps:

1. Transforming random peptide library in plasmids into the appropriate host strain.
2. Washing the host cells in growth medium that represses expression of the peptide library.
3. Resuspending cells in growth medium that represses expression of the peptide library.
4. Growing culture to early log phase.
5. Washing cells in growth medium.
6. Resuspending in growth medium containing inducer(s) of peptide library transcription (and protease if appropriate).
7. Incubating to allow expression of the peptide library.
8. Pelleting cells.
9. Precipitating DNA from supernatent and recover by centrifugation.

In accordance with various embodiments, a protocol for high-throughput bacteriostatic and bactericidal peptide screening can include one or more of the following steps:

1. Transforming random peptide library in plasmids into the appropriate host strain.
2. Washing the cells in growth medium that represses expression of the peptide library.
3. Resuspending cells in growth medium that represses expression of the peptide library.
4. Growing culture to early log phase.
5. Washing cells in growth medium.
6. Resuspending in growth medium containing inducer(s) of peptide library transcription (and protease if appropriate).
7. Incubating to allow expression of the peptide library.
8. Adding ampicillin or other negative selection agent to the culture and incubate until lysis.
9. Pelleting cells and discard supernatant.
10. Washing cell pellet.
11. Isolating plasmid DNA from pelleted cells.

Confirmation of Efficacy Protocol. This protocol applies equally to all plasmid DNA preparations from the three above screens (bacteriolytic, bacteriostatic, and bactericidal). In various embodiments, the protocol can include one or more of the following steps:

1. Transforming cells with plasmids isolated from the bacteriolytic, or bactericidal and bacteriostatic screens.
2. Plating on growth medium that represses expression of the peptides.
3. Growing until colonies form.
4. Replicating onto growth medium containing inducer(s) and medium without inducer(s).
5. Incubating until colonies form on the plate without inducer.
6. Selecting colonies that grow in the absence of inducer only.

In various embodiments, one or more peptide antimicrobials disclosed herein may be used to treat and/or prevent a microbial (e.g., bacterial) infection in a subject (e.g., a human or other animal, including, without limitation, research and veterinary animals). A peptide antimicrobial may be administered alone, in combination with one or more additional peptide antimicrobials, in combination with an antibiotic or other medication, and/or in combination with any suitable pharmaceutically acceptable carrier, excipient, binder, filler, buffer, solvent, moisturizer, surfactant, or preservative. Techniques for formulating drugs are well known in the art. See, e.g., Remington's Pharmaceutical Sciences, Mack Publishing Co., Easton, Pa.

The peptide antimicrobials disclosed herein may be useful for treating diseases caused by Gram positive and Gram negative bacteria, including but not limited to *E. coli, P. aeruginosa, E. faecalis, S. aureus, B. subtilis, S. typhi, P.*

*aeruginosa, S. pyogenes, S. aureus, M. tuberculosis, K. pneumoniae*, and *S. marcescens*.

Peptide antimicrobials may be administered in any therapeutically effective dosage. Dosages will vary depending on the dosage form, route of administration, and peptide.

The following Examples are included to demonstrate particular embodiments of the disclosure. Those of skill in the art should, in light of the present disclosure, appreciate that many changes can be made in the specific embodiments that are disclosed and still obtain a like or similar result without departing from the spirit and scope of the invention.

Example 1

General Materials and Methods

Figure 1:
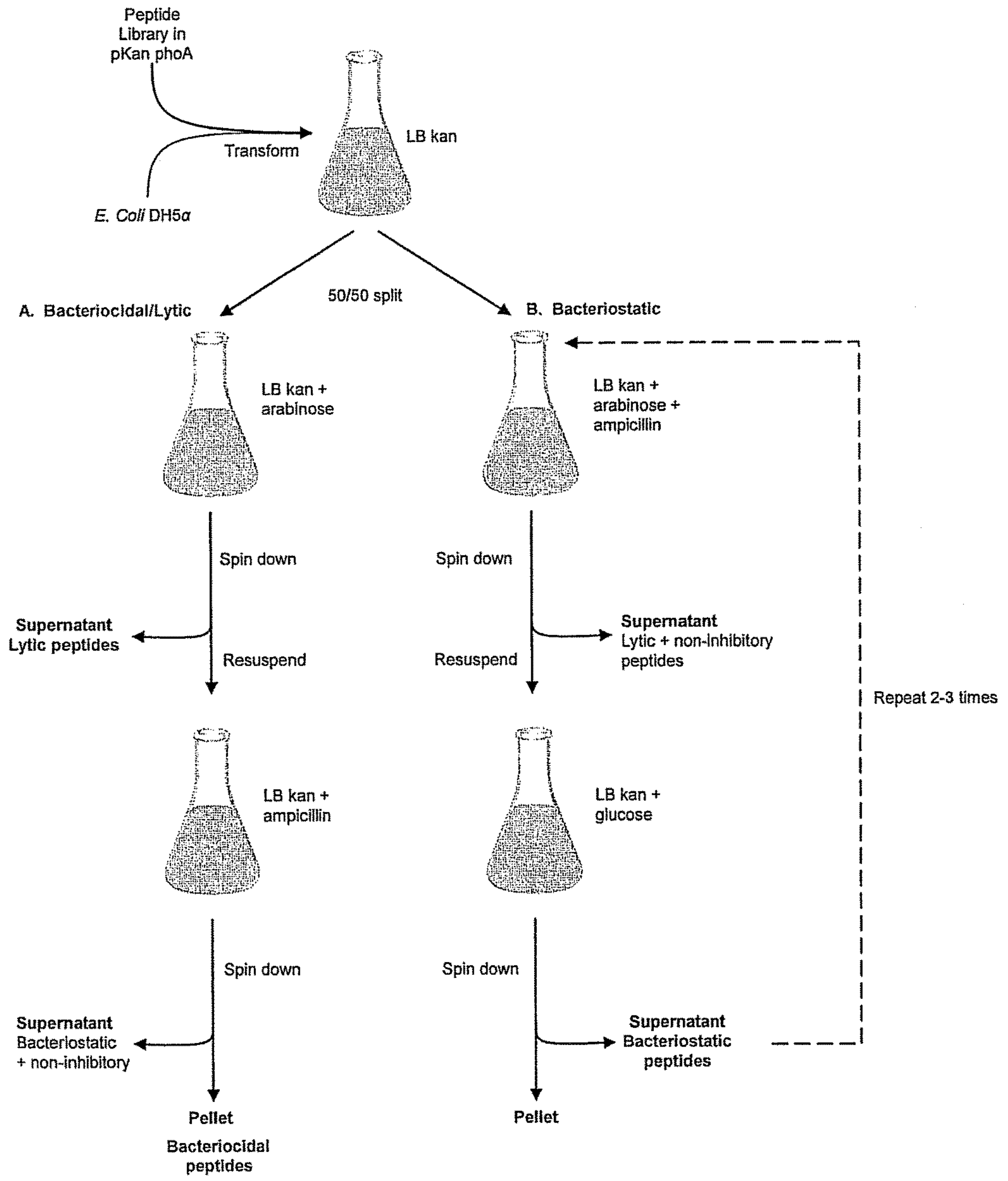
FIGS. 1A and B show an in vivo display overview.
Figure 4A:
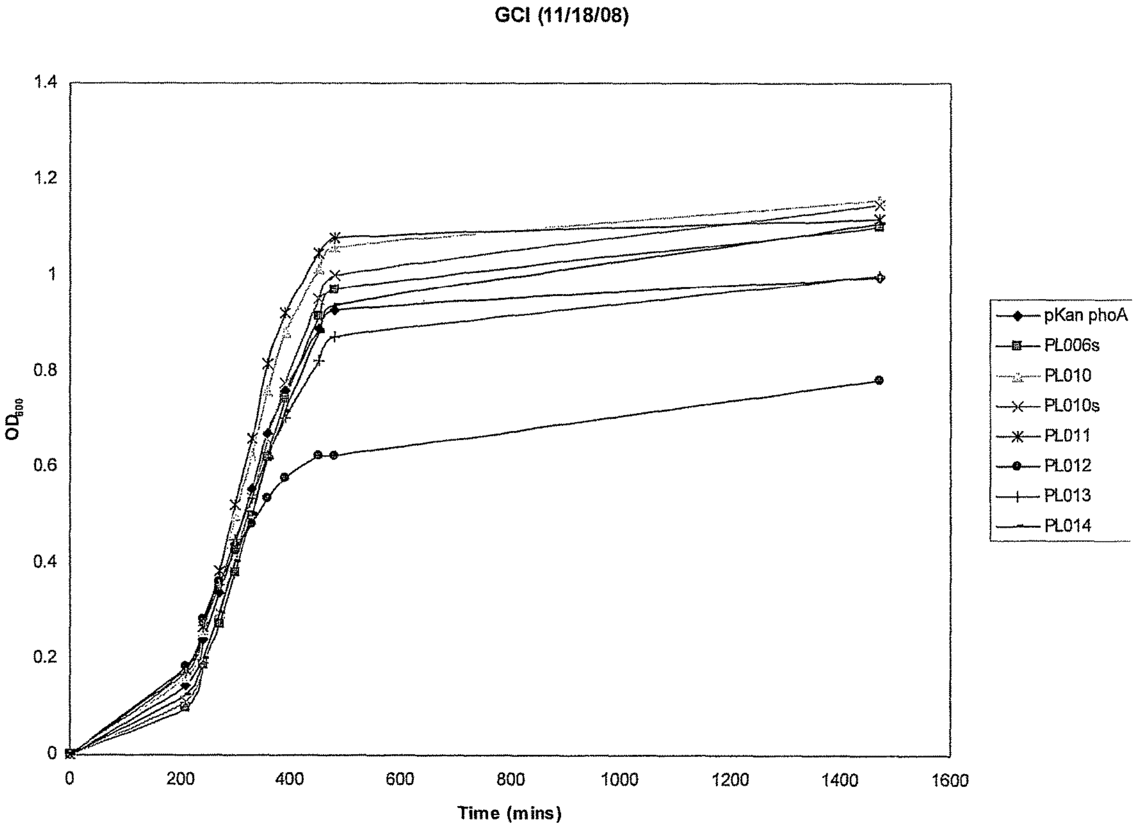
FIGS. 4A-M are graphs showing the growth curves of clones of FIG. 2.
Figure 4B:
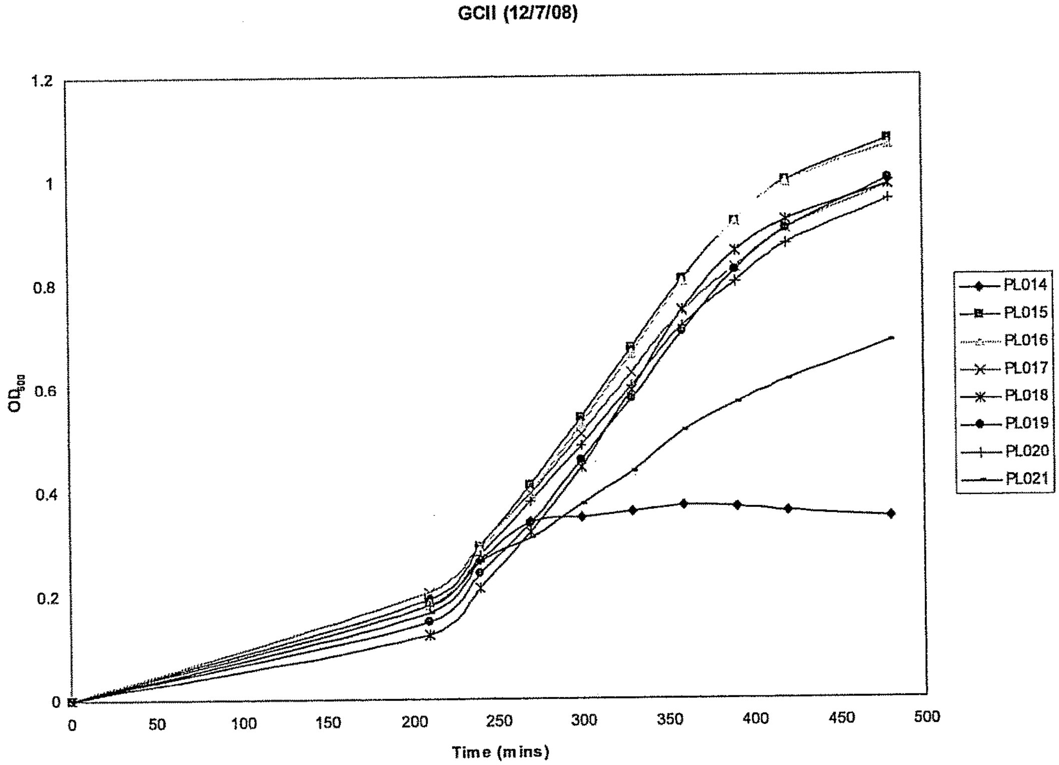
Figure 4C:
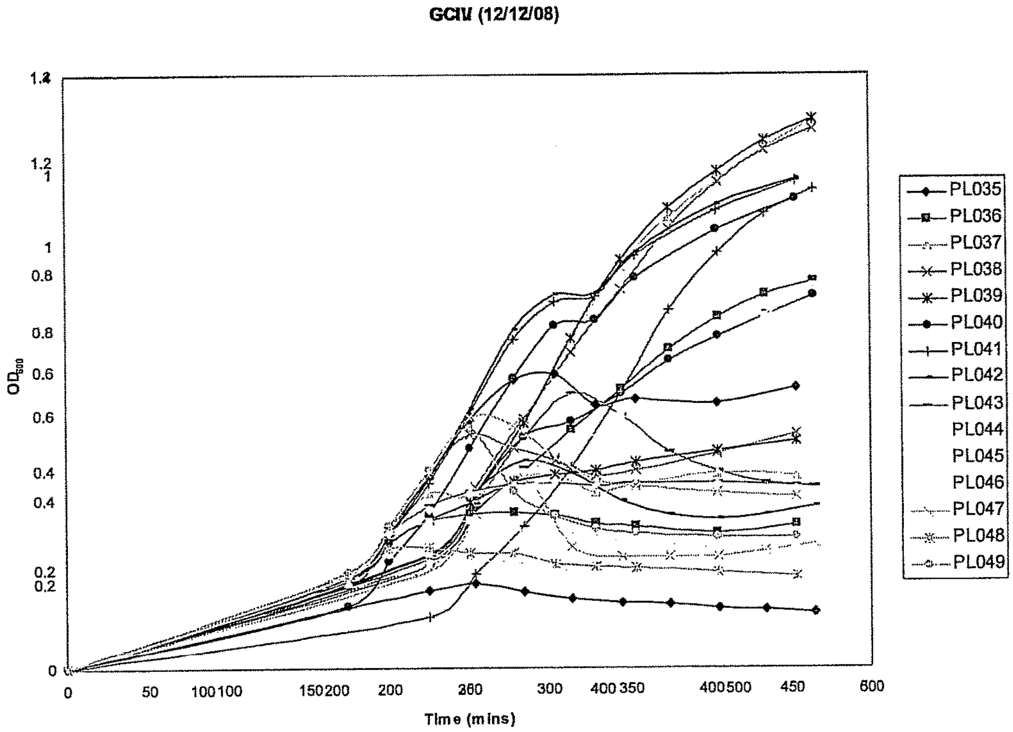
Figure 4D:
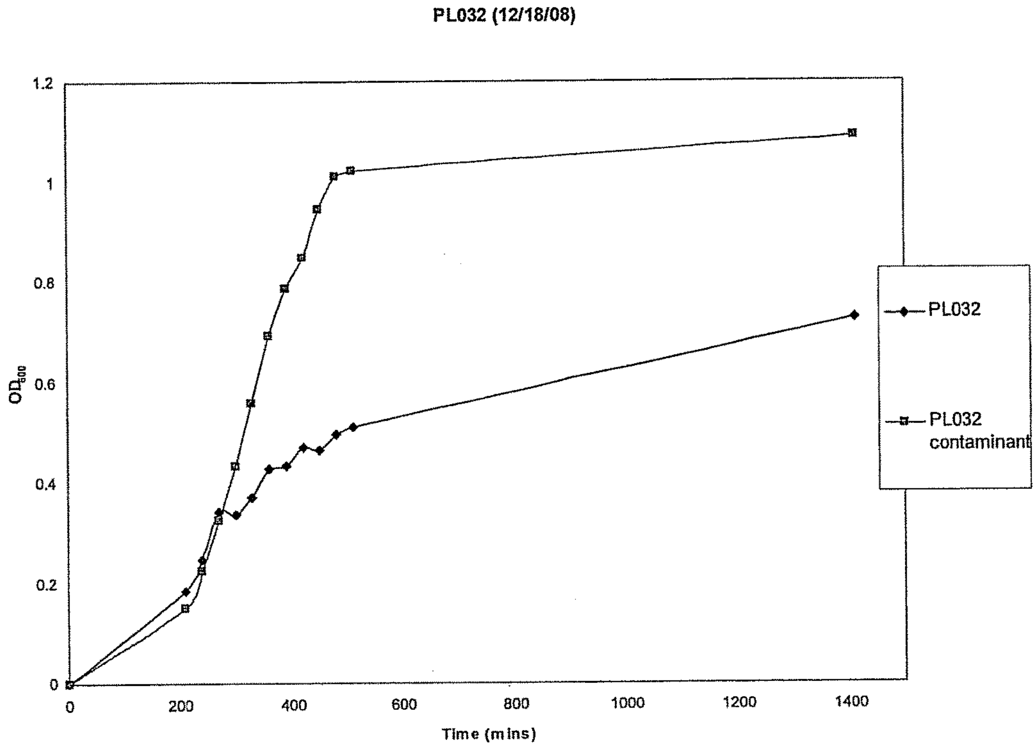
Figure 4E:
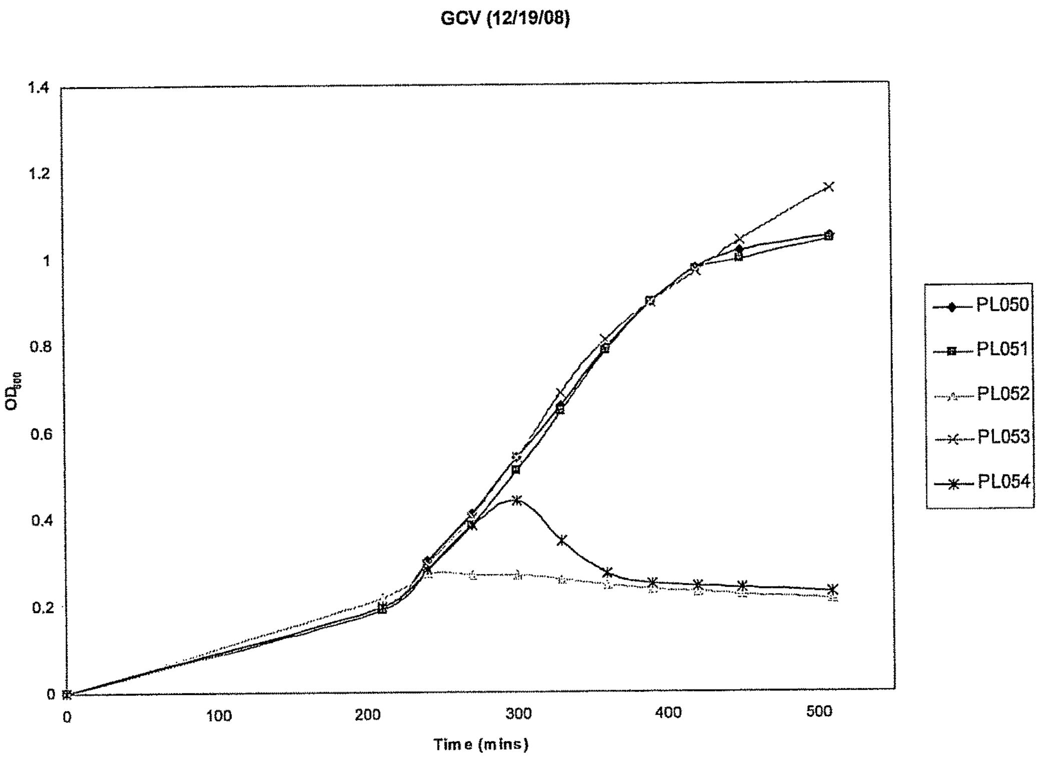
Figure 4F:
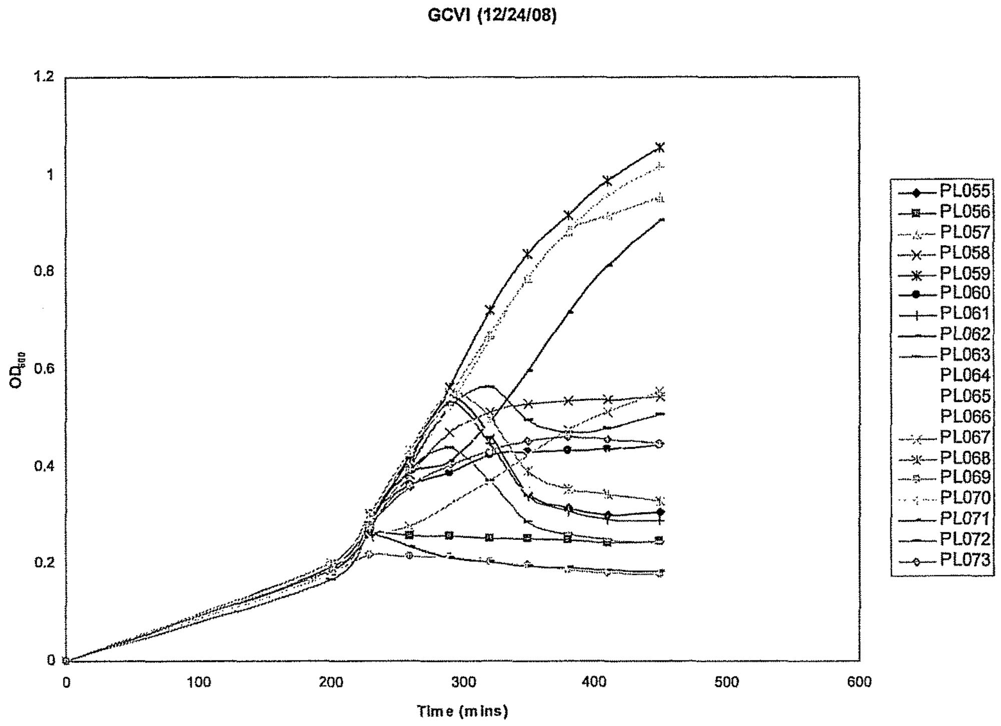
Figure 4G:
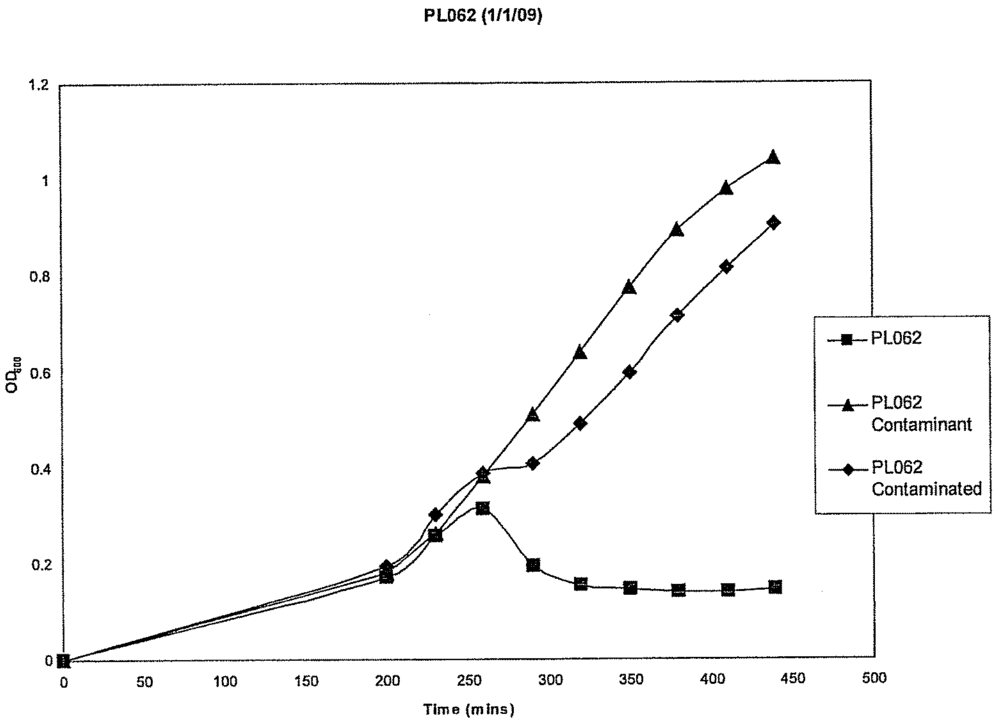
Figure 4H:
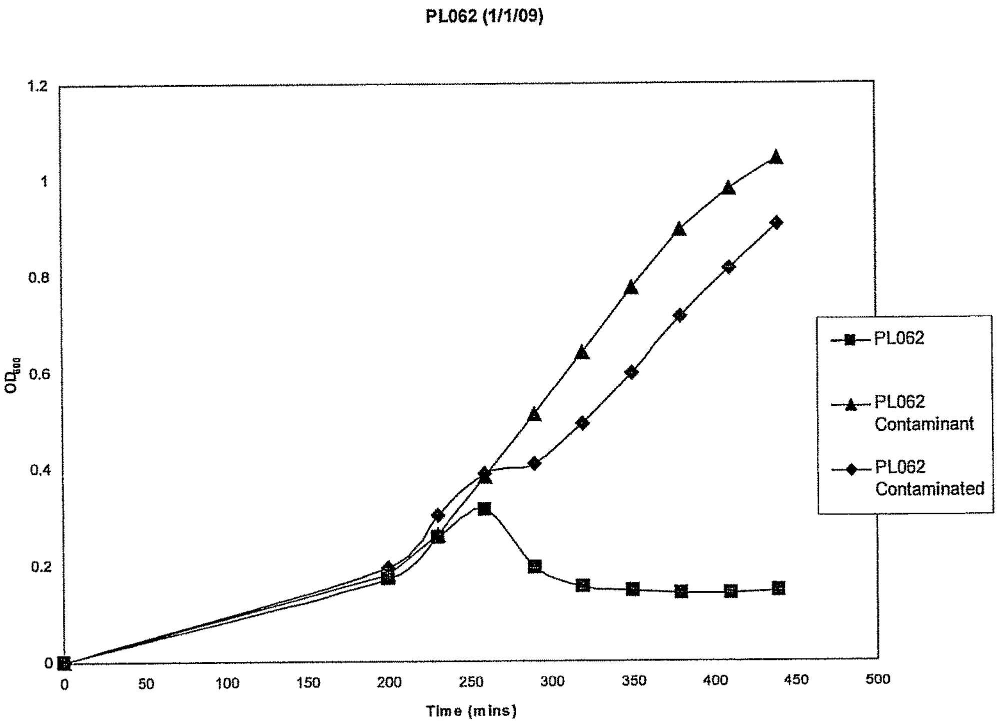
Figure 4I:
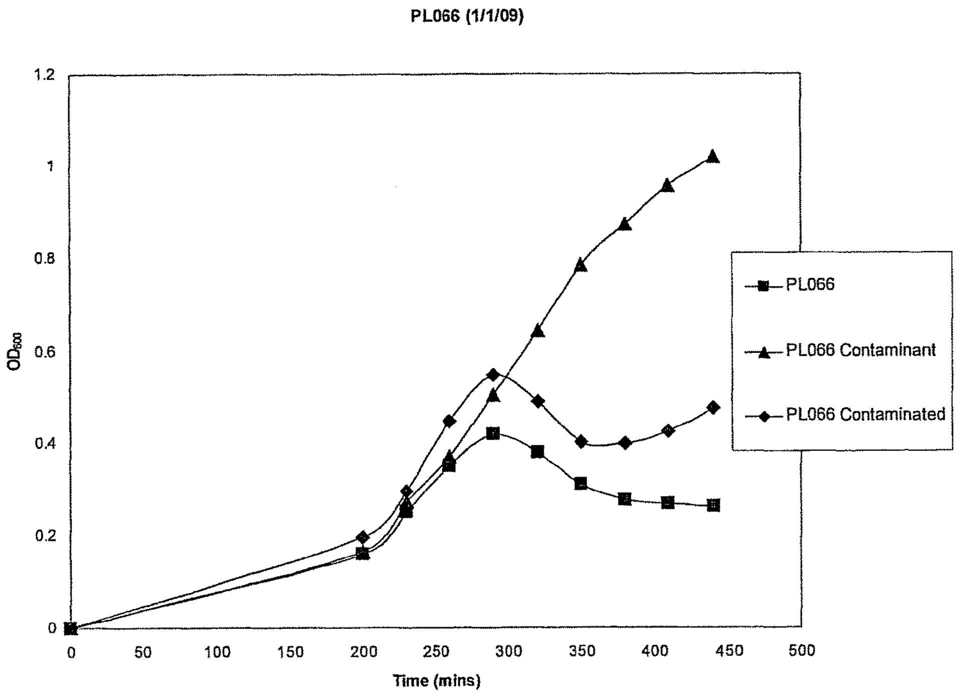
Figure 4J:
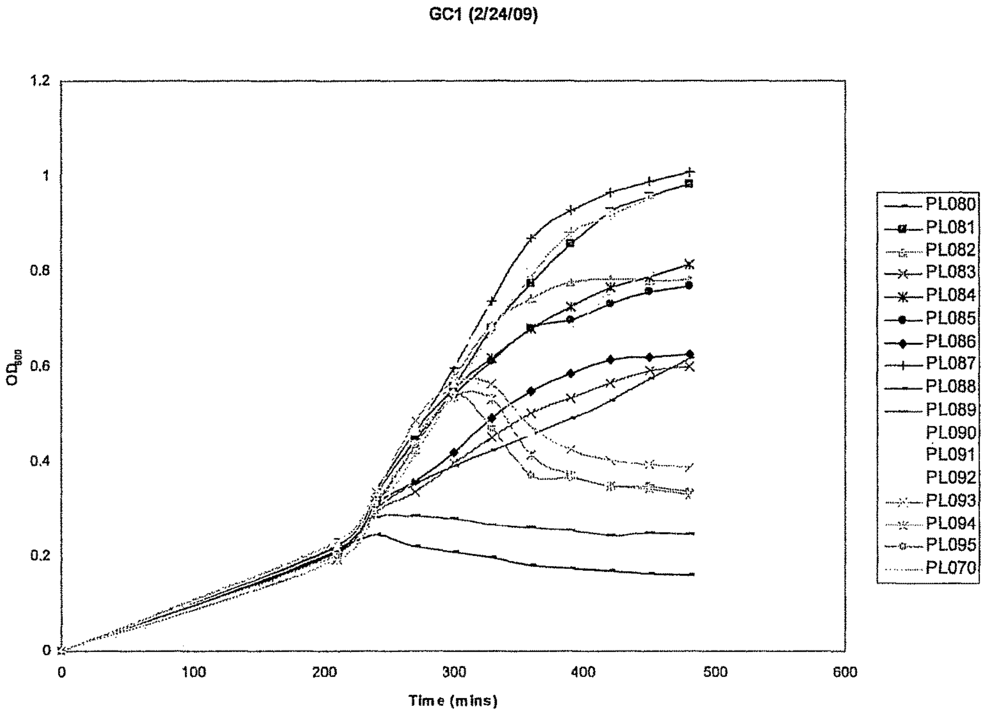
Figure 4K:
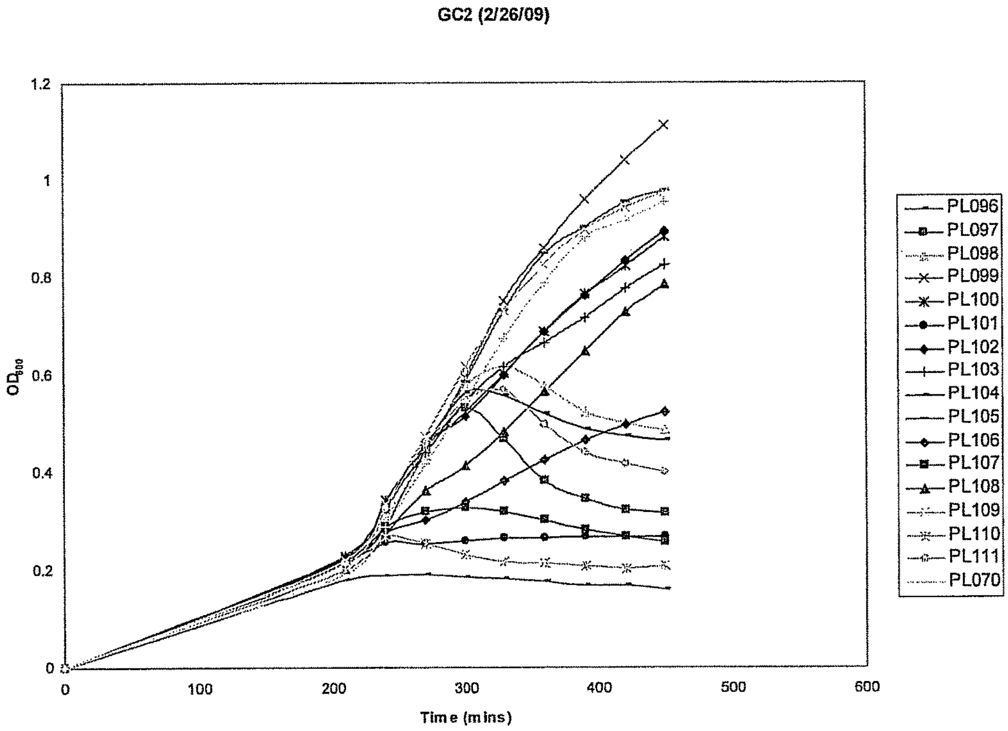
Figure 4L:
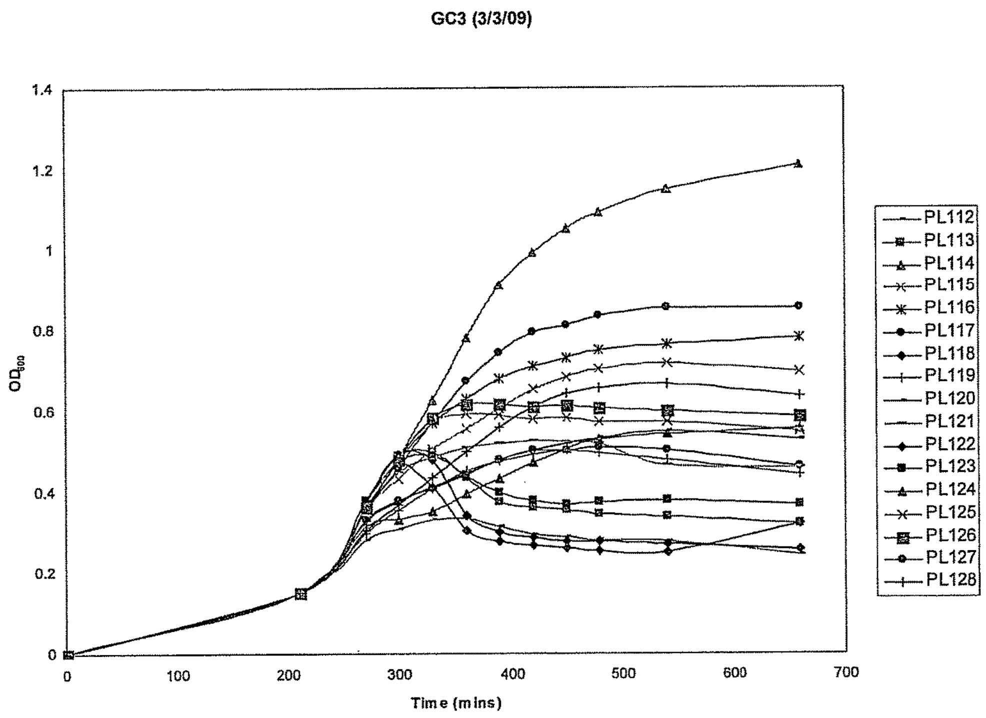
Figure 4M:
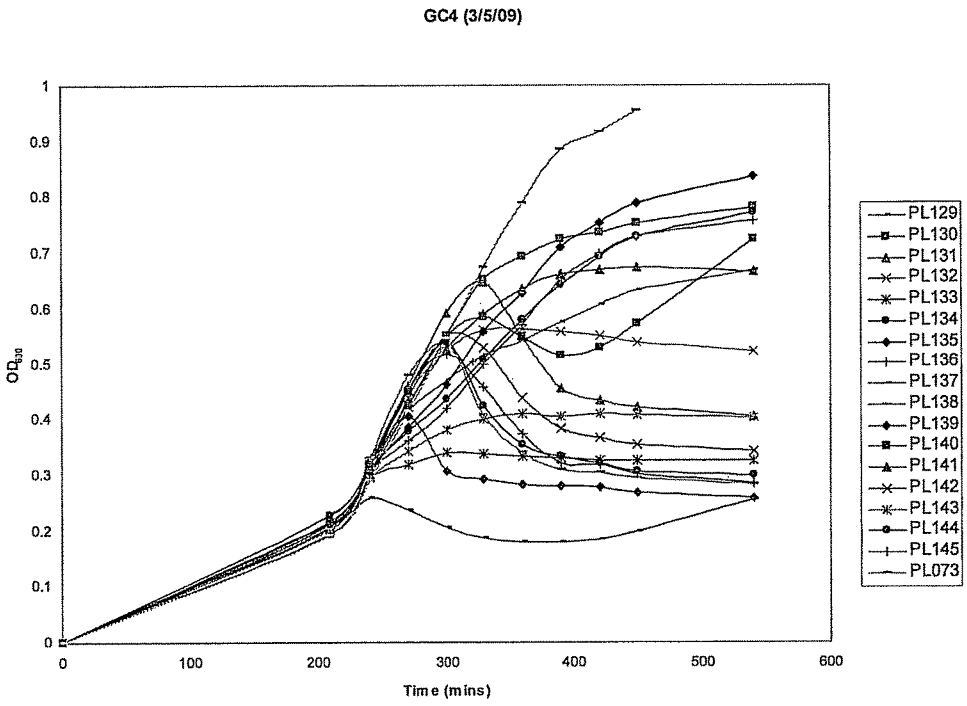

Referring to FIGS. 1A and 1B, transformants were recovered for several hours before the culture was split and entered the two pathways of the screen. FIG. 1A shows a bactericidal/lytic screen; arabinose was added to induce peptide production. Lytic peptides cause cells to release lytic peptide plasmid into the supernatant. Resuspension with ampicillin caused non-inhibitory and bacteriostatic cells to lyse, leaving bactericidal cells intact. FIG. 1B shows a bacteriostatic screen.

Isolation of non-lytic, bactericidal peptides (FIG. 1A). Arabinose and ampicillin were added to lyse non-inhibitory, lytic, and cidal peptide-containing cells. To isolate peptides that kill host cells without causing lysis, cultures were grown to mid-log phase, induced by the addition of 0.2% L-arabinose and further incubated for a period of time sufficient to allow expression of the fusion protein to reach maximal levels (1 hr). Cells were recovered by centrifugation, washed, resuspended and grown to mid-log phase in nonselective medium (LB+0.4% glucose) and subjected to negative selection as described above. Cells from this selection were recovered by centrifugation and used to purify plasmid. EPI300 was transformed with the resulting plasmid and screened by replicating on selective medium. Clones with bactericidal peptides were retained for further analysis.

Isolation of bacteriostatic and weakly inhibitory peptides (FIG. 1B). Negative selection was used to isolate peptides that inhibit growth but are not lethal. Cultures were grown to early-log phase, induced by the addition of 0.2% L-arabinose and further incubated for a period of time sufficient to allow expression of the fusion protein to reach maximal levels (1 hr). Ampicillin (300 μg/ml) was added to the culture and the incubation was continued until the OD600 of the culture stops decreasing. Unlysed cells are recovered by centrifugation, washed, incubated in non-inducing medium (LB+0.4% glucose) overnight and the negative selection procedure repeated. At each stage of the selection, a sample of the recovered cells were plated on nonselective medium and replicated onto selective medium (containing 0.2% L-arabinose) to identify transformants expressing bacteriostatic or weakly inhibitory fusion peptides. Clones with confirmed peptides were retained for further analysis.

Example 2

Construction and Screening of a Random Peptide Library

To construct the random peptide libraries, random codons encoding twelve amino acids were incorporated into a DNA cassette containing the appropriate restriction sequences. The cassette was ligated at either the N-terminus or C-terminus of the display proteins. The amino acids were encoded by the sequence NNK (N=equal representation of A, T, C and G and K=T or G). The resulting ligated plasmids were then transformed into *E. coli* DH5, plated under nonselective conditions, and sequenced to confirm randomness.

To make the random plasmid library, additional transformations are performed. The transformants were pooled, after which plasmids encoding the random peptide sequences were purified. To isolate inhibitory peptides, *E. coli* EPI 300 was transformed with the peptide libraries and screened to identify bacteriolytic, bactericidal, and bacteriostatic peptides, and peptides that specifically inhibit ribosome function using a combination of positive and negative selection strategies.

Figure 5:
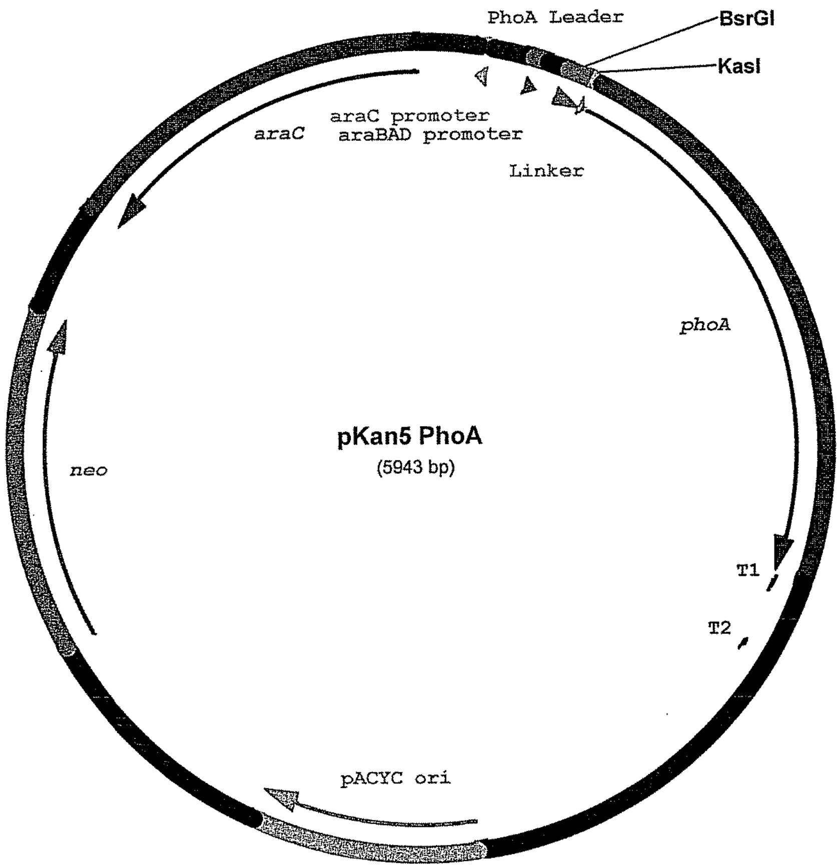
FIG. 5 shows the vector used in screening peptides for anti-growth phenotypes in the periplasm. pKan phoA had the phoA gene under the power of the inducible araBAD promoter
Figure 6:
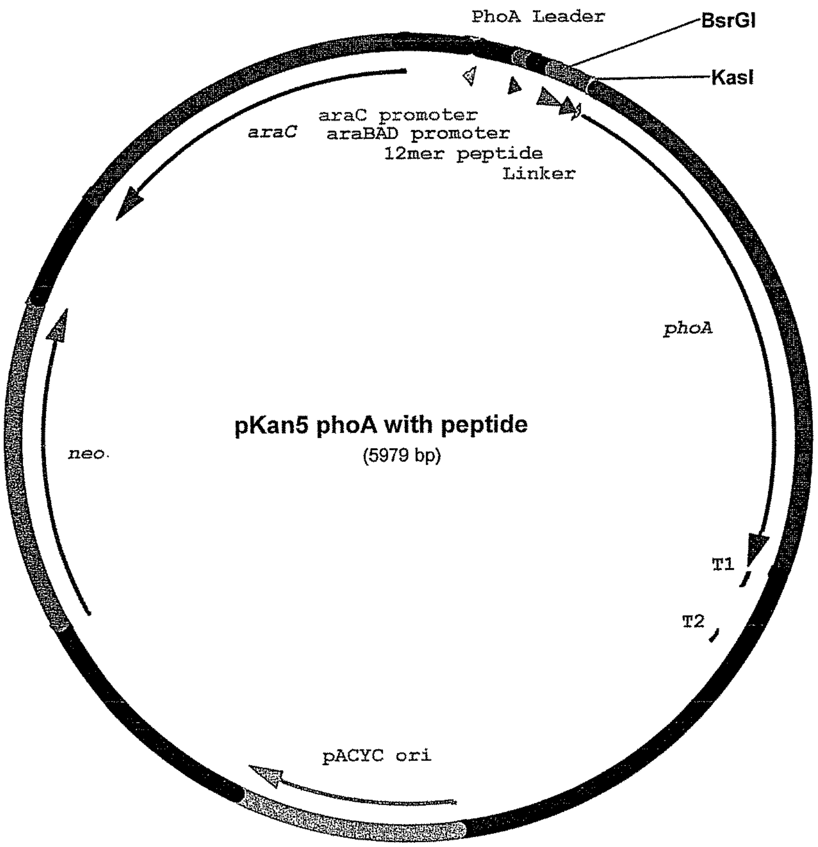
FIG. 6 shows the vector of FIG. 5, with peptide.
Figure 8:
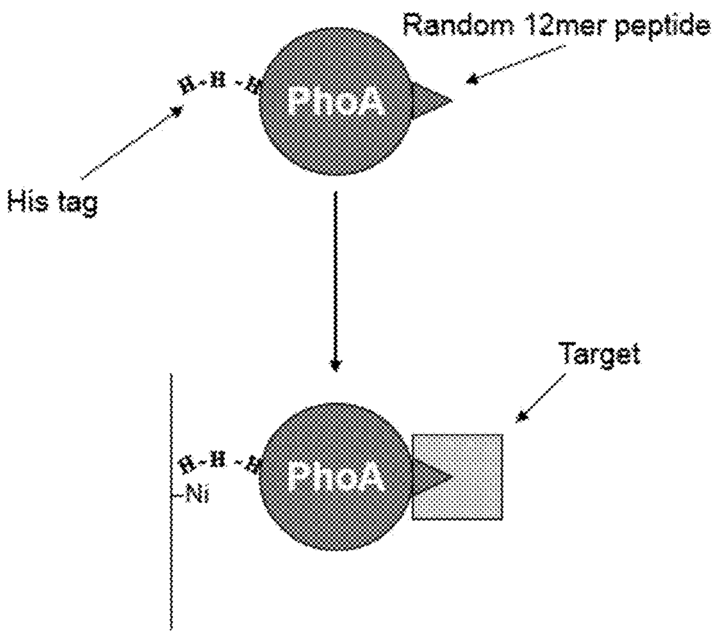
FIG. 8 is a schematic of a display protein.
Figure 9:
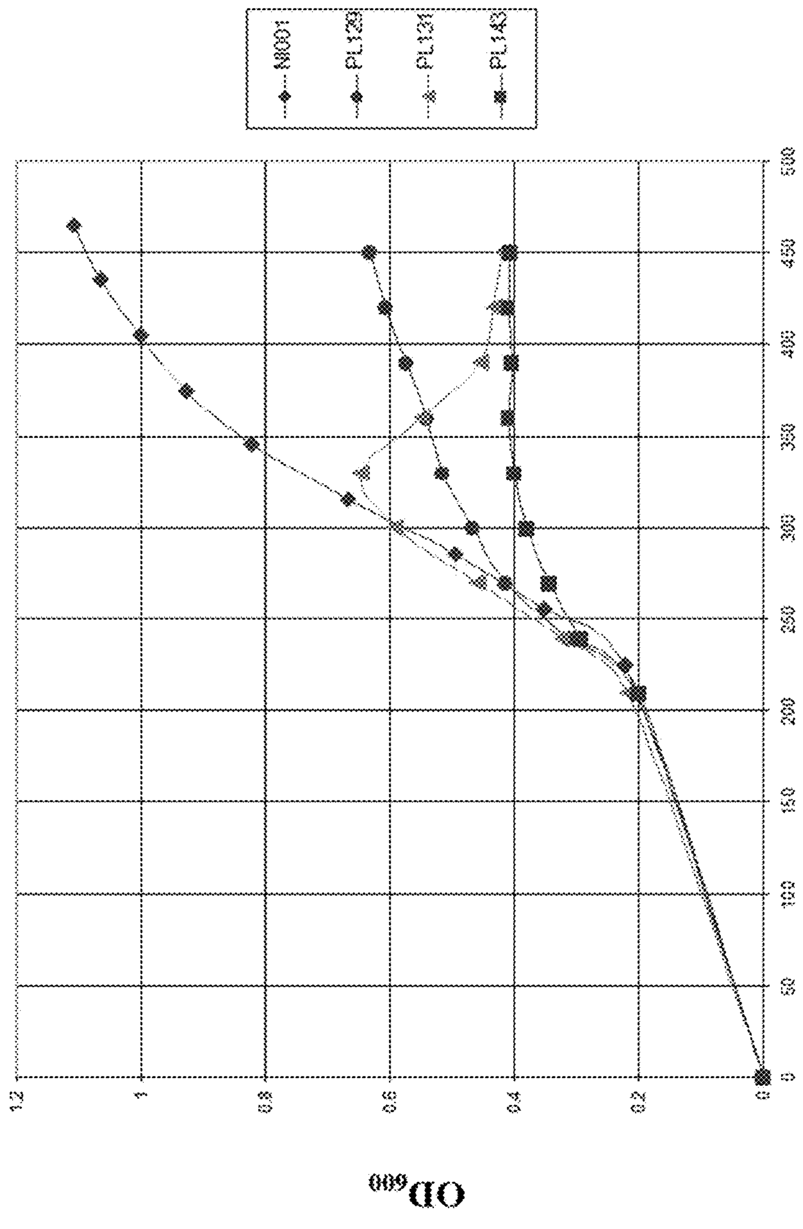
FIG. 9 shows induced growth curves for each type of peptide antimicrobial.

Both the C and N-terminal peptide screens were done in the *E. coli* strain, EPI300, for the ability to induce a higher copy number of plasmid and initiate protein expression. Vector was prepared by cutting with BsrGI-HindIII (C-terminal) or NotI-NcoI (N-terminal) and then ligated to a cassette in a 1:2 molar ratio. The random peptide libraries were constructed by inserting a cassette containing the random dodecamer library, in the appropriate vector. FIG. 5 illustrates a vector used in screening peptides for anti-growth phenotypes in the periplasm. FIG. 6 illustrates pKan phoA had the phoA gene under the power of the inducible araBAD promoter Diversity of the library can be confirmed for example by sequencing 100 transformants in 10 reactions, pooling 10 transformants per reaction. Base bands were expected to be in roughly equal amounts at the randomized positions, except the third position, or K, which was expected to have a 50/50 chance of being G or T.

A library of 1 billion clones was constructed, representing only a fraction of the potential amino acid sequences encoded by (NNK)12. When a single cell *E. coli* bacilli is transformed with one member of this library, it can be induced to express a peptide-PhoA fusion. The disclosed random 12 NNK triplets form a random nucleotide sequence 36 bases long. The random triplets give rise to a random 12 amino acid long peptide following translation. The peptide-PhoA fusion also has a C-terminal (Histidine)6 tag for in vitro purification of the fusion and any potential targets with which it is bound.

Upon expression, the leader peptide of PhoA directs its translocation to the periplasm by directing the translating ribosome to the plasma membrane. The leader peptide and the attached random peptide-PhoA fusion are then translocated through the plasma membrane into the periplasm. At this point the leader peptide is cleaved by a periplasmic peptidase, exposing the random peptide at the N-terminus of the fusion and allowing it to interact with any molecule in the periplasmic environment. The basis of the screens disclosed herein is to extract any random peptide that is able to affect the growth of *E. coli* by binding to and interfering with, preventing, or inhibiting the function of a molecule present in the periplasm.

To undertake this task on a high-throughput scale, a portion of the random peptide library encoded on pKan phoA plasmids was transformed into *E. coli* DH5α, a phoA strain. The cells were allowed to recover in SOC broth and were then transferred to a batch of LB+kanamycin to select for the plasmid; glucose was used to repress any expression of the peptide-PhoA fusion to prevent a particularly lethal peptide from prematurely removing itself from the screen by killing its host early. The cells were grown to mid-log phase; here they are carrying out normal cellular processes at a high rate and the cell density was high enough to recover plasmid DNA. At this point one of three screens were begun, to isolate growth-affecting peptides. Each screen utilized the phenotype of the peptide's expression to remove it from the background of peptides that were non-inhibitory.

As stated, bacteriolytic peptides caused the host cell to lyse or break open, releasing its inter-cellular components into the growth medium. Arabinose was added to a batch of mid-log phase cells to induce the expression of the peptide-PhoA fusion. If a particular peptide was able to cause cell lysis, the plasmid that encoded it would be released into the medium along with all other cellular components. The plasmid DNA could then be recovered using isopropanol precipitation.

As stated, bacteriostatic peptides induced the cell to enter a state of dormancy. While the cell could no longer replicate, if the peptide were to be removed from the cell it could resume growth and replication. Thus, peptides were removed by removing the inducer of its expression, arabinose, and by adding a repressor, glucose, in its stead. Arabinose was initially added to a batch of transformed cells. After a period of time any bacteriostatic peptides were presumed to have stopped their host cells from replicating. At this point it was necessary to remove any background cells or cells that are actively replicating in the presence of their peptides.

Ampicillin, an antibiotic that causes cell lysis only if a cell is actively replicating, is added to the medium. Once lysis of the culture was complete (cell density reaches a minimum) the cells were washed to remove arabinose and ampicillin, and re-suspended in LB broth with glucose to repress any peptide-PhoA fusion expression. This step selected for cells that were not actively replicating in the presence of their peptides, but upon the repression of expression were able to replicate once again. This procedure was repeated two more times to enrich for cells containing plasmids that encoded for bacteriostatic peptides versus ones with non-inhibitory peptides. After this procedure was finished, the plasmid could be extracted from the surviving cells and further analyzed.

As stated previously, bactericidal peptides cause the irreversible death of their host cells. Arabinose was added to a batch culture of mid-log phase cells as above. After a period of induction the cells were washed to remove the arabinose. The cells were re-suspended in LB broth with glucose to repress any expression of the fusion protein. At this point, cells containing plasmids encoding for bactericidal peptides died and could no longer replicate. Ampicillin was added to the broth to lyse all remaining cells in the culture. The bactericidal peptide-containing cells were still intact, so they could be removed from the lysed cells and their plasmids by centrifugation and washing steps to reduce plasmid contamination containing non-inhibitory peptides. The dead cells could be chemically lysed to purify their plasmids.

Numerous periplasmic screens have been performed for the identification of bacteriolytic peptides, encompassing more than 90 million clones. Selected clones have been sequenced and confirmed by induced growth curves, confirming that the disclosed bacteriolytic screen enriches plasmid preparations for peptides that elicit cell lysis. For example, an isolated clone is grown in fresh LB medium to early log phase. Arabinose is added to induced peptide-PhoA fusion expression, and the peptide's effect on growth is observed by measuring the cell density of the culture. Many clones of differing growth phenotypes were analyzed. Bacteriolytic peptides have predominated the extracted clones, which is to be expected given that the bacteriolytic screen was used. Peptides were recovered that had either a bacteriostatic or bactericidal effect and others that have a weakly inhibitory effect as they reduce the rate of *E. coli*'s growth considerably and may find use as precursors to actual peptide hits.

Example 3

Characterization of Inhibitory Peptides Discovered Using In Vivo Display

The affinity tags present on the carrier proteins allow the identification of targets of select inhibitory peptides. Each isolated peptide's intracellular target may be identified using purification techniques. First, the clone will be grown in a medium supplemented with isotopically labeled uridine, thymine and methionine. After induction, the culture is centrifuged to collect the cells and lysed. The target-peptide-fusion protein is then purified by IMAC via the (His)6 tag on the fusion protein. Once the macromolecular nature of the target is identified, mass spectrometry may be used to specifically identify proteins, or nucleic acid sequencing for RNA and DNA.

Synthetic production of selected peptides may then be used for further characterization. Identified target may be purified and used to perform binding assays using any of the following methods: ELISA, surface plasmon resonance, isothermal titration calorimetry, equilibrium dialysis, electrospray mass spectrometry or fluorescence polarization depending on what is suitable for the target.

The spectrum or range of species that the peptide is able to affect was determined by synthesizing the peptide coupled with one of several motifs increasing permeability and adding it to cultures at various concentrations containing bacterial or fungal species of increasing difference. MIC's (minimum inhibitory concentrations) or IC50's were calculated by subjecting select species to the synthetic peptide including *E. coli, Pseudomonas aeruginosa, Staphylococcus aureus, Enterococcus faecalis, Bacillus subtilis, Klebsiella pneumoniae, Serratia marcescens* using the broth dilution method. Growth curves were performed and compared to species exposed to a non-lethal peptide, simultaneously.

Cellular macromolecules may be isotopically labeled in vivo and the target isolated in pull-down experiments in which the target-peptide-fusion protein complex is purified using immobilized metal affinity chromatography (IMAC). The targets may be further characterized by enzymatic digestion. Specific identification of the targets is accomplished using mass spectrometry for protein targets or nucleic acid sequencing for nucleic acid targets. Binding studies may be performed using a variety of methods including but not limited to ELISA, NMR, surface plasmon resonance, isothermal titration calorimetry, equilibrium dialysis, electrospray mass spectrometry, and fluorescence polarization, depending on the nature of the target.

Specific peptides may be selected for further development. Factors affecting which peptides are chosen for further development include the nature of the target, antimicrobial activity, binding constant and solubility. Synthetic peptidomimetic libraries may be synthesized that incorporate the key structural and chemical motifs identified in this study and these libraries are screened against the peptide targets to identify compounds with increased therapeutic potential. These lead compounds may then be subjected to a variety of medicinal chemistry techniques as appropriate, to increase solubility, increase target specificity and decrease toxicity.

Example 4

Peptides Isolated and Sequenced

Peptides isolated using periplasmic bacteriolytic screen are shown in FIG. 2. Phenotype definitions: Bacteriolytic: OD600 of culture decreases in value, correlating with a reduction in the concentration of cells. Bactriostatic/bactericidal: OD600 of culture flatlines, correlating with a complete stop in the growth of the cells and constant cell density. Weakly inhibitory OD600<0.7: Replication is slowed but not stopped. Final OD600 as culture enters stationary phase is less than 0.7. Weakly inhibitory OD600>0.7: Similar to the above, only final OD600 exceeds 0.7. Peptides have only a minor effect on growth. Non-inhibitory: No growth effect was observed versus the expression of PhoA with no peptide at its N-terminus.

Peptide sequences in single letter amino acid code are shown in FIGS. 3A-E.

Five phenotypes were isolated as shown in FIG. 3: (i) Bacteriolytic; (ii) Bacteriostatic/bactercidal; (iii) Weakly inhibitory OD600<0.7; (iv) Weakly inhibitory OD600>0.7 and (v) Non-inhibitory.

After replica plating, clones were grown in LB+30 μg/ml kanamycin. When OD600~0.15, arabinose was added to a final concentration of 0.2%. The OD600 of the culture was then measured every 30 minutes to see the effect of peptide-PhoA fusion expression on the cell. The growth curve results are shown in FIG. 4 A-M.

Example 5

Protocols for High-Throughput Peptide Screening

A. A protocol for High-throughput bacteriolytic peptide screening was as follows:

1. Mix 1 μg of pKan phoA library with 30 μls of DH5α electrocompetent cells.
2. Electroporate mixture at 1.44 kV.
3. Move mixture to 1 ml of SOC broth+0.2% glucose (w/v).
4. Repeat steps 1-3 nine times.
5. Incubate at 37° C. for 1 hr.
6. Centrifuge cells at 7,000 rpm for 5 mins.
7. Pour off supernatant.
8. Gently re-suspend cells in 10 mls pre-warmed LB broth+0.2% glucose.
9. Centrifuge cells at 7,000 rpm for 5 mins.
10. Pour off supernatant.
11. Gently re-suspend cells in 10 mls pre-warmed LB broth+0.2% glucose.
12. Add suspension to 500 mls of LB+30 μg/ml kanamycin+0.2% glucose.
13. Incubate at 37° C. until culture's $OD_{600}$~0.4, centrifuge culture at 7,000 rpm for 5 mins.
14. Pour off supernatant.
15. Gently re-suspend cells in 25 mls of pre-warmed LB.
16. Centrifuge at 7,000 rpm for 5 mins.
17. Pour off supernatant.
18. Gently re-suspend cells in 25 mls of pre-warmed LB.
19. Add suspension to 500 mls of LB+30 μg/ml kanamycin+0.2% arabinose.
20. Incubate at 37° C. for 2 hrs.
21. Remove 21 mls of the culture and place in an oakridge tube.
22. Centrifuge at 13,000 rpm for 10 mins.
23. Pour supernatant into a new oakridge tube and centrifuge at 13,000 rpm for 10 mins.
24. Pour supernatant into a new oakridge tube along with 12.6 mls room temperature isopropanol, 2.1 mls 3M Na Acetate pH 5.2, and 105 μls of 10 μg/ml salmon testes DNA.
25. Centrifuge at 11,000 rpm for 30 mins.
26. Pour off supernatant.
27. Add 5 mls of 70% ethanol, centrifuge at 11,000 rpm for 15 mins.
28. Pour off supernatant.
29. Re-suspend DNA pellet in 500 μls $dH_2O$.
30. Store at −20° C.

B. A protocol for High-throughput bacteriostatic peptide screening was as follows:

1. Mix 1 μg of pKan phoA library with 30 μls of DH5α electrocompetent cells.
2. Electroporate mixture at 1.44 kV.
3. Move mixture to 1 ml of SOC broth+0.2% glucose (w/v).
4. Repeat steps 1-3 nine times.
5. Incubate at 37° C. for 1 hr.
6. Centrifuge cells at 7,000 rpm for 5 mins.
7. Pour off supernatant.
8. Gently re-suspend cells in 10 mls pre-warmed LB broth+0.2% glucose.
9. Centrifuge cells at 7,000 rpm for 5 mins.
10. Pour off supernatant.
11. Gently re-suspend cells in 10 mls pre-warmed LB broth+0.2% glucose.
12. Add suspension to 500 mls of LB+30 μg/ml kanamycin+0.2% glucose.
13. Incubate at 37° C. until culture's $OD_{600}$~0.4, centrifuge culture at 7,000 rpm for 5 mins.
14. Pour off supernatant.
15. Gently re-suspend cells in 25 mls of pre-warmed LB.
16. Centrifuge at 7,000 rpm for 5 mins.
17. Pour off supernatant.
18. Gently re-suspend cells in 25 mls of pre-warmed LB.
19. Add suspension to 500 mls of LB+30 μg/ml kanamycin+0.2% arabinose.
20. Incubate at 37° C. for 2 hrs.
21. Add 500 μls of 300 mg/ml ampicillin to the culture.
22. Continue to incubate for another hour.
23. Centrifuge culture at 7,000 rpm for 10 mins.
24. Pour of supernatant.
25. Gently re-suspend in 25 mls of HN buffer.
26. Centrifuge at 7,000 rpm for 10 mins.
27. Pour off supernatant.
28. Repeat steps 18-20.
29. Gently re-suspend in 25 mls LB.
30. Add to 500 mls of LB++30 μg/ml kanamycin+0.2% glucose.
31. Incubate at 37° C. overnight.
32. Use 1 ml of overnight culture to inoculate 500 mls of LB+30 μg/ml kanamycin+0.2% glucose.
33. Repeat steps 13-25.
34. Repeat steps 13-24.
35. Perform a plasmid preparation of the cells.

C. A protocol for High-throughput bactericidal peptide screening was as follows:

1. Mix 1 μg of pKan phoA library with 30 μls of DH5α electrocompetent cells.
2. Electroporate mixture at 1.44 kV.
3. Move mixture to 1 ml of SOC broth+0.2% glucose (w/v).
4. Repeat steps 1-3 nine times.
5. Incubate at 37° C. for 1 hr.

6. Centrifuge cells at 7,000 rpm for 5 mins.
7. Pour off supernatant.
8. Gently re-suspend cells in 10 mls pre-warmed LB broth+0.2% glucose.
9. Centrifuge cells at 7,000 rpm for 5 mins.
10. Pour off supernatant.
11. Gently re-suspend cells in 10 mls pre-warmed LB broth+0.2% glucose.
12. Add suspension to 500 mls of LB+30 μg/ml kanamycin+0.2% glucose.
13. Incubate at 37° C. until culture's $OD_{600}$~0.4, centrifuge culture at 7,000 rpm for 5 mins.
14. Pour off supernatant.
15. Gently re-suspend cells in 25 mls of pre-warmed LB.
16. Centrifuge at 7,000 rpm for 5 mins.
17. Pour off supernatant.
18. Gently re-suspend cells in 25 mls of pre-warmed LB.
19. Add suspension to 500 mls of LB+30 μg/ml kanamycin+0.2% arabinose.
20. Incubate at 37° C. for 2 hrs.
21. Centrifuge culture at 7,000 rpm for 10 mins.
22. Pour of supernatant.
23. Gently re-suspend cells in 25 mls of pre-warmed LB.
24. Centrifuge at 7,000 rpm for 10 mins.
25. Pour off supernatant.
26. Gently re-suspend cells in 25 mls of pre-warmed LB.
27. Add suspension to 500 mls LB+30 μg/ml kanamycin+0.2% glucose+300 μg/ml ampicillin.
28. Incubate at 37° C. for 3 hrs.
29. Centrifuge culture at 7,000 rpm for 10 mins.
30. Pour off supernatant.
31. Gently re-suspend pellet in 50 mls of $dH_2O$.
32. Centrifuge at 7,000 rpm for 10 mins.
33. Pour off supernatant.
34. Gently re-suspend pellet in 50 mls of $dH_2O$.
35. Centrifuge at 7,000 rpm for 10 mins.
36. Pour of supernatant.
37. Perform a plasmid preparation on the remaining cells.

Confirmation of Efficacy Protocol

This protocol applies equally to all plasmid DNA preparations from the three above screens (bacteriolytic, bacteriostatic, and bactericidal).

7. Mix 1 μl of a plasmid DNA preparation from one of the screens with 30 μls of DH5α electrocompetent cells.
8. Electroporate mixture at 1.44 kV.
9. Move mixture to 1 ml of SOC broth+0.2% glucose (w/v).
10. Repeat steps 1-3 nine times.
11. Incubate at 37° C. for 1 hr.
12. Spread onto a series of LB+30 μg/ml kanamycin+0.2% glucose plates.
13. Incubate overnight at 37° C.
14. Replica plate from these plates first onto an LB+30 μg/ml kanamycin+0.2% arabinose and then to an LB+30 μg/ml kanamycin+0.2% glucose plate.
15. Incubate plates at 37° C. for 8 hrs.
16. Select colonies that did not grow on the arabinose plate for further study.

Example 6

Polynucleotide Sequences

The numbers refer to the nucleotide position in SEQ ID NO:1, which is the DNA sequence of a pKan phoA plasmid.

151-177 araC promoter
276-303 araBAD promoter
358-420 phoA peptide leader
421-435 Linker sequence
436-1785 phoA
1786-1803 His tag
1819-1862 T1 terminator
1994-2023 T2 terminator
2838-3383 pACYC ori
3977-4792 neo
5065-5943 araC SEQ ID NO:2 and 3 shown below are two complimentary strands of DNA containing the NNK 12-mer. SEQ ID NO:2 contains a BsrGI sticky end, and SEQ ID NO:3 contains a KasI sticky end.

(SEQ ID NO: 2)
GTA CAC CCC TGT GAC AAA AGC CDN KNN KNN KNN KNN

KNN KNN KNN KNN KNN KNN KNN KGA AGG CGG CG (SEQ ID NO: 3)
TG GGG ACA CTG TTT TCG GHN MNN MNN MNN MNN MNN

MNN MNN MNN MNN MNN MNN MCT TCC GCC GCC GCG

Example 7

Identification of Antimicrobial Peptides Using a Cytoplasmic System

To avoid bias due to placement of the peptide, two cytoplasmic libraries were constructed; one in which the peptide sequence was fused to the N-terminus of EmGFP and the other in which it was fused to the C-terminus of EmGFP.

Figure 11:
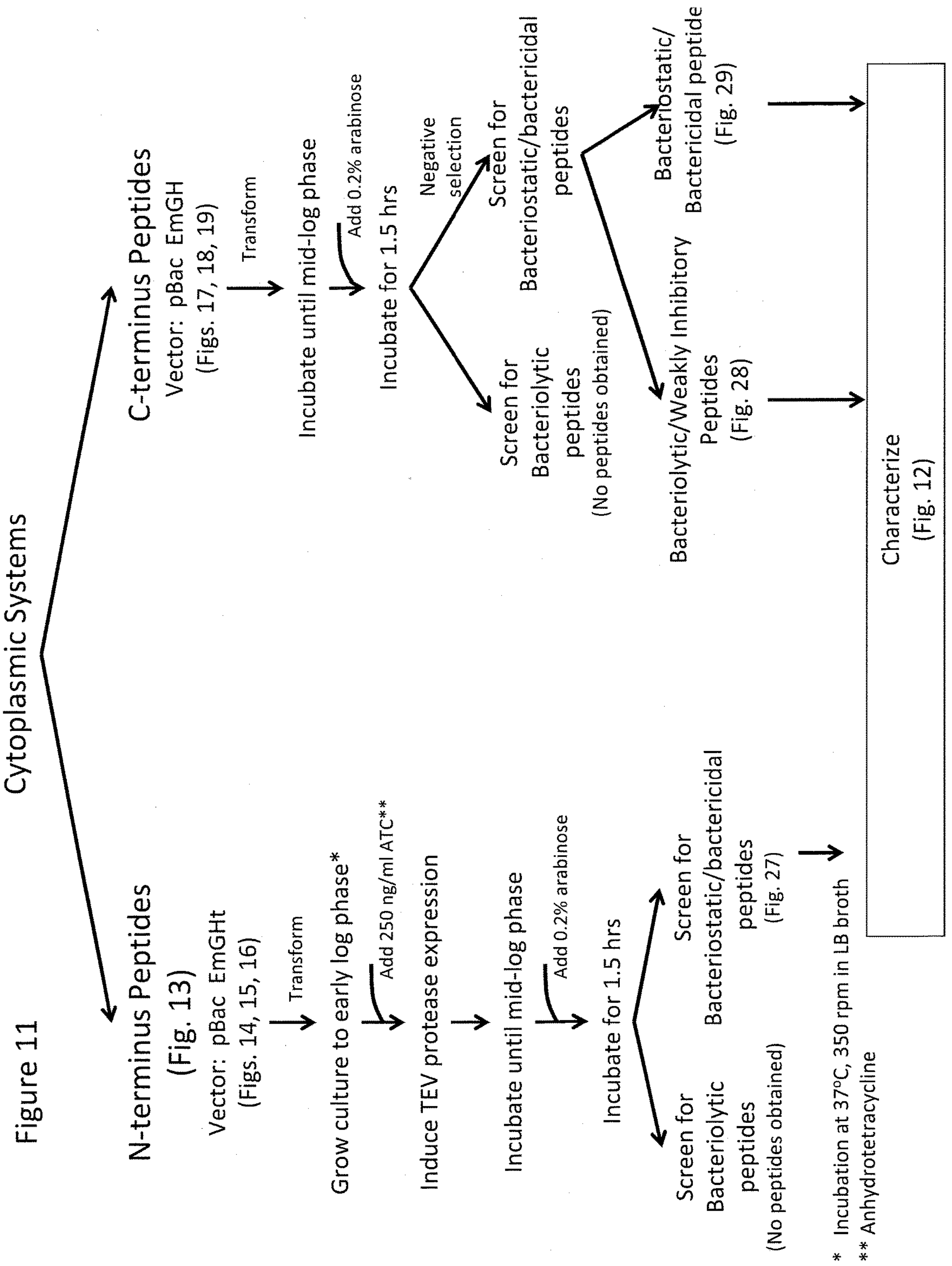
FIG. 11 is a flowchart of a cytoplasmic IVD system.
Figure 14:
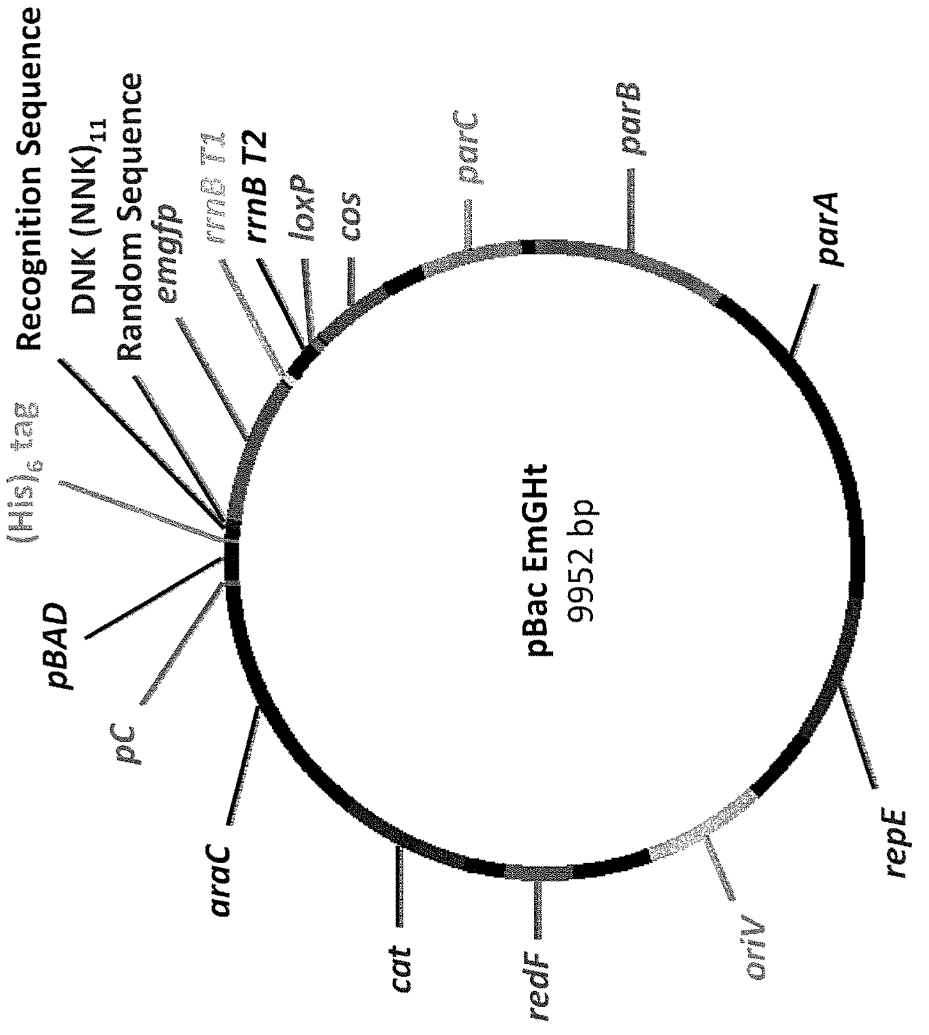
FIG. 14 shows a plasmid construct for expressing N-terminal fusion proteins in the cytoplasm.

The cytoplasmic, N-terminus system (see FIG. 11, left side). To isolate N-terminal inhibitory peptides, the construct pBac-EmGHt was created. The key elements of this plasmid and its sequence are shown FIGS. 14, 15, and 16.

To identify antimicrobial N-terminal peptides, *E. coli* strain EPI301 (an amber suppressor mutant of EPI300 (Epicentre Inc.; Madison, Wis.) containing plasmids pRK603 and pZS4int-tetR (FIG. 13) were transformed with the pBac-EmGHt random library, grown to early log phase and the TEV protease gene was induced by adding anhydrotetracycline (ATC) to a final concentration of 250 ng/ml of culture and the incubation was continued until mid-log phase. At mid-log phase, the peptide fusion construct was induced by adding L-arabinose to a final concentration of 0.2% of culture (w/v), and incubation was continued for 1.5 hrs. In screens to identify bacteriolytic peptides, the culture was centrifuged and plasmid DNA was precipitated from the supernatant and used to transform *E. coli* EPI301 and the transformants were screened on solid medium with or without inducers. No bacteriolytic peptides were identified in the N-terminal cytoplasmic screen. To identify bacteriostatic or bacteriocidal peptides, negative selection was performed in which ampicillin (Cf=500 μg/ml) was added to the mid-log phase cultures to lyse any bacteria that were actively dividing. The non-dividing (dead or static) cells were recovered by centrifugation and their plasmids were isolated and used to transform *E. coli* EPI301. Transformants harboring inhibitory peptides were identified by replica plating on solid media with and without inducers and the plasmids were sequenced to identify the amino acid sequences of the inhibitory peptides. A list of the peptides identified in this screen is provided in FIG. 27.

Figure 17:
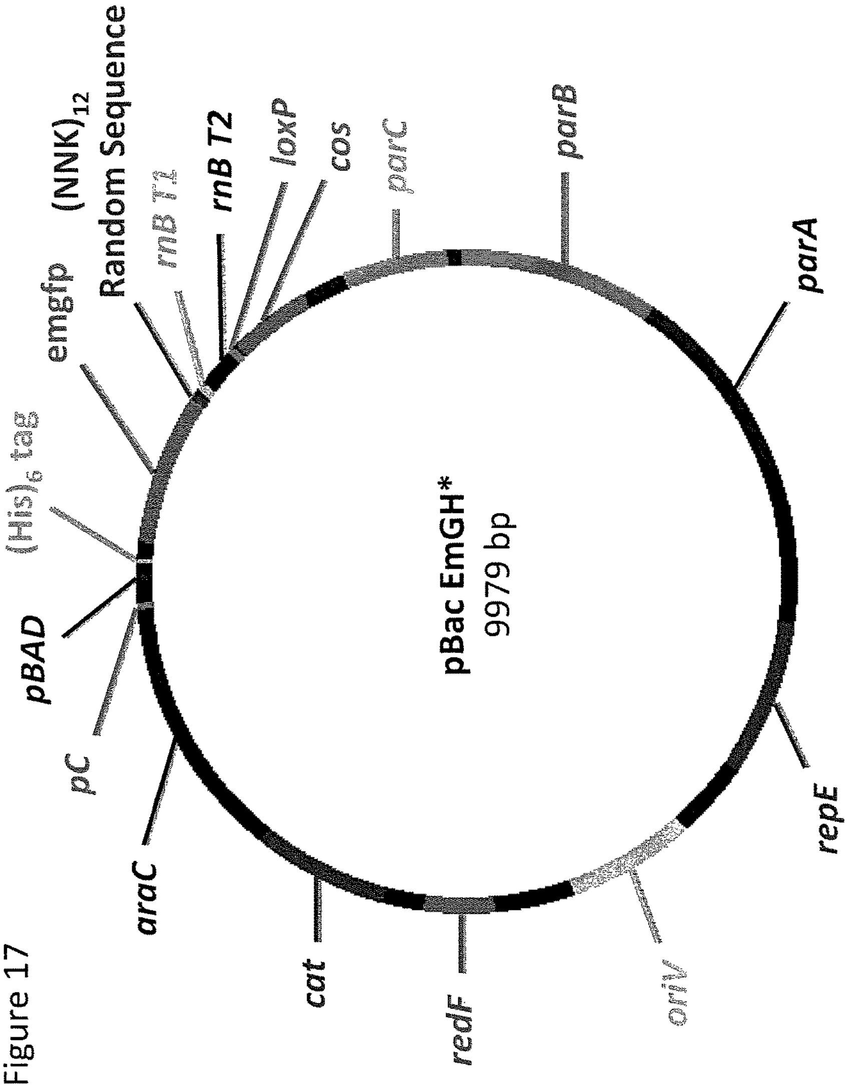
FIG. 17 shows a plasmid construct for expressing C-terminal peptides.

The cytoplasmic, C-terminus system (see FIG. 11, right side). To isolate N-terminal inhibitory peptides, the construct pBac-EmGH was created. The key elements of this plasmid are shown in FIGS. 17, 18, and 19.

To identify antimicrobial C-terminal peptides, *E. coli* EPI301 cells were transformed with the pBac-EmGH random library, grown to mid log phase and L-arabinose was added to a final concentration of 0.2% of culture (w/v) and the incubation was continued for 1.5 hrs. In screens to identify bacteriolytic peptides, the culture was centrifuged and plasmid DNA was precipitated from the supernatant and used to transform *E. coli* EPI301 and the transformants were screened on solid medium with or without inducers. No bacteriolytic peptides were identified in the C-terminal cytoplasmic screen. To identify bacteriostatic or bacteriocidal peptides, negative selection was performed in which ampicillin (Cf=500 μg/ml) was added to the mid-log phase cultures to lyse any bacteria that were actively dividing and the non-dividing (dead or static) cells were recovered by centrifugation, their plasmids were isolated and used to transform *E. coli* EPI301. Transformants harboring inhibitory peptides were identified by replica plating on solid medium with and without inducers and the plasmids were sequenced to identify the amino acid sequence of the inhibitory peptides. Some of these peptides slowed bacterial replication significantly without completely stopping it and were classified as "weakly inhibitory" (see FIG. 28). Other peptides either strongly blocked replication of or killed the cells and were classified as bacteriostatic or bacteriocidal (see FIG. 29).

Example 8

Characterization of Inhibitory Cytoplasmic Peptides

Figure 12:
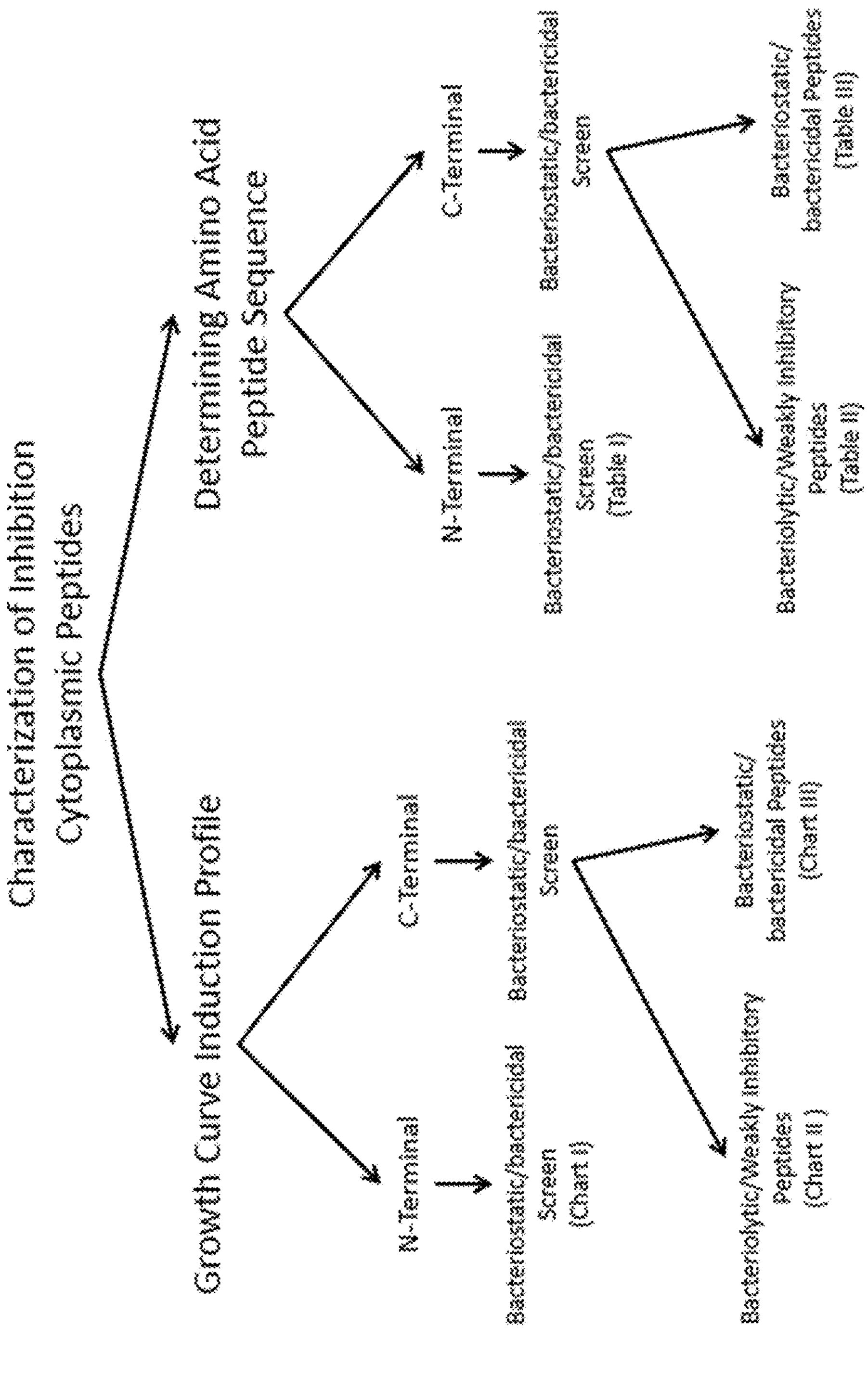
FIG. 12 is a flowchart for characterizing peptide antimicrobials generated using a cytoplasmic IVD system.

Each of the clones isolated in the cytoplasmic screens were characterized to determine their effects on cellular growth and to identify the amino acid sequences of the peptides (see FIG. 12).

Figure 43:
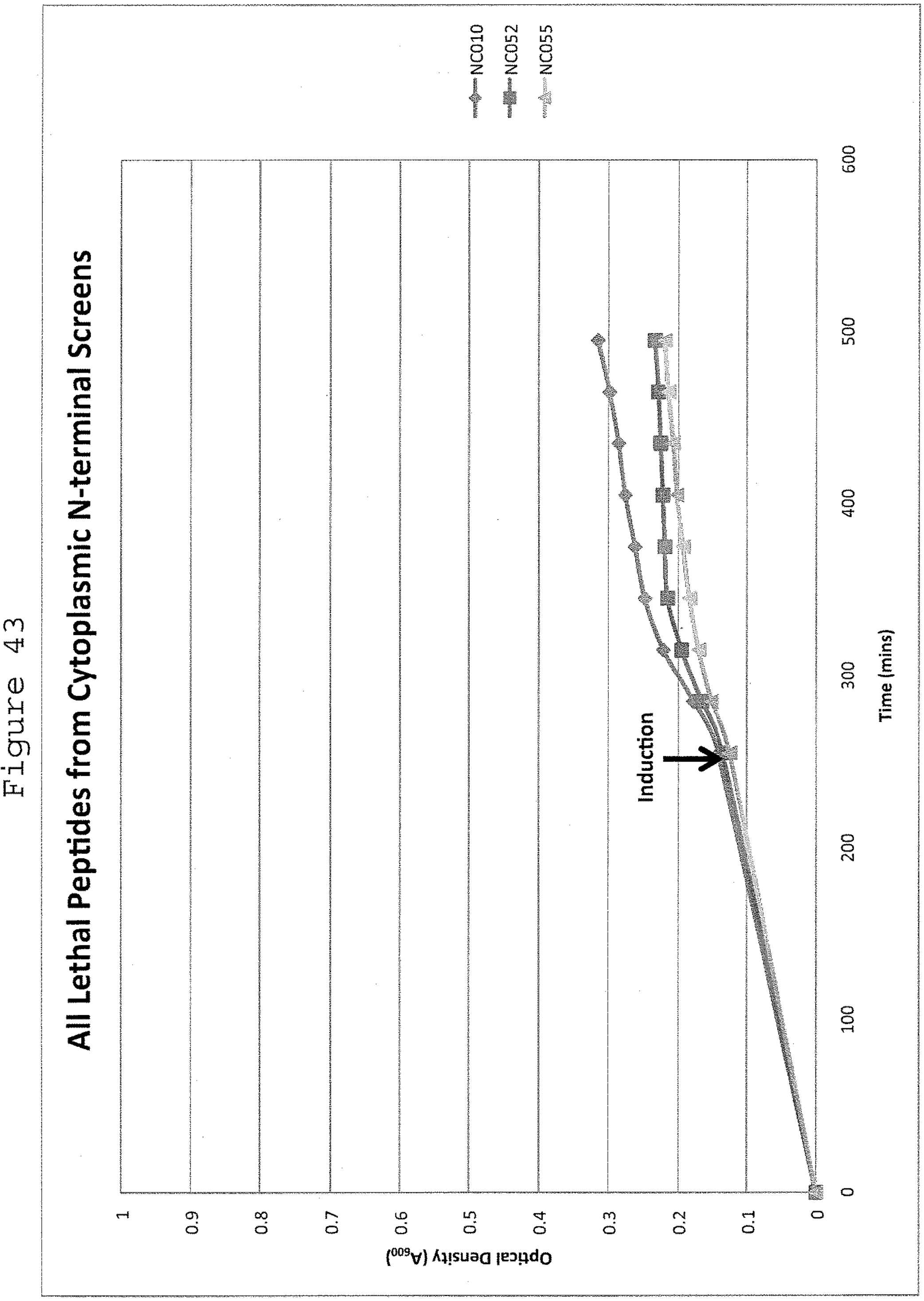
FIG. 43 shows growth curve profiles of bacteria expressing bacteriostatic and bactericidal peptide antimicrobials identified using N-terminal constructs in the cytoplasm.
Figure 44A:
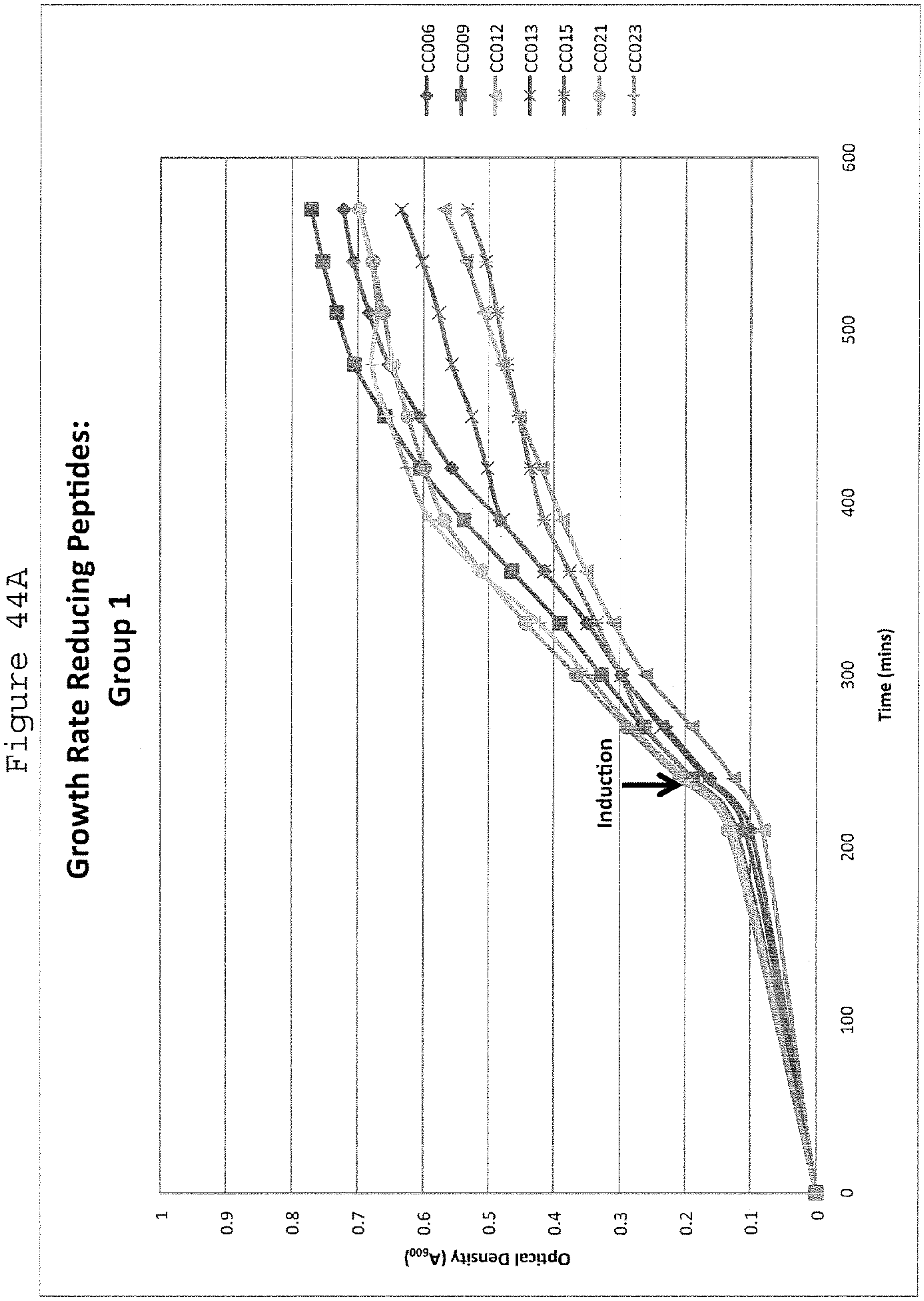
FIGS. 44A-C show growth curve profiles of bacteria expressing growth rate reducing peptide antimicrobials identified using C-terminal constructs.
Figure 44B:
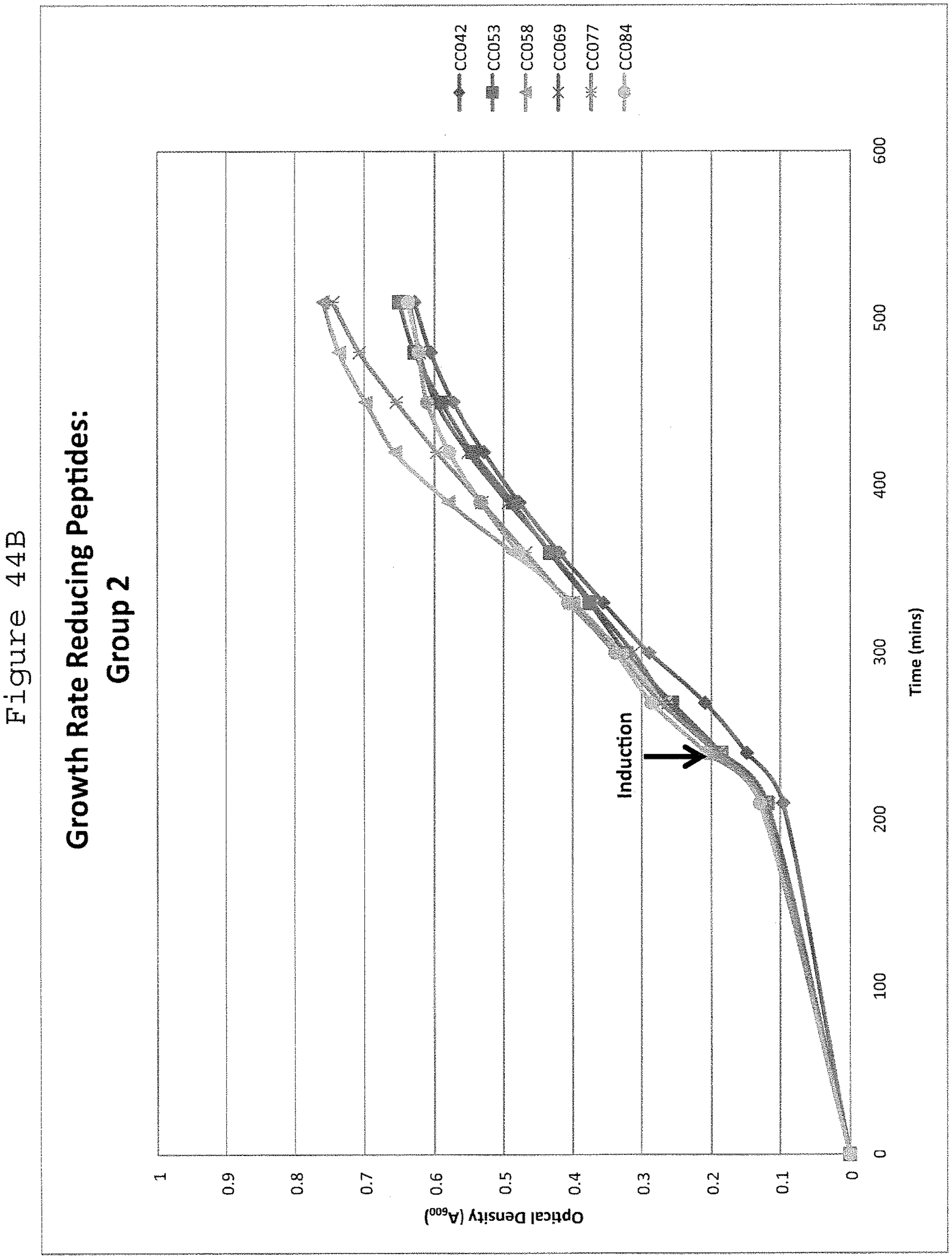
Figure 44C:
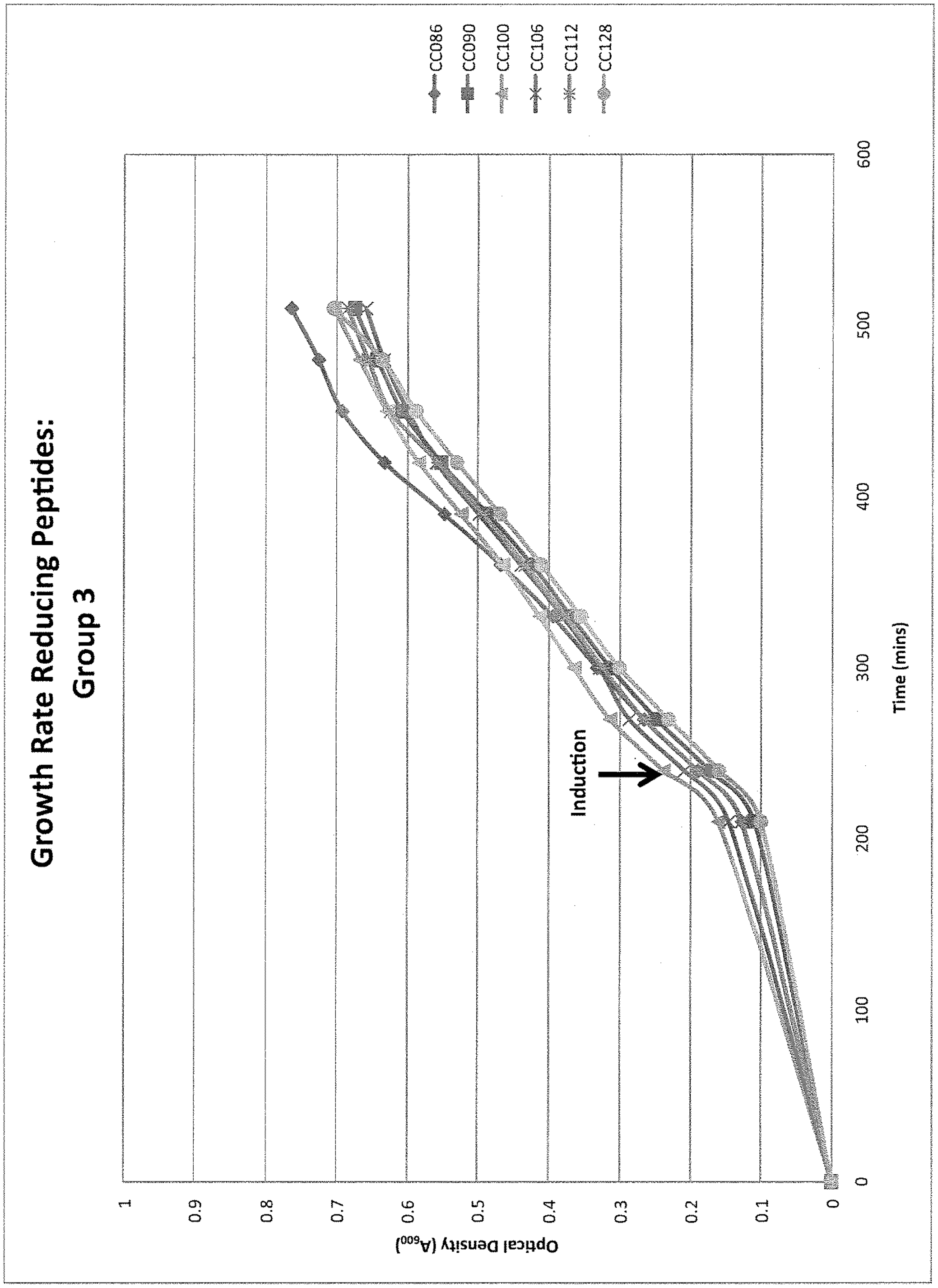
Figure 45A:
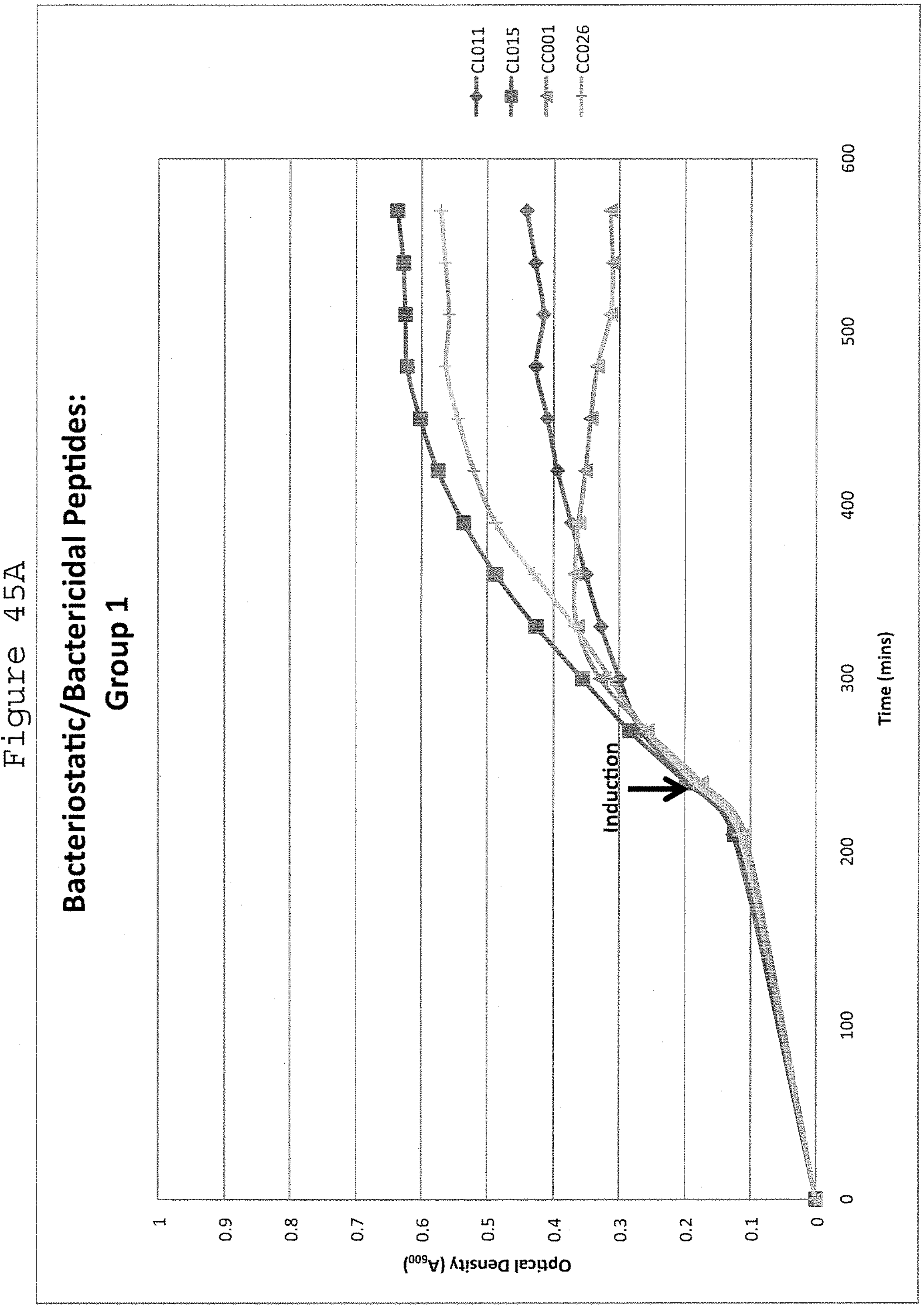
FIGS. 45A-D show growth curve profiles of bacteria expressing bacteriostatic and bactericidal peptide antimicrobials identified using a C-terminal expression system.
Figure 45B:
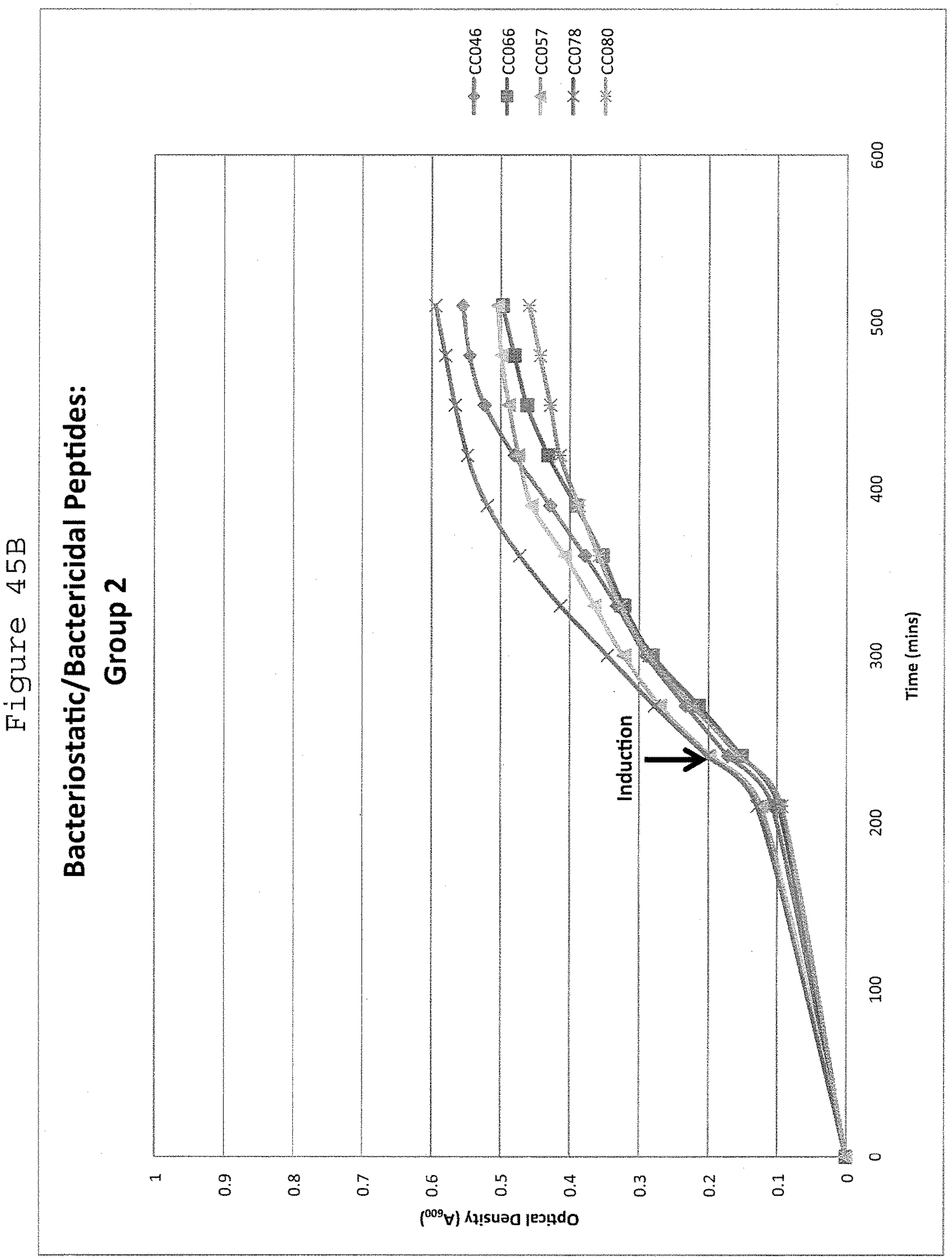
Figure 45C:
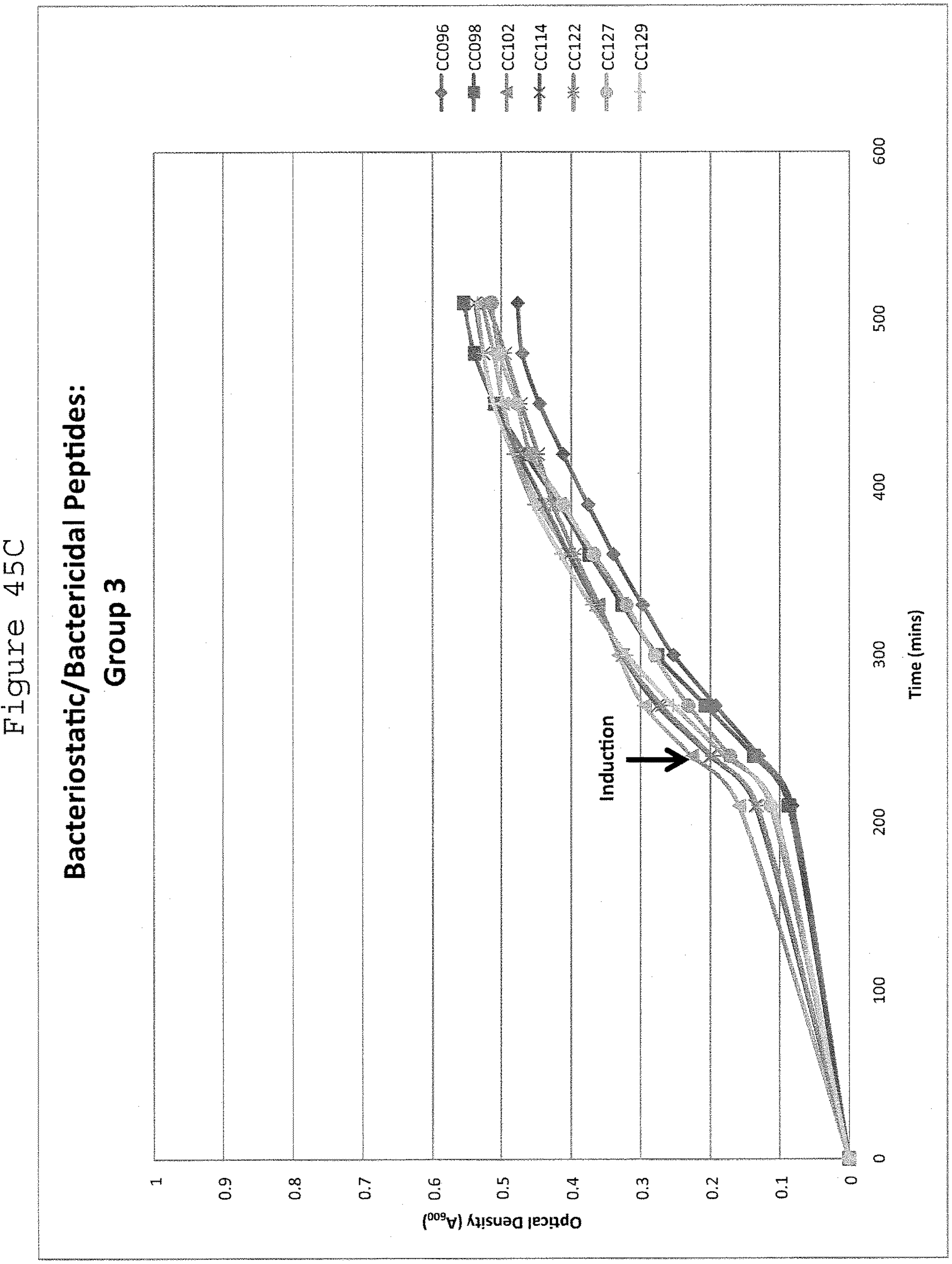
Figure 45D:
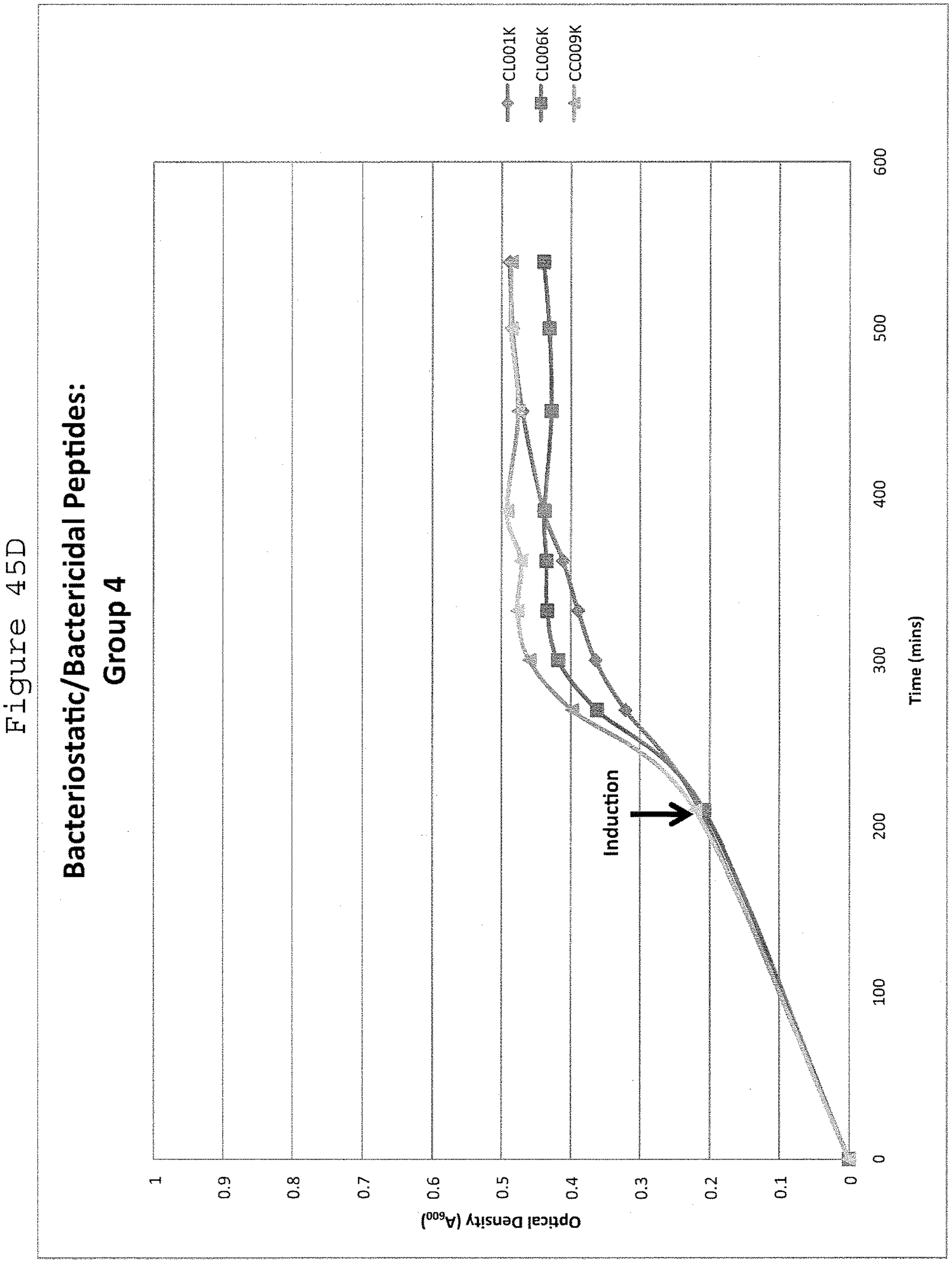
Figure 46A:
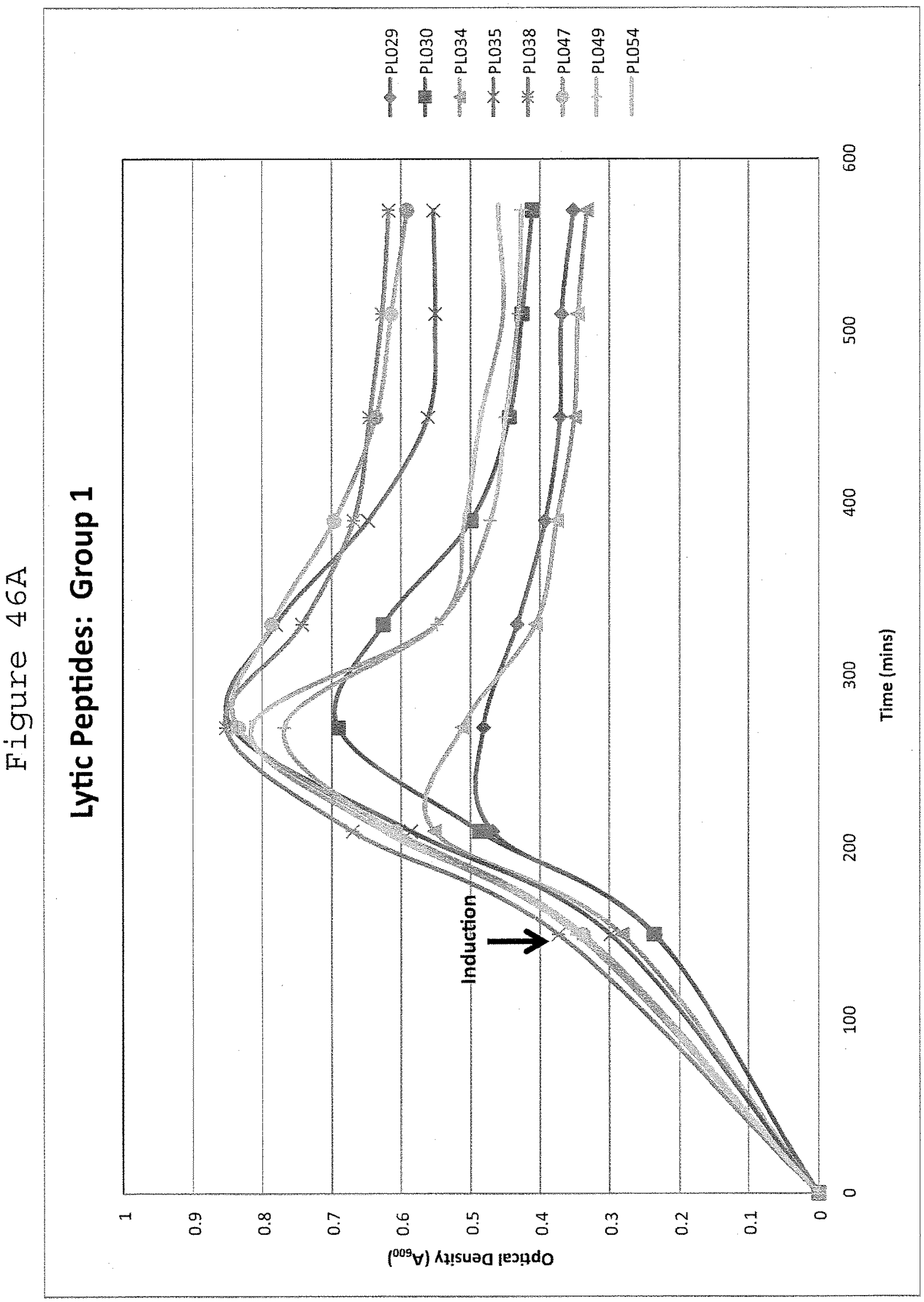
FIGS. 46A-L show growth curve profiles of bacteria expressing bacteriolytic peptide antimicrobials identified using N-terminal constructs in the periplasm.
Figure 46B:
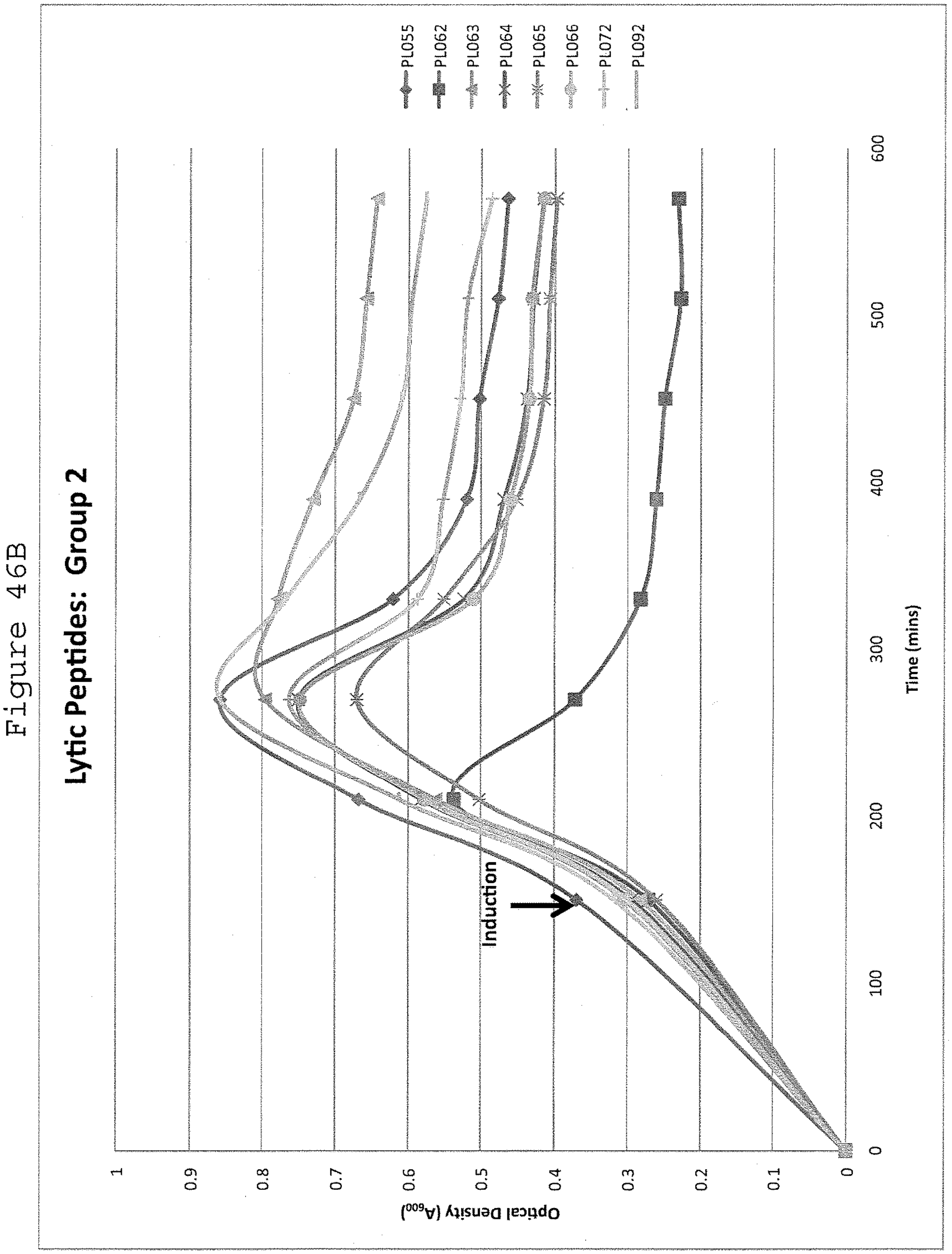
Figure 46C:
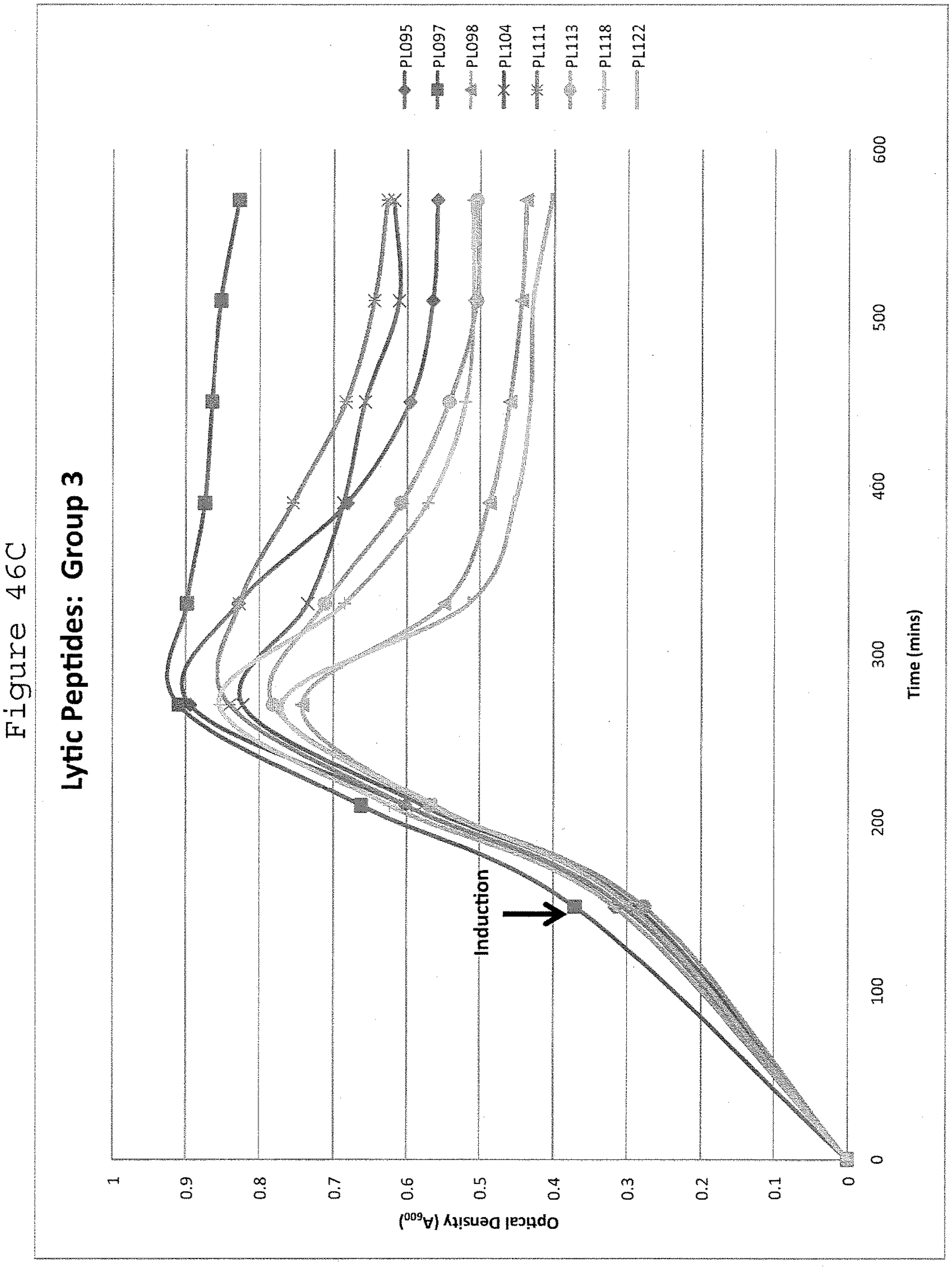
Figure 46D:
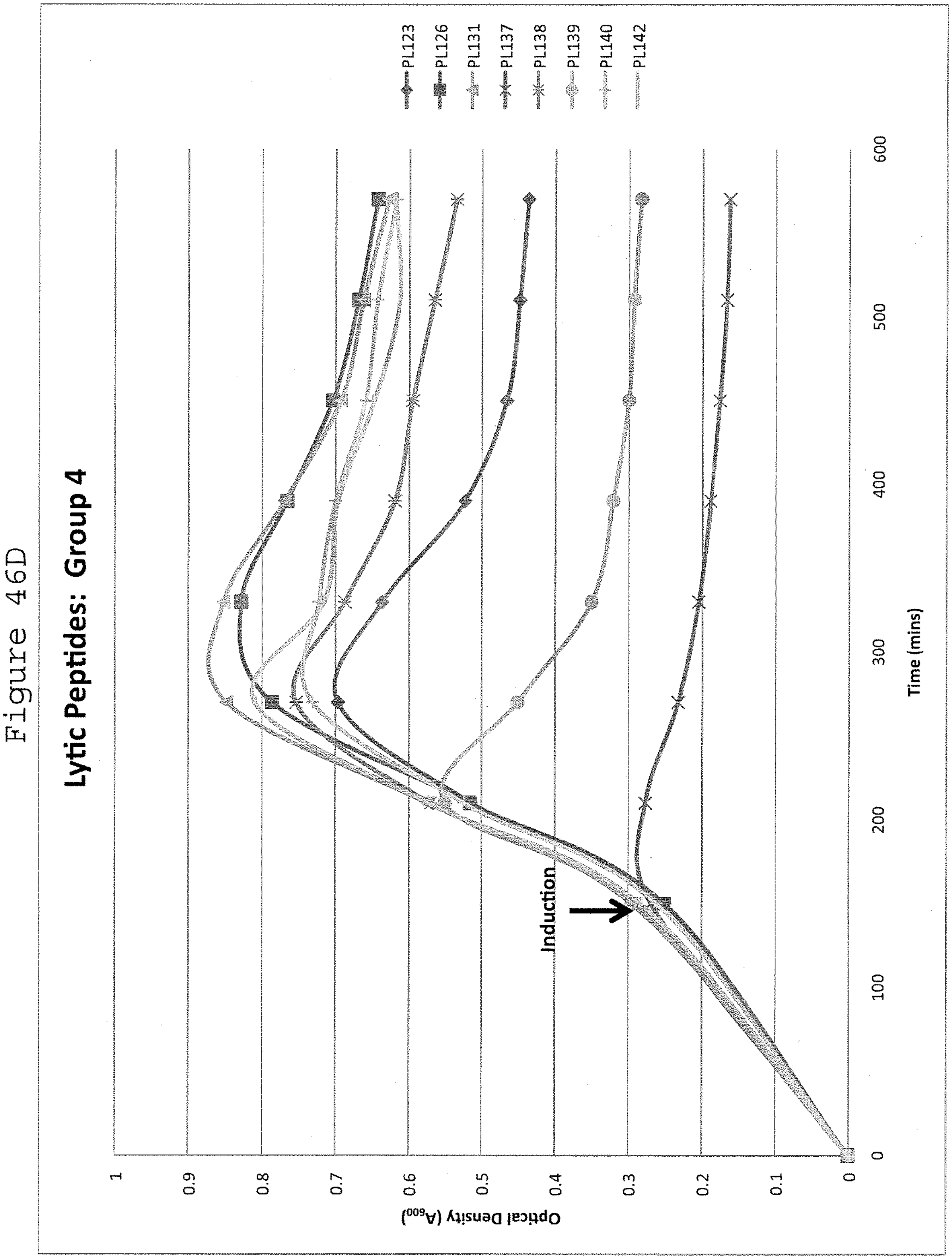
Figure 46E:
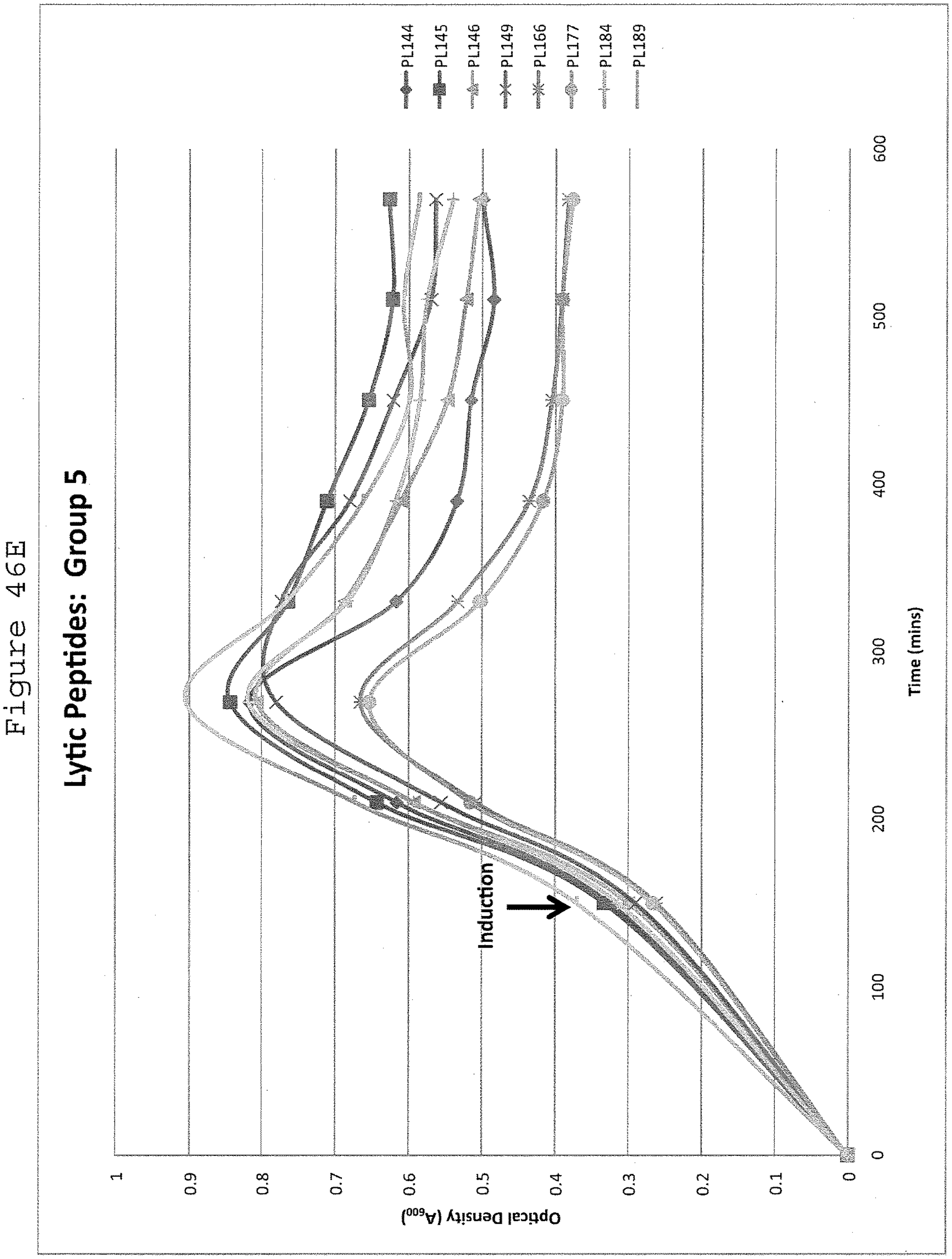
Figure 46F:
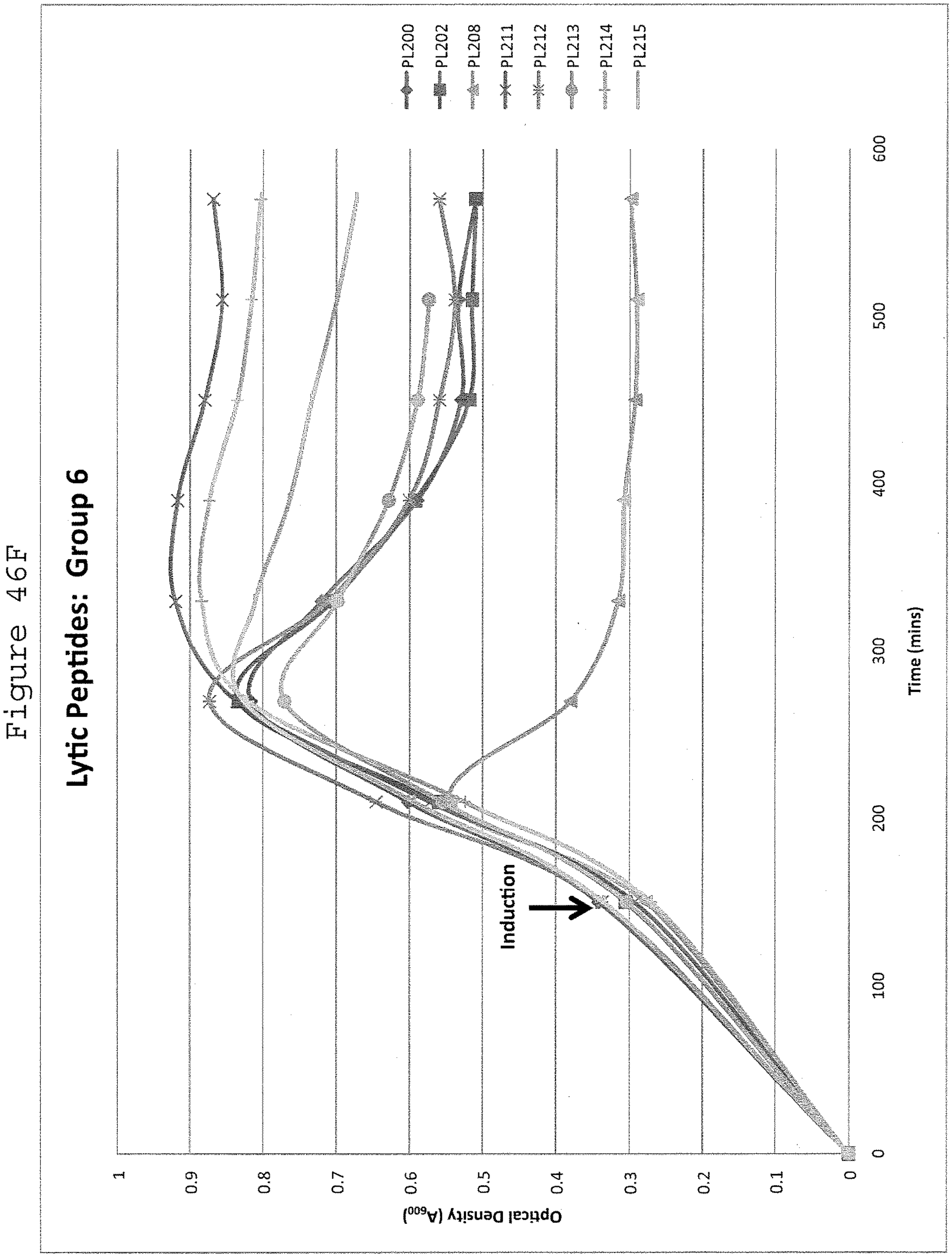
Figure 46G:
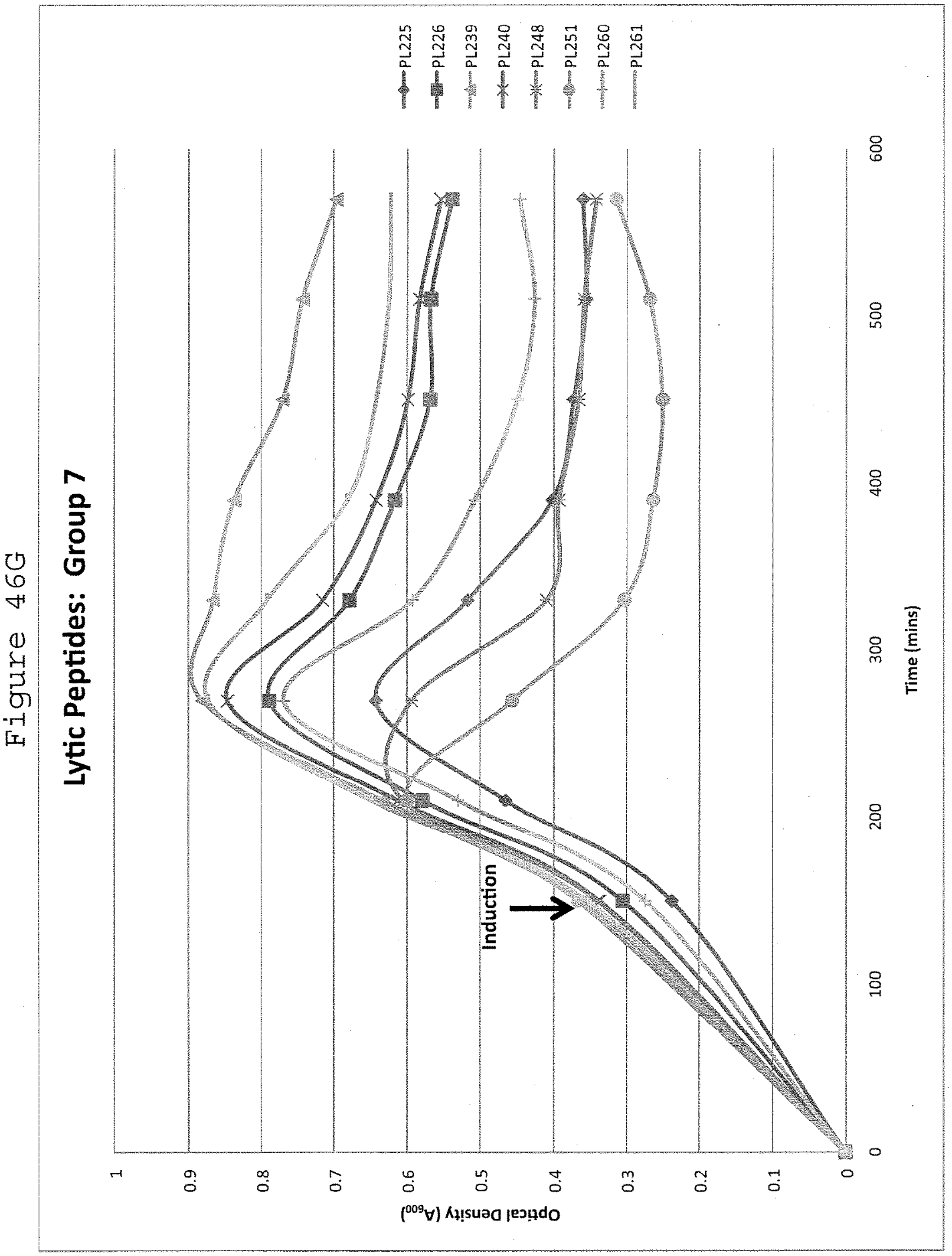
Figure 46H:
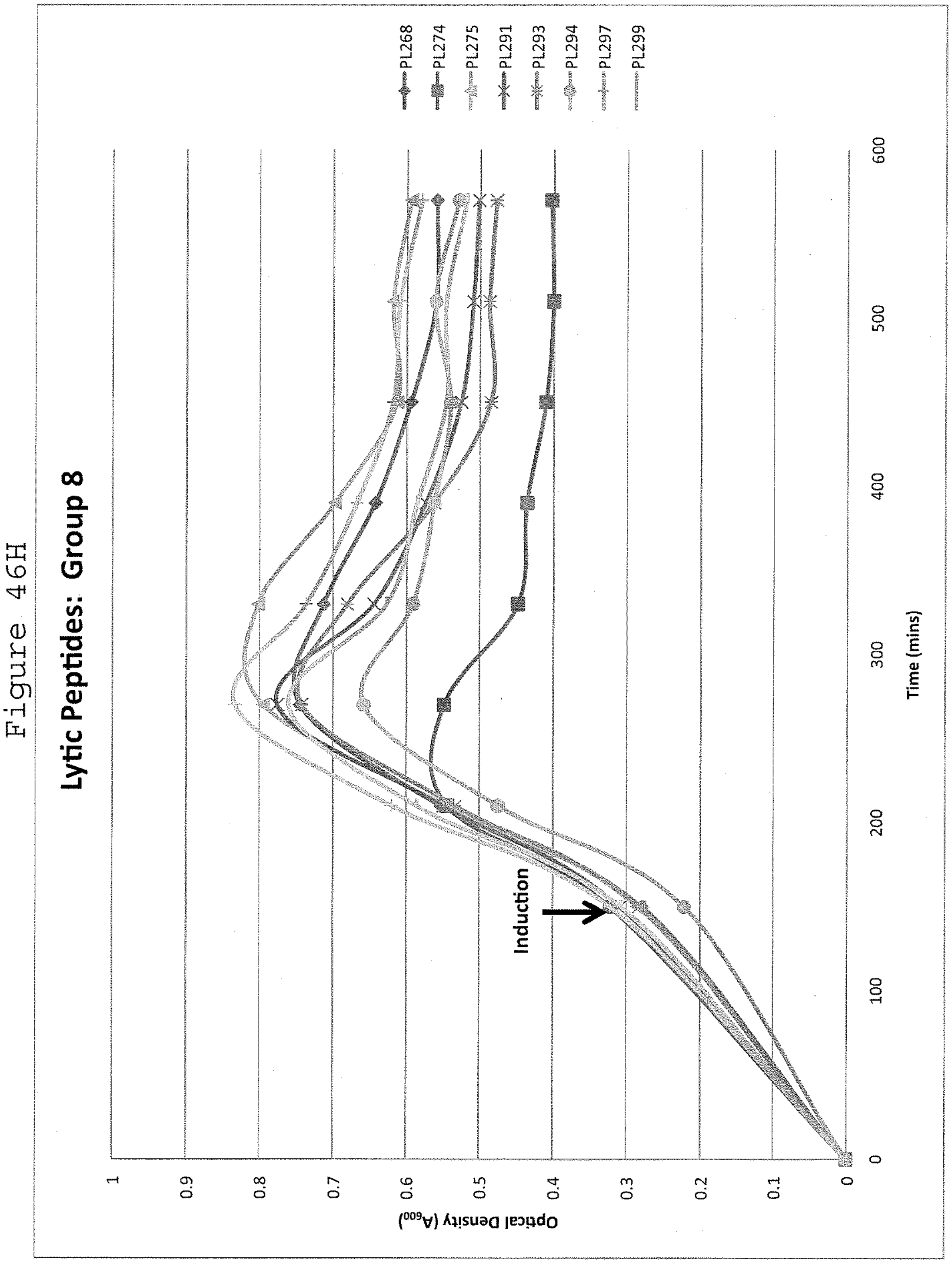
Figure 46I:
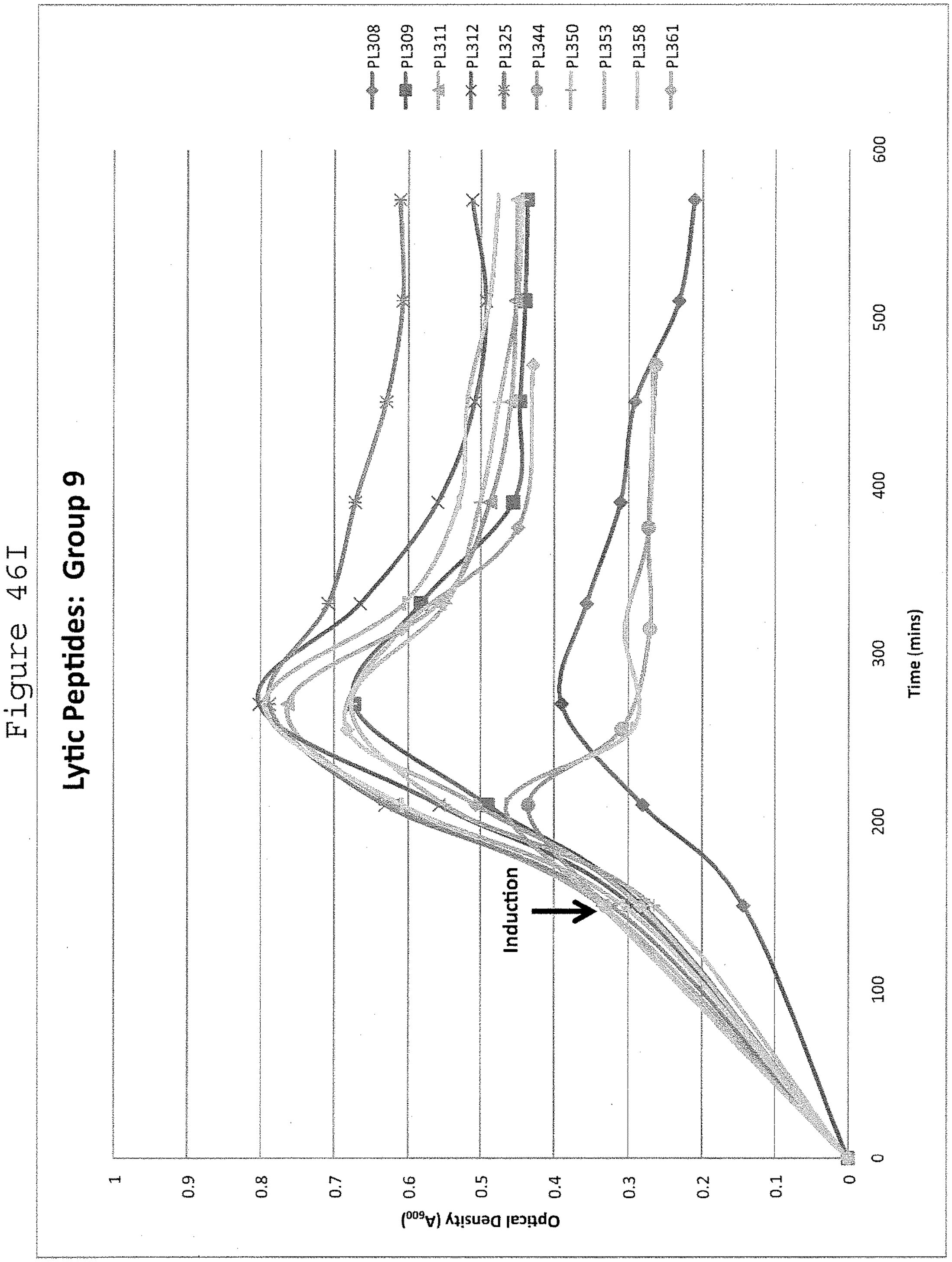
Figure 46J:
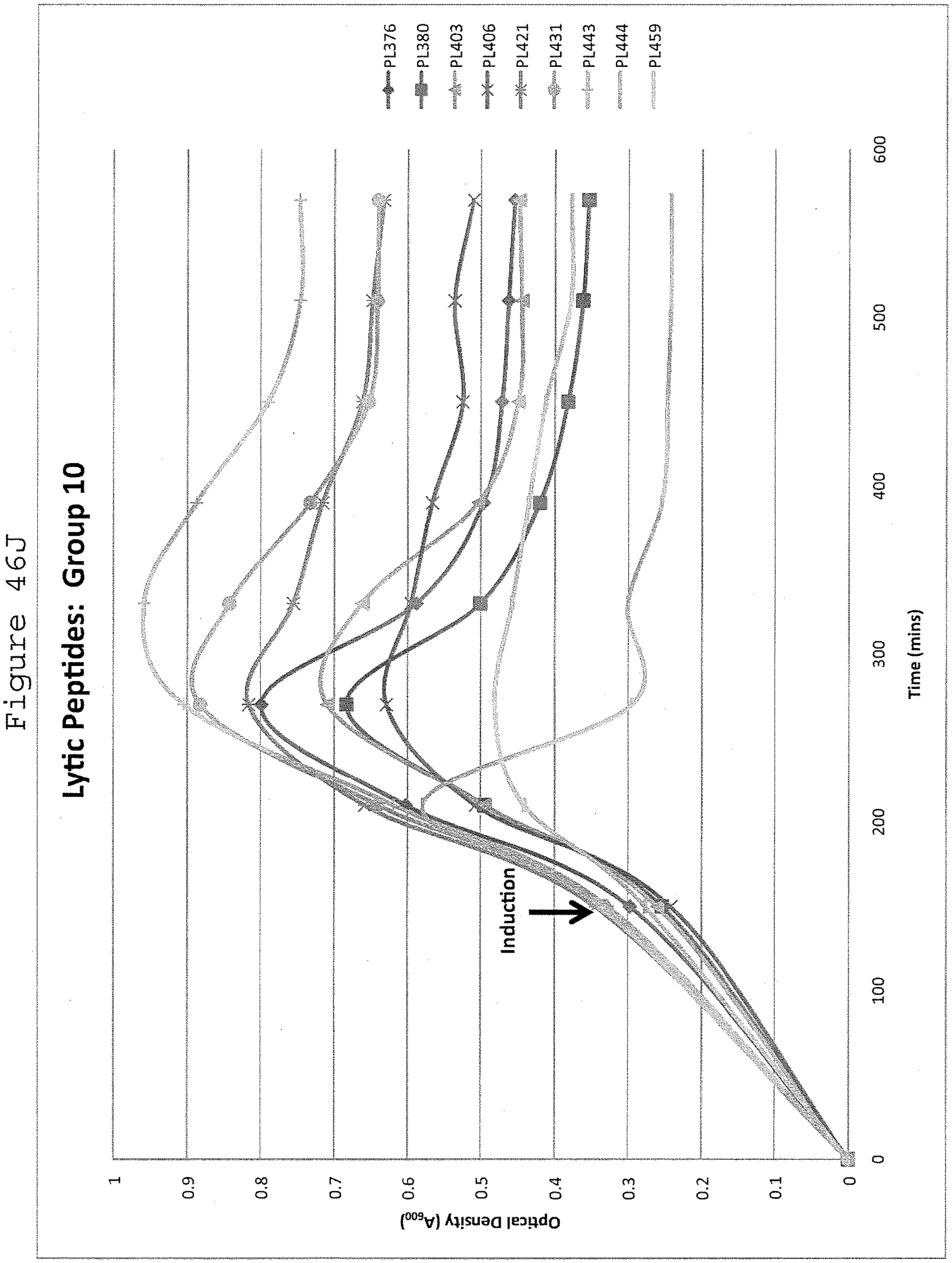
Figure 46K:
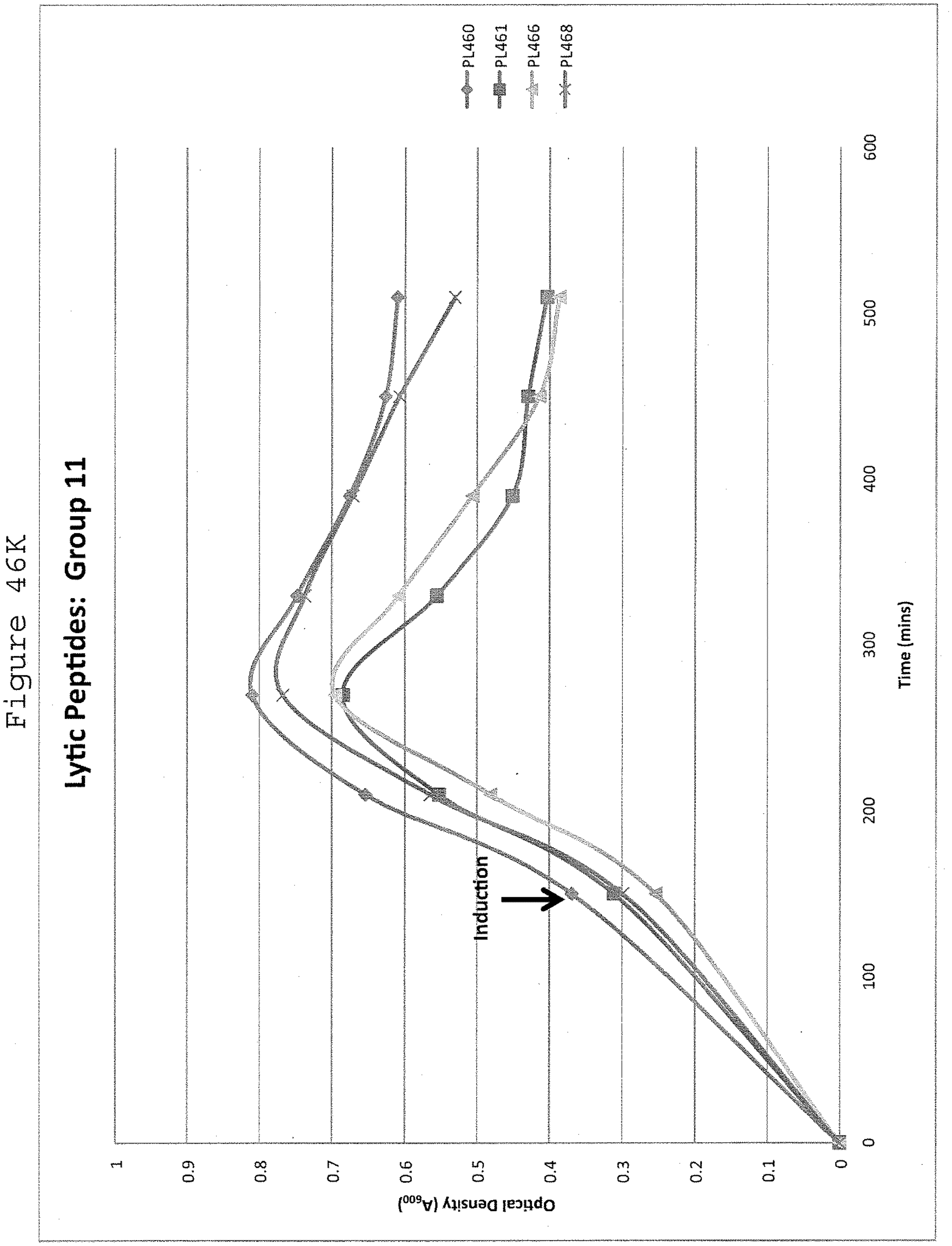
Figure 46L:
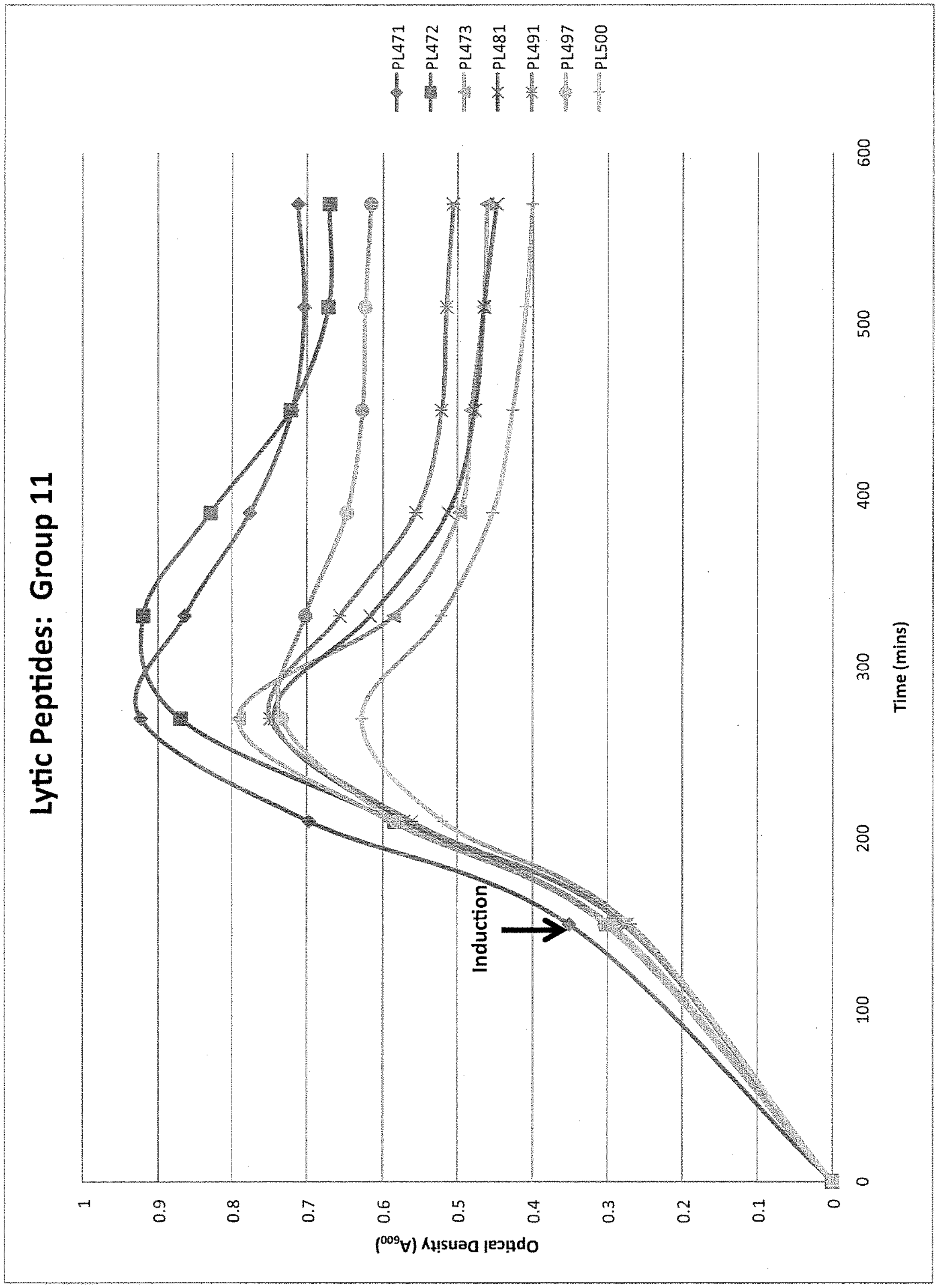
Figure 47A:
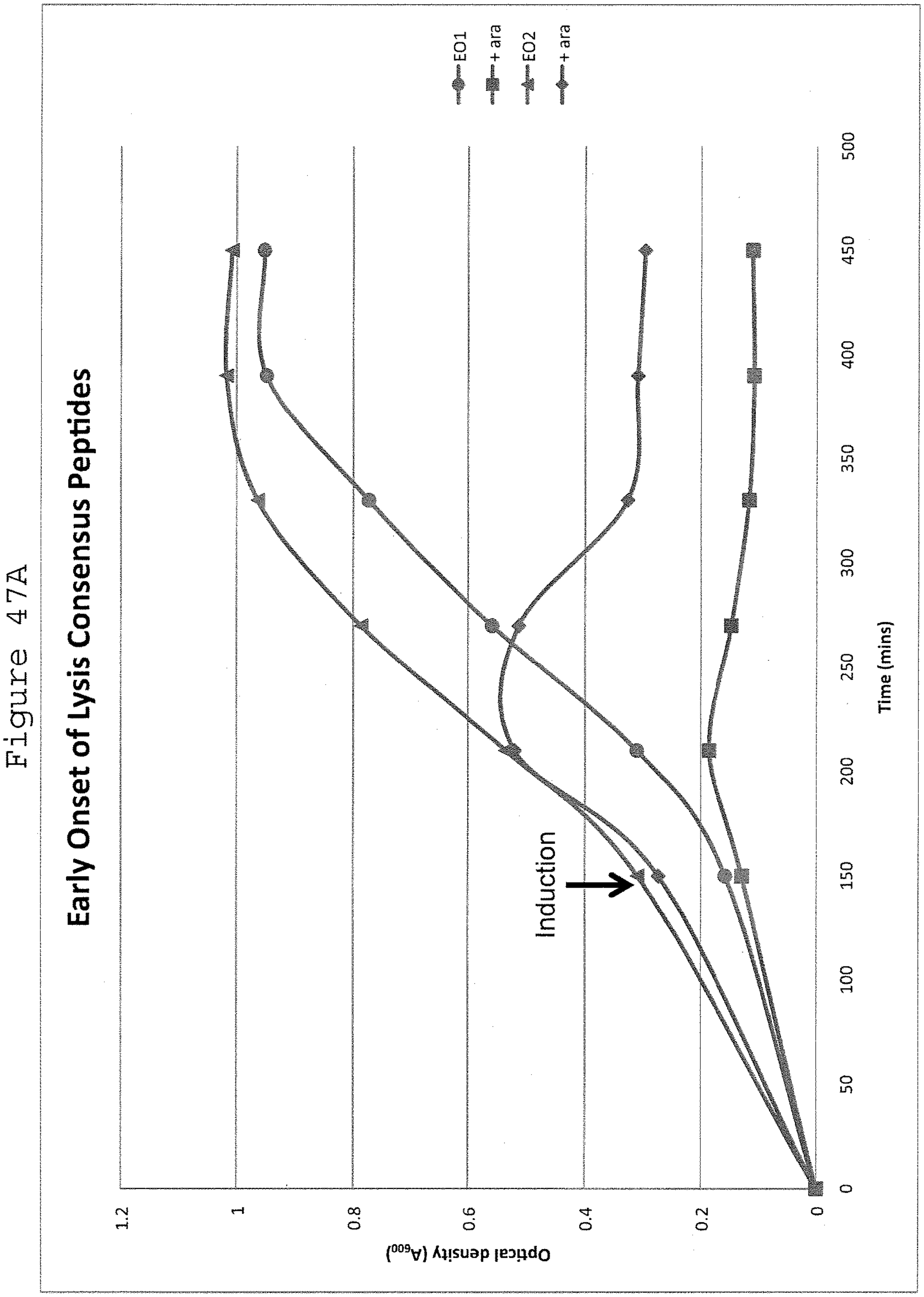
FIGS. 47A-C show growth curve profiles of bacteria expressing consensus peptides derived from the initial bacteriolytic isolates of the periplasmic screen.
Figure 47B:
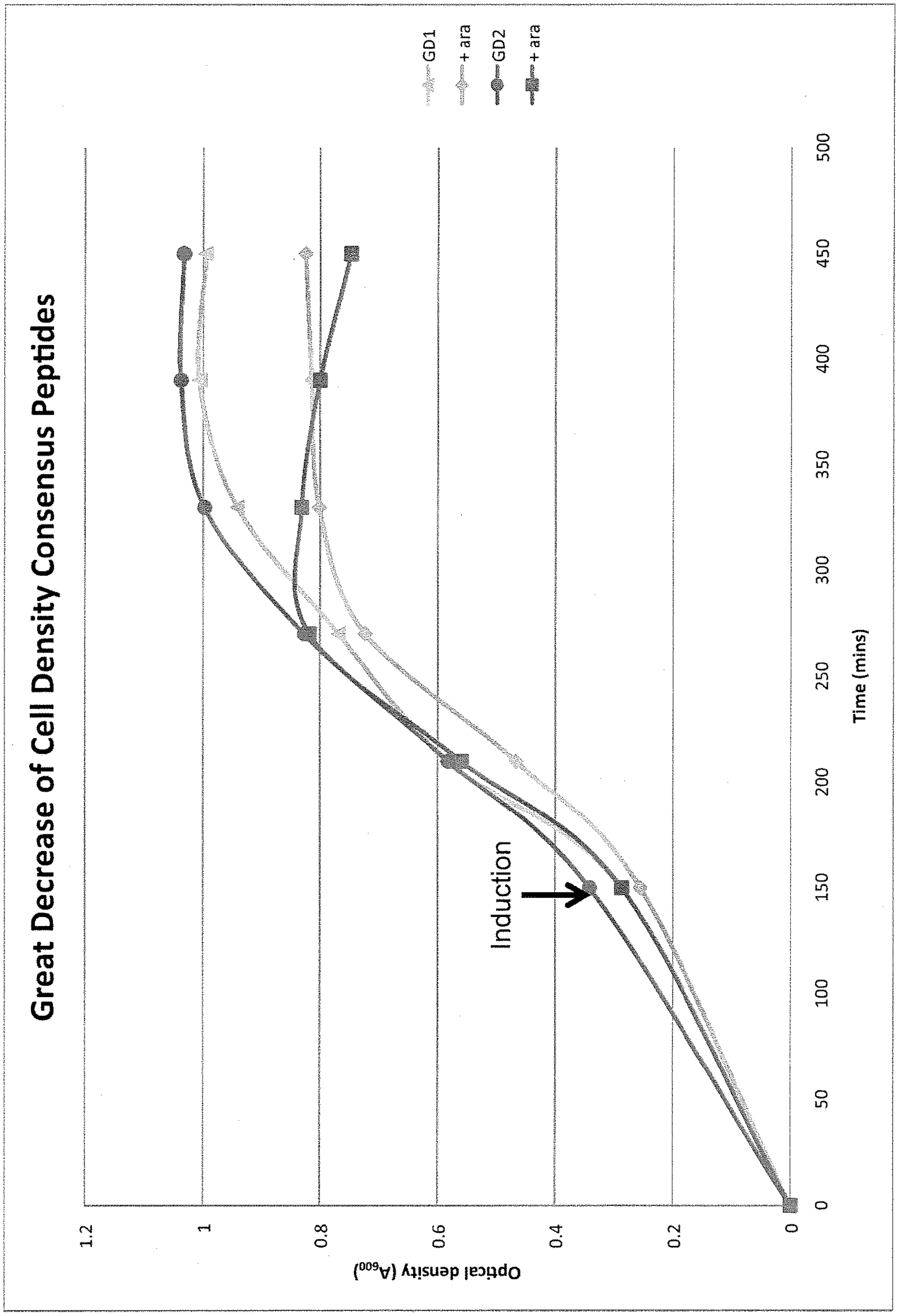
Figure 47C:
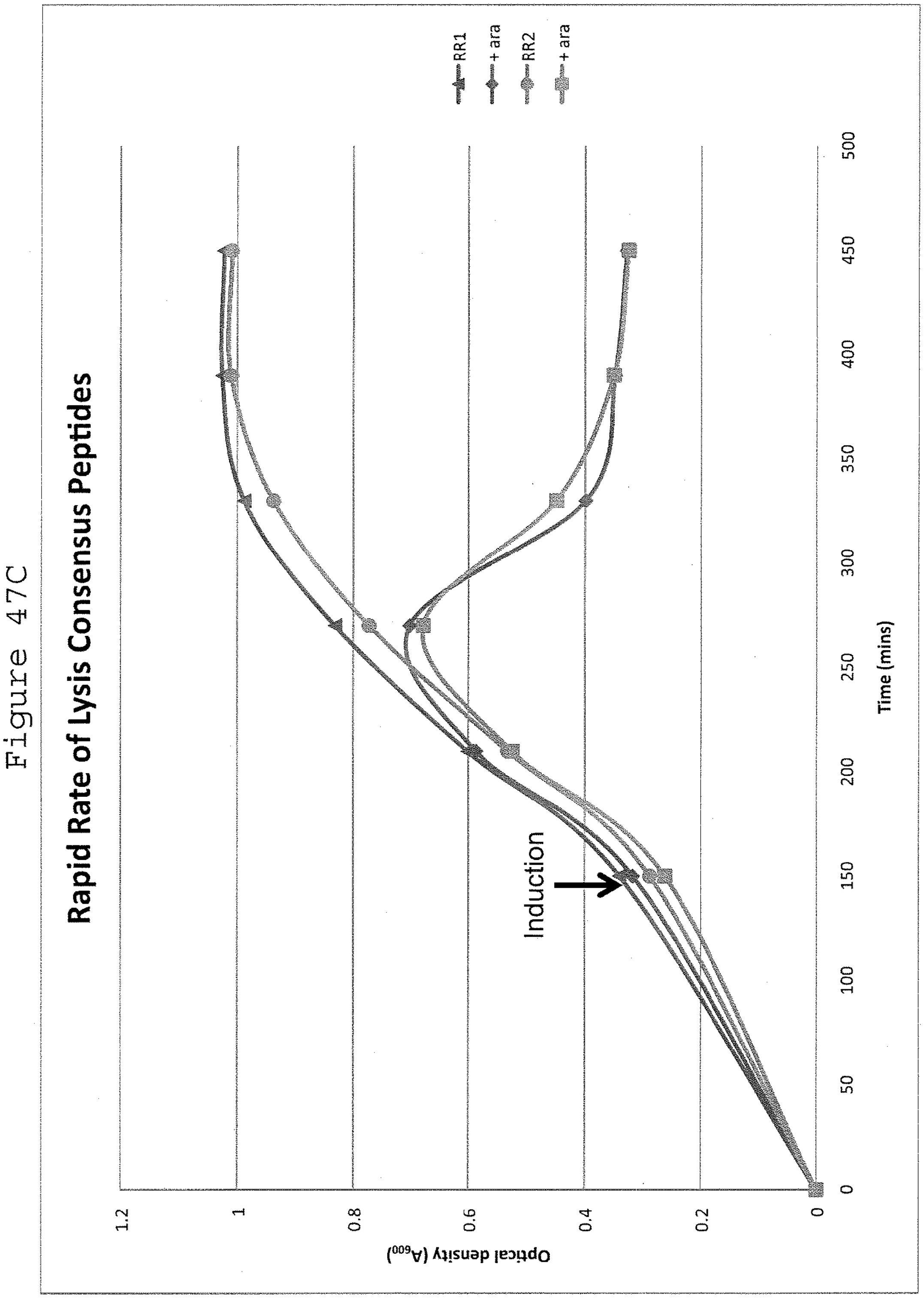
Figure 48A:
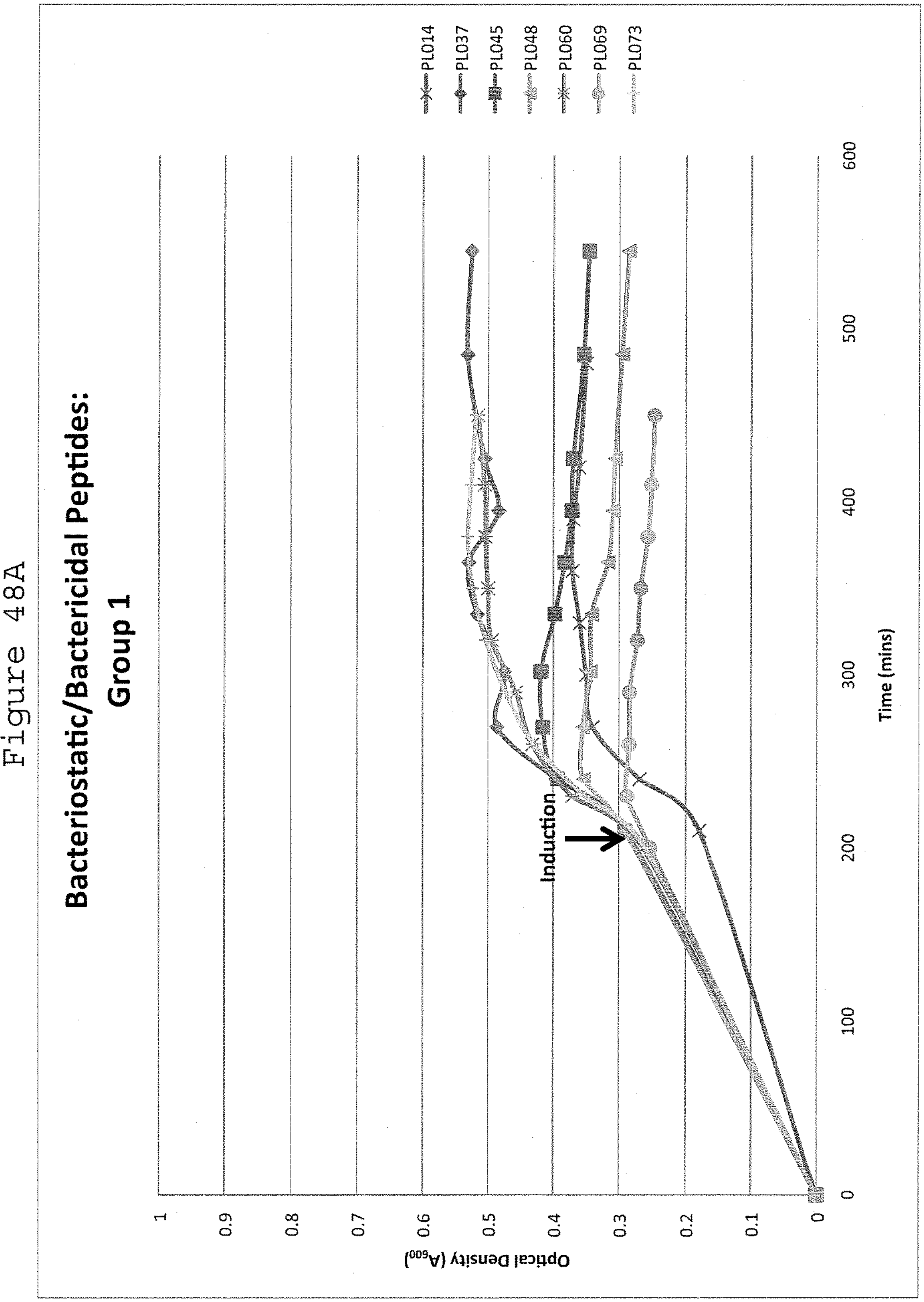
FIGS. 48A-I show growth curve profiles of bacteria expressing bacteriostatic and bactericidal peptide antimicrobials identified using N-terminal constructs in the periplasm.
Figure 48B:
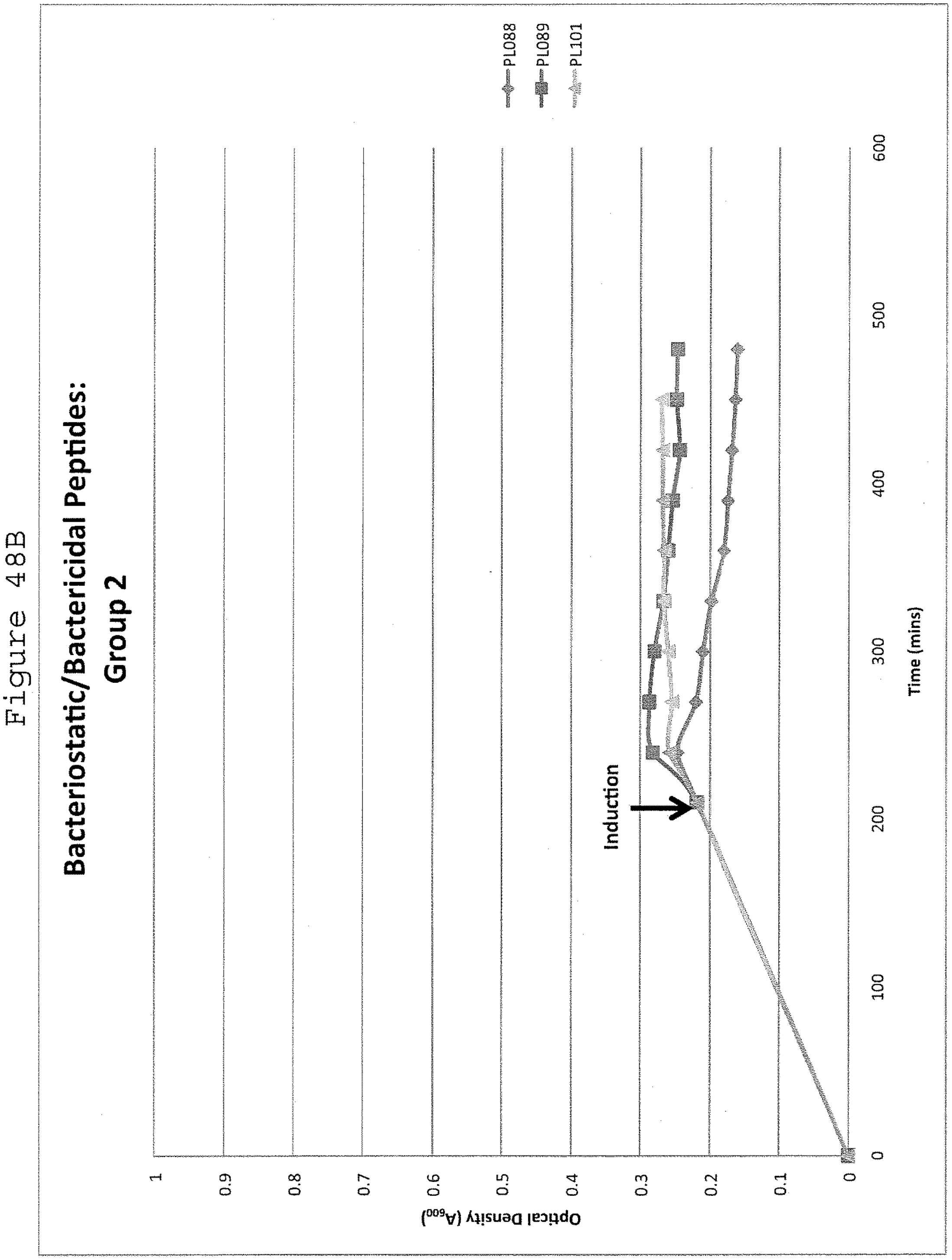
Figure 48C:
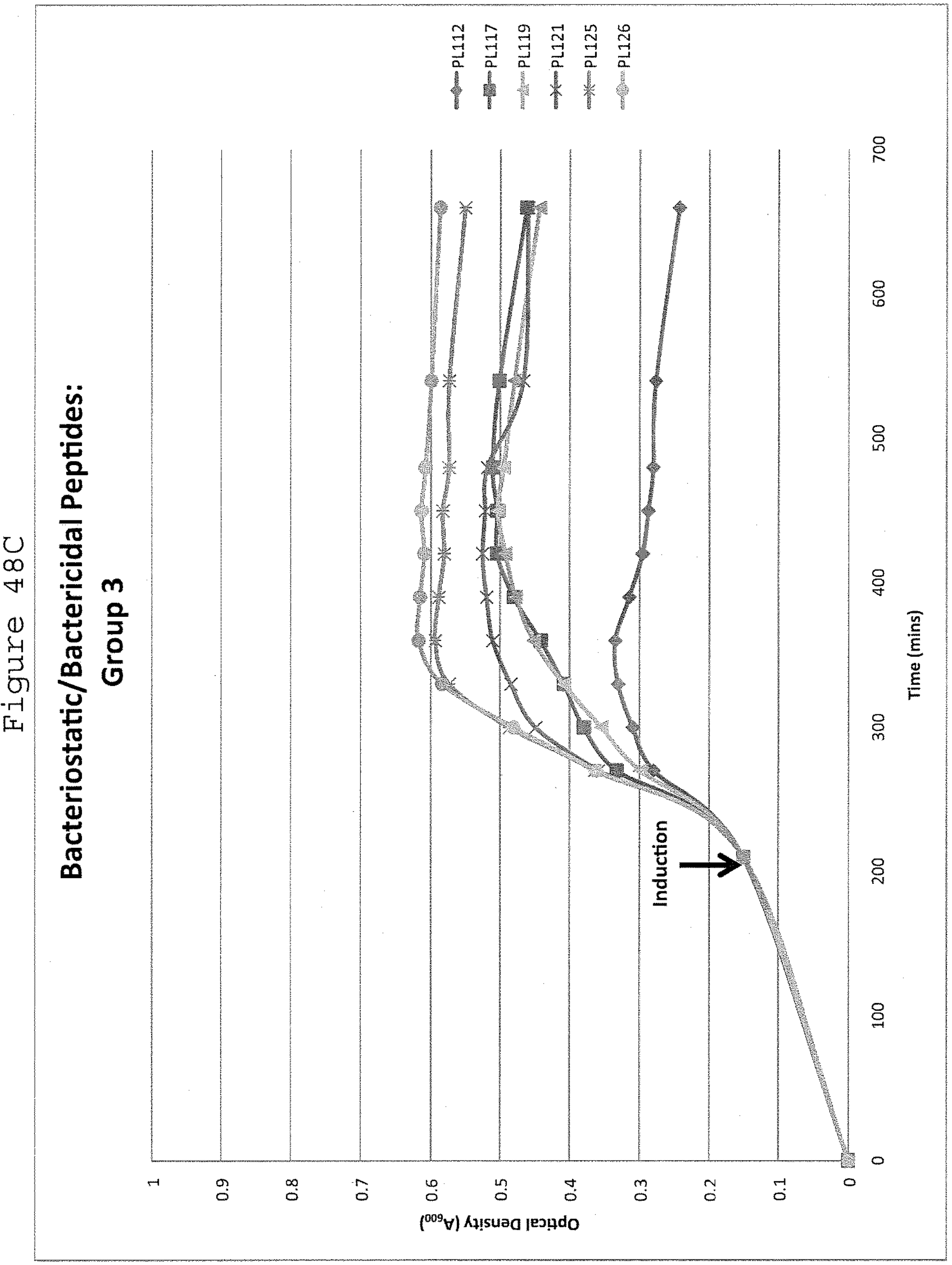
Figure 48D:
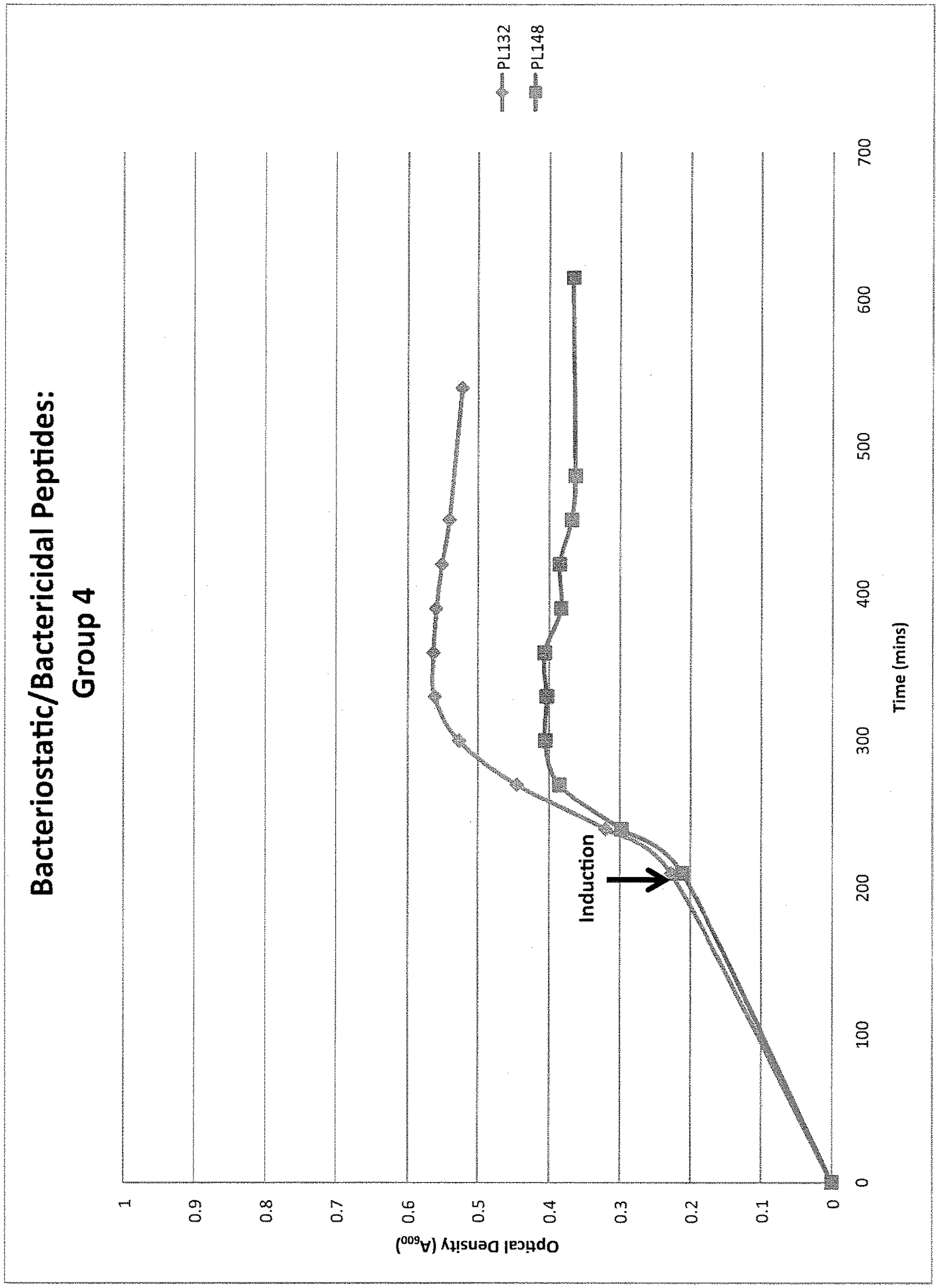
Figure 48E:
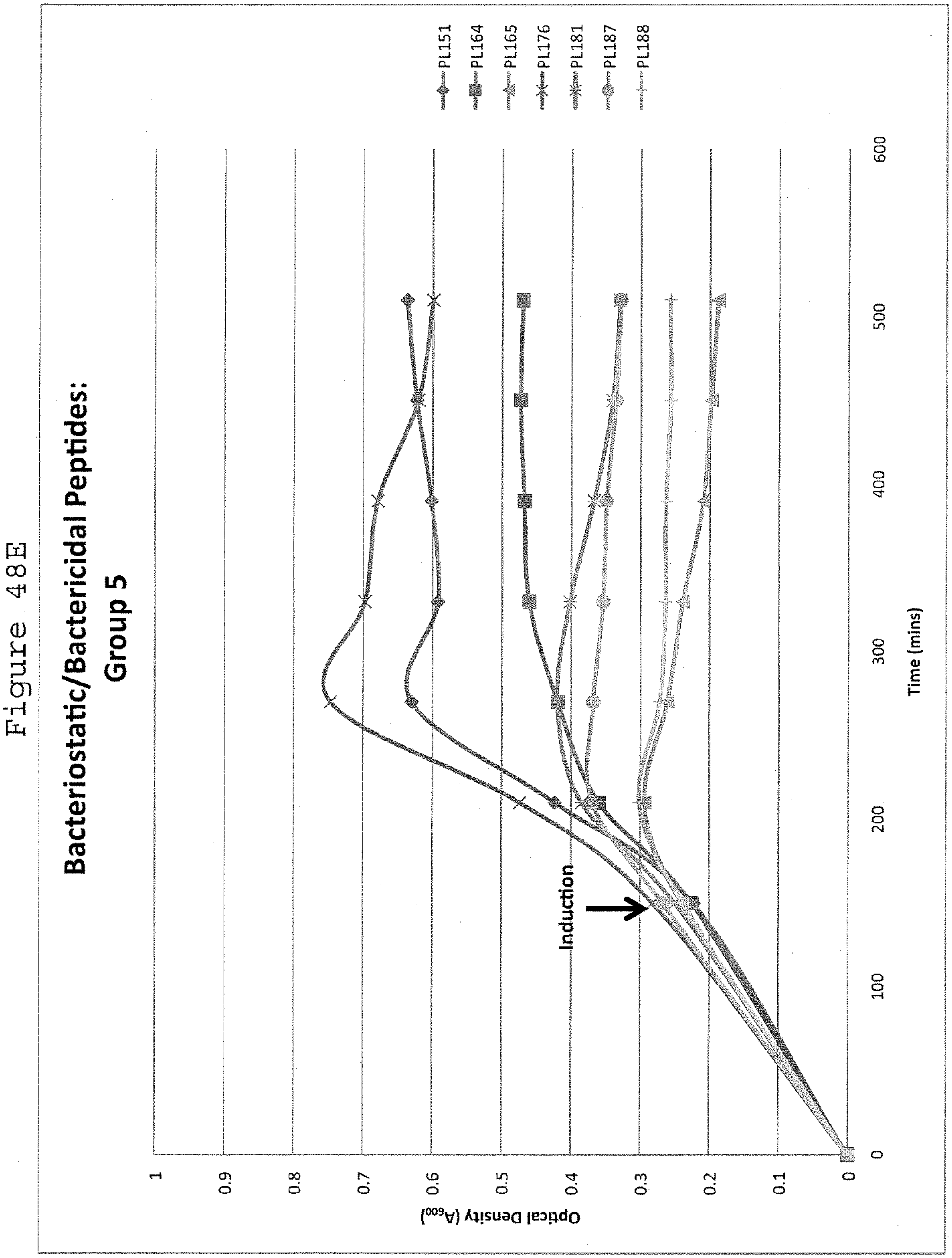
Figure 48F:
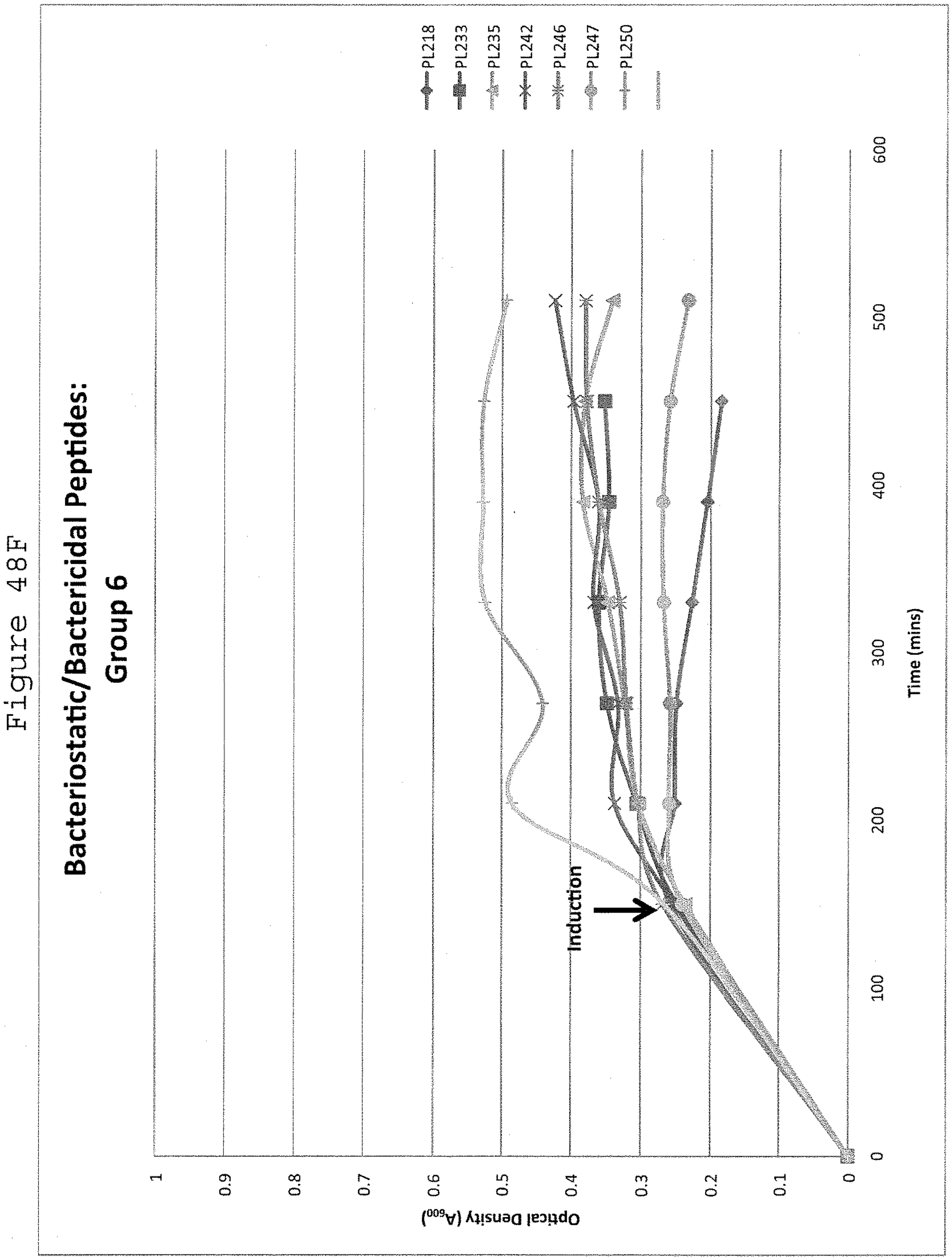
Figure 48G:
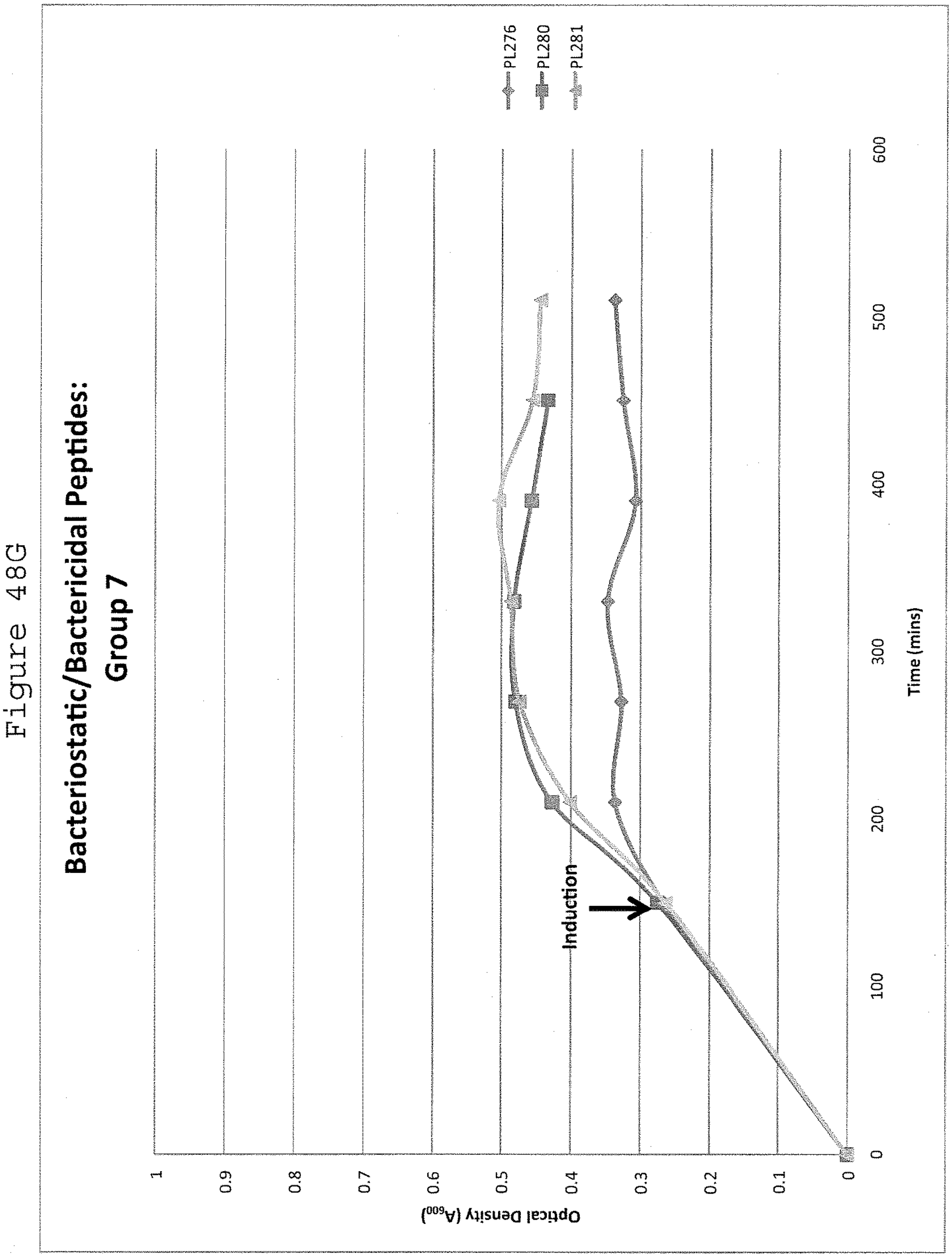
Figure 48H:
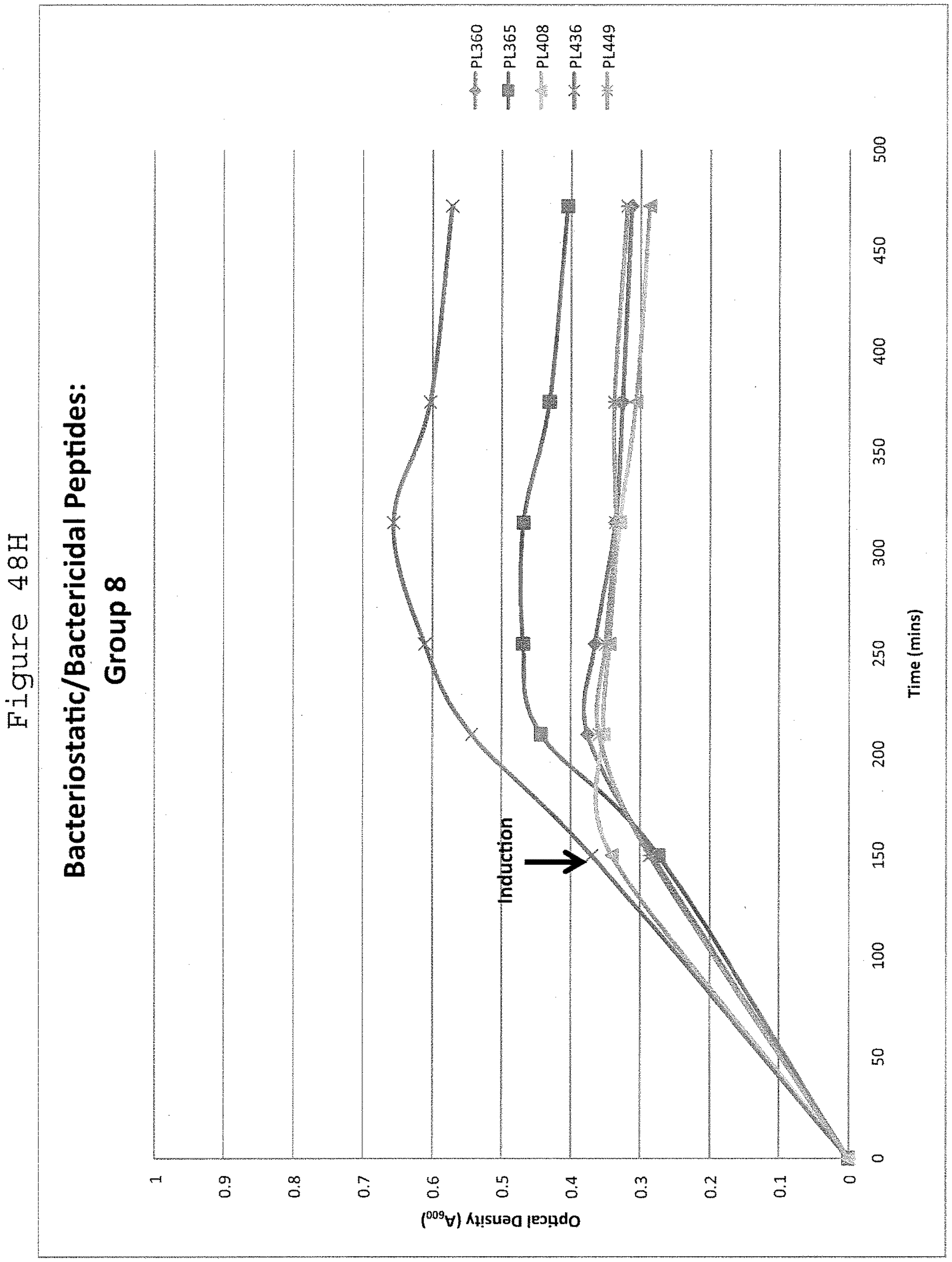
Figure 48I:
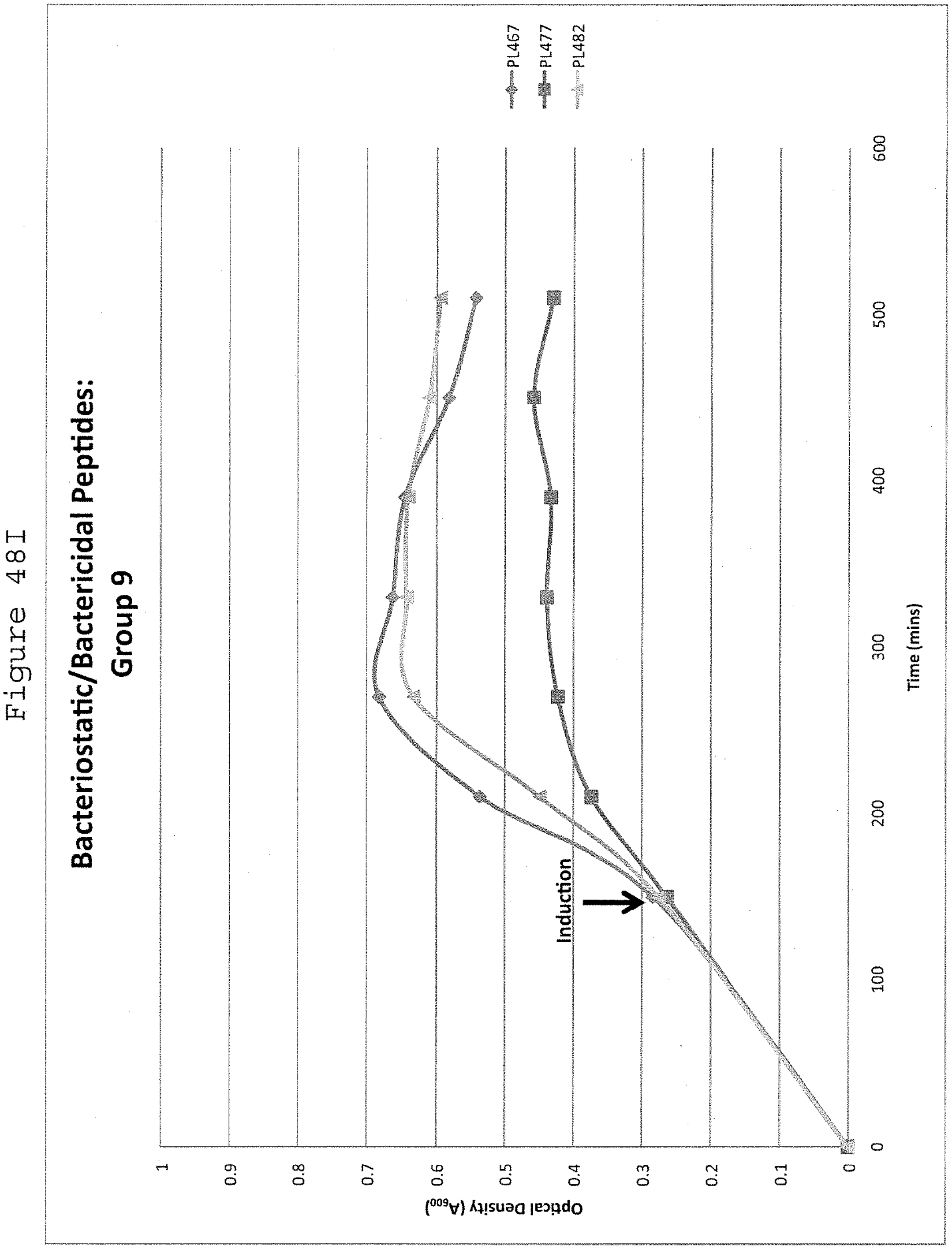
Figure 49A:
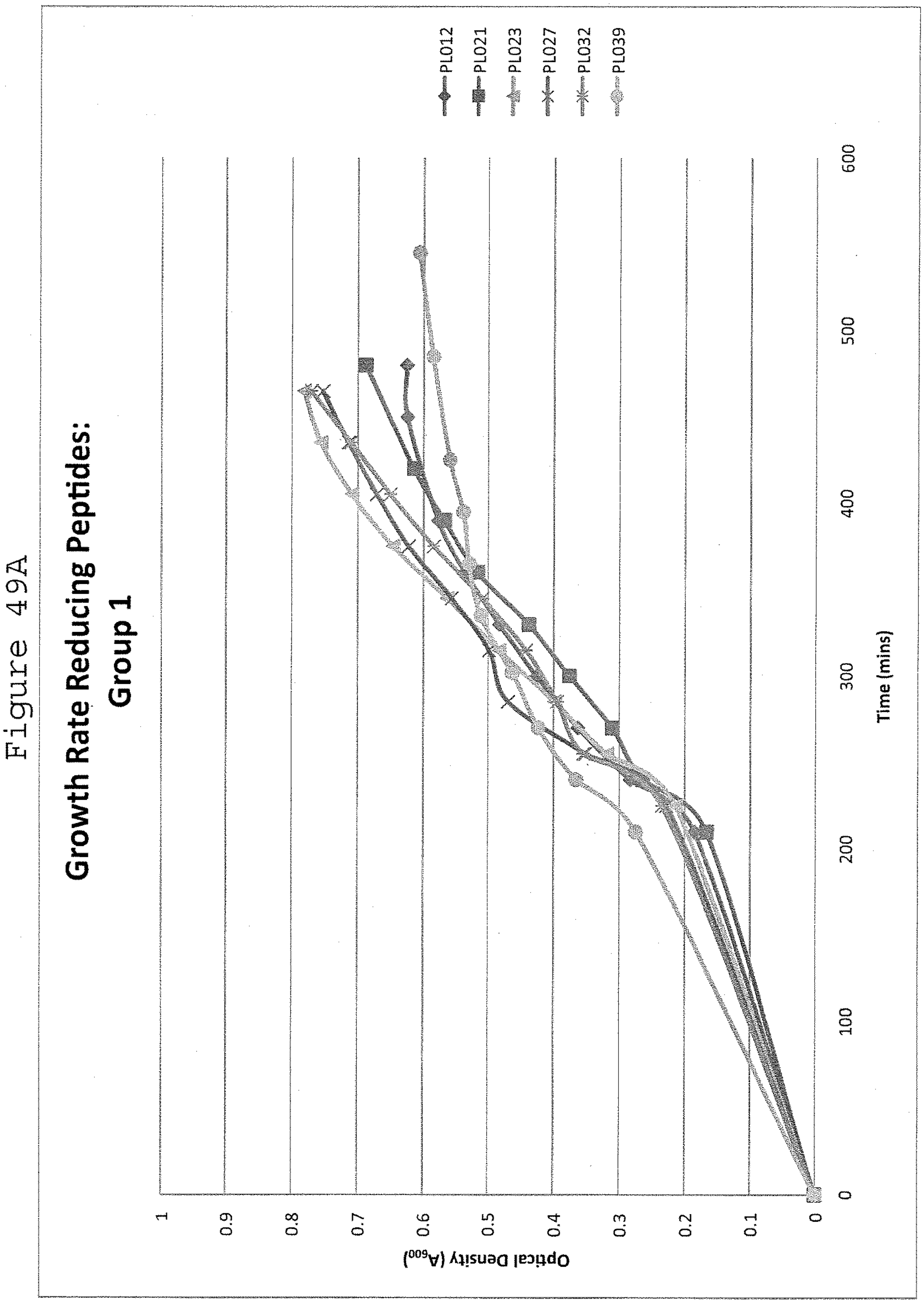
FIGS. 49A-F show growth curve profiles of bacteria expressing growth rate reducing peptide antimicrobials identified using N-terminal constructs.
Figure 49B:
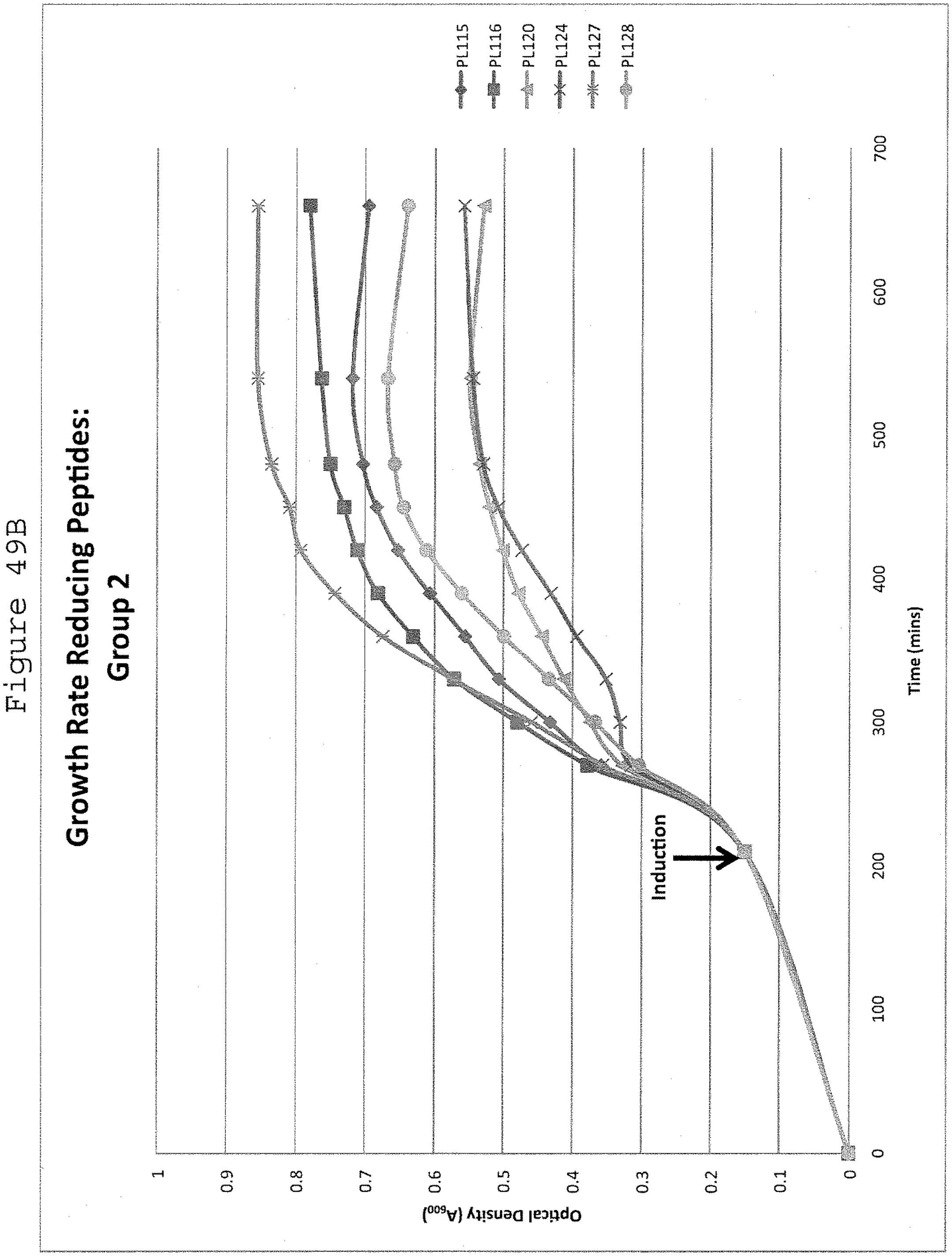
Figure 49C:
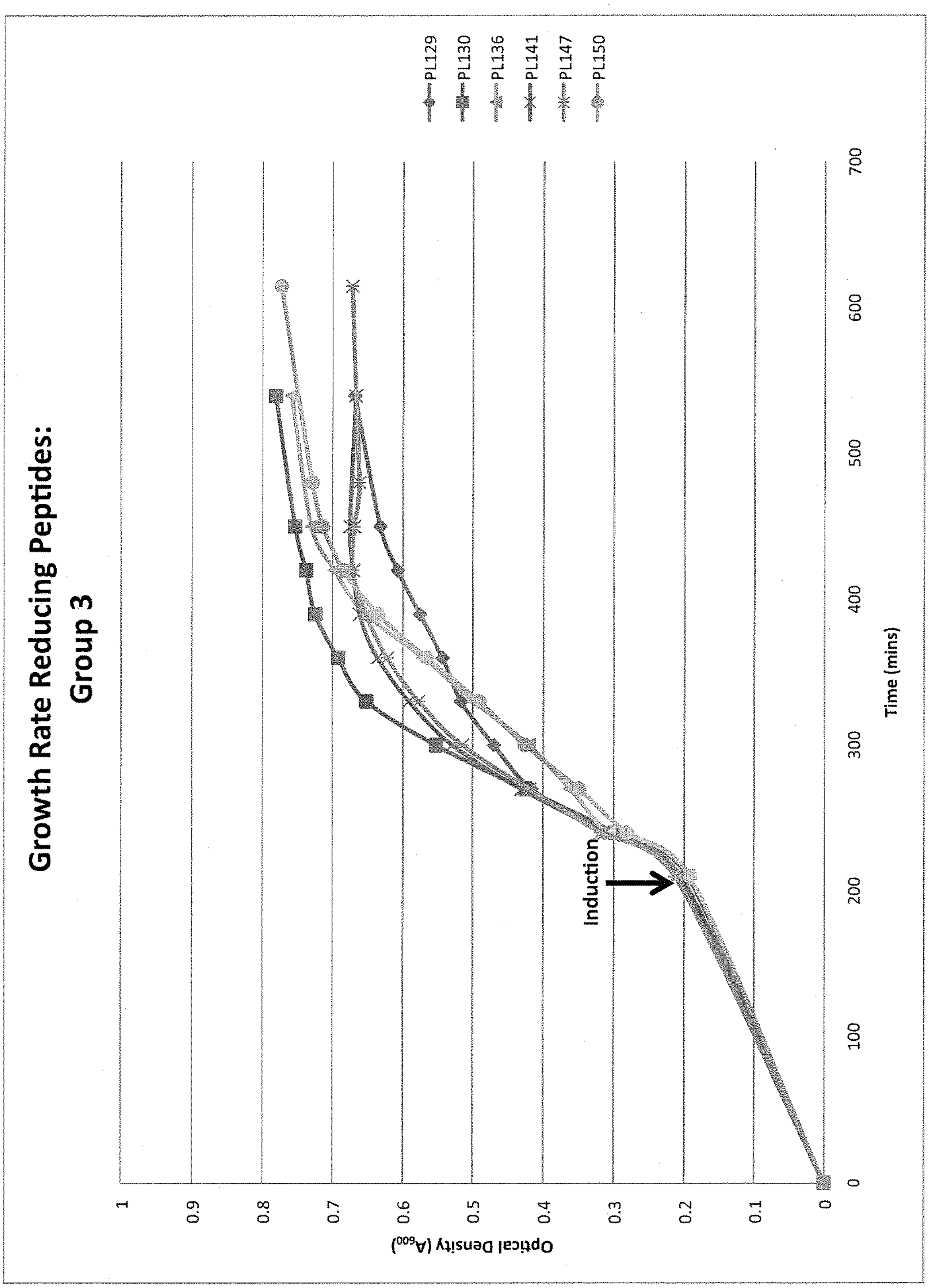
Figure 49D:
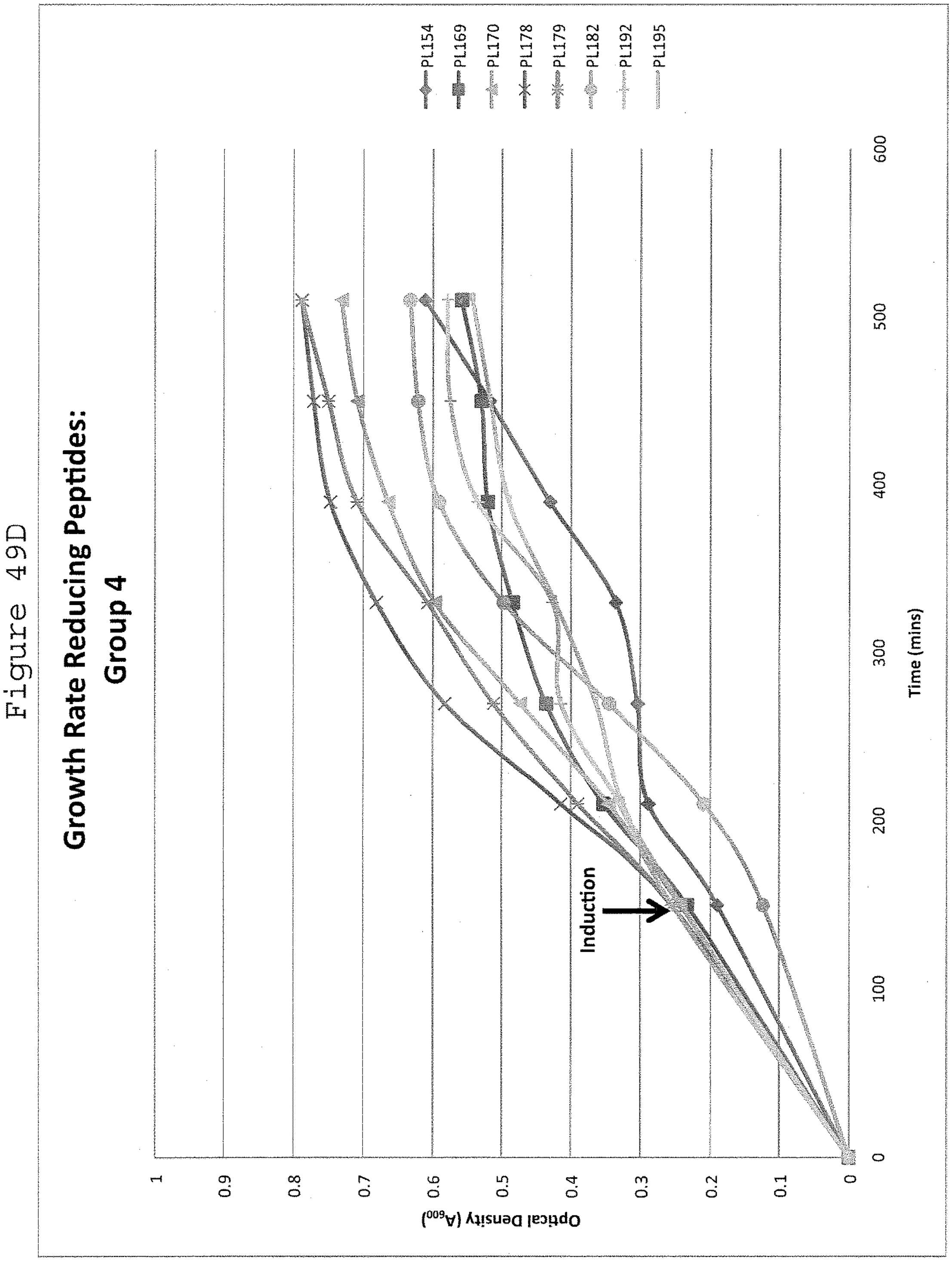
Figure 49E:
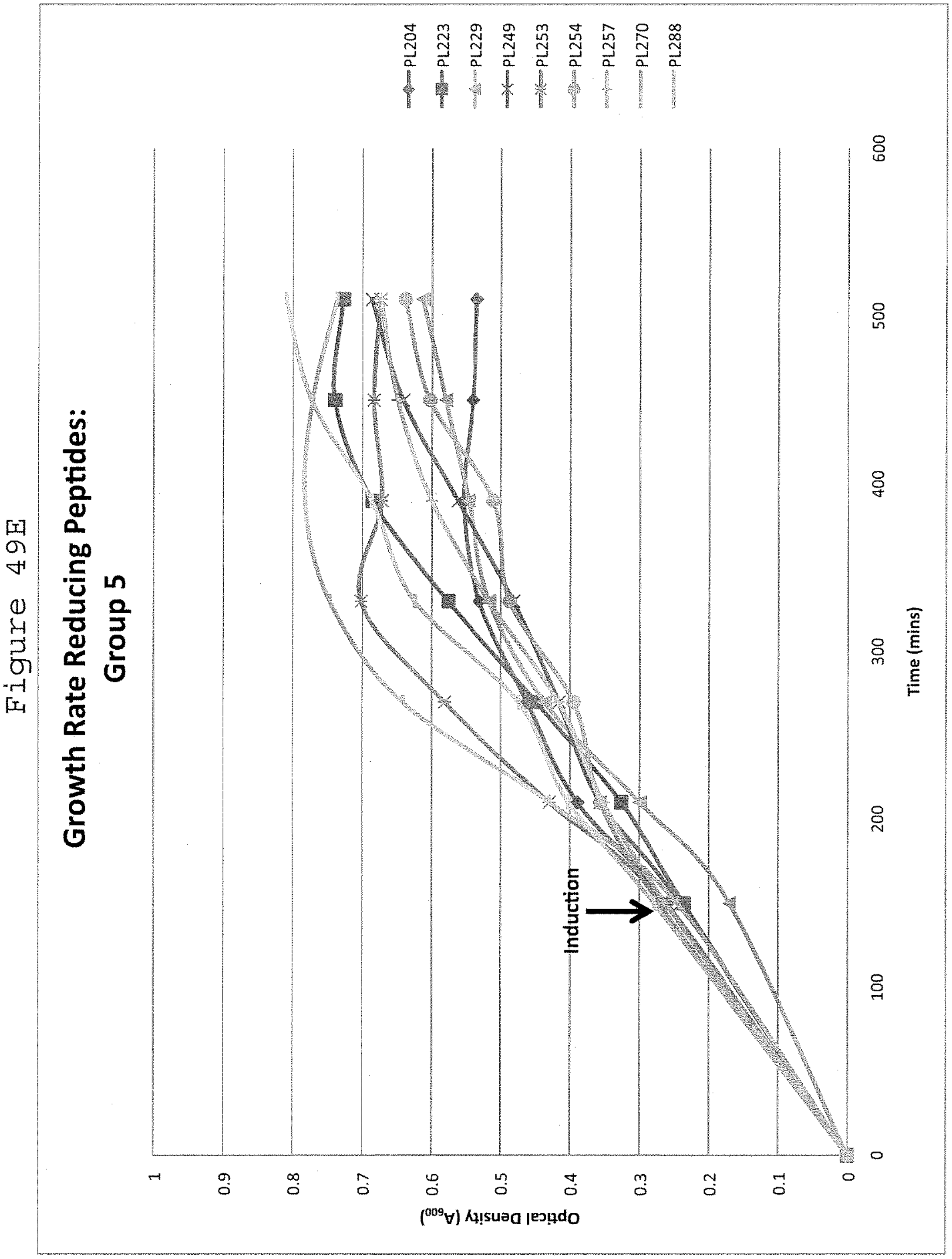
Figure 49F:
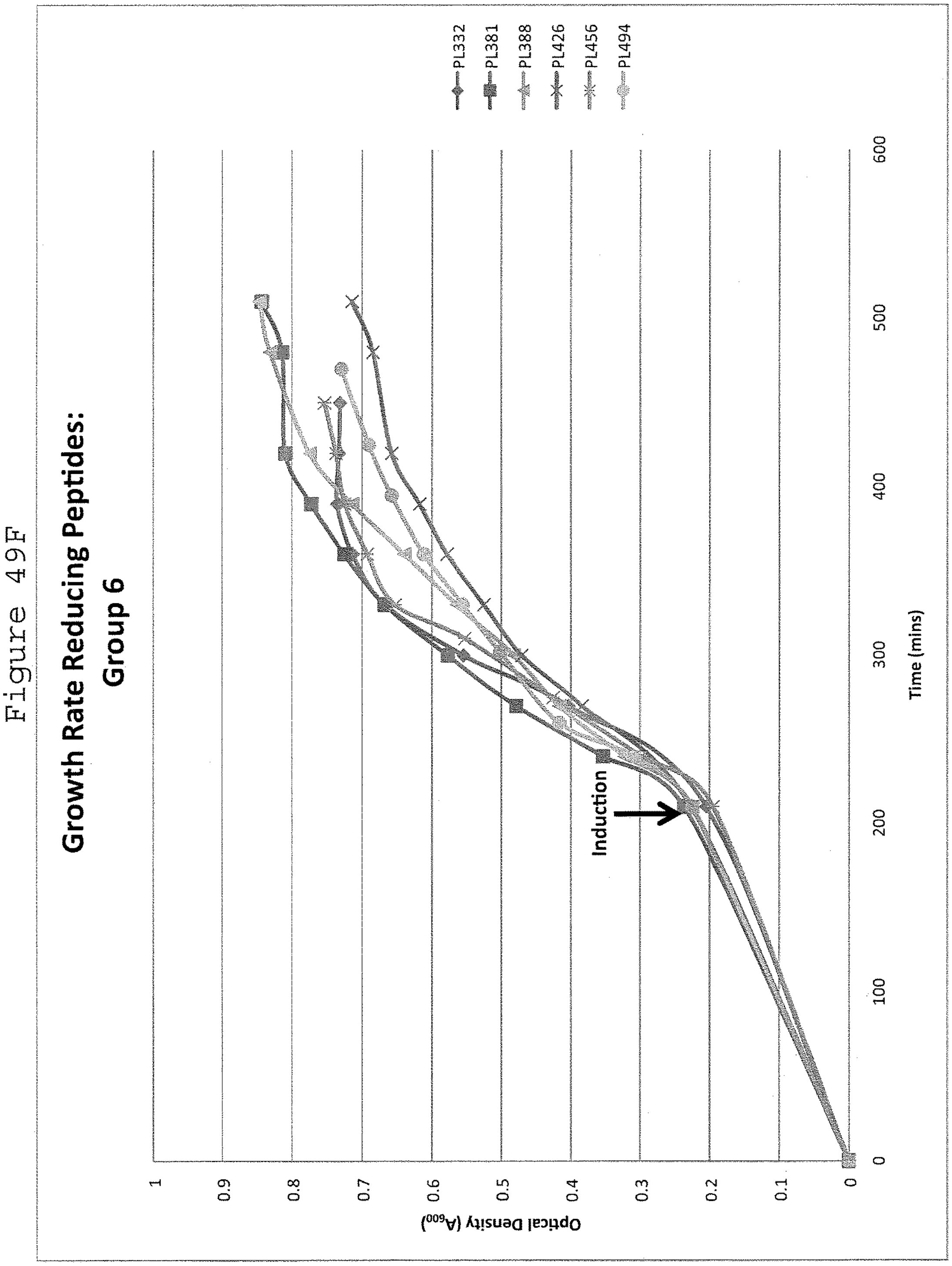
Figure 50A:
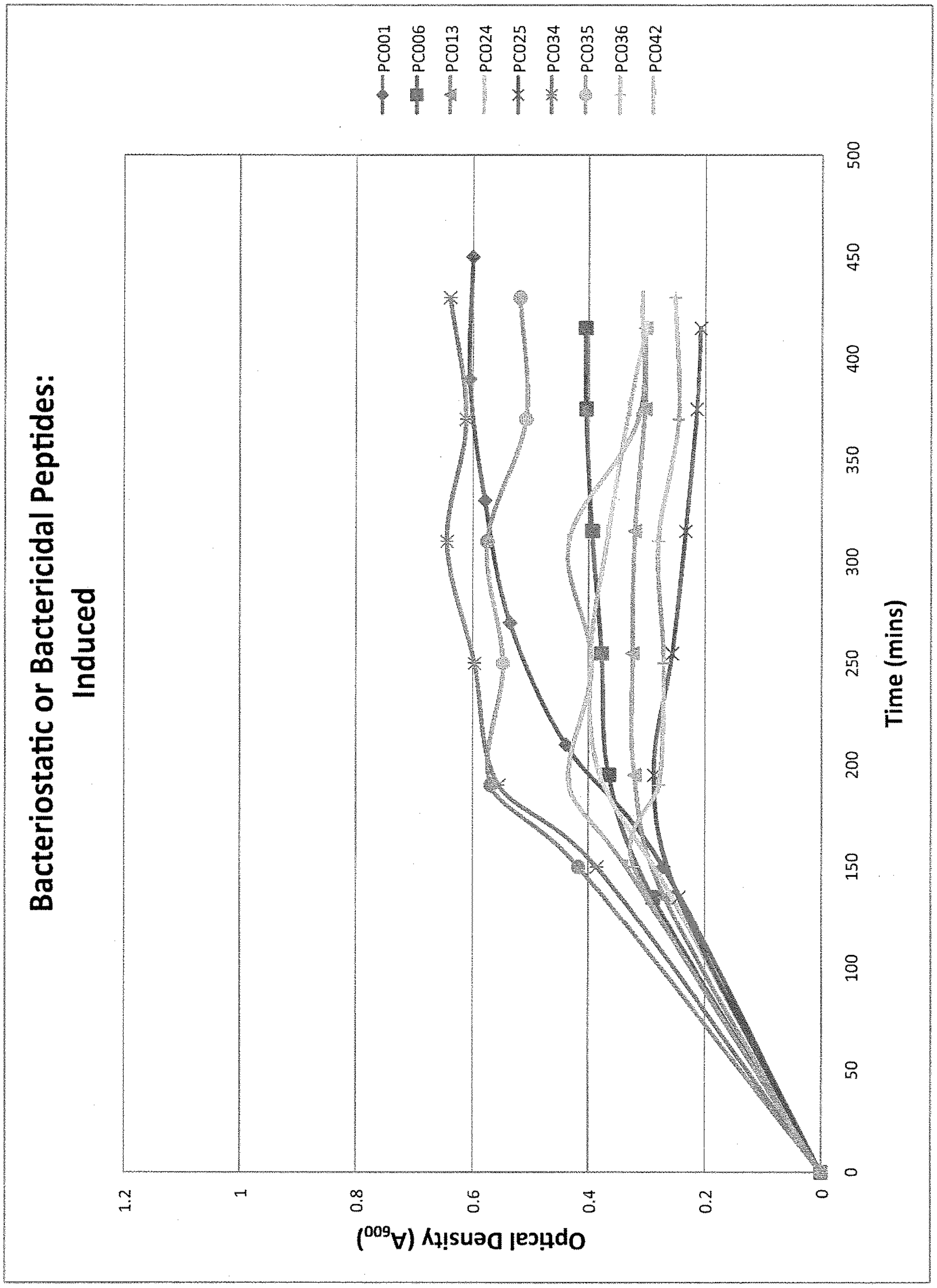
FIGS. 50A-B show growth curve profiles of bacteria expressing bacteriostatic and bactericidal peptide antimicrobials identified using N-terminal constructs in the periplasm.
Figure 50B:
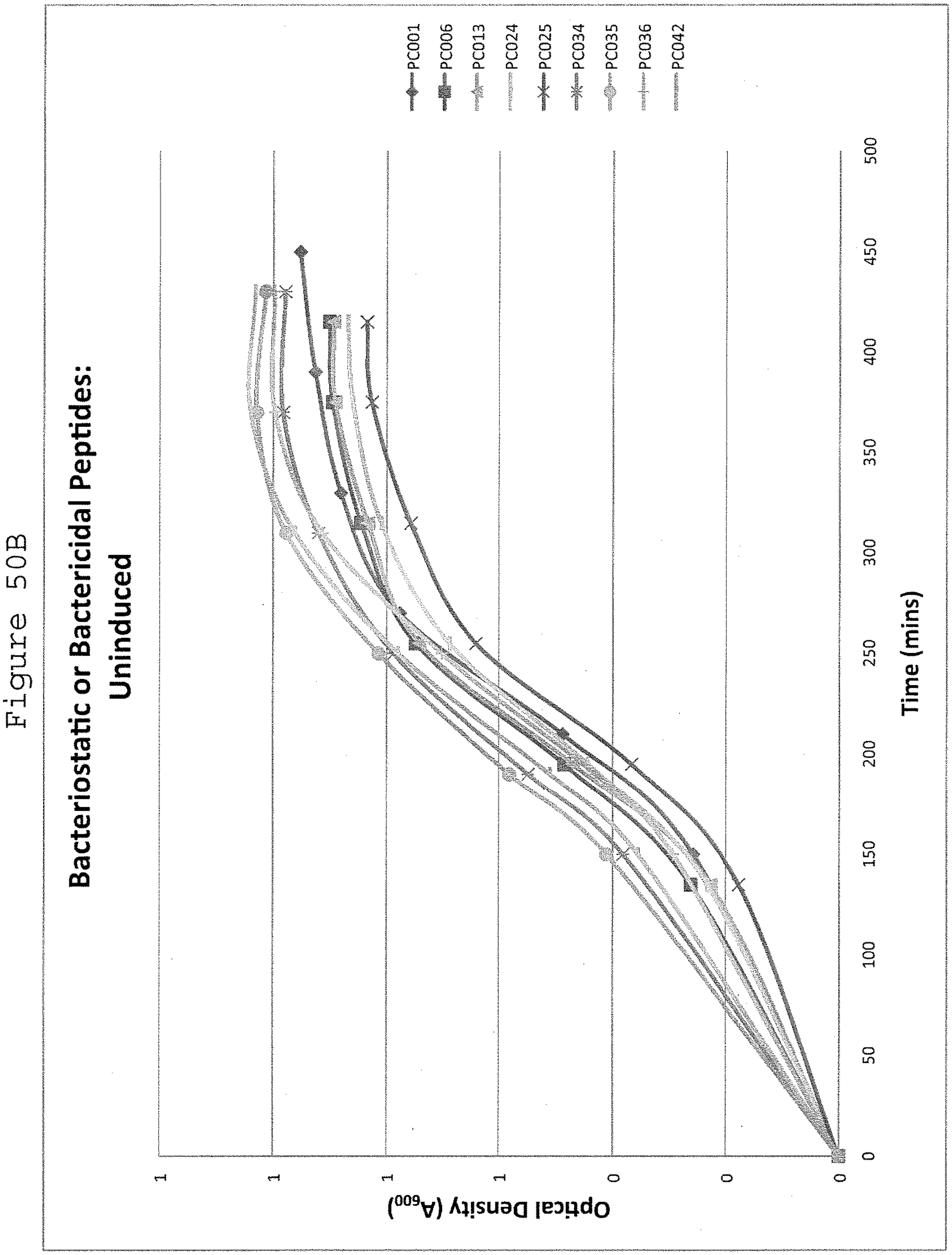

Growth curve induction profiles (see FIG. 12, left side). Pure cultures of *E. coli* EPI301 harboring each of the plasmids encoding inhibitory peptides were grown overnight, used to inoculate LB medium and growth of the cultures was monitored by measuring the optical density of the culture at λ=600 nm ($OD_{600}$). The resulting cultures were grown to early-, mid- or late-log phase and either ATC and L-arabinose (N-terminal peptides) or L-arabinose (C-terminal peptides) were added and the OD600 of each culture was followed. The phenotypes of the N-terminal peptides were consistent with peptides that strongly inhibited growth of the culture without lysing the cells (see FIG. 43). The C-terminal peptides all inhibited growth of the cultures but showed some differences in growth response following induction. Some of the C-terminal peptides lysed the cells while others only slowed the growth rate (see FIGS. 44A-C) and others blocked the growth of the culture (FIGS. 45A-D).

Sequence analysis (FIG. 12, right side). The amino acid sequence of each of the inhibitory peptides isolated in the cytoplasmic screen was determined by sequencing the region on the plasmids containing the randomized peptide sequence. The amino acid sequences of the N-terminal peptides is shown in FIG. 27 and the amino acid sequences of the C-terminal weakly inhibitory and bacteriolytic peptides are shown in FIG. 28 and the amino acid sequences of the strongly inhibitory peptides are shown in FIG. 29.

Example 9

Identification of Antimicrobial Peptides Using the Periplasmic System

Figure 20:
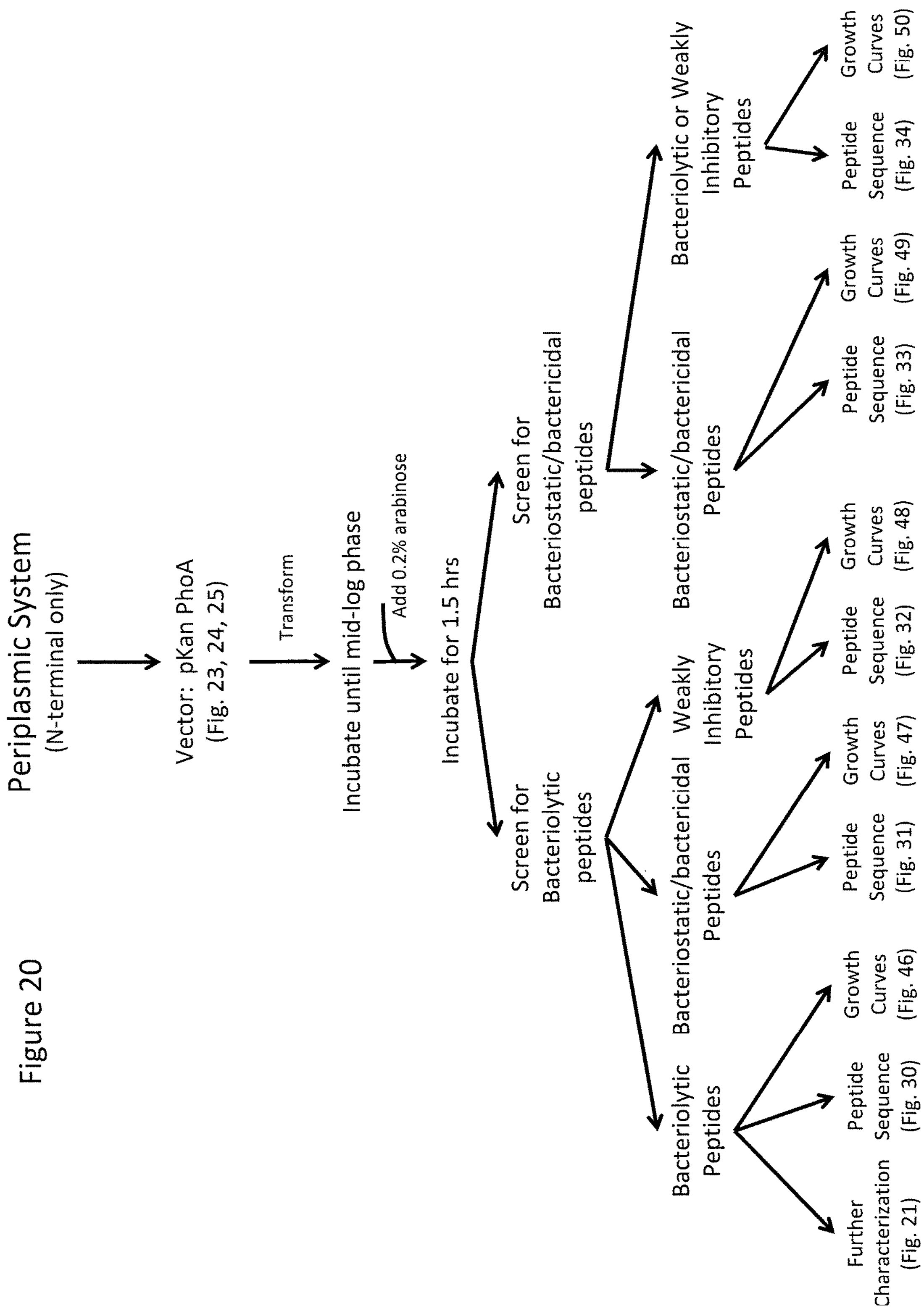
FIG. 20 is a flowchart of a periplasmic IVD system.
Figure 23:
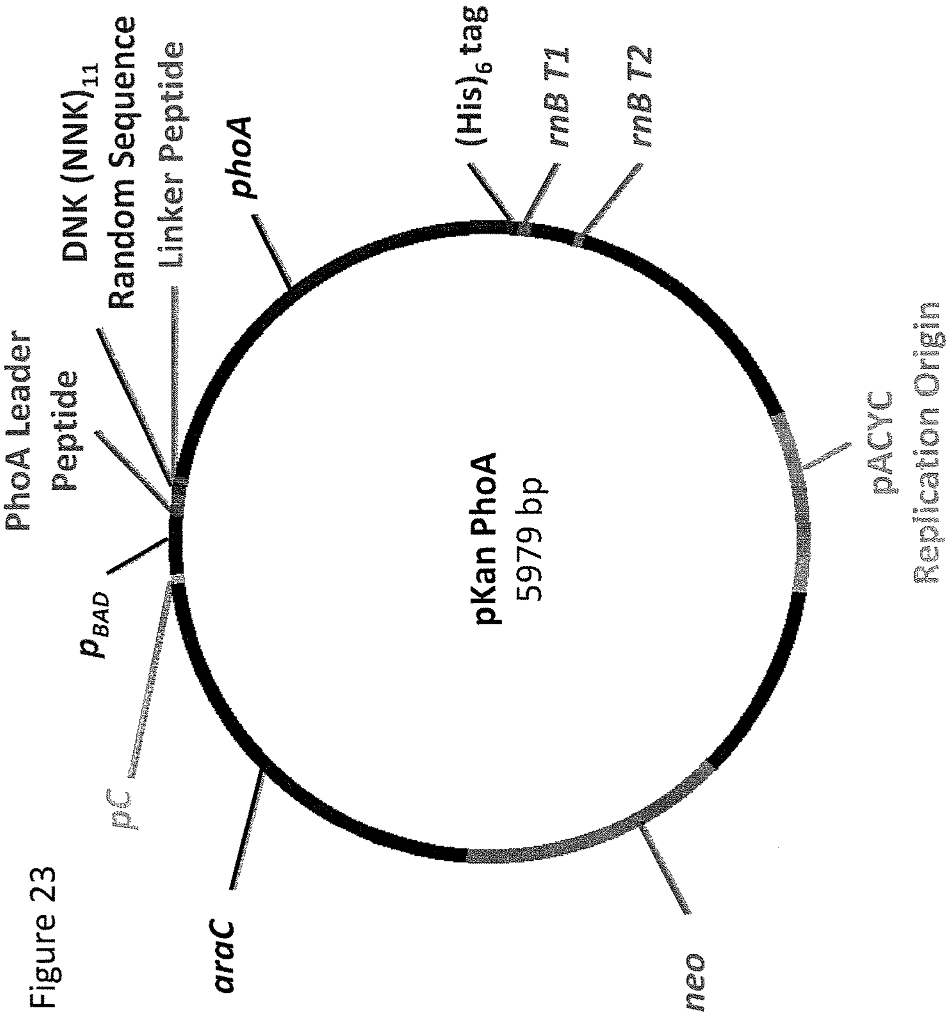
FIG. 23 shows a plasmid construct for expressing N-terminal fusion proteins in the periplasm.

The procedure for isolation of inhibitory peptides using the periplasmic system is illustrated in FIG. 20. Because the periplasmic fusion protein must be synthesized in the cytoplasm and pass through the plasma membrane into the periplasm, the random peptides were placed at the N-terminus of the carrier protein, PhoA. To isolate N-terminal inhibitory peptides, the construct pKan-PhoA (see FIGS. 23, 24, and 25) was created.

To identify antimicrobial periplasmic peptides, *E. coli* DH5α cells were transformed with the pKan-PhoA random library, grown to mid-log phase and L-arabinose was added to a final concentration of 0.2% w/v of culture and the incubation was continued for 1.5 hrs. In screens to identify bacteriolytic peptides, the culture was centrifuged and plasmid DNA was precipitated from the supernatant, used to transform *E. coli* DH5α and the transformants were screened on solid medium with or without inducers. To identify bacteriostatic or bacteriocidal peptides, negative selection was performed in which ampicillin (Cf=500 μg/ml) was added to the induced mid-log phase cultures to lyse any bacteria that were actively dividing and the non-dividing (dead or static) cells were recovered by centrifugation, their plasmids were isolated and used to transform *E. coli* DH5α. Transformants harboring inhibitory peptides were identified by replica plating on solid media with and without inducers and the plasmids were sequenced to identify the amino acid sequence of the inhibitory peptides.

The periplasmic bacteriolytic screen produced inhibitory peptides falling into all three phenotypic categories: bacteriostatic, bacteriocidal/bacteriostatic and weakly inhibitory (FIG. 20 left side). The bacteriolytic clones were sequenced (FIG. 30) and growth curves were performed on each (FIGS. 46A-L). The amino acid sequences of the bacteriolytic isolates were analyzed to identify common sequence motifs that contribute to their antimicrobial activity and these data were used to construct additional peptides in an effort to optimize their antimicrobial activity (see FIG. 21). The bacteriostatic/bacteriocidal peptides and the weakly inhibitory peptides were sequenced (FIGS. 31 and 32) and growth curves were performed (FIGS. 47A-C and 48A-I). The periplasmic screen for bacteriostatic and bacteriocidal also produced peptides that fell into each of the three phenotypic categories (FIG. 20, right side). Each of the isolates was sequenced (FIGS. 33 and 34) and growth curves were performed (FIGS. 49A-F and 50A-B).

Example 10

Further Characterization and Optimization of Bacteriolytic Peptides

Figure 21:
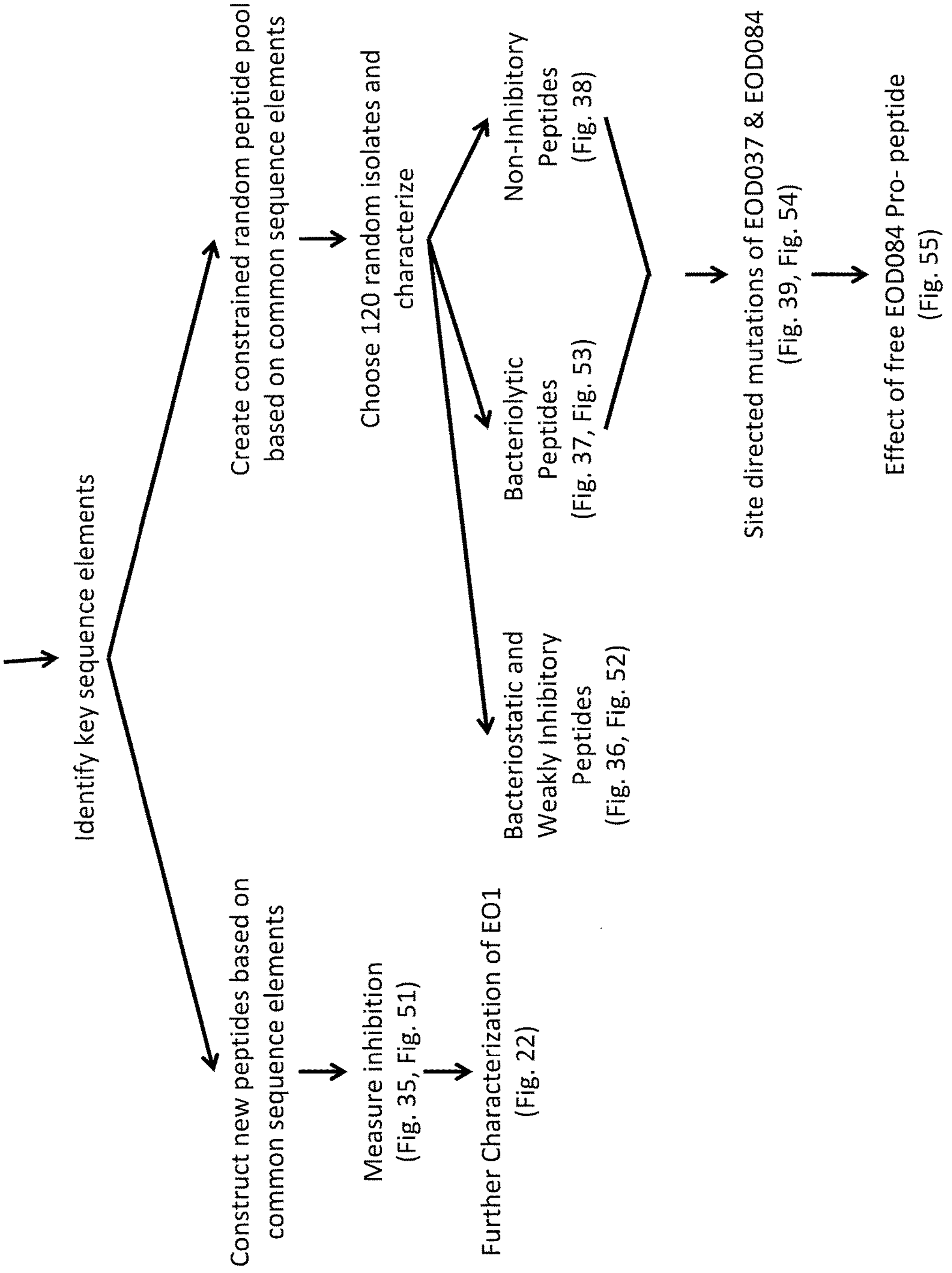
FIG. 21 is a flowchart for characterizing and optimizing bacteriolytic peptide antimicrobials identified using a periplasmic IVD system.

To optimize the antimicrobial activity of the lytic peptides isolated from the periplasmic screen (FIG. 20), the bacteriolytic amino acid sequences were statistically analyzed to identify common motifs or other sequence elements and characteristics that contributed to or detracted from their antimicrobial activity and new peptides were designed, constructed and analyzed (see FIG. 21). The statistical analyses for these peptides are shown in the file labeled Statistics I.

Figure 22:
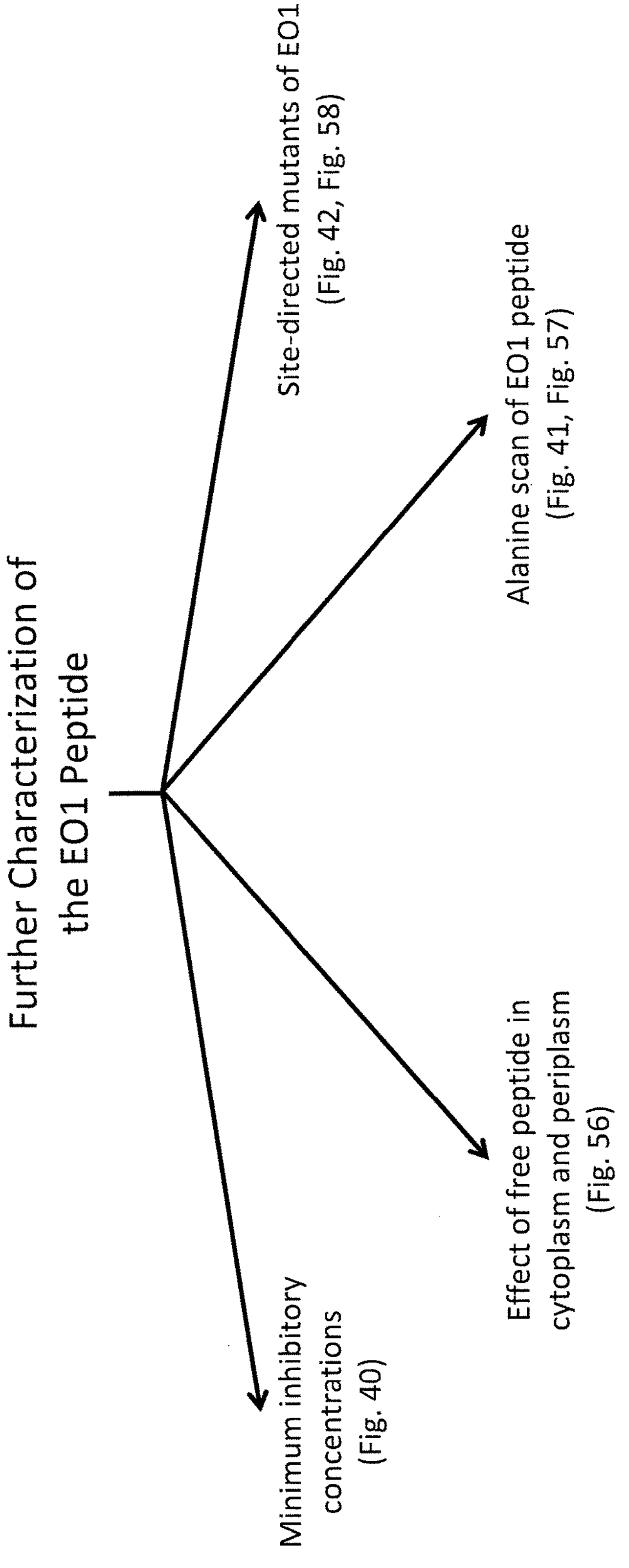
FIG. 22 is an overview of the characterization of the rationally designed EO1 peptide antimicrobial.
Figure 51A:
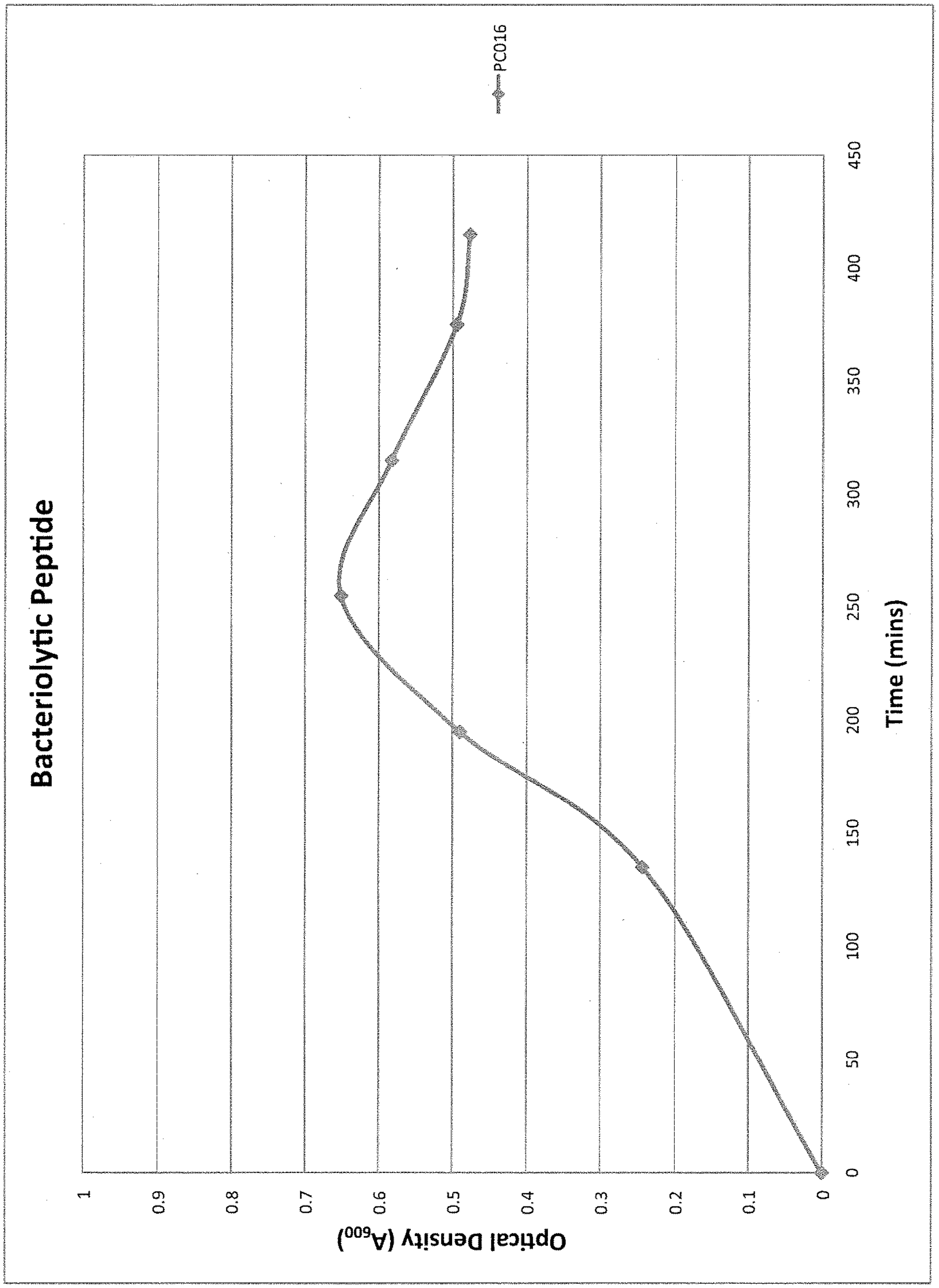
FIGS. 51A-B show growth curve profiles of bacteria expressing bacteriolytic and growth rate reducing peptide antimicrobials identified using N-terminal constructs in the periplasm.
Figure 51B:
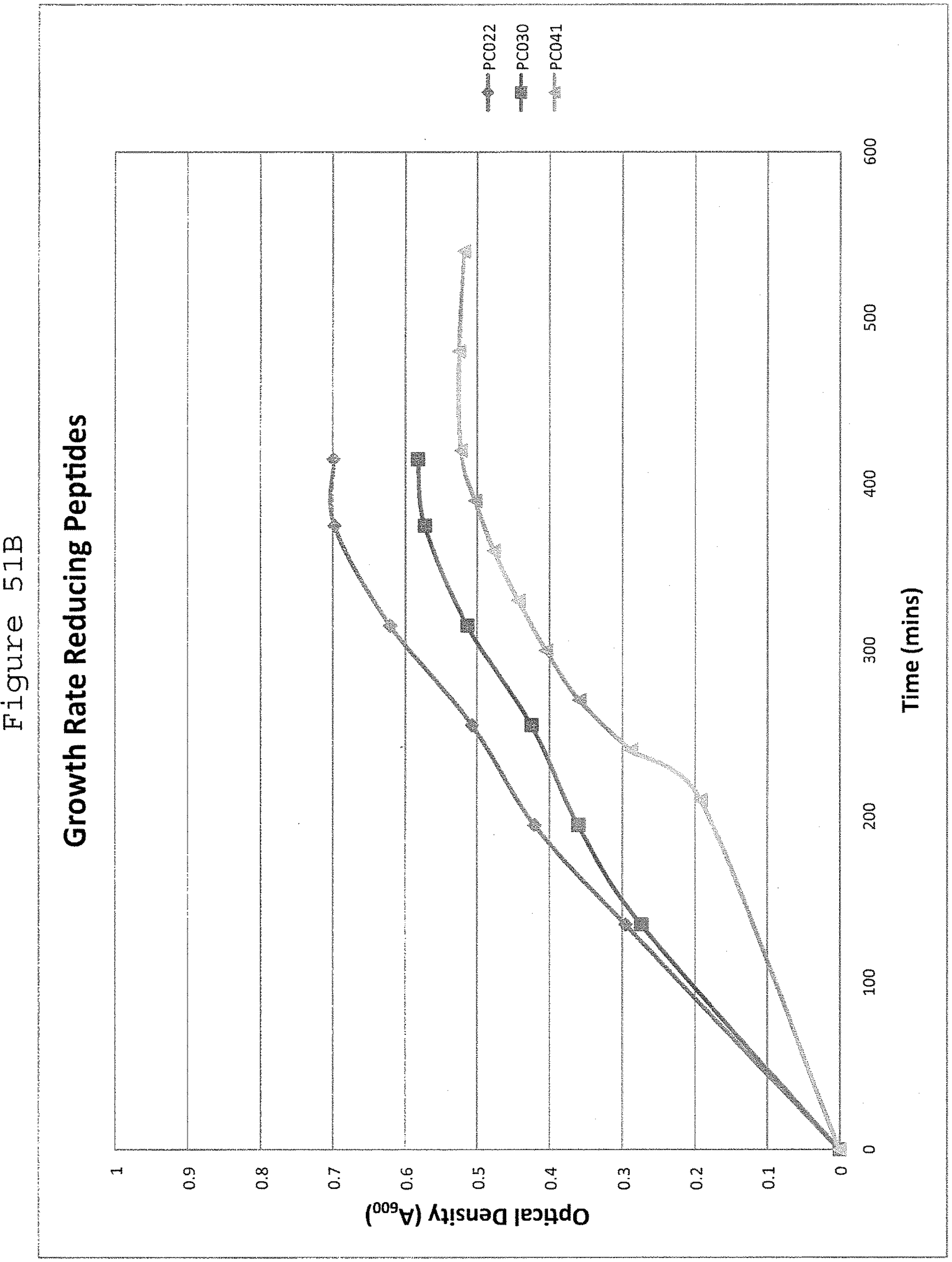

In one set of mutants, common features of the lytic peptides were combined and six new peptides were constructed containing these features and analyzed (FIG. 21, left side). The results of these analyses are shown in FIG. 35 and FIGS. 51A-B. One of the peptides, EO1, showed significantly enhanced antimicrobial activity over the original isolates and was chosen for further study (see FIG. 22).

In another set of experiments, the common features identified in our analysis were used to construct a constrained library of peptide sequences in which variations on each of the elements identified as potentially important for antimicrobial activity were included (FIG. 21, right side). In another set of experiments, the common features identified in our analysis were used to construct a constrained library of peptide sequences in which variations on each of the elements identified as potentially important for antimicrobial activity were included (FIG. 21, right side). The degenerate sequence used to make the constrained peptide library based on analysis of early onset peptide sequences was 5'-WTBNNKYKGCTGNNKAGNYGGTGGCGTS GTNNKNNK-3' (SEQ ID NO: 464), using standard IUPAC nomenclature for DNA nucleotides. "Early onset" refers to peptides listed in FIG. 30 that caused lysis of the cells within one hour of induction. Early onset suggests that lower concentrations of the peptide are required which in turn suggests that the early onset peptides are active at lower concentrations than late onset peptides. The design of the degenerate peptides is derived from the sequences of the early onset peptides in FIG. 30 in an effort to combine characteristics that enhance lysis.

Figure 52A:
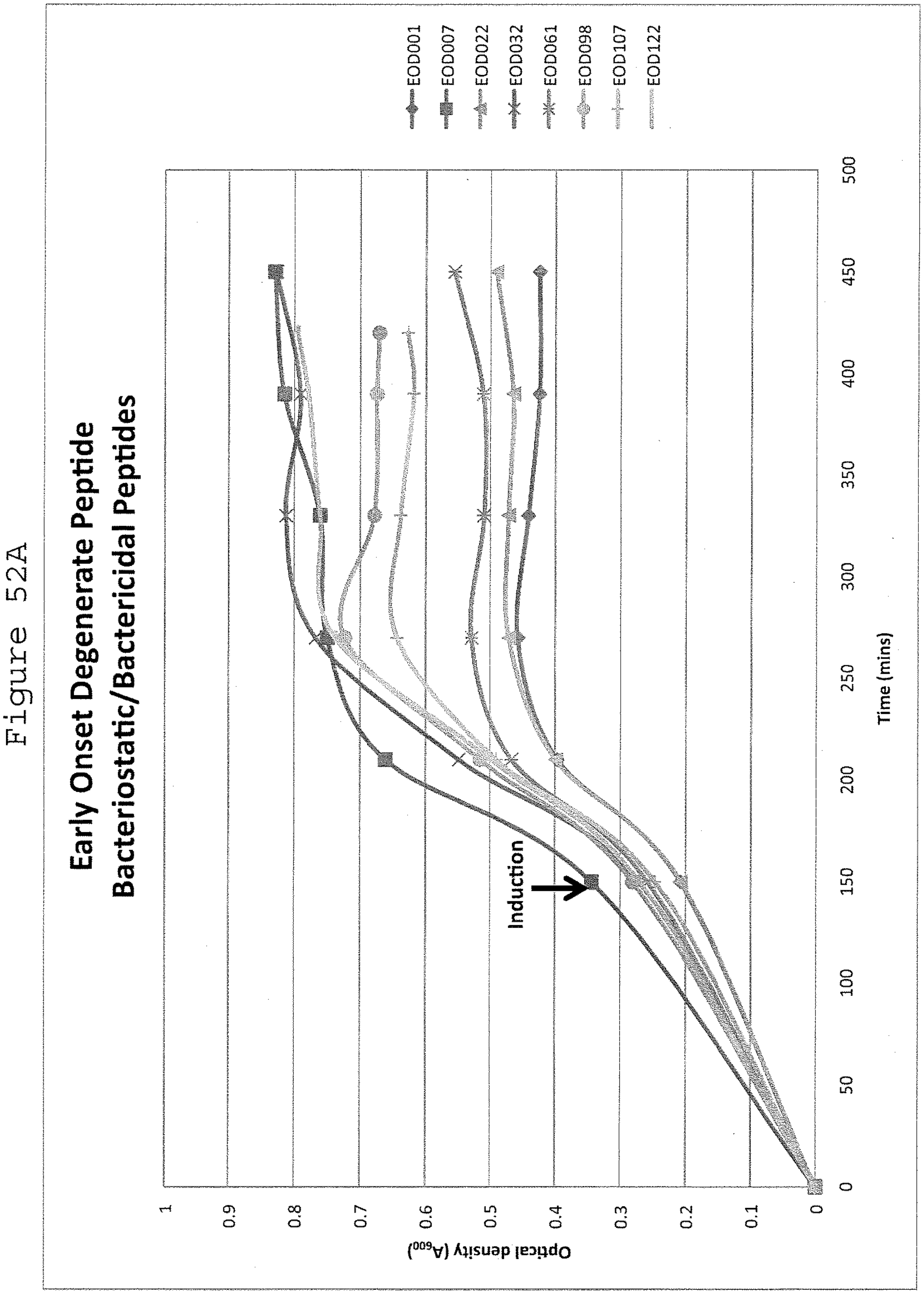
FIGS. 52A-B show growth curve profiles of bacteria expressing bacteriostatic, growth-rate reducing, and bactericidal degenerate peptides derived from the initial early-onset bacteriolytic isolates of the periplasmic screen.
Figure 52B:
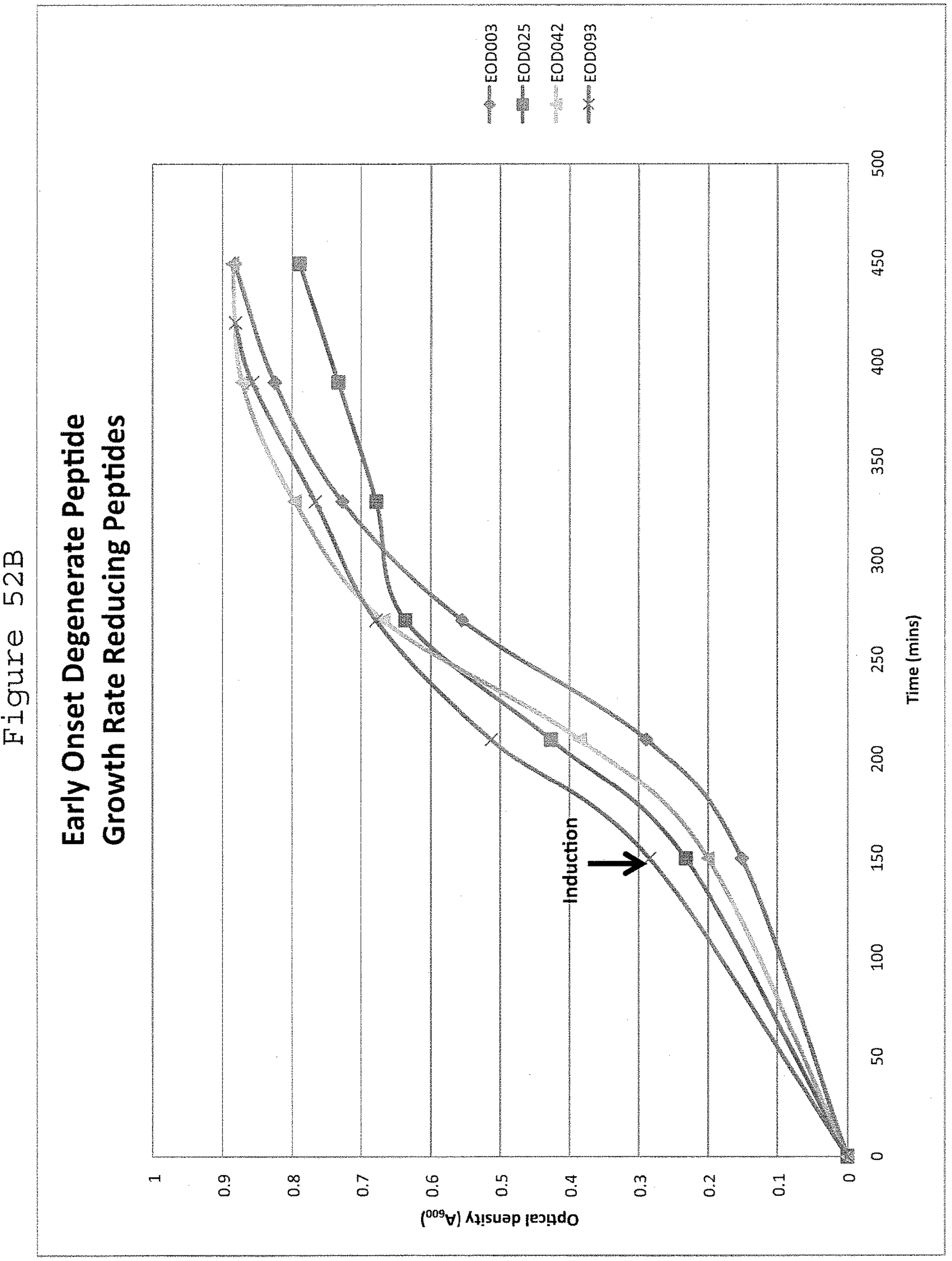
Figure 53A:
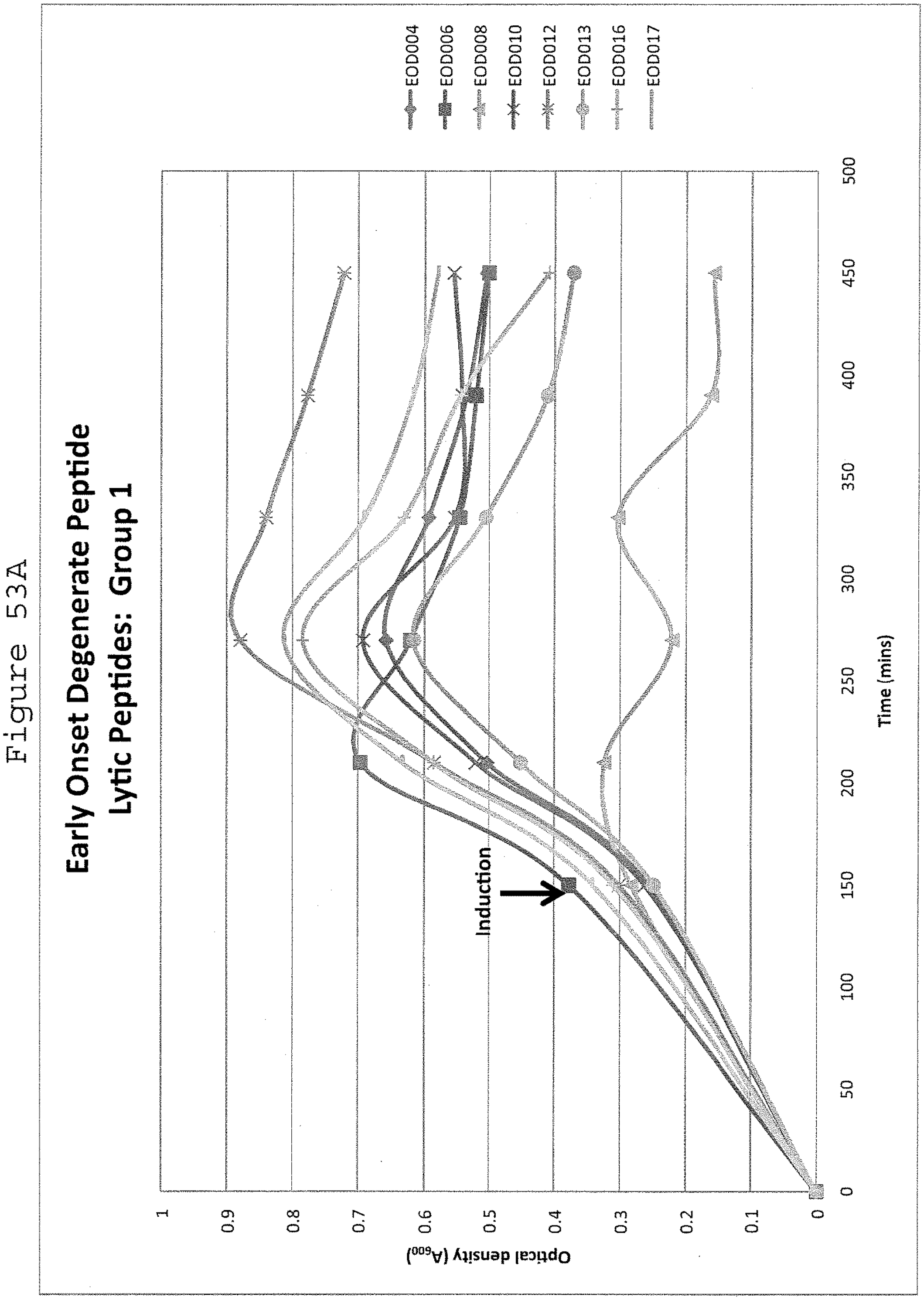
FIGS. 53A-I show growth curve profiles of bacteria expressing bacteriolytic degenerate peptides derived from the initial early-onset bacteriolytic isolates of the periplasmic screen.
Figure 53B:
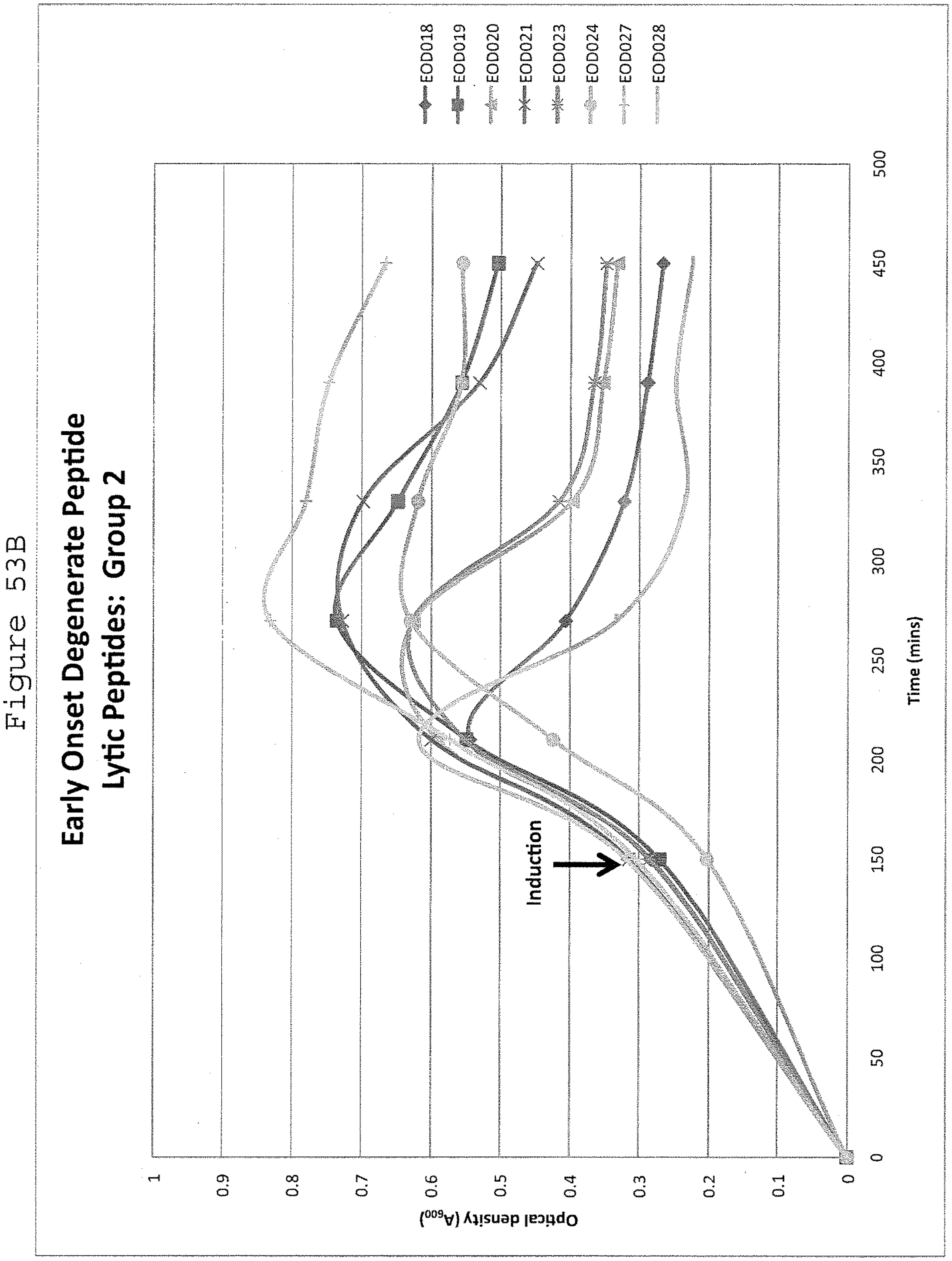
Figure 53C:
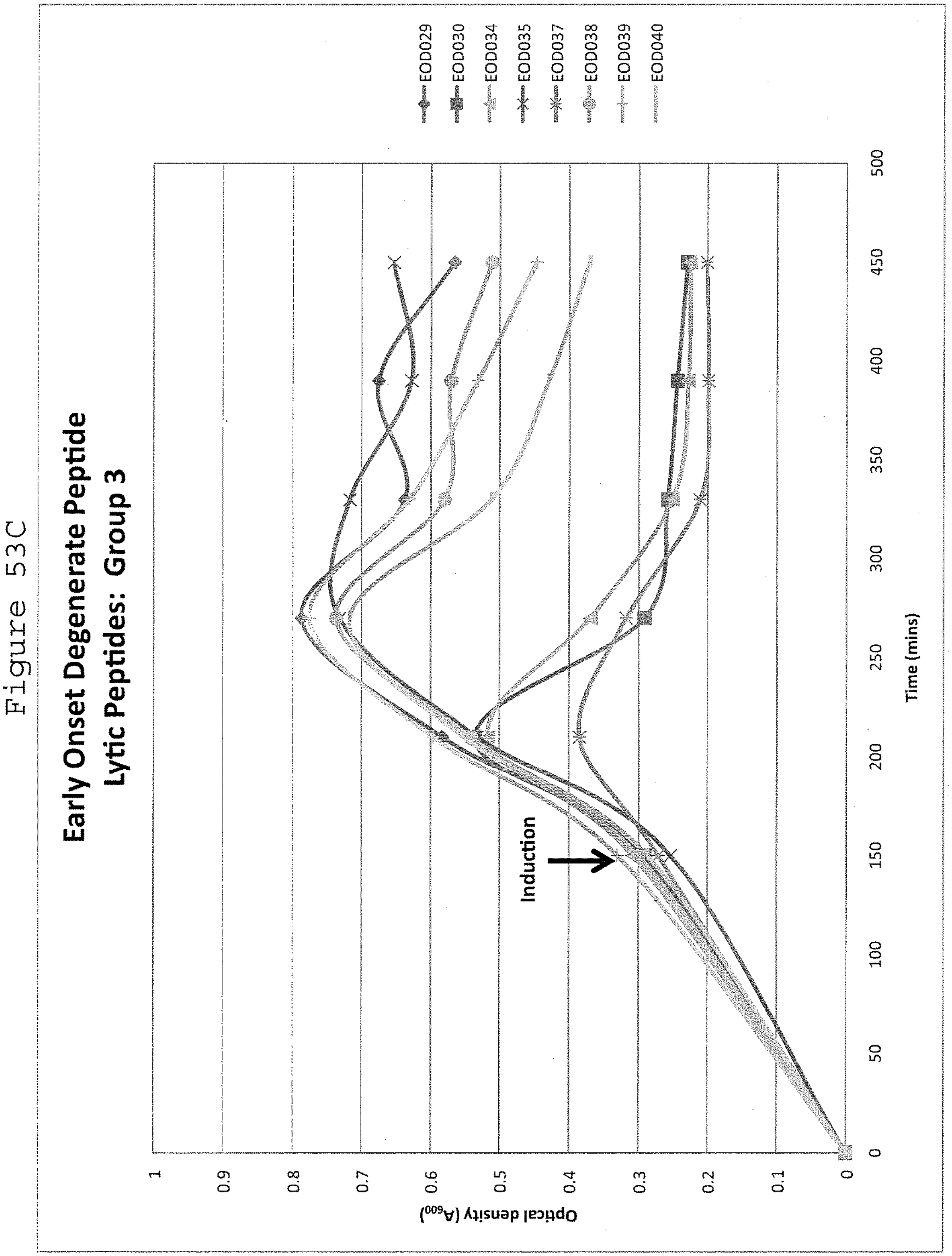
Figure 53D:
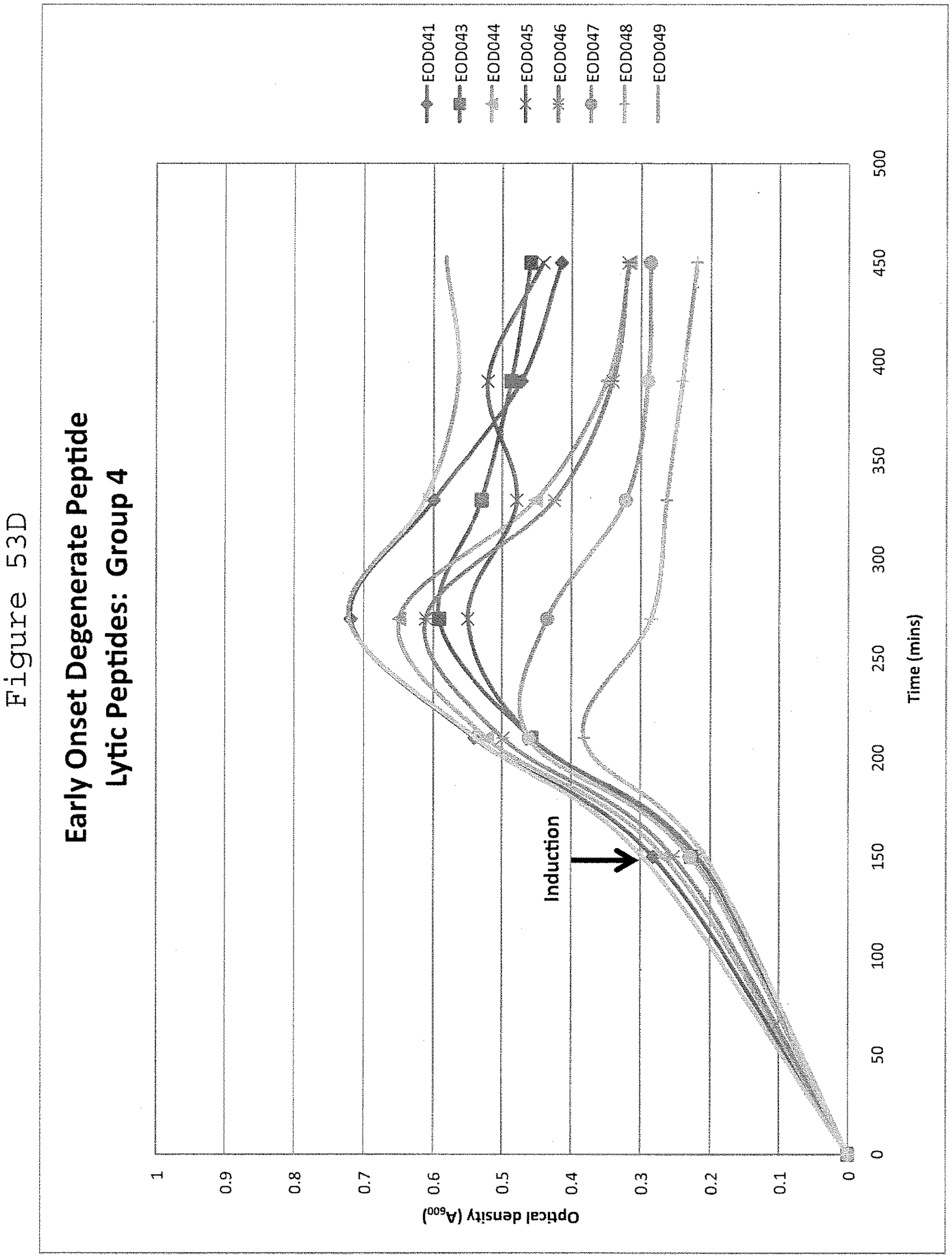
Figure 53E:
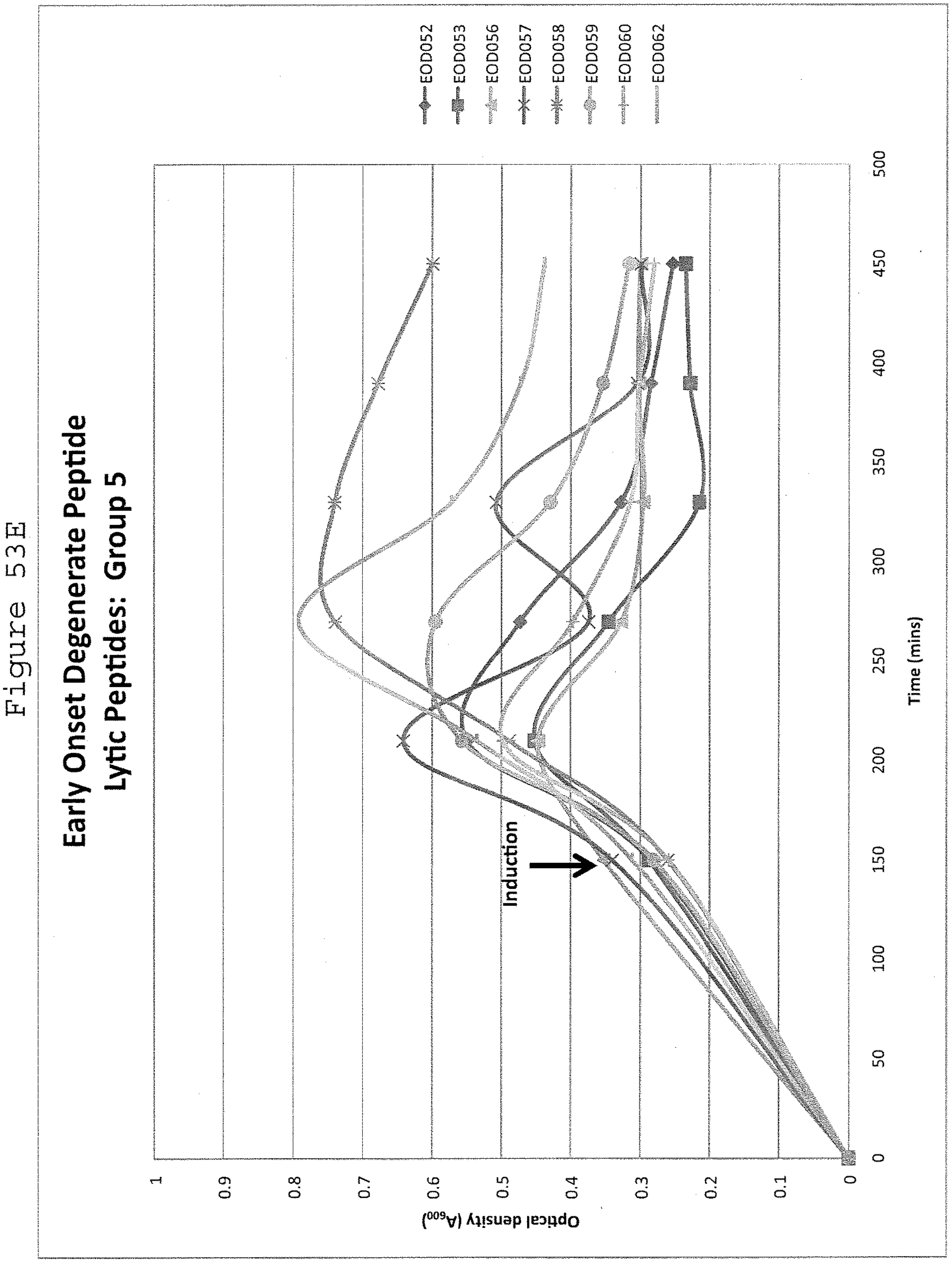
Figure 53F:
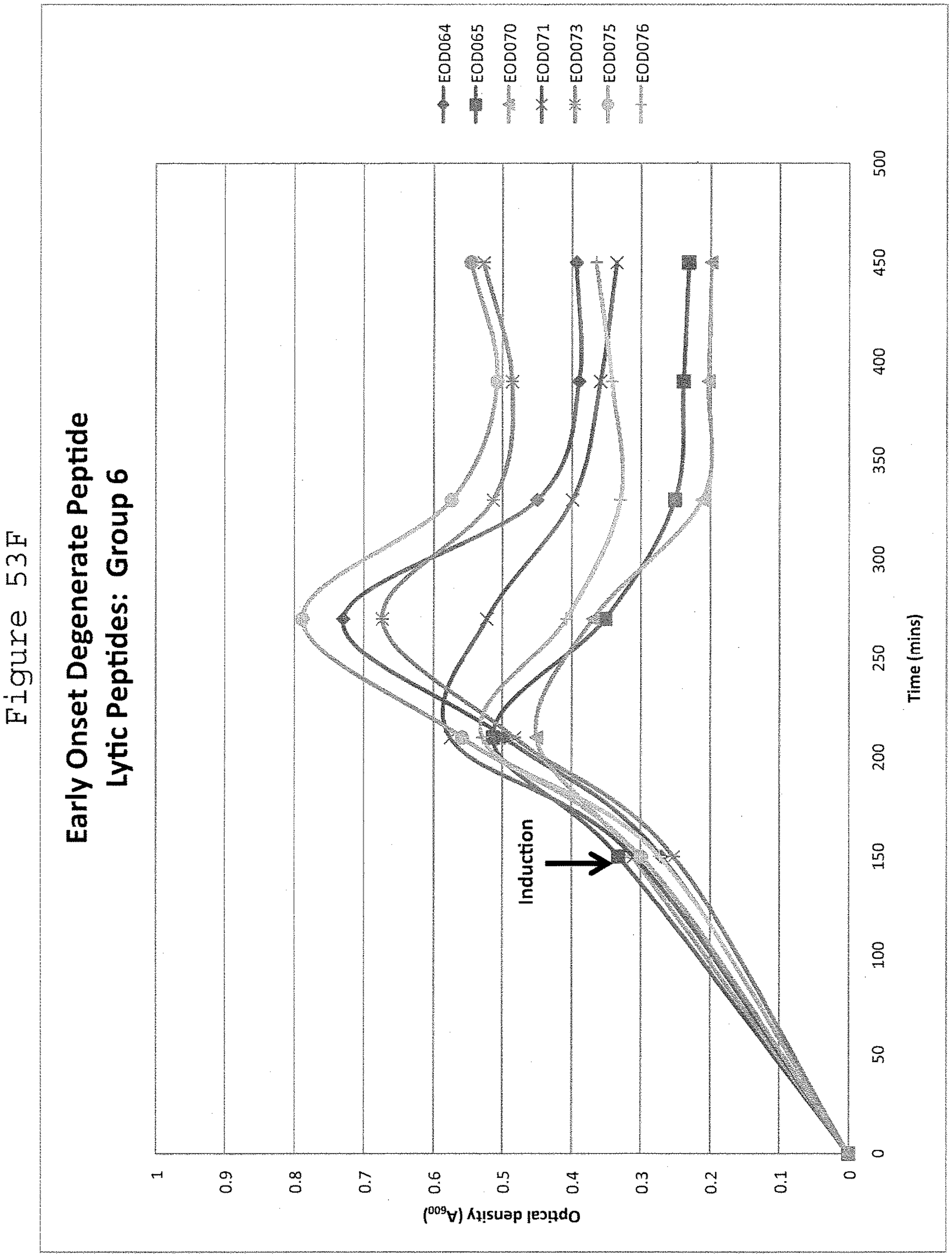
Figure 53G:
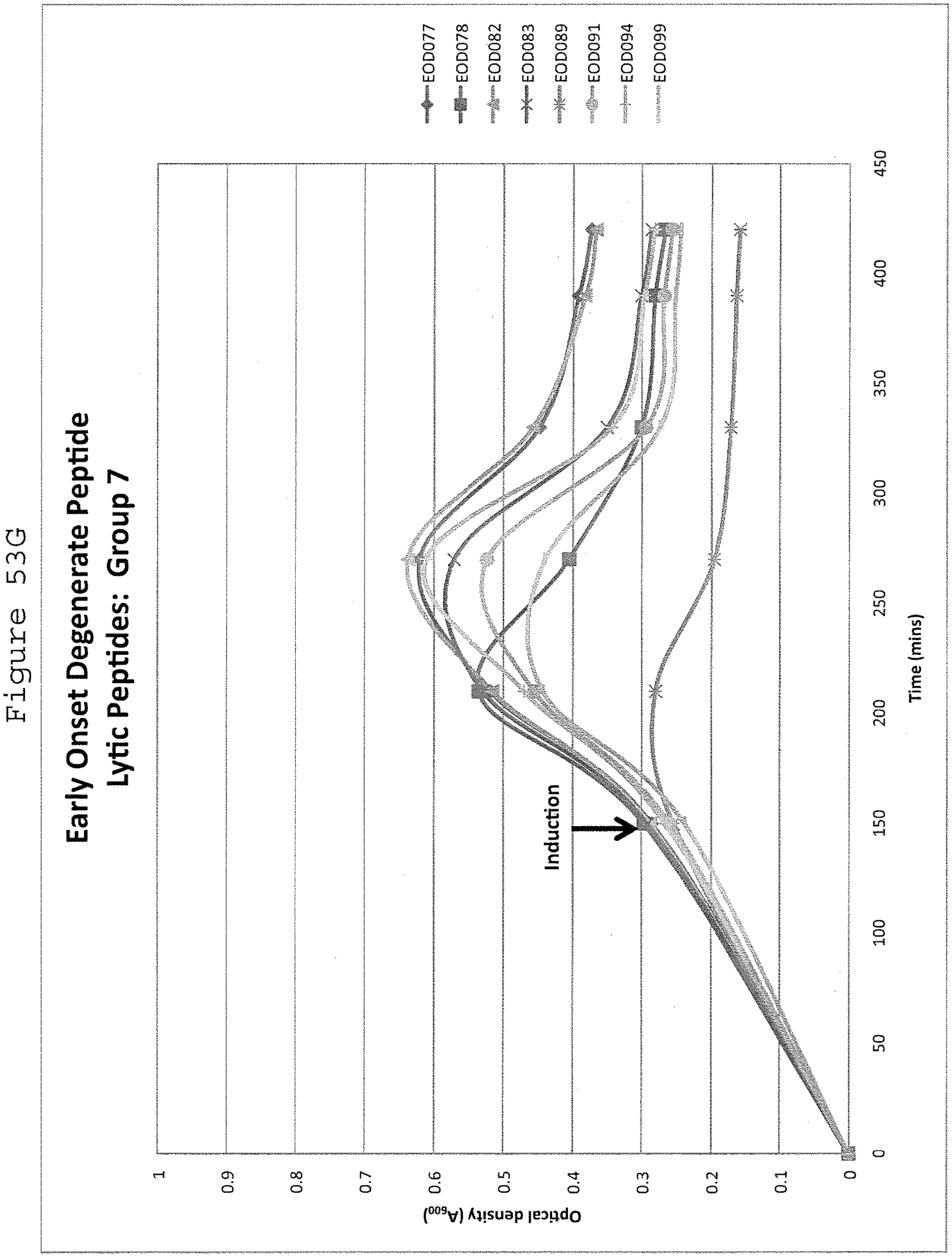
Figure 53H:
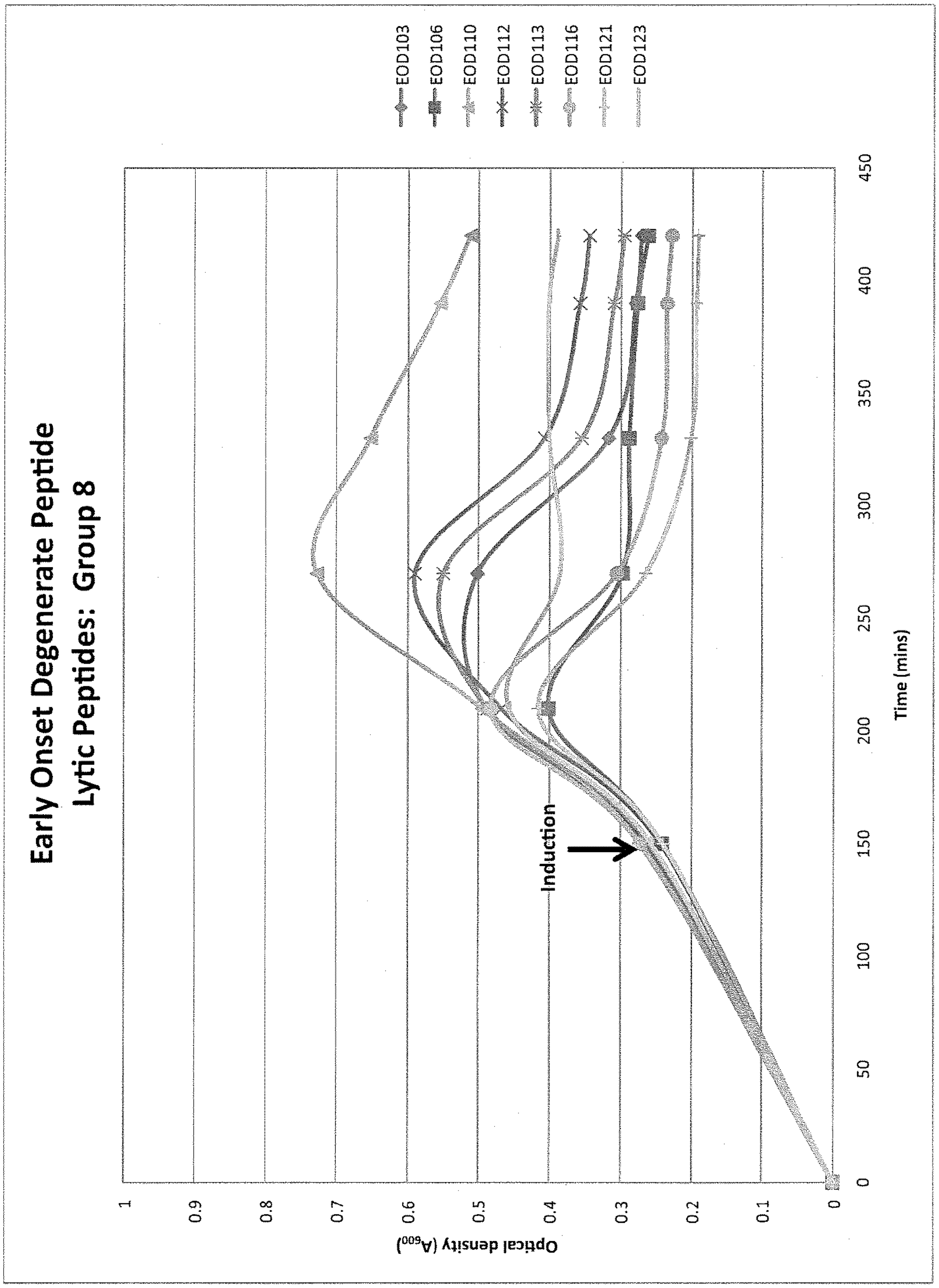
Figure 53I:
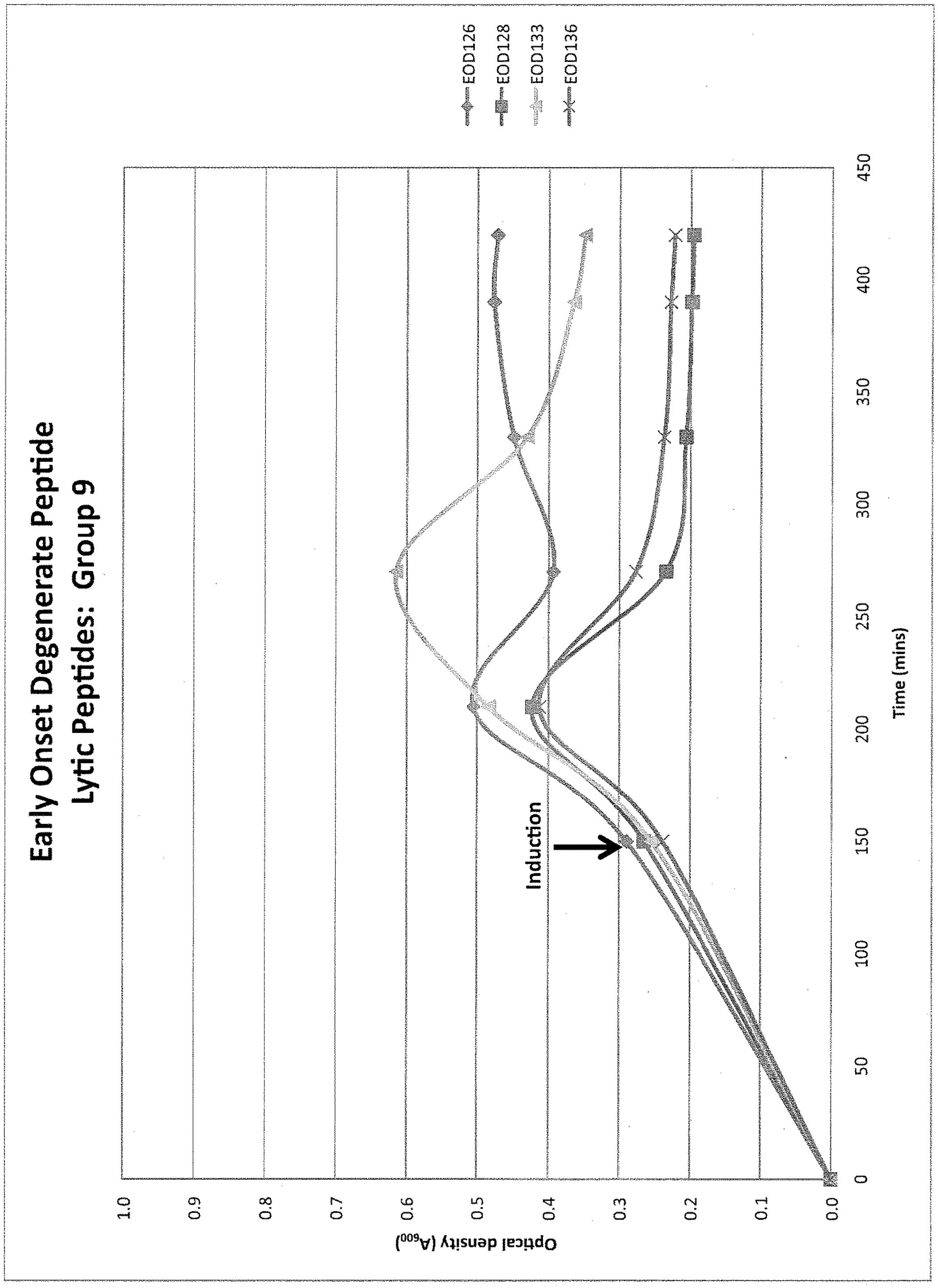
Figure 54A:
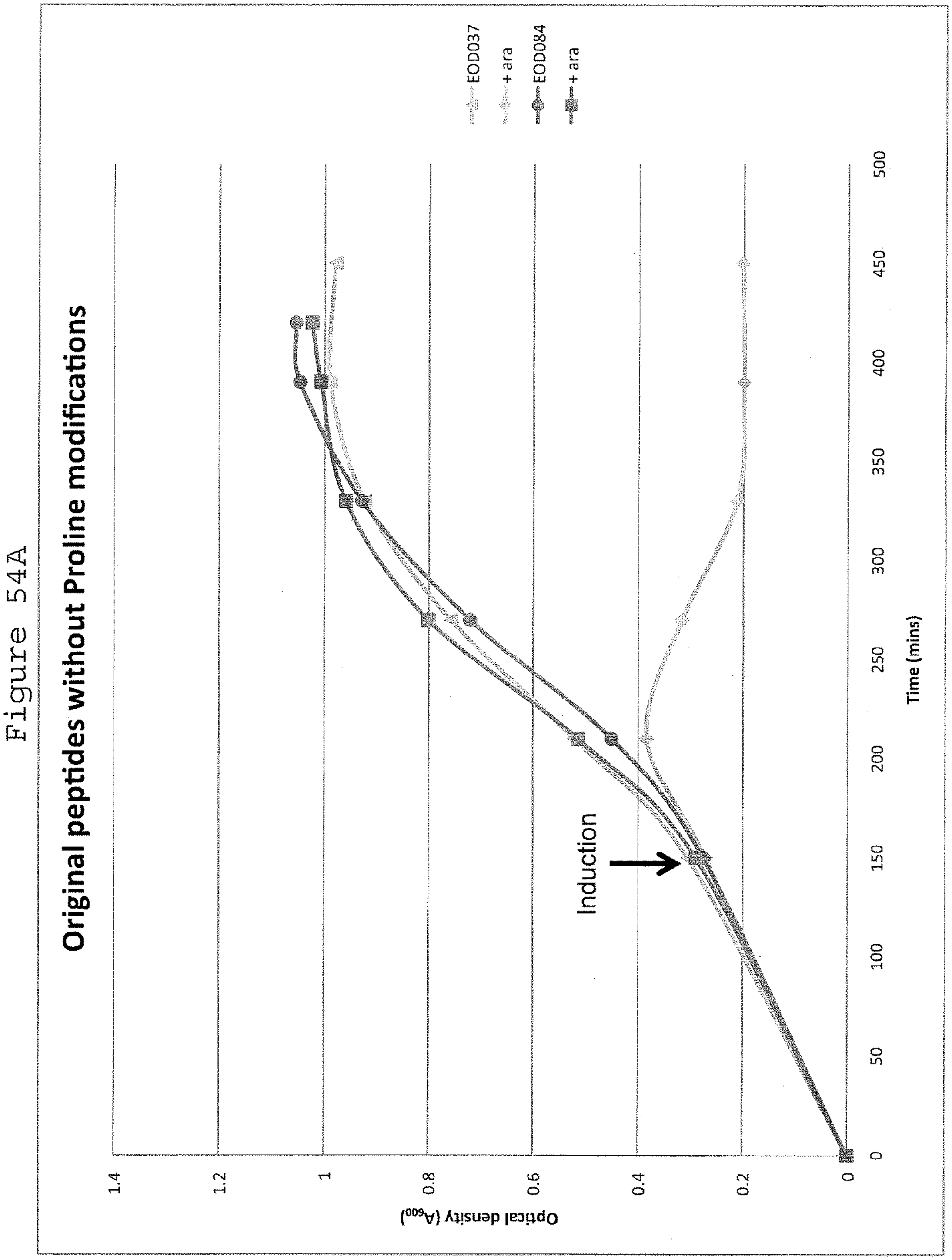
FIGS. 54A-B show growth curve profiles of bacteria for select peptide antimicrobials without proline modifications.
Figure 54B:
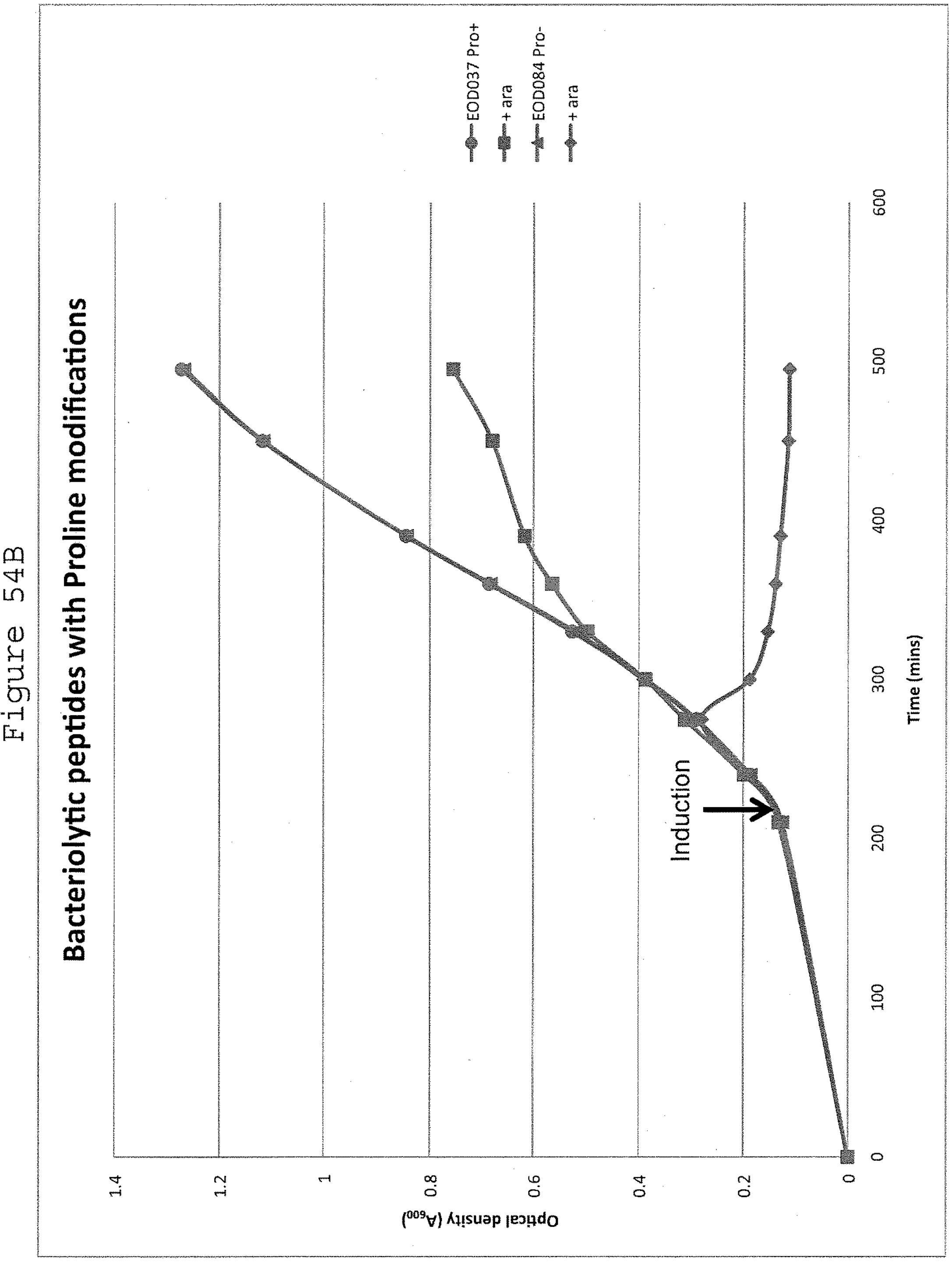

A total of 120 randomly selected clones were screened by growth curve analysis and categorized by their resulting phenotypes. The phenotypes of the isolates are bacteriostatic (FIG. 36, FIGS. 52A-B), weakly inhibitory (FIG. 36, FIGS. 52A-B), bacteriolytic (FIG. 37, FIGS. 53A-I), and non-inhibitory (FIG. 38). The pattern of amino acids in the bacteriolytic peptides and non-inhibitory peptides was also statistically analyzed and these data are located in the files Statistics II and Statistics III respectively. These analyses suggested that alpha helices may be important for antimicrobial activity in some of the peptides and that placement of a proline residue within the alpha helical sequence of an inhibitory peptide might therefore block its antimicrobial activity. To test this hypothesis, an alanine was replaced with a proline in the inhibitory peptide, EOD037, to produce EOD037 Pro+ and a leucine was substituted for the proline in the non-inhibitory peptide, EOD084, to produce EOD084 Pro− and all four of the peptides were analyzed (FIG. 39, FIGS. 54A-B). The results show that in these peptides, the presence of a proline residue does result in loss of antimicrobial activity suggesting that the presence of an alpha helical segment is important.

Figure 55:
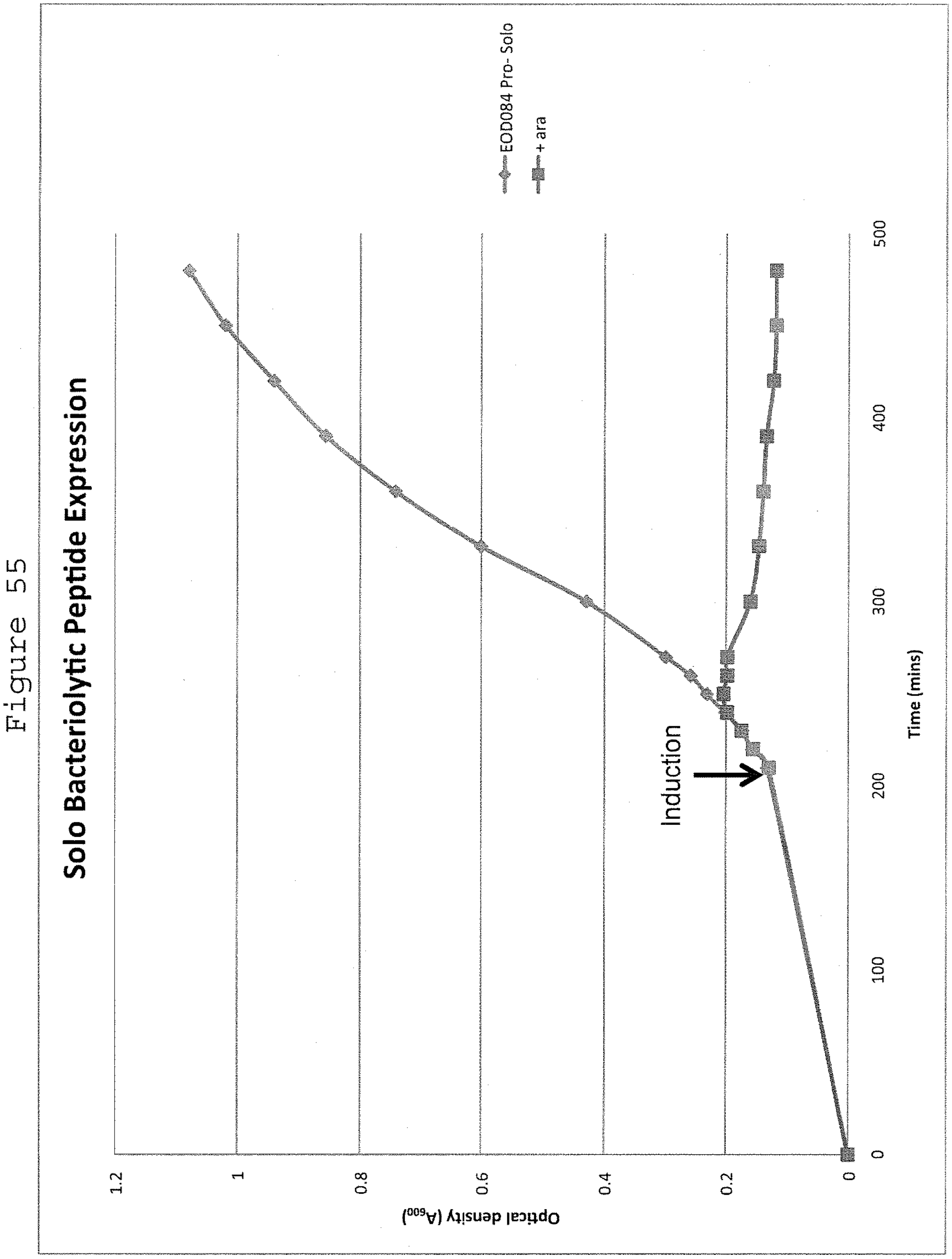
FIG. 55 shows growth curve profiles of bacteria for select peptide antimicrobials with proline modifications expressed as free peptides.

Because the described antimicrobial measurements to date used the peptides expressed as protein fusions, whether the free peptide (not attached to the carrier) would also show antimicrobial activity was evaluated. For this two different sets of experiments were performed. First, special expression vectors that do not contain the carrier protein but produce the peptides in cells as free peptides were created. One vector expresses the free peptides in the cytoplasm and the other vector express the free peptide in the periplasm. These systems were used to test several different peptides and the results of these data are labeled "free peptide" in the tables and charts. EOD084 Pro− retained its antimicrobial activity when expressed in the periplasm in the absence of PhoA (FIG. 39, FIG. 55).

Example 11

Further Characterization of the EO1 Peptide

Several peptides were selected to determine if they retain their antimicrobial activity when added as a purified peptide to growing bacterial cultures. For this, the peptides were synthesized, diluted in growth medium, added to freshly inoculated bacterial cultures, incubated and the lowest concentration of each peptide that completely inhibited the growth of the culture was recorded as its the minimal inhibitory concentration (MIC). These data are provided in the tables containing the lists of peptides and their analyses. For EO1, its MIC against several other bacterial strains were measured and these data show that the EO1 peptide inhibits a broad spectrum of bacteria (Gram positive and Gram negative) at concentrations that are comparable to the MICs of common antibiotics such as chloramphenicol and ampicillin, (FIG. 40).

Figure 56A:
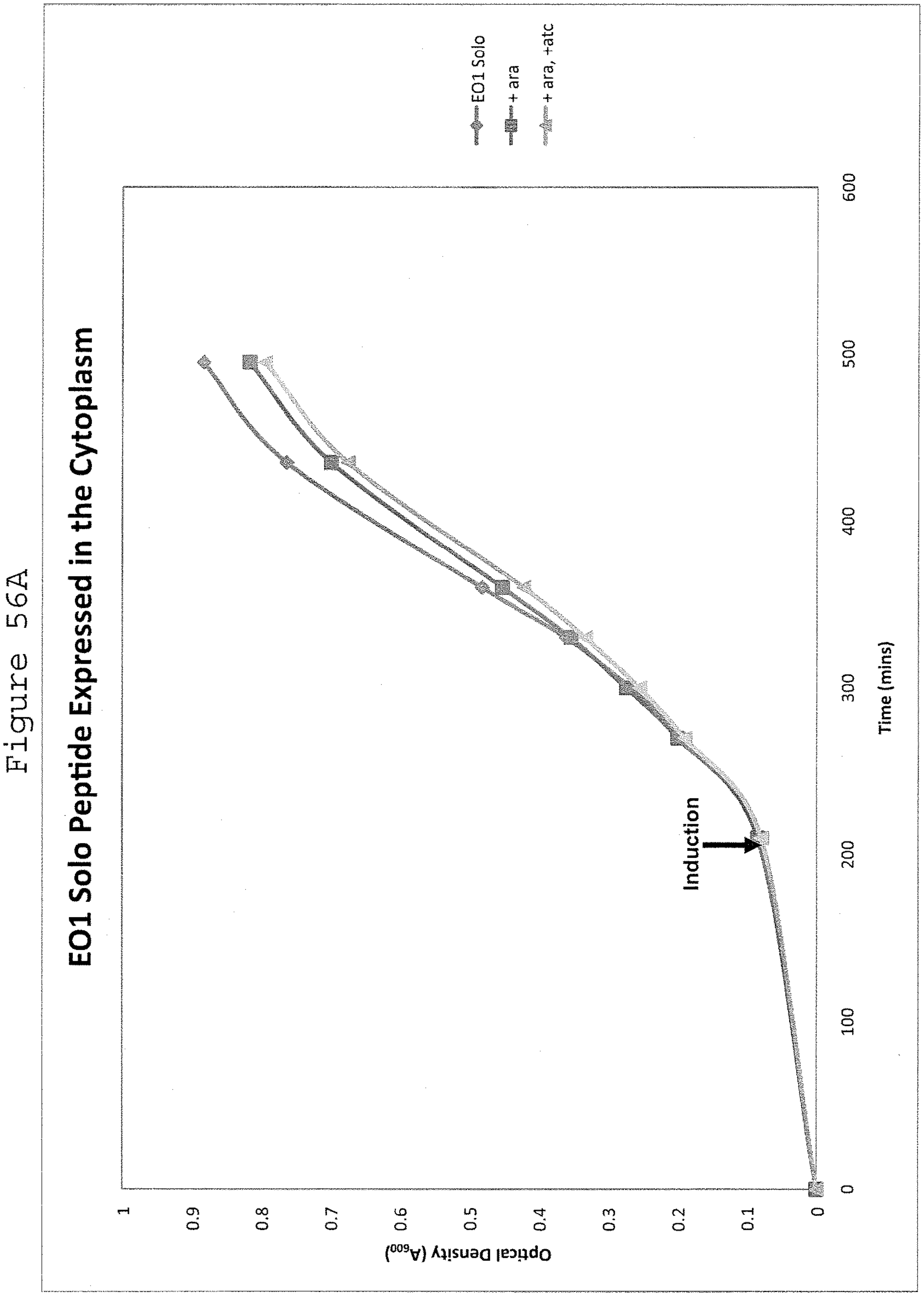
FIGS. 56A-B show growth curve profiles of bacteria expressing EO1 solo (e.g., free) peptide expressed in the cytoplasm and periplasm.
Figure 56B:
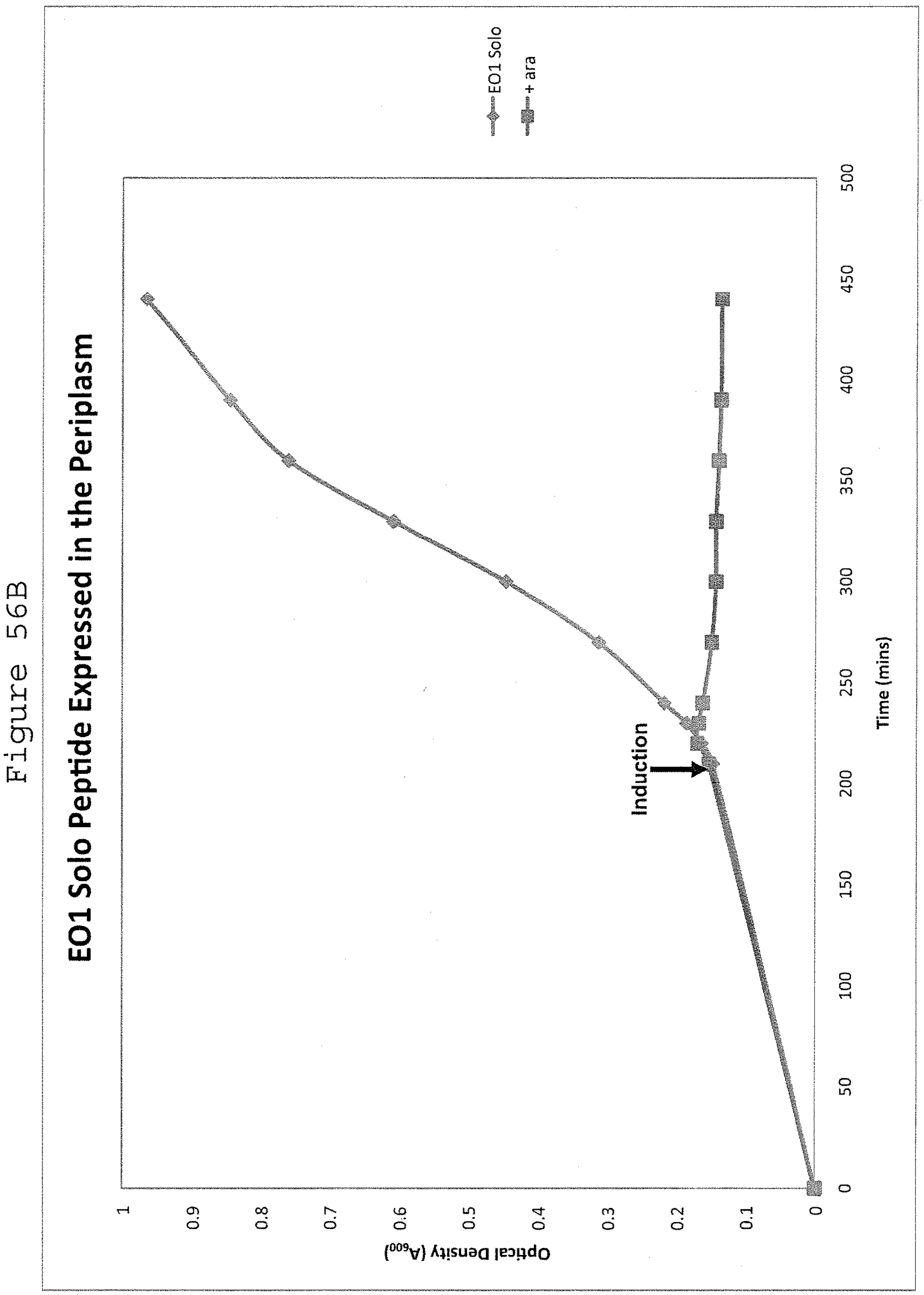

EO1 was also tested to determine if it retained its antimicrobial activity as a free peptide. The free peptide data for peptide EO1 are shown in FIG. 35 and FIGS. 56A-B. These data show that EO1 retains its antimicrobial activity when expressed as a free peptide in the periplasm but not when it is expressed as a free peptide in the cytoplasm.

Figure 57:
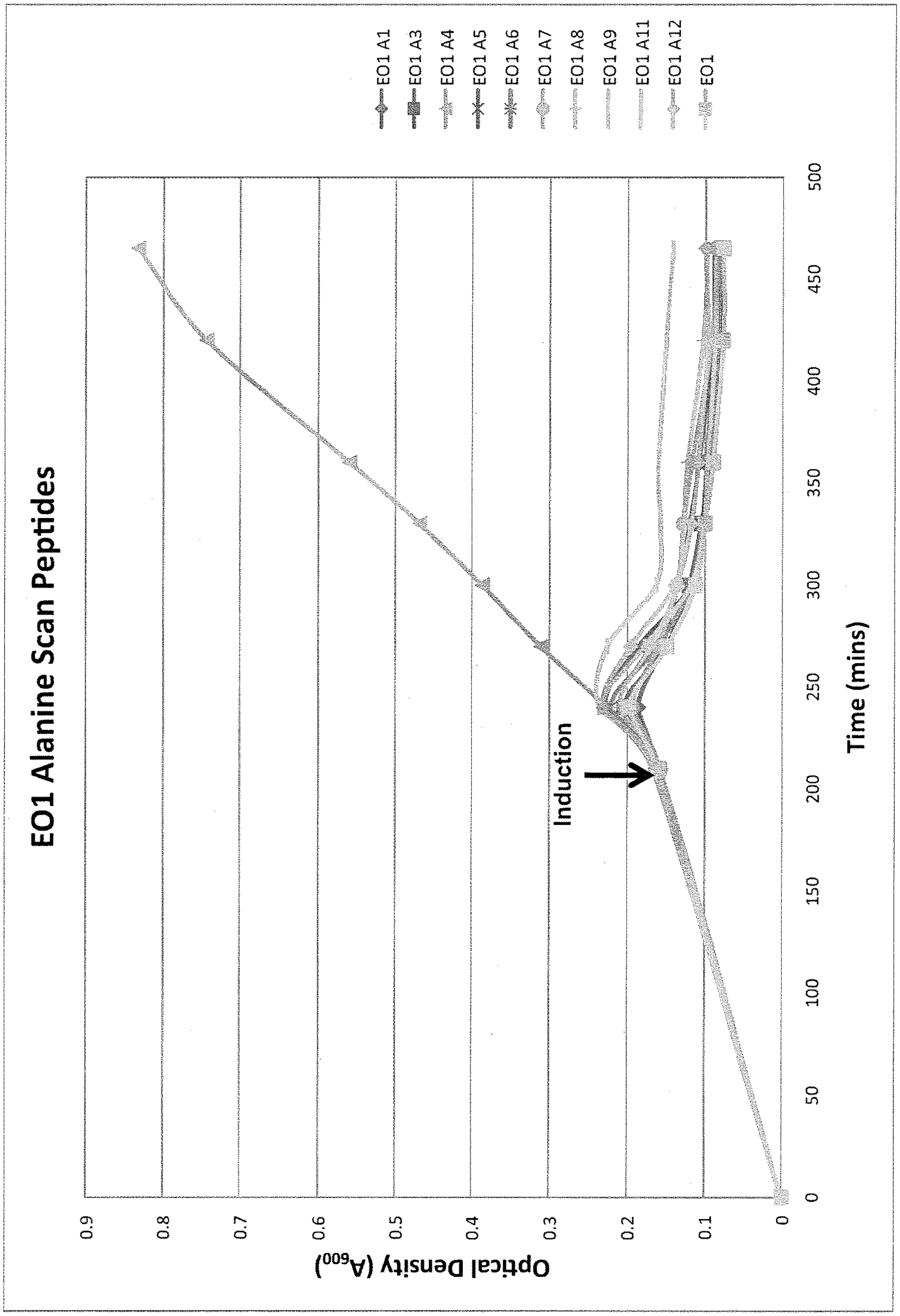
FIG. 57 shows growth curve profiles of bacteria expressing EO1 alanine scan peptides.

Alanine scanning was performed in which substitution of a single alanine for each of the amino acids in EO1 was constructed and analyzed in vivo to determine if substitution of any single amino acid would affect its antimicrobial activity (FIG. 41, FIG. 57). The data show that only replacement of the leucine at position 4 of the peptide significantly affects its antimicrobial activity.

Figure 58A:
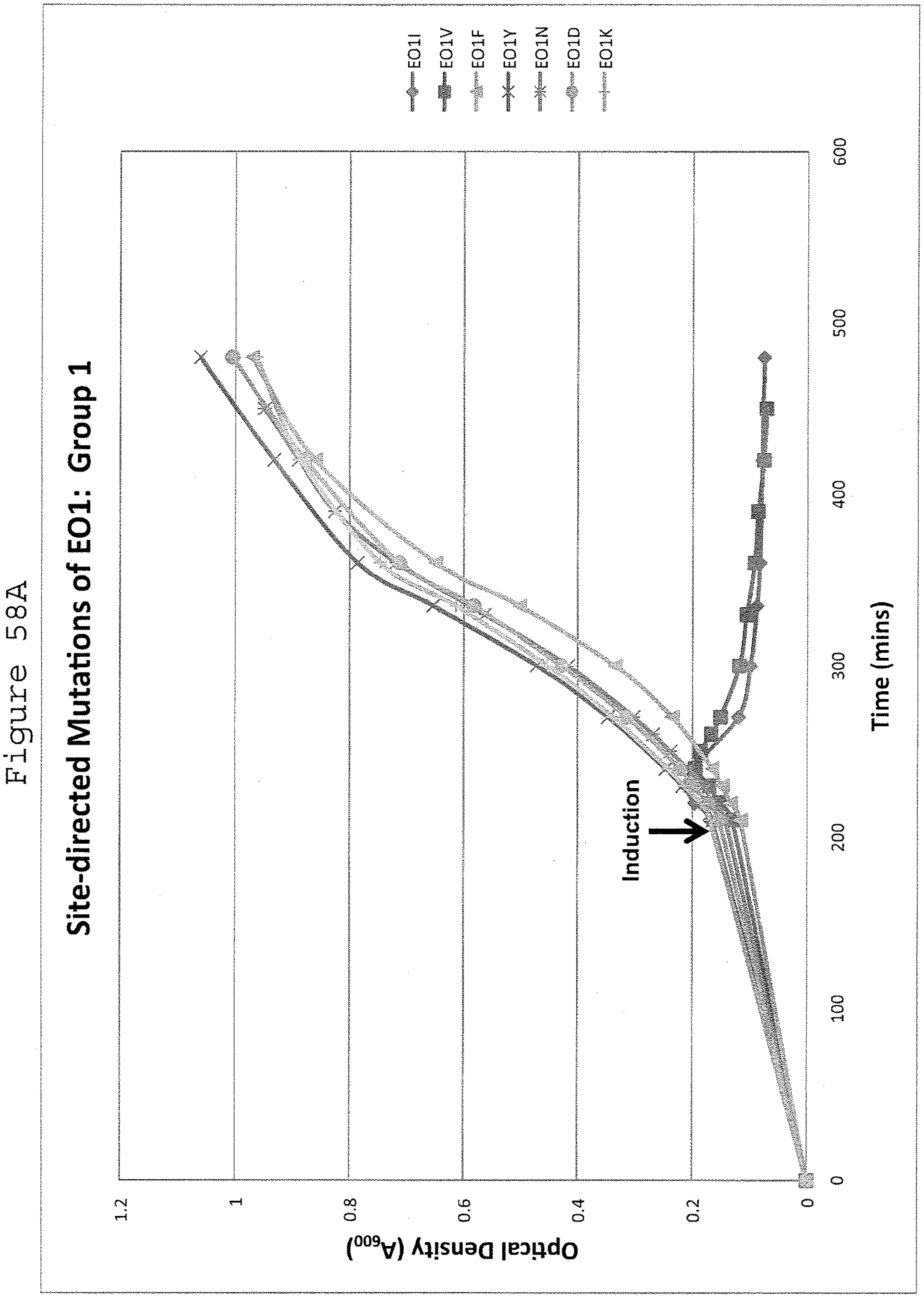
FIGS. 58A-B show growth curve profiles of bacteria expressing EO1 site-directed mutations.
Figure 58B:
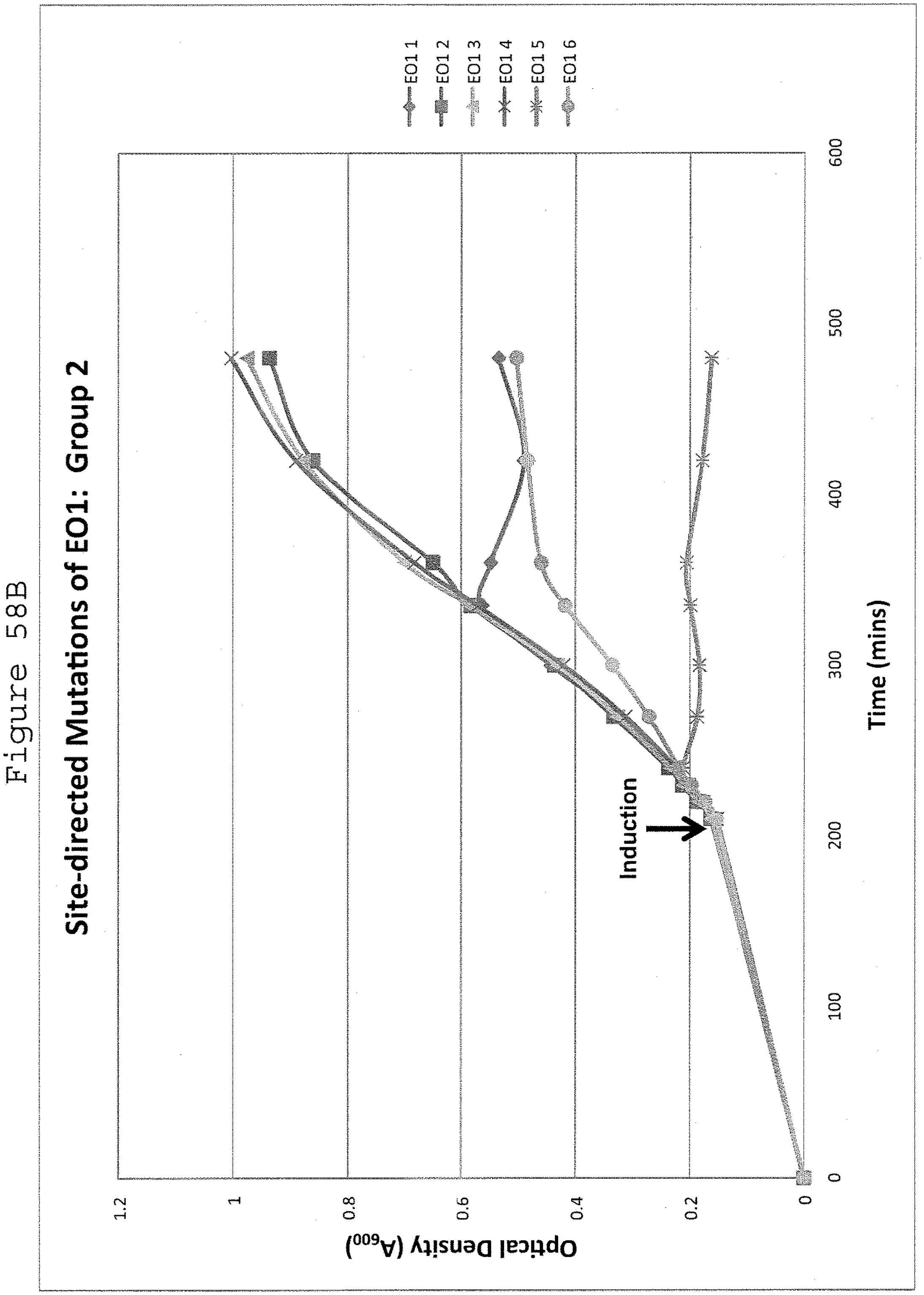

A series of site-directed mutants of EO1 were constructed in an effort to increase its solubility in water but most of these resulted in significant decreases in antimicrobial activity (FIG. 42, Chart FIGS. 58A-B).

Example 12

Consensus Peptide from all Lytic Peptides of the Periplasmic-Bacteriolytic Peptide Screen The following consensus peptide is based on 85 peptides isolated from the periplasmic bacteriolytic peptide screen (FIG. 30) that were shown to exhibit the bacteriolytic growth phenotype (FIGS. 46A-L). More detailed analysis including positional selection against particular amino acids or groups of amino acids shown in FIG. 59.

Figure 26:
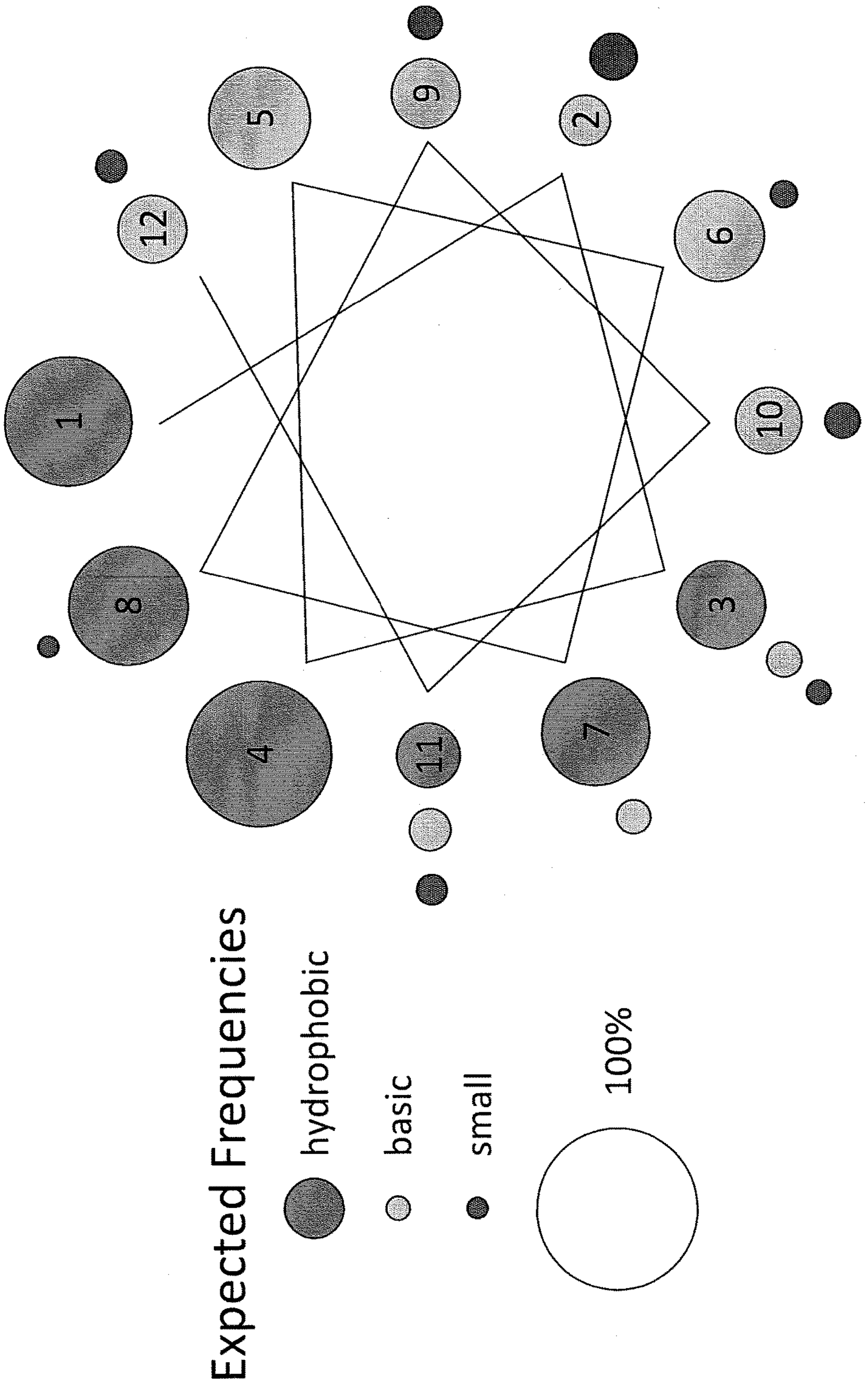
FIG. 26 shows the shows the observed frequencies of amino acids at each position of the bacteriolytic peptide antimicrobials disclosed herein.

Distribution of amino acid residues and groups by position in linear peptide. There is a general bias against acidic amino acids and proline residues. The following data are presented in a linear peptide format proceeding from the N-terminal amino acid to its covalently attached neighboring peptide. However, these peptides fit (there are outliers) to an amphipathic α-helix model where neighboring amino acids are determined by the rotation of the helix. Referring to FIG. 26, a graphical representation of the model is shown. Raw numbers supporting these observations are provided simply to illustrate the model. The raw data were statistically analyzed to determine if the amino acid distributions at each position were random or not and to identify preferences for specific amino acids or groups of amino acids using Chi-squared, and binomial analyses (see FIGS. 59A-H). Since there are 20 amino acids, the random occurrence of any given amino acid is approximately 1/20—this varies slightly depending on the codon because of the NNK sequence randomization used in the initial library construction. Also, if a preference for one type of amino acid is observed for any given position, a corresponding decrease in the other types of amino acids also will be seen at that position. A greater than expected decrease in another category of amino acid would be notable. Thus, in some instances both a preference for one type of amino acid and a selection against another type was seen, whereas in other instances either a selection for or against a particular type of amino acid was seen.

Position 1.

There is a strong preference for hydrophobic amino acids with a specific preference for tryptophan. Out of the 85 peptides analyzed, 75 had a hydrophobic amino acid, 30 of which were tryptophan. Note: In the number one position of the randomized peptide sequence, the randomized codon used for the initial periplasmic screen was DNK instead of NNK to avoid placement of prolines in the first position.

Position 2.

There is a preference for basic and small (glycine, alanine) amino acids and a strong selection against hydrophobic residues (only 6 hydrophobic amino acids were present but we would have expected 35 hydrophobic residues at this position by random chance. Out of 85 peptides analyzed, 27 had a basic amino acid, 21 of which were arginine, 25 had a small amino acid.

Position 3.

There is a preference for hydrophobic amino acids and arginine, a basic amino acid. Out of 85 peptides, 50 have a hydrophobic amino acid, 24 being tryptophan, and 19 have a basic residue, 17 being arginine.

Position 4.

There is a strong preference for hydrophobic residues with a preference for leucine. Out of 85 peptides, 77 have hydrophobic amino acids, 36 of which have leucine.

Position 5.

There is a strong preference for basic amino acids with a preference for arginine and lysine. Out of 85 peptides, 54 have a basic amino acid, 38 of which are arginine and 15 are lysine.

Position 6.

There is a strong preference for basic amino acids, especially arginine and a minor preference for small amino acids as well as a minor selection against hydrophobic amino acids. Out of 85 peptides, 48 have a basic residue, of which 39 are arginine, and 15 of the remaining amino acids are alanine or glycine.

Position 7.

There is a preference for hydrophobic amino acids, split between leucine and tryptophan, a minor preference for basic amino acids, and hydrophilic amino acids are selected against. Out of 85 peptides, 58 have a hydrophobic amino acid, 22 being tryptophan and 22 being leucine, 18 of the remaining 27 amino acids are basic.

Position 8.

There is a strong preference for hydrophobic amino acids tryptophan or leucine with a minor preference for small amino acids. Out of 85 peptides, 63 have a hydrophobic residue, 24 are tryptophan and 20 are leucine, 11 of the remaining 22 are either alanine or glycine.

Position 9.

There is a preference for basic amino acids, overrepresented by arginine with a slight bias towards small residues, particularly glycine. Out of 85 peptides, 37 have a basic amino acid, 31 of which are arginine, and 13 peptides have a glycine residue.

Position 10.

There is a preference for basic amino acids, overrepresented by arginine with a bias towards small amino acids. Out of 85 peptides, 35 have a basic residue, 29 of which are arginine, and 19 peptides have a small amino acid.

Position 11.

There appears to be a strong preference for tryptophan and arginine that drives the distribution here. Out of 85 peptides, 18 are arginine and 15 have a tryptophan.

Position 12.

There is a preference for basic residues, particularly arginine with a slight preference for glycine. Out of 85 peptides 36 have a basic amino acid of which 25 are arginine and 17 peptides have a small amino acid of which 13 are glycine.

Accordingly, in various embodiments, a consensus amino acid sequence for a 12mer peptide antimicrobial can be Xaa1 Xaa2 Xaa3 Xaa4 Xaa5 Xaa6 Xaa7 Xaa8 Xaa9 Xaa10 Xaa11 Xaa12 (SEQ ID NO:465); wherein Xaa1 is a hydrophobic amino acid (in one embodiment, tryptophan);

Xaa2, is a basic or small amino acid (in one embodiment, selected from glycine or alanine) or a basic amino acid (in one embodiment, arginine);

Xaa3 is a hydrophobic amino acid (in one embodiment, tryptophan) or a basic amino acid (in one embodiment, arginine);

Xaa4 is a hydrophobic amino acid (in one embodiment, leucine);

Xaa5 is a basic amino acid (in one embodiment, arginine or lysine);

Xaa6 is a basic amino acid (in one embodiment, arginine) or a small amino acid (in one embodiment, alanine or glycine);

Xaa7 is a hydrophobic amino acid (in one embodiment, selected from leucine or tryptophan) or a basic amino acid;

Xaa8 is a hydrophobic amino acid (in one embodiment, tryptophan or leucine) or a small amino acid (in one embodiment, alanine or glycine);

Xaa9 is a basic amino acid (in one embodiment, arginine) or a small amino acid (in one embodiment, glycine);

Xaa10 is a basic amino acid (in one embodiment, arginine) or a small amino acid (in one embodiment, glycine or alanine);

Xaa11 is tryptophan or arginine;

Xaa12 is a basic amino acid (in one embodiment, arginine) or a small amino acid (in one embodiment, glycine).

Example 13

Further analysis includes target identification utilizing the (His)6 tag to purify and collect the target molecule. Some peptides of various phenotypes have shown that they do not have a protein target. Microscopy is used to determine these peptides' effects on membrane perturbance.

1. A method for identifying an effective peptide antimicrobial, said method comprising:

controllably expressing a random peptide library in one or more microbial cell culture(s), wherein random peptides are encoded by plasmids comprising a nucleic acid sequence which is under the control of an inducible promoter; and identifying microbial cell culture(s) in which microbial cell growth or survival is affected by the peptide expressed by that culture.

2. The method of embodiment 1, comprising growing the one or more microbial cell culture(s) in the absence of an inducer of the inducible promoter before and/or after said controllable expression.
3. The method of embodiment 2, comprising growing the one or more microbial cell culture(s) in the presence of a transcriptional repressor.
4. The method of embodiment 1, comprising adding an inducer of the inducible promoter.
5. The method of embodiment 1, comprising transforming the microbial cells with the plasmids.
6. The method of embodiment 1, comprising contacting the one or more microbial cell culture(s) with an agent that negatively selects against replicating cells.
7. The method of embodiment 6, wherein the agent is ampicillin.
8. The method of embodiment 1, 2, 3, or 4 comprising identifying the peptide sequence of a microbial cell culture in which cell growth or survival is affected.
9. The method of embodiment 1, comprising constructing the plasmid.
10. The method of embodiment 1, wherein the nucleic acid sequence comprises a $NNK_n$ sequence, wherein NNK is a nucleotide triplet that encodes a random amino acid, wherein:
    N is A, T, C or G;
    K is T or G; and
    n is 2-50;
    wherein, optionally, n=12 (SEQ ID NO:462).
11. The method of embodiment 1, wherein the nucleic acid sequence comprises a $DNK(NNK)_n$ sequence, wherein DNK and NNK are nucleotide triplets that encode a random amino acid, wherein:
    N is A, T, C or G;
    K is T or G; and
    D is A, T, or G; and
    n is 1-49;
    wherein, optionally, n=11 (SEQ ID NO:463).
12. The method of any one of embodiments 1-11, wherein the plasmid encodes a leader peptide.
13. The method of embodiment 12, wherein the leader peptide targets the random peptides to the periplasm of gram negative microbial host cells.
14. The method of embodiment 12, wherein the leader peptide is an alkaline phosphatase leader peptide.
15. The method of any one of embodiments 1-11, wherein the inducible promoter is an arabinose inducible promoter ($P_{BAD}$).
16. The method of any one of embodiments 1-11, wherein the nucleic acid sequence encodes a carrier protein.
17. The method of embodiment 16, wherein the carrier protein is alkaline phosphatase, and wherein the C terminus of the random peptide is fused to the N terminus of the alkaline phosphatase protein.
18. The method of embodiment 16, wherein the carrier protein is alkaline phosphatase, and wherein the N terminus of the random peptide is fused to the C terminus of the alkaline phosphatase protein.
19. The method of embodiment 16, wherein the carrier protein is emerald green fluorescent protein, and wherein the C terminus of the random peptide is fused to the N terminus of the emerald green fluorescent protein.
20. The method of embodiment 16, wherein the carrier protein is emerald green fluorescent protein, and wherein the N terminus of the random peptide is fused to the C terminus of the emerald green fluorescent protein.
21. The method of any one of embodiments 1-11, wherein the host cell is a bacterium.
22. The method of embodiment 21, wherein the bacterium is *E. coli.*
23. An antimicrobial peptide comprising the sequence Xaa1 Xaa2 Xaa3 Xaa4 Xaa5 Xaa6 Xaa7 Xaa8 Xaa9 Xaa10 Xaa11 Xaa12 (SEQ ID NO:465); wherein
    Xaa1 is a hydrophobic amino acid;
    Xaa2, is a basic and/or small amino acid;
    Xaa3 is a hydrophobic amino acid or a basic amino acid;
    Xaa4 is a hydrophobic amino acid;
    Xaa5 is a basic amino acid;
    Xaa6 is a basic amino acid and/or a small amino acid;
    Xaa7 is a hydrophobic amino acid or a basic amino acid;
    Xaa8 is a hydrophobic amino acid or a small amino acid;
    Xaa9 is a basic amino acid and/or a small amino acid;
    Xaa10 is a basic amino acid and/or a small amino acid;
    Xaa11 is tryptophan or arginine;
    Xaa12 is a basic amino acid and/or a small amino acid.
24. An antimicrobial peptide comprising the amino acid sequence of any one of SEQ ID NOS:7-461.
25. The antimicrobial peptide of embodiment 24, comprising an amino acid sequence which is at least 85% homologous to the amino acid sequence:

```
                                        (SEQ ID NO: 310)
                FAWLWSWWRARR.
```

26. The antimicrobial peptide of embodiment 25, comprising an amino acid sequence which is at least 85% homologous to the amino acid sequence:

```
                                        (SEQ ID NO: 438)
                FMRLLRWWRRMQ.
```

27. The antimicrobial peptide of embodiment 26, comprising an amino acid sequence which is at least 85% homologous to the amino acid sequence:

```
                                        (SEQ ID NO: 347)
                IRWLARRWRRTF.
```

28. An artificial nucleic acid sequence encoding a peptide comprising the amino acid sequence of any one of SEQ ID NOS:7-461.
29. An expression vector comprising the artificial nucleotide sequence of claim 28.
30. A vector comprising a DNA sequence encoding an inducible promoter and a $(NNK)_n$ sequence of DNA, wherein NNK is a nucleotide triplet that encodes a random amino acid, wherein N is A, T, C or G, K is T or G, and n is 2-50.
31. A vector comprising a DNA sequence encoding an inducible promoter and a $DNK(NNK)_n$ sequence of DNA, wherein NNK is a nucleotide triplet that encodes a random amino acid, wherein N is A, T, C or G, K is T or G, D is A, T, or G; and n is 1-49.
32. An antimicrobial peptide of embodiment 23 comprising the sequence Xaa1 Xaa2 Xaa3 Xaa4 Xaa5 Xaa6 Xaa7 Xaa8 Xaa9 Xaa10 Xaa11 Xaa12 (SEQ ID NO:465); wherein
    Xaa1 is tryptophan;
    Xaa2 is glycine, alanine, or arginine;
    Xaa3 is tryptophan, or arginine;
    Xaa4 is leucine;
    Xaa5 is arginine or lysine;

Xaa6 is arginine, alanine or glycine;
Xaa7 is leucine or tryptophan;
Xaa8 is tryptophan, leucine, alanine or glycine;
Xaa9 is arginine or glycine;
Xaa10 is arginine, glycine or alanine;
Xaa11 is tryptophan or arginine;
Xaa12 is arginine or glycine.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method for isolating an antimicrobial peptide comprising:

obtaining a microbial cell culture comprising microbial cells transformed with a plasmid wherein the microbial cells are transformed with different plasmids, each plasmid comprising a nucleic acid sequence encoding a random peptide wherein expression of the random peptide is under the control of an inducible arabinose promoter, wherein the nucleic acid sequence encoding the random peptide comprises a $DNK(NNK)_n$ sequence, wherein DNK and NNK are nucleotide triplets that encode a random amino acid, wherein:

N is A, T, C or G;

K is T or G; and

D is A, T, or G; and n is 10-49;

culturing the microbial cell culture under a condition that represses expression of the random peptides;

controllably expressing a random peptide library by (i) removing the condition that represses expression from the microbial cell culture; and (ii) adding arabinose to the microbial cell culture, wherein the nucleic acid sequence of the plasmid further encodes a leader peptide and wherein following controllable expression, the leader peptide is at the N-terminus of the random peptide, wherein the microbial cell is a Gram-negative microbial cell comprising a periplasm and wherein the leader peptide targets the random peptide to the periplasm of the Gram negative microbial cell, wherein the leader peptide is an alkaline phosphatase leader peptide;

evaluating the microbial cell culture for evidence of an antimicrobial bacteriolytic, bacteriostatic, or bacteriocidal phenotype and if an antimicrobial phenotype is present;

isolating a nucleic acid sequence encoding a peptide leading to the antimicrobial phenotype.

2. The method of claim 1 wherein n=11.

3. A method of claim 1 wherein the evaluating includes detection of a plasmid in supernatant following centrifugation of the microbial cell culture and wherein the antimicrobial phenotype is bacteriolytic.

4. A method of claim 1 further comprising:

adding a negative selection agent to the microbial cell culture; and removing arabinose and the negative selection agent;

wherein the evaluating includes detection of replicating microbial cells following removal of the arabinose and the negative selection agent and wherein the antimicrobial phenotype is bacteriostatic.

5. A method of claim 4 wherein the negative selection agent is ampicillin.

6. A method of claim 4 further comprising enriching a population of microbial cells expressing a bacteriostatic peptide by:

isolating the replicating microbial cells of claim 4;

culturing the isolated replicating cells under a condition that represses expression of the isolated cells' encoded peptides;

controllably expressing the isolated cells' encoded peptides by (i) removing the condition that represses expression from the microbial cell culture; and (ii) adding arabinose to the microbial cell culture;

adding a negative selection agent to the microbial cell culture; and removing arabinose and the negative selection agent;

thereby enriching the population of microbial cells expressing a bacteriostatic peptide.

7. A method of claim 4 wherein the detection occurs based on examination of growth colonies.

8. A method of claim 1 further comprising:

removing arabinose; and adding a negative selection agent;

wherein the evaluating includes centrifuging the microbial cell culture and removing non-lysed cells from a pellet and wherein the antimicrobial phenotype is bacteriocidal.

9. A method of claim 8 wherein the negative selection agent is ampicillin.

* * * * *

SEQUENCE LISTING

```
<160> NUMBER OF SEQ ID NOS: 465

<210> SEQ ID NO 1
<211> LENGTH: 5943
<212> TYPE: DNA
<213> ORGANISM: Artificial Sequence
<220> FEATURE:
<223> OTHER INFORMATION: pKan phoA plasmid

<400> SEQUENCE: 1

acttttcata ctcccgccat tcagagaaga aaccaattgt ccatattgca tcagacattg      60

ccgtcactgc gtcttttact ggctcttctc gctaaccaaa ccggtaaccc cgcttattaa     120

aagcattctg taacaaagcg ggaccaaagc catgacaaaa acgcgtaaca aaagtgtcta     180

taatcacggc agaaaagtcc acattgatta tttgcacggc gtcacacttt gctatgccat     240
```

-continued

```
agcattttta tccataagat tagcggatcc tacctgacgc tttttatcgc aactctctac    300
tgtttctcca tgcggccgcg aaataatttt gtttaacttt aagaaggaga tatacatatg    360
aaacaaagca ctattgcact ggcactctta ccgttactgt acacccctgt gacaaaagcc    420
gaaggcggcg gcgcccggac accagaaatg cctgttctgg aaaaccgggc tgctcagggc    480
gatattactg cacccggcgg tgctcgccgt ttaacgggtg atcagactgc cgctctgcgt    540
gattctctta gcgataaacc tgcaaaaaat attattttgc tgattggcga tgggatgggg    600
gactcggaaa ttactgccgc acgtaattat gccgaaggtg cgggcggctt ttttaaaggt    660
atagatgcct taccgcttac cgggcaatac actcactatg cgctgaataa aaaaaccggc    720
aaaccggact acgtcaccga ctcggctgca tcagcaaccg cctggtcaac cggtgtcaaa    780
acctataacg gcgcgctggg cgtcgatatt cacgaaaaag atcacccaac gattctggaa    840
atggcaaaag ccgcaggtct ggcgaccggt aacgtttcta ccgcagagtt gcaggatgcc    900
acgcccgctg cgctggtggc acatgtgacc tcgcgcaaat gctacggtcc gagcgcgacc    960
agtgaaaaat gtccgggtaa cgctctggaa aaaggcggaa aaggatcgat taccgaacag   1020
ctgcttaacg ctcgtgccga cgttacgctt ggcggcggcg caaaaacctt tgctgaaacg   1080
gcaaccgctg gtgaatggca gggaaaaacg ctgcgtgaac aggcacaggc gcgtggttat   1140
cagttggtga gcgatgctgc ctcactgaat tcggtgacgg aagcgaatca gcaaaaaccc   1200
ctgcttggcc tgtttgctga cggcaatatg ccagtgcgct ggctaggacc gaaagcaacg   1260
taccatggca atatcgataa gcccgcagtc acctgtacgc caaatccgca acgtaatgac   1320
agtgtaccaa ccctggcgca gatgaccgac aaagccattg aattgttgag taaaaatgag   1380
aaaggctttt tcctgcaagt tgaaggtgcg tcaatcgata aacaggatca tgctgcgaat   1440
ccttgtgggc aaattggcga gacggtcgat ctcgatgaag ccgtacaacg ggcgctggaa   1500
ttcgctaaaa aggagggtaa cacgctggtc atagtcaccg ctgatcacgc ccacgccagc   1560
cagattgttg cgccggatac caaagctccg ggcctcaccc aggcgctaaa taccaaagat   1620
ggcgcagtga tggtgatgag ttacgggaac tccgaagagg attcacaaga acataccggc   1680
agtcagttgc gtattgcggc gtatggcccg catgccgcca atgttgttgg actgaccgac   1740
cagaccgatc tcttctacac catgaaagcc gctctggggc tgaaacatca tcatcatcat   1800
cattaactgt tatctagaat aaaacgaaag gctcagtcga aagactgggc ctttcgtttt   1860
atctgttgtt tgtcggtgaa cgctctcctg agtaggacaa atccgccggg agcggatttg   1920
aacgttgcga agcaacggcc cggagggtgg cgggcaggac gcccgccata aactgccagg   1980
catcaaatta agcagaaggc catcctgacg gatggccttt ttgaattcac tggccgtcgt   2040
tttacaacgt cgtgactggg aaaaccctgg cgttacccaa cttaatcgcc ttgcagcaca   2100
tccccctttc gccagactca ccagtcacag aaaagcatct tacggatggc atgacagtaa   2160
gagaattatg cagtgctgcc ataaccatga gtgataacac tgcggccaac ttacttctga   2220
caacgatcgg aggaccgaag gagctaaccg cttttttgca caacatgggg gatcatgtaa   2280
ctcgccttga tcgttgggaa ccggagctga atgaagccat accaaacgac gagcgtgaca   2340
ccacgatgcc tgcagcaatg gcaacaacgt tgcgcaaact attaactggc gaactactta   2400
ctctagcttc ccggcaacaa ttaatagact ggatggaggc ggataaagtt gcaggaccac   2460
ttctgcgctc ggcccttccg gctggctggt ttattgctga taaatctgga gccggtgagc   2520
gtgggtctcg cggtatcatt gcagcactgg ggccagatgg taagccctcc cgtatcgtag   2580
ttatctacac gacggggagt caggcaacta tggatgaacg aaatagacag atcgctgaga   2640
```

-continued

```
taggtgcctc actgattaag cattggtaac tgtcagacca agtttactca tatatacttt   2700
agattgattt aaaacttcat ttttaattta aaaggatcta ggtgaagatc ctttttgata   2760
atctcatgac caaaatccct taacgtgagt tttcgttcca ctgagcgtca gaccccttaa   2820
taagatgatc ttcttgagat cgttttggtc tgcgcgtaat ctcttgctct gaaaacgaaa   2880
aaaccgcctt gcagggcggt ttttcgaagg ttctctgagc taccaactct ttgaaccgag   2940
gtaactggct tggaggagcg cagtcaccaa aacttgtcct ttcagtttag ccttaaccgg   3000
cgcatgactt caagactaac tcctctaaat caattaccag tggctgctgc cagtggtgct   3060
tttgcatgtc tttccgggtt ggactcaaga cgatagttac cggataaggc gcagcggtcg   3120
gactgaacgg ggggttcgtg catacagtcc agcttggagc gaactgccta cccggaactg   3180
agtgtcaggc gtggaatgag acaaacgcgg ccataacagc ggaatgacac cggtaaaccg   3240
aaaggcagga acaggagagc gcacgaggga gccgccaggg ggaaacgcct ggtatcttta   3300
tagtcctgtc gggtttcgcc accactgatt tgagcgtcag atttcgtgat gcttgtcagg   3360
ggggcggagc ctatggaaaa acggctttgc cgcggccctc tcacttccct gttaagtatc   3420
ttcctggcat cttccaggaa atctccgccc cgttcgtaag ccatttccgc tcgccgcagt   3480
cgaacgaccg agcgtagcga gtcagtgagc gaggaagcgg aatatatcct gtatcacata   3540
ttctgctgac gcaccggtgc agcctttttt ctcctgccac atgaagcact tcactgacac   3600
cctcatcagt gccaacatag taagccagta tacactccgc tagcgctgag gtctgcctcg   3660
tgaagaaggt gttgctgact cataccaggc ctgaatcgcc ccatcatcca gccagaaagt   3720
gagggagcca cggttgatga gagctttgtt gtaggtggac cagttggtga ttttgaactt   3780
ttgctttgcc acggaacggt ctgcgttgtc gggaagatgc gtgatctgat ccttcaactc   3840
agcaaaagtt cgatttattc aacaaagcca cgttgtgtct caaaatctct gatgttacat   3900
tgcacaagat aaaaatatat catcatgaac aataaaactg tctgcttaca taaacagtaa   3960
tacaaggggt gttatgagcc atattcaacg ggaaacgtct tgctcgaggc cgcgattaaa   4020
ttccaacatg gatgctgatt tatatgggta taaatgggct cgcgataatg tcgggcaatc   4080
aggtgcgaca atctatcgat tgtatgggaa gcccgatgcg ccagagttgt ttctgaaaca   4140
tggcaaaggt agcgttgcca atgatgttac agatgagatg gtcagactaa actggctgac   4200
ggaatttatg cctcttccga ccatcaagca ttttatccgt actcctgatg atgcatggtt   4260
actcaccact gcgatccccg ggaaaacagc attccaggta ttagaagaat atcctgattc   4320
aggtgaaaat attgctgatg cgctggcagt gttcctgcgc cggttgcatt cgattcctgt   4380
ttgtaattgt ccttttaaca gcgatcgcgt atttcgtctc gctcaggcgc aatcacgaat   4440
gaataacggt ttggttgatg cgagtgattt tgatgacgag cgtaatggct ggcctgttga   4500
acaagtctgg aaagaaatgc ataaactttt gccattctca ccggattcag tcgtcactca   4560
tggtgatttc tcacttgata accttatttt tgacgagggg aaattaatag gttgtattga   4620
tgttggacga gtcggaatcg cagaccgata ccaggatctt gccatcctat ggaactgcct   4680
cggtgagttt tctccttcat tacagaaacg gctttttcaa aaatatggta ttgataatcc   4740
tgatatgaat aaattgcagt ttcatttgat gctcgatgag tttttctaat cagaattggt   4800
taattggttg taacactggc agagcattac gctgacttga cgggacggcg gctttgttga   4860
ataaatcgaa cttttgctga gttgaaggat cagatcacgc atcttcccga caacgcagac   4920
cgttccgtgg caaagcaaaa gttcaaaatc actagtcgac catggtacca tcgatgcata   4980
```

-continued

```
atgtgcctgt caaatggacg aagcagggat tctgcaaacc ctatgctact ccgtcaagcc   5040

gtcaattgtc tgattcgtta ccaattatga caacttgacg gctacatcat tcactttttc   5100

ttcacaaccg gcacggaact cgctcgggct ggccccggtg cattttttaa atacccgcga   5160

gaaatagagt tgatcgtcaa aaccaacatt gcgaccgacg gtggcgatag gcatccgggt   5220

ggtgctcaaa agcagcttcg cctggctgat acgttggtcc tcgcgccagc ttaagacgct   5280

aatccctaac tgctggcgga aaagatgtga cagacgcgac ggcgacaagc aaacatgctg   5340

tgcgacgctg gcgatatcaa aattgctgtc tgccaggtga tcgctgatgt actgacaagc   5400

ctcgcgtacc cgattatcca tcggtggatg gagcgactcg ttaatcgctt ccatgcgccg   5460

cagtaacaat tgctcaagca gatttatcgc cagcagctcc gaatagcgcc cttccccttg   5520

cccggcgtta atgatttgcc caaacaggtc gctgaaatgc ggctggtgcg cttcatccgg   5580

gcgaaagaac cccgtattgg caaatattga cggccagtta agccattcat gccagtaggc   5640

gcgcggacga aagtaaaccc actggtgata ccattcgcga gcctccggat gacgaccgta   5700

gtgatgaatc tctcctggcg ggaacagcaa aatatcaccc ggtcggcaaa caaattctcg   5760

tccctgattt ttcaccaccc cctgaccgcg aatggtgaga ttgagaatat aacctttcat   5820

tcccagcggt cggtcgataa aaaaatcgag ataaccgttg gcctcaatcg gcgttaaacc   5880

cgccaccaga tgggcattaa acgagtatcc cggcagcagg ggatcatttt gcgcttcagc   5940

cat                                                                 5943


<210> SEQ ID NO 2
<211> LENGTH: 68
<212> TYPE: DNA
<213> ORGANISM: Artificial Sequence
<220> FEATURE:
<223> OTHER INFORMATION: Complementary DNA containing a NNK 12-mer and a
      BsrGI sticky end
<220> FEATURE:
<221> NAME/KEY: misc_feature
<222> LOCATION: (23)..(23)
<223> OTHER INFORMATION: d=a, g or t
<220> FEATURE:
<221> NAME/KEY: misc_feature
<222> LOCATION: (24)..(57)
<223> OTHER INFORMATION: n=g, a, t or c
<220> FEATURE:
<221> NAME/KEY: misc_feature
<222> LOCATION: (25)..(58)
<223> OTHER INFORMATION: k=g or t

<400> SEQUENCE: 2

gtacacccct gtgacaaaag ccdnknnknn knnknnknnk nnknnknnkn nknnknnkga     60

aggcggcg                                                              68


<210> SEQ ID NO 3
<211> LENGTH: 68
<212> TYPE: DNA
<213> ORGANISM: Artificial Sequence
<220> FEATURE:
<223> OTHER INFORMATION: Complementary DNA containing a NNK 12-mer and a
      KasI sticky end
<220> FEATURE:
<221> NAME/KEY: misc_feature
<222> LOCATION: (19)..(19)
<223> OTHER INFORMATION: h=a. c or t
<220> FEATURE:
<221> NAME/KEY: misc_feature
<222> LOCATION: (20)..(53)
<223> OTHER INFORMATION: n=g, a, t or c
<220> FEATURE:
<221> NAME/KEY: misc_feature
```

<222> LOCATION: (21)..(54)
<223> OTHER INFORMATION: m=a or c

<400> SEQUENCE: 3
tggggacact gttttcgghn mnnmnnmnnm nnmnnmnnmn nmnnmnnmnn mnnmcttccg 60
ccgccgcg 68

<210> SEQ ID NO 4
<211> LENGTH: 9952
<212> TYPE: DNA
<213> ORGANISM: Artificial Sequence
<220> FEATURE:
<223> OTHER INFORMATION: pBac-EmGHt construct
<220> FEATURE:
<221> NAME/KEY: misc_feature
<222> LOCATION: (173)..(173)
<223> OTHER INFORMATION: d=a, g or t
<220> FEATURE:
<221> NAME/KEY: misc_feature
<222> LOCATION: (174)..(207)
<223> OTHER INFORMATION: n=g, a, t or c
<220> FEATURE:
<221> NAME/KEY: misc_feature
<222> LOCATION: (175)..(208)
<223> OTHER INFORMATION: k=g or t

<400> SEQUENCE: 4
gacgcttttt atcgcaactc tctactgttt ctccatgcgg ccgcgaaata attttgttta 60
actttaagaa ggagatatac atatgcgggg ttctcatcat catcatcatc atggtatggc 120
tagcatgact ggtggacagc aaatgggtcg ggaaaacctg tacttccagg gcdnknnknn 180
knnknnknnk nnknnknnkn nknnknnkga aggcggcggc gccatggtga gcaagggcga 240
ggagctgttc accggggtgg tgcccatcct ggtcgagctg gacggcgacg taaacggcca 300
caagttcagc gtgtccggcg agggcgaggg cgatgccacc tacggcaagc tgaccctgaa 360
gttcatctgc accaccggca agctgcccgt gccctggccc accctcgtga ccaccttgac 420
ctacggcgtg cagtgcttcg cccgctaccc cgaccacatg aagcagcacg acttcttcaa 480
gtccgccatg cccgaaggct acgtccagga gcgcaccatc ttcttcaagg acgacggcaa 540
ctacaagacc cgcgccgagg tgaagttcga gggcgacacc ctggtgaacc gcatcgagct 600
gaagggcatc gacttcaagg aggacggcaa catcctgggg cacaagctgg agtacaacta 660
caacagccac aaggtctata tcaccgccga caagcagaag aacggcatca aggtgaactt 720
caagacccgc cacaacatcg aggacggcag cgtgcagctc gccgaccact accagcagaa 780
cacccccatc ggcgacggcc ccgtgctgct gcccgacaac cactacctga gcacccagtc 840
cgccctgagc aaagacccca acgagaagcg cgatcacatg gtcctgctgg agttcgtgac 900
cgccgccggg atcactctcg gcatggacga gctgtacaag taactcgaga agcttctaga 960
ataaaacgaa aggctcagtc gaaagactgg gcctttcgtt ttatctgttg tttgtcggtg 1020
aacgctctcc tgagtaggac aaatccgccg ggagcggatt tgaacgttgc gaagcaacgg 1080
cccggagggt ggcgggcagg acgcccgcca taaactgcca ggcatcaaat taagcagaag 1140
gccatcctga cggatggcct ttttgaattc atgccgtaat aggccgcatc gaatataact 1200
tcgtataatg tatgctatac gaagttatta gcgatgagct cggacttcca ttgttcattc 1260
cacggacaaa aacagagaaa ggaaacgaca gaggccaaaa agctcgcttt cagcacctgt 1320
cgtttccttt cttttcagag ggtattttaa ataaaaacat taagttatga cgaagaagaa 1380
cggaaacgcc ttaaaccgga aaattttcat aaatagcgaa aacccgcgag gtcgccgccc 1440

-continued

```
cgtaacctgt cggatcaccg gaaaggaccc gtaaagtgat aatgattatc atctacatat   1500
cacaacgtgc gtggaggcca tcaaaccacg tcaaataatc aattatgacg caggtatcgt   1560
attaattgat ctgcatcaac ttaacgtaaa aacaacttca gacaatacaa atcagcgaca   1620
ctgaatacgg ggcaacctca tgtccgagct cgcgagctcg tcgacagcga cacacttgca   1680
tcggatgcag cccggttaac gtgccggcac ggcctgggta accaggtatt ttgtccacat   1740
aaccgtgcgc aaaatgttgt ggataagcag gacacagcag caatccacag caggcataca   1800
accgcacacc gaggttactc cgttctacag gttacgacga catgtcaata cttgcccttg   1860
acaggcattg atggaatcgt agtctcacgc tgatagtctg atcgacaata caagtgggac   1920
cgtggtccca gaccgataat cagaccgaca acacgagtgg gatcgtggtc ccagactaat   1980
aatcagaccg acgatacgag tgggaccgtg gtcccagact aataatcaga ccgacgatac   2040
gagtgggacc gtggttccag actaataatc agaccgacga tacgagtggg accgtggtcc   2100
cagactaata atcagaccga cgatacgagt gggaccatgg tcccagacta ataatcagac   2160
cgacgatacg agtgggaccg tggtcccagt ctgattatca gaccgacgat acgagtggga   2220
ccgtggtccc agactaataa tcagaccgac gatacgagtg ggaccgtggt cccagactaa   2280
taatcagacc gacgatacga gtgggaccgt ggtcccagtc tgattatcag accgacgata   2340
caagtggaac agtgggccca gagagaatat tcaggccagt tatgctttct ggcctgtaac   2400
aaaggacatt aagtaaagac agataaacgt agactaaaac gtggtcgcat cagggtgctg   2460
gcttttcaag ttccttaaga atggcctcaa ttttctctat acactcagtt ggaacacgag   2520
acctgtccag gttaagcacc attttatcgc ccttatacaa tactgtcgct ccaggagcaa   2580
actgatgtcg tgagcttaaa ctagttcttg atgcagatga cgttttaagc acagaagtta   2640
aaagagtgat aacttcttca gcttcaaata tcaccccagc ttttttctgc tcatgaaggt   2700
tagatgcctg ctgcttaagt aattcctctt tatctgtaaa ggctttttga agtgcatcac   2760
ctgaccgggc agatagttca ccggggtgag aaaaaagagc aacaactgat ttaggcaatt   2820
tggcggtgtt gatacagcgg gtaataatct tacgtgaaat attttccgca tcagccagcg   2880
cagaaatatt tccagcaaat tcattctgca atcggcttgc ataacgctga ccacgttcat   2940
aagcacttgt tgggcgataa tcgttaccca atctggataa tgcagccatc tgctcatcat   3000
ccagctcgcc aaccagaaca cgataatcac tttcggtaag tgcagcagct ttacgacggc   3060
gactcccatc ggcaatttct atgacaccag atactcttcg accgaacgcc ggtgtctgtt   3120
gaccagtcag tagaaaagaa gggatgagat catccagtgc gtcctcagta agcagctcct   3180
ggtcacgttc attacctgac catacccgag aggtcttctc aacactatca ccccggagca   3240
cttcaagagt aaacttcaca tcccgaccac atacaggcaa agtaatggca ttaccgcgag   3300
ccattactcc tacgcgcgca attaacgaat ccaccatcgg ggcagctggt gtcgataacg   3360
aagtatcttc aaccggttga gtattgagcg tatgttttgg aataacaggc gcacgcttca   3420
ttatctaatc tcccagcgtg gtttaatcag acgatcgaaa atttcattgc agacaggttc   3480
ccaaatagaa agagcatttc tccaggcacc agttgaagag cgttgatcaa tggcctgttc   3540
aaaaacagtt ctcatccgga tctgaccttt accaacttca tccgtttcac gtacaacatt   3600
ttttagaacc atgcttcccc aggcatcccg aatttgctcc tccatccacg gggactgaga   3660
gccattgcta ttgctgtatt tggtaagcaa aatacgtaca tcaggctcga accctttaag   3720
atcaacgttc ttgagcagat cacgaagcat atcgaaaaac tgcagtgcgg aggtgtagtc   3780
aaacaactca gcaggcgtgg gaacaatcag cacatcagca gcacatacga cattaatcgt   3840
```

-continued

```
gccgataccc aggttaggcg cgctgtcaat aactatgaca tcatagtcat gagcaacagt   3900
ttcaatggcc agtcggagca tcaggtgtgg atcggtgggc agtttacctt catcaaattt   3960
gcccattaac tcagtttcaa tacggtgcag agccagacag gaaggaataa tgtcaagccc   4020
cggccagcaa gtgggcttta ttgcataagt gacatcgtcc ttttccccaa gatagaaagg   4080
caggagagtg tcttctgcat gaatatgaag atctggtacc catccgtgat acattgaggc   4140
tgttccctgg gggtcgttac cttccacgag caaaacacgt agccccttca gagccagatc   4200
ctgagcaaga tgaacagaaa ctgaggtttt gtaaacgcca cctttatggg cagcaacccc   4260
gatcaccggt ggaaatacgt cttcagcacg tcgcaatcgc gtaccaaaca catcacgcat   4320
atgattaatt tgttcaattg tataaccaac acgttgctca acccgtcctc gaatttccat   4380
atccgggtgc ggtagtcgcc ctgctttctc ggcatctctg atagcctgag aagaaacccc   4440
aactaaatcc gctgcttcac ctattctcca gcgccgggtt attttcctcg cttccgggct   4500
gtcatcatta aactgtgcaa tggcgatagc cttcgtcatt tcatgaccag cgtttatgca   4560
ctggttaagt gtttccatga gtttcattct gaacatcctt taatcattgc tttgcgtttt   4620
tttattaaat cttgcaattt actgcaaagc aacaacaaaa tcgcaaagtc atcaaaaaac   4680
cgcaaagttg tttaaaataa gagcaacact acaaaaggag ataagaagag cacatacctc   4740
agtcacttat tatcactagc gctcgccgca gccgtgtaac cgagcatagc gagcgaactg   4800
gcgaggaagc aaagaagaac tgttctgtca gatagctctt acgctcagcg caagaagaaa   4860
tatccaccgt gggaaaaact ccaggtagag gtacacacgc ggatagccaa ttcagagtaa   4920
taaactgtga taatcaaccc tcatcaatga tgacgaacta acccccgata tcaggtcaca   4980
tgacgaaggg aaagagaagg aaatcaactg tgacaaactg ccctcaaatt tggcttcctt   5040
aaaaattaca gttcaaaaag tatgagaaaa tccatgcagg ctgaaggaaa cagcaaaact   5100
gtgacaaatt accctcagta ggtcagaaca aatgtgacga accaccctca aatctgtgac   5160
agataaccct cagactatcc tgtcgtcatg gaagtgatat cgcggaagga aaatacgata   5220
tgagtcgtct ggcggccttt ctttttctca atgtatgaga ggcgcattgg agttctgctg   5280
ttgatctcat taacacagac ctgcaggaag cggcggcgga agtcaggcat acgctggtaa   5340
ctttgaggca gctggtaacg ctctatgatc cagtcgattt tcagagagac gatgcctgag   5400
ccatccggct tacgatactg acacagggat tcgtataaac gcatggcata cggattggtg   5460
atttcttttg tttcactaag ccgaaactgc gtaaaccggt tctgtaaccc gataaagaag   5520
ggaatgagat atgggttgat atgtacgctg taaagccctc tggatggact gtgcgcacgt   5580
ttgataaacc aaggaaaaga ttcatagcct ttttcatcgc cggcatcctc ttcagggcga   5640
taaaaaacca cttccttccc cgcgaaactc ttcaatgcct gccgtatatc cttactggct   5700
tccgcagagg tcaatccgaa tatttcagca tatttagcaa catggatctc gcagataccg   5760
tcatgttcct gtagggtgcc atcagatttt ctgatctggt caacgaacag atacagcata   5820
cgtttttgat cccgggagag actatatgcc gcctcagtga ggtcgtttga ctggacgatt   5880
cgcgggctat tttacgttt cttgtgattg ataaccgctg tttccgccat gacagatcca   5940
tgtgaagtgt gacaagtttt tagattgtca cactaaataa aaaagagtca ataagcaggg   6000
ataactttgt gaaaaaacag cttcttctga gggcaatttg tcacagggtt aagggcaatt   6060
tgtcacagac aggactgtca tttgagggtg atttgtcaca ctgaaagggc aatttgtcac   6120
aacaccttct ctagaaccag catggataaa ggcctacaag gcgctctaaa aaagaagatc   6180
```

-continued

```
taaaaactat aaaaaaaata attataaaaa tatccccgtg gataagtgga taaccccaag   6240
ggaagttttt tcaggcatcg tgtgtaagca gaatatataa gtgctgttcc ctggtgcttc   6300
ctcgctcact cgaccgggag ggttcgagaa ggggggcac ccccccttcgg cgtgcgcggt   6360
cacgcgcaca gggcgcagcc ctggttaaaa acaaggttta taaatattgg tttaaaagca   6420
ggttaaaaga caggttagcg gtggccgaaa aacgggcgga aacccttgca aatgctggat   6480
tttctgcctg tggacagccc ctcaaatgtc aataggtgcg cccctcatct gtcagcactc   6540
tgcccctcaa gtgtcaagga tcgcgcccct catctgtcag tagtcgcgcc cctcaagtgt   6600
caataccgca gggcacttat ccccaggctt gtccacatca tctgtgggaa actcgcgtaa   6660
aatcaggcgt tttcgccgat ttgcgaggct ggccagctcc acgtcgccgg ccgaaatcga   6720
gcctgcccct catctgtcaa cgccgcgccg ggtgagtcgg cccctcaagt gtcaacgtcc   6780
gcccctcatc tgtcagtgag ggccaagttt tccgcgaggt atccacaacg ccggcggccg   6840
gccgcggtgt ctcgcacacg gcttcgacgg cgtttctggc gcgtttgcag ggccatagac   6900
ggccgccagc ccagcggcga gggcaaccag ctcgagggct tcgccctgtc gctcgactgc   6960
ggcgagcact actggctgta aaaggacaga ccacatcatg gttctgtgtt cattaggttg   7020
ttctgtccat tgctgacata atccgctcca cttcaacgta acaccgcacg aagatttcta   7080
ttgttcctga aggcatattc aaatcgtttt cgttaccgct tgcaggcatc atgacagaac   7140
actacttcct ataaacgcta cacaggctcc tgagattaat aatgcggatc tctacgataa   7200
tgggagattt tcccgactgt ttcgttcgct tctcagtgga taacagccag cttctctgtt   7260
taacagacaa aaacagcata tccactcagt tccacatttc catataaagg ccaaggcatt   7320
tattctcagg ataattgttt cagcatcgca accgcatcag actccggcat cgcaaactgc   7380
acccggtgcc gggcagccac atccagcgca aaaaccttcg tgtagacttc cgttgaactg   7440
atggacttat gtcccatcag gctttgcaga actttcagcg gtataccggc atacagcatg   7500
tgcatcgcat aggaatggcg gaacgtatgt ggtgtgaccg gaacagagaa cgtcacaccg   7560
tcagcagcag cggcggcaac cgcctcccca atccaggtcc tgaccgttct gtccgtcact   7620
tcccagatcc gcgctttctc tgtccttcct gtgcgacggt tacgccgctc catgagctta   7680
tcgcgaataa atacctgtga cggaagatca cttcgcagaa taaataaatc ctggtgtccc   7740
tgttgatacc gggaagccct gggccaactt ttggcgaaaa tgagacgttg atcggcacgt   7800
aagaggttcc aactttcacc ataatgaaat aagatcacta ccgggcgtat tttttgagtt   7860
atcgagattt tcaggagcta aggaagctaa aatggagaaa aaaatcactg gatataccac   7920
cgttgatata tcccaatggc atcgtaaaga acattttgag gcatttcagt cagttgctca   7980
atgtacctat aaccagaccg ttcagctgga tattacggcc tttttaaaga ccgtaaagaa   8040
aaataagcac aagttttatc cggcctttat tcacattctt gcccgcctga tgaatgctca   8100
tccggaattt cgtatggcaa tgaaagacgg tgagctggtg atatgggata gtgttcaccc   8160
ttgttacacc gttttccatg agcaaactga aacgttttca tcgctctgga gtgaatacca   8220
cgacgatttc cggcagtttc tacacatata ttcgcaagat gtggcgtgtt acggtgaaaa   8280
cctggcctat ttccctaaag ggtttattga gaatatgttt ttcgtctcag ccaatccctg   8340
ggtgagtttc accagttttg atttaaacgt ggccaatatg gacaacttct tcgcccccgt   8400
tttcaccatg ggcaaatatt atacgcaagg cgacaaggtg ctgatgccgc tggcgattca   8460
ggttcatcat gccgtttgtg atggcttcca tgtcggcaga atgcttaatg aattacaaca   8520
gtactgcgat gagtggcagg gcggggcgta attttttttaa ggcagttatt ggtgccctta   8580
```

```
aacgcctggt tgctacgcct gaataagtga taataagcgg atgaatggca gaaattcgat   8640

gataagctgt caaacatgag aattggtcga cggcccgggc ggccatcgaa gcctataggt   8700

accatcgatg cataatgtgc ctgtcaaatg gacgaagcag ggattctgca aaccctatgc   8760

tactccgtca agccgtcaat tgtctgattc gttaccaatt atgacaactt gacggctaca   8820

tcattcactt tttcttcaca accggcacgg aactcgctcg ggctggcccc ggtgcatttt   8880

ttaaataccc gcgagaaata gagttgatcg tcaaaaccaa cattgcgacc gacggtggcg   8940

ataggcatcc gggtggtgct caaaagcagc ttcgcctggc tgatacgttg gtcctcgcgc   9000

cagcttaaga cgctaatccc taactgctgg cggaaaagat gtgacagacg cgacggcgac   9060

aagcaaacat gctgtgcgac gctggcgata tcaaaattgc tgtctgccag gtgatcgctg   9120

atgtactgac aagcctcgcg tacccgatta tccatcggtg gatggagcga ctcgttaatc   9180

gcttccatgc gccgcagtaa caattgctca agcagattta tcgccagcag ctccgaatag   9240

cgcccttccc cttgcccggc gttaatgatt tgcccaaaca ggtcgctgaa atgcggctgg   9300

tgcgcttcat ccgggcgaaa gaaccccgta ttggcaaata ttgacggcca gttaagccat   9360

tcatgccagt aggcgcgcgg acgaaagtaa acccactggt gataccattc gcgagcctcc   9420

ggatgacgac cgtagtgatg aatctctcct ggcgggaaca gcaaaatatc acccggtcgg   9480

caaacaaatt ctcgtccctg atttttcacc accccctgac cgcgaatggt gagattgaga   9540

atataacctt tcattcccag cggtcggtcg ataaaaaaat cgagataacc gttggcctca   9600

atcggcgtta aacccgccac cagatgggca ttaaacgagt atcccggcag caggggatca   9660

ttttgcgctt cagccatact tttcatactc ccgccattca gagaagaaac caattgtcca   9720

tattgcatca gacattgccg tcactgcgtc ttttactggc tcttctcgct aaccaaaccg   9780

gtaaccccgc ttattaaaag cattctgtaa caaagcggga ccaaagccat gacaaaaacg   9840

cgtaacaaaa gtgtctataa tcacggcaga aaagtccaca ttgattattt gcacggcgtc   9900

acactttgct atgccatagc atttttatcc ataagattag cggatcctac ct            9952
```

<210> SEQ ID NO 5
<211> LENGTH: 9979
<212> TYPE: DNA
<213> ORGANISM: Artificial Sequence
<220> FEATURE:
<223> OTHER INFORMATION: pBac-EmGH construct
<220> FEATURE:
<221> NAME/KEY: misc_feature
<222> LOCATION: (932)..(966)
<223> OTHER INFORMATION: n=g, a, t or c
<220> FEATURE:
<221> NAME/KEY: misc_feature
<222> LOCATION: (934)..(967)
<223> OTHER INFORMATION: k=g or t

<400> SEQUENCE: 5

```
gacgcttttt atcgcaactc tctactgttt ctccatgcgg ccgcgaaata attttgttta     60

actttaagaa ggagatatac atatgcgggg ttctcatcat catcatcatc atggtatggc    120

tagcatgact ggtggacagc aaatgggtcg ggatctgtac gacgatgacg ataaggatcg    180

atggggatcc gaattcgcca ccatggtgag caagggcgag gagctgttca ccggggtggt    240

gcccatcctg gtcgagctgg acggcgacgt aaacggccac aagttcagcg tgtccggcga    300

gggcgagggc gatgccacct acggcaagct gaccctgaag ttcatctgca ccaccggcaa    360

gctgcccgtg ccctggccca ccctcgtgac caccttgacc tacggcgtgc agtgcttcgc    420
```

-continued

```
ccgctacccc gaccacatga agcagcacga cttcttcaag tccgccatgc ccgaaggcta    480
cgtccaggag cgcaccatct tcttcaagga cgacggcaac tacaagaccc gcgccgaggt    540
gaagttcgag ggcgacaccc tggtgaaccg catcgagctg aagggcatcg acttcaagga    600
ggacggcaac atcctggggc acaagctgga gtacaactac aacagccaca aggtctatat    660
caccgccgac aagcagaaga acggcatcaa ggtgaacttc aagacccgcc acaacatcga    720
ggacggcagc gtgcagctcg ccgaccacta ccagcagaac acccccatcg gcgacggccc    780
cgtgctgctg cccgacaacc actacctgag cacccagtcc gccctgagca aagaccccaa    840
cgagaagcgc gatcacatgg tcctgctgga gttcgtgacc gccgccggga tcactctcgg    900
catggacgag ctgtacaagg gcggcggcga annknnknnk nnknnknnkn nknnknnknn    960
knnknnktaa ctcgagaagc ttctagaata aaacgaaagg ctcagtcgaa agactgggcc   1020
tttcgtttta tctgttgttt gtcggtgaac gctctcctga gtaggacaaa tccgccggga   1080
gcggatttga acgttgcgaa gcaacggccc ggagggtggc gggcaggacg cccgccataa   1140
actgccaggc atcaaattaa gcagaaggcc atcctgacgg atggcctttt tgaattcatg   1200
ccgtaatagg ccgcatcgaa tataacttcg tataatgtat gctatacgaa gttattagcg   1260
atgagctcgg acttccattg ttcattccac ggacaaaaac agagaaagga aacgacagag   1320
gccaaaaagc tcgctttcag cacctgtcgt ttcctttctt ttcagagggt attttaaata   1380
aaaacattaa gttatgacga agaagaacgg aaacgcctta aaccggaaaa ttttcataaa   1440
tagcgaaaac ccgcgaggtc gccgccccgt aacctgtcgg atcaccggaa aggacccgta   1500
aagtgataat gattatcatc tacatatcac aacgtgcgtg gaggccatca aaccacgtca   1560
aataatcaat tatgacgcag gtatcgtatt aattgatctg catcaactta acgtaaaaac   1620
aacttcagac aatacaaatc agcgacactg aatacggggc aacctcatgt ccgagctcgc   1680
gagctcgtcg acagcgacac acttgcatcg gatgcagccc ggttaacgtg ccggcacggc   1740
ctgggtaacc aggtattttg tccacataac cgtgcgcaaa atgttgtgga taagcaggac   1800
acagcagcaa tccacagcag gcatacaacc gcacaccgag gttactccgt tctacaggtt   1860
acgacgacat gtcaatactt gcccttgaca ggcattgatg gaatcgtagt ctcacgctga   1920
tagtctgatc gacaatacaa gtgggaccgt ggtcccagac cgataatcag accgacaaca   1980
cgagtgggat cgtggtccca gactaataat cagaccgacg atacgagtgg gaccgtggtc   2040
ccagactaat aatcagaccg acgatacgag tgggaccgtg gttccagact aataatcaga   2100
ccgacgatac gagtgggacc gtggtcccag actaataatc agaccgacga tacgagtggg   2160
accatggtcc cagactaata atcagaccga cgatacgagt gggaccgtgg tcccagtctg   2220
attatcagac cgacgatacg agtgggaccg tggtcccaga ctaataatca gaccgacgat   2280
acgagtggga ccgtggtccc agactaataa tcagaccgac gatacgagtg ggaccgtggt   2340
cccagtctga ttatcagacc gacgatacaa gtggaacagt gggcccagag agaatattca   2400
ggccagttat gctttctggc ctgtaacaaa ggacattaag taaagacaga taaacgtaga   2460
ctaaaacgtg gtcgcatcag ggtgctggct tttcaagttc cttaagaatg gcctcaattt   2520
tctctataca ctcagttgga acacgagacc tgtccaggtt aagcaccatt ttatcgccct   2580
tatacaatac tgtcgctcca ggagcaaact gatgtcgtga gcttaaacta gttcttgatg   2640
cagatgacgt tttaagcaca gaagttaaaa gagtgataac ttcttcagct tcaaatatca   2700
ccccagcttt tttctgctca tgaaggttag atgcctgctg cttaagtaat tcctctttat   2760
ctgtaaaggc tttttgaagt gcatcacctg accgggcaga tagttcaccg ggtgagaaa    2820
```

```
aaagagcaac aactgattta ggcaatttgg cggtgttgat acagcgggta ataatcttac   2880
gtgaaatatt ttccgcatca gccagcgcag aaatatttcc agcaaattca ttctgcaatc   2940
ggcttgcata acgctgacca cgttcataag cacttgttgg gcgataatcg ttacccaatc   3000
tggataatgc agccatctgc tcatcatcca gctcgccaac cagaacacga taatcacttt   3060
cggtaagtgc agcagcttta cgacggcgac tcccatcggc aatttctatg acaccagata   3120
ctcttcgacc gaacgccggt gtctgttgac cagtcagtag aaaagaaggg atgagatcat   3180
ccagtgcgtc ctcagtaagc agctcctggt cacgttcatt acctgaccat acccgagagg   3240
tcttctcaac actatcaccc cggagcactt caagagtaaa cttcacatcc cgaccacata   3300
caggcaaagt aatggcatta ccgcgagcca ttactcctac gcgcgcaatt aacgaatcca   3360
ccatcggggc agctggtgtc gataacgaag tatcttcaac cggttgagta ttgagcgtat   3420
gttttggaat aacaggcgca cgcttcatta tctaatctcc cagcgtggtt taatcagacg   3480
atcgaaaatt tcattgcaga caggttccca aatagaaaga gcatttctcc aggcaccagt   3540
tgaagagcgt tgatcaatgg cctgttcaaa aacagttctc atccggatct gacctttacc   3600
aacttcatcc gtttcacgta caacattttt tagaaccatg cttccccagg catcccgaat   3660
ttgctcctcc atccacgggg actgagagcc attgctattg ctgtatttgg taagcaaaat   3720
acgtacatca ggctcgaacc ctttaagatc aacgttcttg agcagatcac gaagcatatc   3780
gaaaaactgc agtgcggagg tgtagtcaaa caactcagca ggcgtgggaa caatcagcac   3840
atcagcagca catacgacat taatcgtgcc gatacccagg ttaggcgcgc tgtcaataac   3900
tatgacatca tagtcatgag caacagtttc aatggccagt cggagcatca ggtgtggatc   3960
ggtgggcagt ttaccttcat caaatttgcc cattaactca gtttcaatac ggtgcagagc   4020
cagacaggaa ggaataatgt caagccccgg ccagcaagtg ggctttattg cataagtgac   4080
atcgtccttt tccccaagat agaaaggcag gagagtgtct tctgcatgaa tatgaagatc   4140
tggtacccat ccgtgataca ttgaggctgt tccctggggg tcgttacctt ccacgagcaa   4200
aacacgtagc cccttcagag ccagatcctg agcaagatga acagaaactg aggttttgta   4260
aacgccacct ttatgggcag caaccccgat caccggtgga aatacgtctt cagcacgtcg   4320
caatcgcgta ccaaacacat cacgcatatg attaatttgt tcaattgtat aaccaacacg   4380
ttgctcaacc cgtcctcgaa tttccatatc cgggtgcggt agtcgccctg ctttctcggc   4440
atctctgata gcctgagaag aaaccccaac taaatccgct gcttcaccta ttctccagcg   4500
ccgggttatt ttcctcgctt ccgggctgtc atcattaaac tgtgcaatgg cgatagcctt   4560
cgtcatttca tgaccagcgt ttatgcactg gttaagtgtt tccatgagtt tcattctgaa   4620
catcctttaa tcattgcttt gcgttttttt attaaatctt gcaatttact gcaaagcaac   4680
aacaaaatcg caaagtcatc aaaaaaccgc aaagttgttt aaaataagag caacactaca   4740
aaaggagata agaagagcac atacctcagt cacttattat cactagcgct cgccgcagcc   4800
gtgtaaccga gcatagcgag cgaactggcg aggaagcaaa gaagaactgt tctgtcagat   4860
agctcttacg ctcagcgcaa gaagaaatat ccaccgtggg aaaaactcca ggtagaggta   4920
cacacgcgga tagccaattc agagtaataa actgtgataa tcaaccctca tcaatgatga   4980
cgaactaacc cccgatatca ggtcacatga cgaagggaaa gagaaggaaa tcaactgtga   5040
caaactgccc tcaaatttgg cttccttaaa aattacagtt caaaaagtat gagaaaatcc   5100
atgcaggctg aaggaaacag caaaactgtg acaaattacc ctcagtaggt cagaacaaat   5160
```

-continued gtgacgaacc accctcaaat ctgtgacaga taaccctcag actatcctgt cgtcatggaa 5220
gtgatatcgc ggaaggaaaa tacgatatga gtcgtctggc ggcctttctt tttctcaatg 5280
tatgagaggc gcattggagt tctgctgttg atctcattaa cacagacctg caggaagcgg 5340
cggcggaagt caggcatacg ctggtaactt tgaggcagct ggtaacgctc tatgatccag 5400
tcgattttca gagagacgat gcctgagcca tccggcttac gatactgaca cagggattcg 5460
tataaacgca tggcatacgg attggtgatt tcttttgttt cactaagccg aaactgcgta 5520
aaccggttct gtaacccgat aaagaaggga atgagatatg ggttgatatg tacgctgtaa 5580
agccctctgg atggactgtg cgcacgtttg ataaaccaag gaaaagattc atagcctttt 5640
tcatcgccgg catcctcttc agggcgataa aaaaccactt ccttccccgc gaaactcttc 5700
aatgcctgcc gtatatcctt actggcttcc gcagaggtca atccgaatat ttcagcatat 5760
ttagcaacat ggatctcgca gataccgtca tgttcctgta gggtgccatc agattttctg 5820
atctggtcaa cgaacagata cagcatacgt tttgatccc gggagagact atatgccgcc 5880
tcagtgaggt cgtttgactg gacgattcgc gggctatttt tacgtttctt gtgattgata 5940
accgctgttt ccgccatgac agatccatgt gaagtgtgac aagtttttag attgtcacac 6000
taaataaaaa agagtcaata agcagggata actttgtgaa aaaacagctt cttctgaggg 6060
caatttgtca cagggttaag ggcaatttgt cacagacagg actgtcattt gagggtgatt 6120
tgtcacactg aaagggcaat ttgtcacaac accttctcta gaaccagcat ggataaaggc 6180
ctacaaggcg ctctaaaaaa gaagatctaa aaactataaa aaaaataatt ataaaaatat 6240
ccccgtggat aagtggataa ccccaaggga agttttttca ggcatcgtgt gtaagcagaa 6300
tatataagtg ctgttccctg gtgcttcctc gctcactcga ccgggagggt tcgagaaggg 6360
ggggcacccc ccttcggcgt gcgcggtcac gcgcacaggg cgcagccctg gttaaaaaca 6420
aggtttataa atattggttt aaaagcaggt taaaagacag gttagcggtg gccgaaaaac 6480
gggcggaaac ccttgcaaat gctggatttt ctgcctgtgg acagcccctc aaatgtcaat 6540
aggtgcgccc ctcatctgtc agcactctgc ccctcaagtg tcaaggatcg cgcccctcat 6600
ctgtcagtag tcgcgcccct caagtgtcaa taccgcaggg cacttatccc caggcttgtc 6660
cacatcatct gtgggaaact cgcgtaaaat caggcgtttt cgccgatttg cgaggctggc 6720
cagctccacg tcgccggccg aaatcgagcc tgcccctcat ctgtcaacgc cgcgccgggt 6780
gagtcggccc ctcaagtgtc aacgtccgcc cctcatctgt cagtgagggc caagttttcc 6840
gcgaggtatc cacaacgccg gcggccggcc gcggtgtctc gcacacggct tcgacggcgt 6900
ttctggcgcg tttgcagggc catagacggc cgccagccca gcggcgaggg caaccagctc 6960
gagggcttcg ccctgtcgct cgactgcggc gagcactact ggctgtaaaa ggacagacca 7020
catcatggtt ctgtgttcat taggttgttc tgtccattgc tgacataatc cgctccactt 7080
caacgtaaca ccgcacgaag atttctattg ttcctgaagg catattcaaa tcgttttcgt 7140
taccgcttgc aggcatcatg acagaacact acttcctata aacgctacac aggctcctga 7200
gattaataat gcggatctct acgataatgg gagattttcc cgactgtttc gttcgcttct 7260
cagtggataa cagccagctt ctctgtttaa cagacaaaaa cagcatatcc actcagttcc 7320
acatttccat ataaaggcca aggcatttat tctcaggata attgtttcag catcgcaacc 7380
gcatcagact ccggcatcgc aaactgcacc cggtgccggg cagccacatc cagcgcaaaa 7440
accttcgtgt agacttccgt tgaactgatg gacttatgtc ccatcaggct ttgcagaact 7500
ttcagcggta taccggcata cagcatgtgc atcgcatagg aatggcggaa cgtatgtggt 7560

```
gtgaccggaa cagagaacgt cacaccgtca gcagcagcgg cggcaaccgc ctccccaatc   7620
caggtcctga ccgttctgtc cgtcacttcc cagatccgcg ctttctctgt ccttcctgtg   7680
cgacggttac gccgctccat gagcttatcg cgaataaata cctgtgacgg aagatcactt   7740
cgcagaataa ataaatcctg gtgtccctgt tgataccggg aagccctggg ccaacttttg   7800
gcgaaaatga gacgttgatc ggcacgtaag aggttccaac tttcaccata atgaaataag   7860
atcactaccg ggcgtatttt ttgagttatc gagattttca ggagctaagg aagctaaaat   7920
ggagaaaaaa atcactggat ataccaccgt tgatatatcc caatggcatc gtaaagaaca   7980
ttttgaggca tttcagtcag ttgctcaatg tacctataac cagaccgttc agctggatat   8040
tacggccttt ttaaagaccg taaagaaaaa taagcacaag ttttatccgg cctttattca   8100
cattcttgcc cgcctgatga atgctcatcc ggaatttcgt atggcaatga aagacggtga   8160
gctggtgata tgggatagtg ttcacccttg ttacaccgtt ttccatgagc aaactgaaac   8220
gttttcatcg ctctggagtg aataccacga cgatttccgg cagtttctac acatatattc   8280
gcaagatgtg gcgtgttacg gtgaaaacct ggcctatttc cctaaagggt ttattgagaa   8340
tatgtttttc gtctcagcca atccctgggt gagtttcacc agttttgatt taaacgtggc   8400
caatatggac aacttcttcg cccccgtttt caccatgggc aaatattata cgcaaggcga   8460
caaggtgctg atgccgctgg cgattcaggt tcatcatgcc gtttgtgatg gcttccatgt   8520
cggcagaatg cttaatgaat tacaacagta ctgcgatgag tggcagggcg gggcgtaatt   8580
tttttaaggc agttattggt gcccttaaac gcctggttgc tacgcctgaa taagtgataa   8640
taagcggatg aatggcagaa attcgatgat aagctgtcaa acatgagaat tggtcgacgg   8700
cccgggcggc catcgaagcc tataggtacc atcgatgcat aatgtgcctg tcaaatggac   8760
gaagcaggga ttctgcaaac cctatgctac tccgtcaagc cgtcaattgt ctgattcgtt   8820
accaattatg acaacttgac ggctacatca ttcacttttt cttcacaacc ggcacggaac   8880
tcgctcgggc tggccccggt gcattttttta aatacccgcg agaaatagag ttgatcgtca   8940
aaaccaacat tgcgaccgac ggtggcgata ggcatccggg tggtgctcaa aagcagcttc   9000
gcctggctga tacgttggtc ctcgcgccag cttaagacgc taatccctaa ctgctggcgg   9060
aaaagatgtg acagacgcga cggcgacaag caaacatgct gtgcgacgct ggcgatatca   9120
aaattgctgt ctgccaggtg atcgctgatg tactgacaag cctcgcgtac ccgattatcc   9180
atcggtggat ggagcgactc gttaatcgct tccatgcgcc gcagtaacaa ttgctcaagc   9240
agatttatcg ccagcagctc cgaatagcgc ccttcccctt gcccggcgtt aatgatttgc   9300
ccaaacaggt cgctgaaatg cggctggtgc gcttcatccg ggcgaaagaa ccccgtattg   9360
gcaaatattg acggccagtt aagccattca tgccagtagg cgcgcggacg aaagtaaacc   9420
cactggtgat accattcgcg agcctccgga tgacgaccgt agtgatgaat ctctcctggc   9480
gggaacagca aaatatcacc cggtcggcaa acaaattctc gtccctgatt tttcaccacc   9540
ccctgaccgc gaatggtgag attgagaata taacctttca ttcccagcgg tcggtcgata   9600
aaaaaatcga gataaccgtt ggcctcaatc ggcgttaaac ccgccaccag atgggcatta   9660
aacgagtatc ccggcagcag gggatcattt tgcgcttcag ccatactttt catactcccg   9720
ccattcagag aagaaaccaa ttgtccatat tgcatcagac attgccgtca ctgcgtcttt   9780
tactggctct tctcgctaac caaaccggta accccgctta ttaaaagcat tctgtaacaa   9840
agcgggacca aagccatgac aaaaacgcgt aacaaaagtg tctataatca cggcagaaaa   9900
```

```
gtccacattg attatttgca cggcgtcaca ctttgctatg ccatagcatt tttatccata   9960

agattagcgg atcctacct                                                9979


<210> SEQ ID NO 6
<211> LENGTH: 5979
<212> TYPE: DNA
<213> ORGANISM: Artificial Sequence
<220> FEATURE:
<223> OTHER INFORMATION: pKan PhoA construct
<220> FEATURE:
<221> NAME/KEY: misc_feature
<222> LOCATION: (146)..(146)
<223> OTHER INFORMATION: d=a, g or t
<220> FEATURE:
<221> NAME/KEY: misc_feature
<222> LOCATION: (147)..(180)
<223> OTHER INFORMATION: n=g, a, t or c
<220> FEATURE:
<221> NAME/KEY: misc_feature
<222> LOCATION: (148)..(181)
<223> OTHER INFORMATION: k=g or t

<400> SEQUENCE: 6

gacgcttttt atcgcaactc tctactgttt ctccatgcgg ccgcgaaata attttgttta     60

actttaagaa ggagatatac atatgaaaca aagcactatt gcactggcac tcttaccgtt    120

actgtacacc cctgtgacaa aagccdnknn knnknnknnk nnknnknnkn nknnknnknn    180

kgaaggcggc ggcgcccgga caccagaaat gcctgttctg gaaaaccggg ctgctcaggg    240

cgatattact gcacccggcg gtgctcgccg tttaacgggt gatcagactg ccgctctgcg    300

tgattctctt agcgataaac ctgcaaaaaa tattattttg ctgattggcg atgggatggg    360

ggactcggaa attactgccg cacgtaatta tgccgaaggt gcgggcggct tttttaaagg    420

tatagatgcc ttaccgctta ccgggcaata cactcactat gcgctgaata aaaaaaccgg    480

caaaccggac tacgtcaccg actcggctgc atcagcaacc gcctggtcaa ccggtgtcaa    540

aacctataac ggcgcgctgg gcgtcgatat tcacgaaaaa gatcacccaa cgattctgga    600

aatggcaaaa gccgcaggtc tggcgaccgg taacgtttct accgcagagt tgcaggatgc    660

cacgcccgct gcgctggtgg cacatgtgac ctcgcgcaaa tgctacggtc cgagcgcgac    720

cagtgaaaaa tgtccgggta acgctctgga aaaaggcgga aaaggatcga ttaccgaaca    780

gctgcttaac gctcgtgccg acgttacgct tggcggcggc gcaaaaacct ttgctgaaac    840

ggcaaccgct ggtgaatggc agggaaaaac gctgcgtgaa caggcacagg cgcgtggtta    900

tcagttggtg agcgatgctg cctcactgaa ttcggtgacg gaagcgaatc agcaaaaacc    960

cctgcttggc ctgtttgctg acggcaatat gccagtgcgc tggctaggac cgaaagcaac   1020

gtaccatggc aatatcgata agcccgcagt cacctgtacg ccaaatccgc aacgtaatga   1080

cagtgtacca accctggcgc agatgaccga caaagccatt gaattgttga gtaaaaatga   1140

gaaaggcttt ttcctgcaag ttgaaggtgc gtcaatcgat aaacaggatc atgctgcgaa   1200

tccttgtggg caaattggcg agacggtcga tctcgatgaa gccgtacaac gggcgctgga   1260

attcgctaaa aaggagggta acacgctggt catagtcacc gctgatcacg cccacgccag   1320

ccagattgtt gcgccggata ccaaagctcc gggcctcacc caggcgctaa ataccaaaga   1380

tggcgcagtg atggtgatga gttacgggaa ctccgaagag gattcacaag aacataccgg   1440

cagtcagttg cgtattgcgg cgtatggccc gcatgccgcc aatgttgttg gactgaccga   1500

ccagaccgat ctcttctaca ccatgaaagc cgctctgggg ctgaaacatc atcatcatca   1560

tcattaactg ttatctagaa taaaacgaaa ggctcagtcg aaagactggg cctttcgttt   1620
```

tatctgttgt ttgtcggtga acgctctcct gagtaggaca aatccgccgg gagcggattt 1680
gaacgttgcg aagcaacggc ccggagggtg gcgggcagga cgcccgccat aaactgccag 1740
gcatcaaatt aagcagaagg ccatcctgac ggatggcctt tttgaattca ctggccgtcg 1800
ttttacaacg tcgtgactgg gaaaaccctg gcgttaccca acttaatcgc cttgcagcac 1860
atcccccttt cgccagactc accagtcaca gaaaagcatc ttacggatgg catgacagta 1920
agagaattat gcagtgctgc cataaccatg agtgataaca ctgcggccaa cttacttctg 1980
acaacgatcg gaggaccgaa ggagctaacc gcttttttgc acaacatggg ggatcatgta 2040
actcgccttg atcgttggga accggagctg aatgaagcca taccaaacga cgagcgtgac 2100
accacgatgc ctgcagcaat ggcaacaacg ttgcgcaaac tattaactgg cgaactactt 2160
actctagctt cccggcaaca attaatagac tggatggagg cggataaagt tgcaggacca 2220
cttctgcgct cggcccttcc ggctggctgg tttattgctg ataaatctgg agccggtgag 2280
cgtgggtctc gcggtatcat tgcagcactg gggccagatg gtaagccctc ccgtatcgta 2340
gttatctaca cgacggggag tcaggcaact atggatgaac gaaatagaca gatcgctgag 2400
ataggtgcct cactgattaa gcattggtaa ctgtcagacc aagtttactc atatatactt 2460
tagattgatt taaaacttca tttttaattt aaaaggatct aggtgaagat cctttttgat 2520
aatctcatga ccaaaatccc ttaacgtgag ttttcgttcc actgagcgtc agacccctta 2580
ataagatgat cttcttgaga tcgttttggt ctgcgcgtaa tctcttgctc tgaaaacgaa 2640
aaaaccgcct tgcagggcgg tttttcgaag gttctctgag ctaccaactc tttgaaccga 2700
ggtaactggc ttggaggagc gcagtcacca aaacttgtcc tttcagttta gccttaaccg 2760
gcgcatgact tcaagactaa ctcctctaaa tcaattacca gtggctgctg ccagtggtgc 2820
ttttgcatgt ctttccgggt tggactcaag acgatagtta ccggataagg cgcagcggtc 2880
ggactgaacg gggggttcgt gcatacagtc cagcttggag cgaactgcct acccggaact 2940
gagtgtcagg cgtggaatga gacaaacgcg gccataacag cggaatgaca ccggtaaacc 3000
gaaaggcagg aacaggagag cgcacgaggg agccgccagg gggaaacgcc tggtatcttt 3060
atagtcctgt cgggtttcgc caccactgat ttgagcgtca gatttcgtga tgcttgtcag 3120
gggggcggag cctatggaaa aacggctttg ccgcggccct ctcacttccc tgttaagtat 3180
cttcctggca tcttccagga aatctccgcc ccgttcgtaa gccatttccg ctcgccgcag 3240
tcgaacgacc gagcgtagcg agtcagtgag cgaggaagcg gaatatatcc tgtatcacat 3300
attctgctga cgcaccggtg cagccttttt tctcctgcca catgaagcac ttcactgaca 3360
ccctcatcag tgccaacata gtaagccagt atacactccg ctagcgctga ggtctgcctc 3420
gtgaagaagg tgttgctgac tcataccagg cctgaatcgc cccatcatcc agccagaaag 3480
tgagggagcc acggttgatg agagctttgt tgtaggtgga ccagttggtg attttgaact 3540
tttgctttgc cacggaacgg tctgcgttgt cgggaagatg cgtgatctga tccttcaact 3600
cagcaaaagt tcgatttatt caacaaagcc acgttgtgtc tcaaaatctc tgatgttaca 3660
ttgcacaaga taaaaatata tcatcatgaa caataaaact gtctgcttac ataaacagta 3720
atacaagggg tgttatgagc catattcaac gggaaacgtc ttgctcgagg ccgcgattaa 3780
attccaacat ggatgctgat ttatatgggt ataaatgggc tcgcgataat gtcgggcaat 3840
caggtgcgac aatctatcga ttgtatggga agcccgatgc gccagagttg tttctgaaac 3900
atggcaaagg tagcgttgcc aatgatgtta cagatgagat ggtcagacta aactggctga 3960

-continued

```
cggaatttat gcctcttccg accatcaagc attttatccg tactcctgat gatgcatggt   4020

tactcaccac tgcgatcccc gggaaaacag cattccaggt attagaagaa tatcctgatt   4080

caggtgaaaa tattgctgat gcgctggcag tgttcctgcg ccggttgcat tcgattcctg   4140

tttgtaattg tccttttaac agcgatcgcg tatttcgtct cgctcaggcg caatcacgaa   4200

tgaataacgg tttggttgat gcgagtgatt ttgatgacga gcgtaatggc tggcctgttg   4260

aacaagtctg gaaagaaatg cataaacttt tgccattctc accggattca gtcgtcactc   4320

atggtgattt ctcacttgat aaccttattt ttgacgaggg gaaattaata ggttgtattg   4380

atgttggacg agtcggaatc gcagaccgat accaggatct tgccatccta tggaactgcc   4440

tcggtgagtt ttctccttca ttacagaaac ggctttttca aaaatatggt attgataatc   4500

ctgatatgaa taaattgcag tttcatttga tgctcgatga gtttttctaa tcagaattgg   4560

ttaattggtt gtaacactgg cagagcatta cgctgacttg acgggacggc ggctttgttg   4620

aataaatcga acttttgctg agttgaagga tcagatcacg catcttcccg acaacgcaga   4680

ccgttccgtg gcaaagcaaa agttcaaaat cactagtcga ccatggtacc atcgatgcat   4740

aatgtgcctg tcaaatggac gaagcaggga ttctgcaaac cctatgctac tccgtcaagc   4800

cgtcaattgt ctgattcgtt accaattatg acaacttgac ggctacatca ttcacttttt   4860

cttcacaacc ggcacggaac tcgctcgggc tggccccggt gcatttttta aatacccgcg   4920

agaaatagag ttgatcgtca aaaccaacat tgcgaccgac ggtggcgata ggcatccggg   4980

tggtgctcaa aagcagcttc gcctggctga tacgttggtc ctcgcgccag cttaagacgc   5040

taatccctaa ctgctggcgg aaaagatgtg acagacgcga cggcgacaag caaacatgct   5100

gtgcgacgct ggcgatatca aaattgctgt ctgccaggtg atcgctgatg tactgacaag   5160

cctcgcgtac ccgattatcc atcggtggat ggagcgactc gttaatcgct tccatgcgcc   5220

gcagtaacaa ttgctcaagc agatttatcg ccagcagctc cgaatagcgc ccttcccctt   5280

gcccggcgtt aatgatttgc ccaaacaggt cgctgaaatg cggctggtgc gcttcatccg   5340

ggcgaaagaa ccccgtattg gcaaatattg acggccagtt aagccattca tgccagtagg   5400

cgcgcggacg aaagtaaacc cactggtgat accattcgcg agcctccgga tgacgaccgt   5460

agtgatgaat ctctcctggc gggaacagca aaatatcacc cggtcggcaa acaaattctc   5520

gtccctgatt tttcaccacc ccctgaccgc gaatggtgag attgagaata taacctttca   5580

ttcccagcgg tcggtcgata aaaaaatcga gataaccgtt ggcctcaatc ggcgttaaac   5640

ccgccaccag atgggcatta aacgagtatc ccggcagcag gggatcattt tgcgcttcag   5700

ccatactttt catactcccg ccattcagag aagaaaccaa ttgtccatat tgcatcagac   5760

attgccgtca ctgcgtcttt tactggctct tctcgctaac caaaccggta accccgctta   5820

ttaaaagcat tctgtaacaa agcgggacca aagccatgac aaaaacgcgt aacaaaagtg   5880

tctataatca cggcagaaaa gtccacattg attatttgca cggcgtcaca ctttgctatg   5940

ccatagcatt tttatccata agattagcgg atcctacct                          5979
```

```
<210> SEQ ID NO 7
<211> LENGTH: 12
<212> TYPE: PRT
<213> ORGANISM: Artificial Sequence
<220> FEATURE:
<223> OTHER INFORMATION: Antimicrobial peptide PL012

<400> SEQUENCE: 7

Gly Ile Gly Ala Ile Val Gly Val Leu Ile Leu Gly
```

1 5 10

<210> SEQ ID NO 8
<211> LENGTH: 12
<212> TYPE: PRT
<213> ORGANISM: Artificial Sequence
<220> FEATURE:
<223> OTHER INFORMATION: Antimicrobial peptide PL014

<400> SEQUENCE: 8

Trp Thr Val Arg Val Asp Val Ile Glu Ser Arg Trp
1 5 10

<210> SEQ ID NO 9
<211> LENGTH: 12
<212> TYPE: PRT
<213> ORGANISM: Artificial Sequence
<220> FEATURE:
<223> OTHER INFORMATION: Antimicrobial peptide PL021

<400> SEQUENCE: 9

Ala Leu Leu Val Ala Met Trp Ala Gly Val Ala Gly
1 5 10

<210> SEQ ID NO 10
<211> LENGTH: 12
<212> TYPE: PRT
<213> ORGANISM: Artificial Sequence
<220> FEATURE:
<223> OTHER INFORMATION: Antimicrobial peptide PL023

<400> SEQUENCE: 10

Val Cys Glu Cys Gly Pro Arg Val Thr Leu Thr Gln
1 5 10

<210> SEQ ID NO 11
<211> LENGTH: 12
<212> TYPE: PRT
<213> ORGANISM: Artificial Sequence
<220> FEATURE:
<223> OTHER INFORMATION: Antimicrobial peptide PL027

<400> SEQUENCE: 11

Leu Thr Thr Ile Cys Arg Trp Met Arg Arg Arg Asp
1 5 10

<210> SEQ ID NO 12
<211> LENGTH: 12
<212> TYPE: PRT
<213> ORGANISM: Artificial Sequence
<220> FEATURE:
<223> OTHER INFORMATION: Antimicrobial peptide PL029

<400> SEQUENCE: 12

Met Thr Lys Met Phe Arg Arg Trp Arg Thr Asn Lys
1 5 10

<210> SEQ ID NO 13
<211> LENGTH: 12
<212> TYPE: PRT
<213> ORGANISM: Artificial Sequence
<220> FEATURE:
<223> OTHER INFORMATION: Antimicrobial peptide PL030

<400> SEQUENCE: 13

Leu Gly Trp Leu Arg Gly Lys Ala Leu Gly Arg Gly
1 5 10

<210> SEQ ID NO 14
<211> LENGTH: 12
<212> TYPE: PRT
<213> ORGANISM: Artificial Sequence
<220> FEATURE:
<223> OTHER INFORMATION: Antimicrobial peptide PL034

<400> SEQUENCE: 14

Phe Ala Ala Val Val Arg Trp Val Arg Gly Arg Ala
1 5 10

<210> SEQ ID NO 15
<211> LENGTH: 12
<212> TYPE: PRT
<213> ORGANISM: Artificial Sequence
<220> FEATURE:
<223> OTHER INFORMATION: Antimicrobial peptide PL032

<400> SEQUENCE: 15

Phe Lys Trp Val Leu Ala Arg Leu Thr Gln Ser Ser
1 5 10

<210> SEQ ID NO 16
<211> LENGTH: 12
<212> TYPE: PRT
<213> ORGANISM: Artificial Sequence
<220> FEATURE:
<223> OTHER INFORMATION: Antimicrobial peptide PL035

<400> SEQUENCE: 16

Tyr Gly Lys Ala Arg Arg Trp Leu Gly Arg Trp Thr
1 5 10

<210> SEQ ID NO 17
<211> LENGTH: 12
<212> TYPE: PRT
<213> ORGANISM: Artificial Sequence
<220> FEATURE:
<223> OTHER INFORMATION: Antimicrobial peptide PL037

<400> SEQUENCE: 17

Phe Arg Trp Leu Tyr Arg Leu Phe Met Phe Arg Leu
1 5 10

<210> SEQ ID NO 18
<211> LENGTH: 12
<212> TYPE: PRT
<213> ORGANISM: Artificial Sequence
<220> FEATURE:
<223> OTHER INFORMATION: Antimicrobial peptide PL038

<400> SEQUENCE: 18

Ile Ser Trp Leu Gly Gly Leu Leu Gly Arg Arg Glu
1 5 10

<210> SEQ ID NO 19
<211> LENGTH: 12
<212> TYPE: PRT
<213> ORGANISM: Artificial Sequence
<220> FEATURE:
<223> OTHER INFORMATION: Antimicrobial peptide PL039

<400> SEQUENCE: 19

Cys Glu Ser Gly Lys Ser Tyr Arg Ile Gly Lys Trp
1 5 10

<210> SEQ ID NO 20
<211> LENGTH: 12
<212> TYPE: PRT
<213> ORGANISM: Artificial Sequence
<220> FEATURE:
<223> OTHER INFORMATION: Antimicrobial peptide PL045

<400> SEQUENCE: 20

Cys Ile Leu Val Val Leu Val His Leu Phe Val Ala
1 5 10

<210> SEQ ID NO 21
<211> LENGTH: 12
<212> TYPE: PRT
<213> ORGANISM: Artificial Sequence
<220> FEATURE:
<223> OTHER INFORMATION: Antimicrobial peptide PL047

<400> SEQUENCE: 21

Ile Arg Ala Phe Arg Ser Phe Thr Gln Leu Leu Cys
1 5 10

<210> SEQ ID NO 22
<211> LENGTH: 12
<212> TYPE: PRT
<213> ORGANISM: Artificial Sequence
<220> FEATURE:
<223> OTHER INFORMATION: Antimicrobial peptide PL048

<400> SEQUENCE: 22

Val Thr Leu Gly Leu Val Met Leu Ala Val Ser Leu
1 5 10

<210> SEQ ID NO 23
<211> LENGTH: 12
<212> TYPE: PRT
<213> ORGANISM: Artificial Sequence
<220> FEATURE:
<223> OTHER INFORMATION: Antimicrobial peptide PL049

<400> SEQUENCE: 23

Trp Arg Tyr Leu Leu Gly Arg Gly Lys Arg Arg Lys
1 5 10

<210> SEQ ID NO 24
<211> LENGTH: 12
<212> TYPE: PRT
<213> ORGANISM: Artificial Sequence
<220> FEATURE:
<223> OTHER INFORMATION: Antimicrobial peptide PL054

<400> SEQUENCE: 24

Trp Gly Ser Leu Met Leu Lys Trp Arg Arg Thr Arg
1 5 10

<210> SEQ ID NO 25
<211> LENGTH: 12
<212> TYPE: PRT
<213> ORGANISM: Artificial Sequence
<220> FEATURE:
<223> OTHER INFORMATION: Antimicrobial peptide PL055

<400> SEQUENCE: 25

Leu Lys Trp Ile Arg Ser Leu Leu Val Arg Gly Arg
1 5 10

<210> SEQ ID NO 26
<211> LENGTH: 12
<212> TYPE: PRT
<213> ORGANISM: Artificial Sequence
<220> FEATURE:
<223> OTHER INFORMATION: Antimicrobial peptide PL060

<400> SEQUENCE: 26

Leu Ser Trp Val Trp Arg Gln Leu Gly Gly Ala Trp
1 5 10

<210> SEQ ID NO 27
<211> LENGTH: 12
<212> TYPE: PRT
<213> ORGANISM: Artificial Sequence
<220> FEATURE:
<223> OTHER INFORMATION: Antimicrobial peptide PL061

<400> SEQUENCE: 27

Ile Lys Trp Ile Arg Ser Leu Leu Val Arg Gly Arg
1 5 10

<210> SEQ ID NO 28
<211> LENGTH: 12
<212> TYPE: PRT
<213> ORGANISM: Artificial Sequence
<220> FEATURE:
<223> OTHER INFORMATION: Antimicrobial peptide PL062

<400> SEQUENCE: 28

Phe Ala Arg Leu His Lys Trp Phe Gln Arg Arg Lys
1 5 10

<210> SEQ ID NO 29
<211> LENGTH: 12
<212> TYPE: PRT
<213> ORGANISM: Artificial Sequence
<220> FEATURE:
<223> OTHER INFORMATION: Antimicrobial peptide PL063

<400> SEQUENCE: 29

Ile Lys Leu Leu Arg Ile Leu Ser Gln Lys Trp Arg
1 5 10

<210> SEQ ID NO 30
<211> LENGTH: 12
<212> TYPE: PRT
<213> ORGANISM: Artificial Sequence
<220> FEATURE:
<223> OTHER INFORMATION: Antimicrobial peptide PL064

<400> SEQUENCE: 30

Trp Val Trp Leu Ser Arg Trp Leu Arg Arg Gly Trp
1 5 10

<210> SEQ ID NO 31
<211> LENGTH: 12
<212> TYPE: PRT
<213> ORGANISM: Artificial Sequence
<220> FEATURE:
<223> OTHER INFORMATION: Antimicrobial peptide PL065

<400> SEQUENCE: 31

Leu Lys Gly Leu Lys Arg Trp Trp Arg Pro Glu His
1 5 10

<210> SEQ ID NO 32

<211> LENGTH: 12
<212> TYPE: PRT
<213> ORGANISM: Artificial Sequence
<220> FEATURE:
<223> OTHER INFORMATION: Antimicrobial peptide PL066

<400> SEQUENCE: 32

Trp Lys Trp Leu Gln Ser Leu Trp Gly Cys Glu Val
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Antimicrobial peptide PL068

<400> SEQUENCE: 33

Trp Lys Trp Leu Gln Ser Leu Trp Gly Cys Glu Val
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Antimicrobial peptide PL069

<400> SEQUENCE: 34

Phe Phe Cys Leu Trp Val Leu Tyr Leu Gly Thr Pro
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Antimicrobial peptide PL072

<400> SEQUENCE: 35

Trp Arg Gly Val Arg Lys Val Trp Arg Arg Met Arg
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Antimicrobial peptide PL073

<400> SEQUENCE: 36

Asn Val Arg Ile Ile Val Asp Met Thr Ile Ser Ala
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Antimicrobial peptide PL088

<400> SEQUENCE: 37

Ile Ile Val Leu Val Phe Val Thr Tyr Leu Thr Ala
1               5                   10

<210> SEQ ID NO 38
<211> LENGTH: 12

<212> TYPE: PRT
<213> ORGANISM: Artificial Sequence
<220> FEATURE:
<223> OTHER INFORMATION: Antimicrobial peptide PL092

<400> SEQUENCE: 38

Tyr Cys Trp Leu Arg Glu Lys Leu Gly Gly Gly Gln
1 5 10

<210> SEQ ID NO 39
<211> LENGTH: 12
<212> TYPE: PRT
<213> ORGANISM: Artificial Sequence
<220> FEATURE:
<223> OTHER INFORMATION: Antimicrobial peptide PL093

<400> SEQUENCE: 39

Tyr Cys Trp Leu Arg Glu Lys Leu Gly Gly Gly Gln
1 5 10

<210> SEQ ID NO 40
<211> LENGTH: 12
<212> TYPE: PRT
<213> ORGANISM: Artificial Sequence
<220> FEATURE:
<223> OTHER INFORMATION: Antimicrobial peptide PL094

<400> SEQUENCE: 40

Tyr Cys Trp Lys Arg Glu Lys Leu Gly Gly Gly Gln
1 5 10

<210> SEQ ID NO 41
<211> LENGTH: 12
<212> TYPE: PRT
<213> ORGANISM: Artificial Sequence
<220> FEATURE:
<223> OTHER INFORMATION: Antimicrobial peptide PL095

<400> SEQUENCE: 41

Trp Gln Leu Val Arg Arg Leu Leu Gly Gln Leu Gly
1 5 10

<210> SEQ ID NO 42
<211> LENGTH: 12
<212> TYPE: PRT
<213> ORGANISM: Artificial Sequence
<220> FEATURE:
<223> OTHER INFORMATION: Antimicrobial peptide PL097

<400> SEQUENCE: 42

Trp Val Thr Ala Arg Asp Trp Val Lys Ser Trp Trp
1 5 10

<210> SEQ ID NO 43
<211> LENGTH: 12
<212> TYPE: PRT
<213> ORGANISM: Artificial Sequence
<220> FEATURE:
<223> OTHER INFORMATION: Antimicrobial peptide PL098

<400> SEQUENCE: 43

Trp Arg Arg Trp Lys Met Arg Gly Arg Ala Arg Val
1 5 10

<210> SEQ ID NO 44
<211> LENGTH: 12
<212> TYPE: PRT

<213> ORGANISM: Artificial Sequence
<220> FEATURE:
<223> OTHER INFORMATION: Antimicrobial peptide PL101

<400> SEQUENCE: 44

Ile Leu Tyr Leu Cys Val Leu Ser Val Ser Arg Asn
1 5 10

<210> SEQ ID NO 45
<211> LENGTH: 12
<212> TYPE: PRT
<213> ORGANISM: Artificial Sequence
<220> FEATURE:
<223> OTHER INFORMATION: Antimicrobial peptide PL104

<400> SEQUENCE: 45

Met Gly Met Leu Arg Trp Leu Phe Ser Phe Trp Arg
1 5 10

<210> SEQ ID NO 46
<211> LENGTH: 12
<212> TYPE: PRT
<213> ORGANISM: Artificial Sequence
<220> FEATURE:
<223> OTHER INFORMATION: Antimicrobial peptide PL111

<400> SEQUENCE: 46

Leu Ser Arg Ala Lys Ala Leu Leu Lys Arg Ala Lys
1 5 10

<210> SEQ ID NO 47
<211> LENGTH: 12
<212> TYPE: PRT
<213> ORGANISM: Artificial Sequence
<220> FEATURE:
<223> OTHER INFORMATION: Antimicrobial peptide PL112

<400> SEQUENCE: 47

Gly Leu Trp Gly Lys Trp Glu Pro Gly Gly Gln Gly
1 5 10

<210> SEQ ID NO 48
<211> LENGTH: 12
<212> TYPE: PRT
<213> ORGANISM: Artificial Sequence
<220> FEATURE:
<223> OTHER INFORMATION: Antimicrobial peptide PL113

<400> SEQUENCE: 48

Cys Arg Tyr Leu Arg Leu Leu Trp Ser Asn Ile Arg
1 5 10

<210> SEQ ID NO 49
<211> LENGTH: 12
<212> TYPE: PRT
<213> ORGANISM: Artificial Sequence
<220> FEATURE:
<223> OTHER INFORMATION: Antimicrobial peptide PL114

<400> SEQUENCE: 49

Gln Ala Glu Ser Ser Met Ile Ala Pro Ser Gln Cys
1 5 10

<210> SEQ ID NO 50
<211> LENGTH: 12
<212> TYPE: PRT
<213> ORGANISM: Artificial Sequence
<220> FEATURE:
<223> OTHER INFORMATION: Antimicrobial peptide PL115

<400> SEQUENCE: 50

Val Leu Ser Ala Asn Ile Trp Ala Gly Met Arg Phe
1 5 10

<210> SEQ ID NO 51
<211> LENGTH: 12
<212> TYPE: PRT
<213> ORGANISM: Artificial Sequence
<220> FEATURE:
<223> OTHER INFORMATION: Antimicrobial peptide PL116

<400> SEQUENCE: 51

Ile Val Ile Cys Cys Val Gly Val Leu Thr His Pro
1 5 10

<210> SEQ ID NO 52
<211> LENGTH: 12
<212> TYPE: PRT
<213> ORGANISM: Artificial Sequence
<220> FEATURE:
<223> OTHER INFORMATION: Antimicrobial peptide PL117

<400> SEQUENCE: 52

Val Ile Gly Thr Val Met Cys Thr Leu Thr Trp Gly
1 5 10

<210> SEQ ID NO 53
<211> LENGTH: 12
<212> TYPE: PRT
<213> ORGANISM: Artificial Sequence
<220> FEATURE:
<223> OTHER INFORMATION: Antimicrobial peptide PL118

<400> SEQUENCE: 53

Tyr Arg Arg Val Gly Gly Trp Leu Arg Arg Val Leu
1 5 10

<210> SEQ ID NO 54
<211> LENGTH: 12
<212> TYPE: PRT
<213> ORGANISM: Artificial Sequence
<220> FEATURE:
<223> OTHER INFORMATION: Antimicrobial peptide PL119

<400> SEQUENCE: 54

Thr Ser Asp Leu Glu Thr Gln Ser Gly Gly Arg Leu
1 5 10

<210> SEQ ID NO 55
<211> LENGTH: 12
<212> TYPE: PRT
<213> ORGANISM: Artificial Sequence
<220> FEATURE:
<223> OTHER INFORMATION: Antimicrobial peptide PL120

<400> SEQUENCE: 55

Ile Val Thr Thr Asn His Val Leu Val Cys Thr Tyr
1 5 10

<210> SEQ ID NO 56
<211> LENGTH: 12
<212> TYPE: PRT
<213> ORGANISM: Artificial Sequence
<220> FEATURE:

<223> OTHER INFORMATION: Antimicrobial peptide PL121

<400> SEQUENCE: 56

Asp Gly Met Phe Arg Met Thr Leu Leu Thr Ser Trp
1 5 10

<210> SEQ ID NO 57
<211> LENGTH: 12
<212> TYPE: PRT
<213> ORGANISM: Artificial Sequence
<220> FEATURE:
<223> OTHER INFORMATION: Antimicrobial peptide PL122

<400> SEQUENCE: 57

Val Asn Trp Trp Arg Arg Cys Trp Lys Gln Trp His
1 5 10

<210> SEQ ID NO 58
<211> LENGTH: 12
<212> TYPE: PRT
<213> ORGANISM: Artificial Sequence
<220> FEATURE:
<223> OTHER INFORMATION: Antimicrobial peptide PL123

<400> SEQUENCE: 58

Trp Thr Trp Ile Lys Arg Val Leu Gln Glu Met Gly
1 5 10

<210> SEQ ID NO 59
<211> LENGTH: 12
<212> TYPE: PRT
<213> ORGANISM: Artificial Sequence
<220> FEATURE:
<223> OTHER INFORMATION: Antimicrobial peptide PL124

<400> SEQUENCE: 59

Leu Leu Val Ser Leu Pro Val Leu Leu Ser Cys Gly
1 5 10

<210> SEQ ID NO 60
<211> LENGTH: 12
<212> TYPE: PRT
<213> ORGANISM: Artificial Sequence
<220> FEATURE:
<223> OTHER INFORMATION: Antimicrobial peptide PL125

<400> SEQUENCE: 60

Leu Asn Trp Leu Arg Gly Trp Thr Gly Leu Val Gly
1 5 10

<210> SEQ ID NO 61
<211> LENGTH: 12
<212> TYPE: PRT
<213> ORGANISM: Artificial Sequence
<220> FEATURE:
<223> OTHER INFORMATION: Antimicrobial peptide PL126

<400> SEQUENCE: 61

Trp Thr Arg Phe Met Arg Ala Leu Gly Phe Thr Gln
1 5 10

<210> SEQ ID NO 62
<211> LENGTH: 12
<212> TYPE: PRT
<213> ORGANISM: Artificial Sequence
<220> FEATURE:
<223> OTHER INFORMATION: Antimicrobial peptide PL127

<400> SEQUENCE: 62

Tyr Cys Pro Gly Pro Ser Val Glu Ile Arg Arg Cys
1 5 10

<210> SEQ ID NO 63
<211> LENGTH: 12
<212> TYPE: PRT
<213> ORGANISM: Artificial Sequence
<220> FEATURE:
<223> OTHER INFORMATION: Antimicrobial peptide PL128

<400> SEQUENCE: 63

Leu Tyr Ala Phe Gly Thr Cys Glu Phe Ser Val Met
1 5 10

<210> SEQ ID NO 64
<211> LENGTH: 12
<212> TYPE: PRT
<213> ORGANISM: Artificial Sequence
<220> FEATURE:
<223> OTHER INFORMATION: Antimicrobial peptide PL129

<400> SEQUENCE: 64

Tyr Tyr Thr Phe Ile Leu Pro Leu Ser Leu Ser Cys
1 5 10

<210> SEQ ID NO 65
<211> LENGTH: 12
<212> TYPE: PRT
<213> ORGANISM: Artificial Sequence
<220> FEATURE:
<223> OTHER INFORMATION: Antimicrobial peptide PL130

<400> SEQUENCE: 65

Met Glu Arg Val Arg Lys Trp Phe Asn Glu Gly Arg
1 5 10

<210> SEQ ID NO 66
<211> LENGTH: 12
<212> TYPE: PRT
<213> ORGANISM: Artificial Sequence
<220> FEATURE:
<223> OTHER INFORMATION: Antimicrobial peptide PL131

<400> SEQUENCE: 66

Tyr Ser Ala Ile Lys Arg Arg Leu Leu Gln Gly Arg
1 5 10

<210> SEQ ID NO 67
<211> LENGTH: 12
<212> TYPE: PRT
<213> ORGANISM: Artificial Sequence
<220> FEATURE:
<223> OTHER INFORMATION: Antimicrobial peptide PL132

<400> SEQUENCE: 67

Ile Thr Phe Trp Ser Phe Val Phe Thr Met Arg Trp
1 5 10

<210> SEQ ID NO 68
<211> LENGTH: 12
<212> TYPE: PRT
<213> ORGANISM: Artificial Sequence
<220> FEATURE:
<223> OTHER INFORMATION: Antimicrobial peptide PL136

<400> SEQUENCE: 68

Phe Gln Leu Glu Phe Ser Val Ala Val Gly Ala Val
1 5 10

<210> SEQ ID NO 69
<211> LENGTH: 12
<212> TYPE: PRT
<213> ORGANISM: Artificial Sequence
<220> FEATURE:
<223> OTHER INFORMATION: Antimicrobial peptide PL137

<400> SEQUENCE: 69

Leu Ser Leu Ala Ile Glu Phe Ser Leu Ser Val Gln
1 5 10

<210> SEQ ID NO 70
<211> LENGTH: 12
<212> TYPE: PRT
<213> ORGANISM: Artificial Sequence
<220> FEATURE:
<223> OTHER INFORMATION: Antimicrobial peptide PL138

<400> SEQUENCE: 70

Trp Arg Trp Val Ser Arg Lys Trp Gln Thr Arg Gly
1 5 10

<210> SEQ ID NO 71
<211> LENGTH: 12
<212> TYPE: PRT
<213> ORGANISM: Artificial Sequence
<220> FEATURE:
<223> OTHER INFORMATION: Antimicrobial peptide PL139

<400> SEQUENCE: 71

Met Ala Trp Leu Ala Gln Trp Trp Gly Ala Arg Arg
1 5 10

<210> SEQ ID NO 72
<211> LENGTH: 12
<212> TYPE: PRT
<213> ORGANISM: Artificial Sequence
<220> FEATURE:
<223> OTHER INFORMATION: Antimicrobial peptide PL140

<400> SEQUENCE: 72

Val Asn Ala Trp Arg Lys Leu Ala Gln Ile Trp Arg
1 5 10

<210> SEQ ID NO 73
<211> LENGTH: 12
<212> TYPE: PRT
<213> ORGANISM: Artificial Sequence
<220> FEATURE:
<223> OTHER INFORMATION: Antimicrobial peptide PL141

<400> SEQUENCE: 73

Tyr Cys Ala His Leu Ser Cys Thr Val Cys Val Tyr
1 5 10

<210> SEQ ID NO 74
<211> LENGTH: 12
<212> TYPE: PRT
<213> ORGANISM: Artificial Sequence
<220> FEATURE:
<223> OTHER INFORMATION: Antimicrobial peptide PL142

<400> SEQUENCE: 74

Ile Gly Leu Leu Lys Arg Leu Val Thr Thr Arg Ser
1               5                   10

<210> SEQ ID NO 75
<211> LENGTH: 12
<212> TYPE: PRT
<213> ORGANISM: Artificial Sequence
<220> FEATURE:
<223> OTHER INFORMATION: Antimicrobial peptide PL144

<400> SEQUENCE: 75

Trp Asp Arg Val Ile Lys Trp Leu Arg Cys Gly Lys
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Antimicrobial peptide PL145

<400> SEQUENCE: 76

Gly Arg Leu Val Ala Arg Val Trp Arg Lys Trp Lys
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Antimicrobial peptide PL062c

<400> SEQUENCE: 77

Phe Tyr Leu Asn Ile Cys Ala Cys Trp Pro Ser Asn
1               5                   10

<210> SEQ ID NO 78
<211> LENGTH: 12
<212> TYPE: PRT
<213> ORGANISM: Artificial Sequence
<220> FEATURE:
<223> OTHER INFORMATION: Antimicrobial peptide PL066c

<400> SEQUENCE: 78

Trp Pro Arg Gly Arg Gln Glu Leu Ala Gly Arg Glu
1               5                   10

<210> SEQ ID NO 79
<211> LENGTH: 12
<212> TYPE: PRT
<213> ORGANISM: Artificial Sequence
<220> FEATURE:
<223> OTHER INFORMATION: Antimicrobial peptide NC010

<400> SEQUENCE: 79

Trp Trp Ile Val Pro Leu Leu Leu Pro Val Leu Leu
1               5                   10

<210> SEQ ID NO 80
<211> LENGTH: 12
<212> TYPE: PRT
<213> ORGANISM: Artificial Sequence
<220> FEATURE:
<223> OTHER INFORMATION: Antimicrobial peptide NC052

<400> SEQUENCE: 80

-continued

Met Arg Val Thr Leu Leu Cys Val Met Ile Leu Phe
1 5 10

<210> SEQ ID NO 81
<211> LENGTH: 12
<212> TYPE: PRT
<213> ORGANISM: Artificial Sequence
<220> FEATURE:
<223> OTHER INFORMATION: Antimicrobial peptide NC055

<400> SEQUENCE: 81

Ala Met Ser Leu Ala Cys Trp Leu Leu Phe Phe Pro
1 5 10

<210> SEQ ID NO 82
<211> LENGTH: 12
<212> TYPE: PRT
<213> ORGANISM: Artificial Sequence
<220> FEATURE:
<223> OTHER INFORMATION: Antimicrobial peptide CC006

<400> SEQUENCE: 82

Ala Leu Leu Arg Ser Val Phe Trp Phe Cys Cys Leu
1 5 10

<210> SEQ ID NO 83
<211> LENGTH: 12
<212> TYPE: PRT
<213> ORGANISM: Artificial Sequence
<220> FEATURE:
<223> OTHER INFORMATION: Antimicrobial peptide CC009

<400> SEQUENCE: 83

Val Met Trp Leu Asn Val Cys Asn Leu Val Ser Ala
1 5 10

<210> SEQ ID NO 84
<211> LENGTH: 12
<212> TYPE: PRT
<213> ORGANISM: Artificial Sequence
<220> FEATURE:
<223> OTHER INFORMATION: Antimicrobial peptide CC012

<400> SEQUENCE: 84

Phe Ala Asn Tyr Leu Gly Val Arg Gln Thr Leu Pro
1 5 10

<210> SEQ ID NO 85
<211> LENGTH: 12
<212> TYPE: PRT
<213> ORGANISM: Artificial Sequence
<220> FEATURE:
<223> OTHER INFORMATION: Antimicrobial peptide CC013

<400> SEQUENCE: 85

Trp Leu Phe Cys Trp Trp Phe Cys Phe Phe Met Thr
1 5 10

<210> SEQ ID NO 86
<211> LENGTH: 12
<212> TYPE: PRT
<213> ORGANISM: Artificial Sequence
<220> FEATURE:
<223> OTHER INFORMATION: Antimicrobial peptide CC015

<400> SEQUENCE: 86

Leu Leu Tyr Ala Leu Phe Val Ser Cys Leu Pro Phe 1 5 10

<210> SEQ ID NO 87
<211> LENGTH: 12
<212> TYPE: PRT
<213> ORGANISM: Artificial Sequence
<220> FEATURE:
<223> OTHER INFORMATION: Antimicrobial peptide CC021

<400> SEQUENCE: 87

Gly Ser Gly His Tyr Thr Leu Val Arg Thr Pro Pro
1 5 10

<210> SEQ ID NO 88
<211> LENGTH: 12
<212> TYPE: PRT
<213> ORGANISM: Artificial Sequence
<220> FEATURE:
<223> OTHER INFORMATION: Antimicrobial peptide CC23

<400> SEQUENCE: 88

Met Leu Ser Leu Ile Val Met Gln Phe Ile Gln Leu
1 5 10

<210> SEQ ID NO 89
<211> LENGTH: 12
<212> TYPE: PRT
<213> ORGANISM: Artificial Sequence
<220> FEATURE:
<223> OTHER INFORMATION: Antimicrobial peptide CC042

<400> SEQUENCE: 89

Cys Met Arg Met Cys Glu Glu Val Gly Val Ser Asp
1 5 10

<210> SEQ ID NO 90
<211> LENGTH: 12
<212> TYPE: PRT
<213> ORGANISM: Artificial Sequence
<220> FEATURE:
<223> OTHER INFORMATION: Antimicrobial peptide CC053

<400> SEQUENCE: 90

Gly Ala Arg Arg Phe Leu Tyr Pro Met Gly Phe Gly
1 5 10

<210> SEQ ID NO 91
<211> LENGTH: 12
<212> TYPE: PRT
<213> ORGANISM: Artificial Sequence
<220> FEATURE:
<223> OTHER INFORMATION: Antimicrobial peptide CC058

<400> SEQUENCE: 91

Phe Val Asp Lys Cys Leu Leu Phe Val Tyr Ser Leu
1 5 10

<210> SEQ ID NO 92
<211> LENGTH: 12
<212> TYPE: PRT
<213> ORGANISM: Artificial Sequence
<220> FEATURE:
<223> OTHER INFORMATION: Antimicrobial peptide CC069

<400> SEQUENCE: 92

Leu Leu Met Trp Ala Cys Ala Thr Val Phe Met Gly
1 5 10

<210> SEQ ID NO 93
<211> LENGTH: 12
<212> TYPE: PRT
<213> ORGANISM: Artificial Sequence
<220> FEATURE:
<223> OTHER INFORMATION: Antimicrobial peptide CC077

<400> SEQUENCE: 93

Ser Val Ser Gly Val Trp Gly Phe Gly His Val Leu
1 5 10

<210> SEQ ID NO 94
<211> LENGTH: 12
<212> TYPE: PRT
<213> ORGANISM: Artificial Sequence
<220> FEATURE:
<223> OTHER INFORMATION: Antimicrobial peptide CC084

<400> SEQUENCE: 94

Trp Leu Phe Val Leu Val Ser Gly Val Phe Thr Leu
1 5 10

<210> SEQ ID NO 95
<211> LENGTH: 12
<212> TYPE: PRT
<213> ORGANISM: Artificial Sequence
<220> FEATURE:
<223> OTHER INFORMATION: Antimicrobial peptide CC086

<400> SEQUENCE: 95

Ile Leu Ile Gly Leu Leu Phe Met Met Met Asp Ala
1 5 10

<210> SEQ ID NO 96
<211> LENGTH: 12
<212> TYPE: PRT
<213> ORGANISM: Artificial Sequence
<220> FEATURE:
<223> OTHER INFORMATION: Antimicrobial peptide CC090

<400> SEQUENCE: 96

Trp Leu Ile Tyr Leu Leu Ile Thr Ser Phe Gln Leu
1 5 10

<210> SEQ ID NO 97
<211> LENGTH: 12
<212> TYPE: PRT
<213> ORGANISM: Artificial Sequence
<220> FEATURE:
<223> OTHER INFORMATION: Antimicrobial peptide CC100

<400> SEQUENCE: 97

Trp Val Trp Ala Asn Met Met Asn Trp Cys Ala Cys
1 5 10

<210> SEQ ID NO 98
<211> LENGTH: 12
<212> TYPE: PRT
<213> ORGANISM: Artificial Sequence
<220> FEATURE:
<223> OTHER INFORMATION: Antimicrobial peptide CC106

<400> SEQUENCE: 98

Phe Met Asn Tyr Val Val Lys Phe Phe Cys Met Gln
1 5 10

<210> SEQ ID NO 99
<211> LENGTH: 12
<212> TYPE: PRT
<213> ORGANISM: Artificial Sequence
<220> FEATURE:
<223> OTHER INFORMATION: Antimicrobial peptide CC112

<400> SEQUENCE: 99

Ile Leu Leu Ser Val Pro Trp Ala Leu Phe Leu Thr
1 5 10

<210> SEQ ID NO 100
<211> LENGTH: 12
<212> TYPE: PRT
<213> ORGANISM: Artificial Sequence
<220> FEATURE:
<223> OTHER INFORMATION: Antimicrobial peptide CC128

<400> SEQUENCE: 100

Asn Phe Val Asn Arg Gly Ser Trp Leu Met Thr Arg
1 5 10

<210> SEQ ID NO 101
<211> LENGTH: 12
<212> TYPE: PRT
<213> ORGANISM: Artificial Sequence
<220> FEATURE:
<223> OTHER INFORMATION: Antimicrobial peptide CL011

<400> SEQUENCE: 101

Trp Val Tyr Leu Leu Leu Ser Cys Thr Gly Trp Phe
1 5 10

<210> SEQ ID NO 102
<211> LENGTH: 12
<212> TYPE: PRT
<213> ORGANISM: Artificial Sequence
<220> FEATURE:
<223> OTHER INFORMATION: Antimicrobial peptide CL015

<400> SEQUENCE: 102

Arg Ser Ala Ile Gln Glu Val Asn Leu Met Val Gly
1 5 10

<210> SEQ ID NO 103
<211> LENGTH: 12
<212> TYPE: PRT
<213> ORGANISM: Artificial Sequence
<220> FEATURE:
<223> OTHER INFORMATION: Antimicrobial peptide CC001

<400> SEQUENCE: 103

Ala Gln His Asp Gln Arg Gly Leu Val Tyr Val Arg
1 5 10

<210> SEQ ID NO 104
<211> LENGTH: 12
<212> TYPE: PRT
<213> ORGANISM: Artificial Sequence
<220> FEATURE:
<223> OTHER INFORMATION: Antimicrobial peptide CC026

<400> SEQUENCE: 104

Ala Ile Leu Thr Ile Leu Leu Gly Leu Gly Leu Leu
1 5 10

<210> SEQ ID NO 105
<211> LENGTH: 12
<212> TYPE: PRT
<213> ORGANISM: Artificial Sequence
<220> FEATURE:
<223> OTHER INFORMATION: Antimicrobial peptide CC046

<400> SEQUENCE: 105

Leu Phe Leu Thr Phe Leu Val Ser Phe Ala Trp Asn
1 5 10

<210> SEQ ID NO 106
<211> LENGTH: 12
<212> TYPE: PRT
<213> ORGANISM: Artificial Sequence
<220> FEATURE:
<223> OTHER INFORMATION: Antimicrobial peptide CC057

<400> SEQUENCE: 106

Met Phe Ser Cys Leu Leu Gln Val Leu Cys Val Val
1 5 10

<210> SEQ ID NO 107
<211> LENGTH: 12
<212> TYPE: PRT
<213> ORGANISM: Artificial Sequence
<220> FEATURE:
<223> OTHER INFORMATION: Antimicrobial peptide CC066

<400> SEQUENCE: 107

Phe Ser Ser Gln Asn Asp Tyr Pro Ser Arg Pro Pro
1 5 10

<210> SEQ ID NO 108
<211> LENGTH: 12
<212> TYPE: PRT
<213> ORGANISM: Artificial Sequence
<220> FEATURE:
<223> OTHER INFORMATION: Antimicrobial peptide CC078

<400> SEQUENCE: 108

Gly Leu Ala Arg Gly Pro Pro Gly Gly Trp Arg Gly
1 5 10

<210> SEQ ID NO 109
<211> LENGTH: 12
<212> TYPE: PRT
<213> ORGANISM: Artificial Sequence
<220> FEATURE:
<223> OTHER INFORMATION: Antimicrobial peptide CC080

<400> SEQUENCE: 109

Phe Tyr Met Ile Pro Glu Asn Phe Trp Val Asp Trp
1 5 10

<210> SEQ ID NO 110
<211> LENGTH: 12
<212> TYPE: PRT
<213> ORGANISM: Artificial Sequence
<220> FEATURE:
<223> OTHER INFORMATION: Antimicrobial peptide CC096

<400> SEQUENCE: 110

Trp Leu Ala Arg Val Asp Tyr Leu Tyr Thr Val Ser
1 5 10

<210> SEQ ID NO 111

-continued

<211> LENGTH: 12
<212> TYPE: PRT
<213> ORGANISM: Artificial Sequence
<220> FEATURE:
<223> OTHER INFORMATION: Antimicrobial peptide CC098

<400> SEQUENCE: 111

Gln Tyr Gly Trp Lys Gln Glu Tyr Gly Arg His Gly
1 5 10

<210> SEQ ID NO 112
<211> LENGTH: 12
<212> TYPE: PRT
<213> ORGANISM: Artificial Sequence
<220> FEATURE:
<223> OTHER INFORMATION: Antimicrobial peptide CC102

<400> SEQUENCE: 112

Gln Val Leu Ser Phe Leu Val Ser Trp Leu Ala Gln
1 5 10

<210> SEQ ID NO 113
<211> LENGTH: 12
<212> TYPE: PRT
<213> ORGANISM: Artificial Sequence
<220> FEATURE:
<223> OTHER INFORMATION: Antimicrobial peptide CC114

<400> SEQUENCE: 113

Val Asp Leu Cys Trp Leu Arg Ser Glu Arg Arg Val
1 5 10

<210> SEQ ID NO 114
<211> LENGTH: 12
<212> TYPE: PRT
<213> ORGANISM: Artificial Sequence
<220> FEATURE:
<223> OTHER INFORMATION: Antimicrobial peptide CC122

<400> SEQUENCE: 114

Leu Asp Phe Trp Phe Ala Pro Gly Leu Asp Pro Pro
1 5 10

<210> SEQ ID NO 115
<211> LENGTH: 12
<212> TYPE: PRT
<213> ORGANISM: Artificial Sequence
<220> FEATURE:
<223> OTHER INFORMATION: Antimicrobial peptide CC127

<400> SEQUENCE: 115

Ser Trp Leu Leu Phe Phe Phe Ile Ser Ser Ser Arg
1 5 10

<210> SEQ ID NO 116
<211> LENGTH: 12
<212> TYPE: PRT
<213> ORGANISM: Artificial Sequence
<220> FEATURE:
<223> OTHER INFORMATION: Antimicrobial peptide CC129

<400> SEQUENCE: 116

Ser Ser Ser Ser Ser Ser Ser Ser Ser Ser Ser Ser
1 5 10

<210> SEQ ID NO 117
<211> LENGTH: 12

<212> TYPE: PRT
<213> ORGANISM: Artificial Sequence
<220> FEATURE:
<223> OTHER INFORMATION: Antimicrobial peptide CL001K

<400> SEQUENCE: 117

Asp Thr Lys Ser Ala Leu Val Val Ala Leu Ile His
1 5 10

<210> SEQ ID NO 118
<211> LENGTH: 12
<212> TYPE: PRT
<213> ORGANISM: Artificial Sequence
<220> FEATURE:
<223> OTHER INFORMATION: Antimicrobial peptide CLO06K

<400> SEQUENCE: 118

Arg Val Leu Asp Leu Val Pro Tyr Ala Pro Asp Ala
1 5 10

<210> SEQ ID NO 119
<211> LENGTH: 12
<212> TYPE: PRT
<213> ORGANISM: Artificial Sequence
<220> FEATURE:
<223> OTHER INFORMATION: Antimicrobial peptide CC009K

<400> SEQUENCE: 119

Leu Ala Phe Phe Phe Phe Ile Ser Ala Ser Leu Gly
1 5 10

<210> SEQ ID NO 120
<211> LENGTH: 12
<212> TYPE: PRT
<213> ORGANISM: Artificial Sequence
<220> FEATURE:
<223> OTHER INFORMATION: Antimicrobial peptide PL029

<400> SEQUENCE: 120

Met Thr Lys Met Phe Arg Arg Trp Arg Thr Asn Lys
1 5 10

<210> SEQ ID NO 121
<211> LENGTH: 12
<212> TYPE: PRT
<213> ORGANISM: Artificial Sequence
<220> FEATURE:
<223> OTHER INFORMATION: Antimicrobial peptide PL030

<400> SEQUENCE: 121

Leu Gly Trp Leu Arg Gly Lys Ala Leu Gly Arg Gly
1 5 10

<210> SEQ ID NO 122
<211> LENGTH: 12
<212> TYPE: PRT
<213> ORGANISM: Artificial Sequence
<220> FEATURE:
<223> OTHER INFORMATION: Antimicrobial peptide PL034

<400> SEQUENCE: 122

Phe Ala Ala Val Val Arg Trp Val Arg Gly Arg Ala
1 5 10

<210> SEQ ID NO 123
<211> LENGTH: 12
<212> TYPE: PRT

<213> ORGANISM: Artificial Sequence
<220> FEATURE:
<223> OTHER INFORMATION: Antimicrobial peptide PL035

<400> SEQUENCE: 123

Tyr Gly Lys Ala Arg Arg Trp Leu Gly Arg Trp Thr
1 5 10

<210> SEQ ID NO 124
<211> LENGTH: 12
<212> TYPE: PRT
<213> ORGANISM: Artificial Sequence
<220> FEATURE:
<223> OTHER INFORMATION: Antimicrobial peptide PL038

<400> SEQUENCE: 124

Ile Ser Trp Leu Gly Gly Leu Leu Gly Arg Arg Glu
1 5 10

<210> SEQ ID NO 125
<211> LENGTH: 12
<212> TYPE: PRT
<213> ORGANISM: Artificial Sequence
<220> FEATURE:
<223> OTHER INFORMATION: Antimicrobial peptide PL047

<400> SEQUENCE: 125

Ile Arg Ala Phe Arg Ser Phe Thr Gln Leu Leu Cys
1 5 10

<210> SEQ ID NO 126
<211> LENGTH: 12
<212> TYPE: PRT
<213> ORGANISM: Artificial Sequence
<220> FEATURE:
<223> OTHER INFORMATION: Antimicrobial peptide PL049

<400> SEQUENCE: 126

Trp Arg Tyr Leu Leu Gly Arg Gly Lys Arg Arg Lys
1 5 10

<210> SEQ ID NO 127
<211> LENGTH: 12
<212> TYPE: PRT
<213> ORGANISM: Artificial Sequence
<220> FEATURE:
<223> OTHER INFORMATION: Antimicrobial peptide PL054

<400> SEQUENCE: 127

Trp Gly Ser Leu Met Leu Lys Trp Arg Arg Thr Arg
1 5 10

<210> SEQ ID NO 128
<211> LENGTH: 12
<212> TYPE: PRT
<213> ORGANISM: Artificial Sequence
<220> FEATURE:
<223> OTHER INFORMATION: Antimicrobial peptide PL055

<400> SEQUENCE: 128

Ile Lys Trp Ile Arg Ser Leu Leu Val Arg Gly Arg
1 5 10

<210> SEQ ID NO 129
<211> LENGTH: 12
<212> TYPE: PRT
<213> ORGANISM: Artificial Sequence
<220> FEATURE:
<223> OTHER INFORMATION: Antimicrobial peptide PL062

<400> SEQUENCE: 129

Phe Ala Arg Leu His Lys Trp Phe Gln Arg Arg Lys
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Antimicrobial peptide PL063

<400> SEQUENCE: 130

Ile Lys Leu Leu Arg Ile Leu Ser Gln Lys Trp Arg
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Antimicrobial peptide PL064

<400> SEQUENCE: 131

Trp Val Trp Leu Ser Arg Trp Leu Arg Arg Gly Trp
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Antimicrobial peptide PL065

<400> SEQUENCE: 132

Leu Lys Gly Leu Lys Arg Trp Trp Arg Pro Glu His
1               5                   10

<210> SEQ ID NO 133
<211> LENGTH: 12
<212> TYPE: PRT
<213> ORGANISM: Artificial Sequence
<220> FEATURE:
<223> OTHER INFORMATION: Antimicrobial peptide PL066

<400> SEQUENCE: 133

Trp Lys Trp Leu Gln Ser Leu Trp Gly Cys Glu Val
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Antimicrobial peptide PL072

<400> SEQUENCE: 134

Trp Arg Gly Val Arg Lys Val Trp Arg Arg Met Arg
1               5                   10

<210> SEQ ID NO 135
<211> LENGTH: 12
<212> TYPE: PRT
<213> ORGANISM: Artificial Sequence
<220> FEATURE:

<223> OTHER INFORMATION: Antimicrobial peptide PL092

<400> SEQUENCE: 135

Tyr Cys Trp Leu Arg Glu Lys Leu Gly Gly Gly Gln
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Antimicrobial peptide PL095

<400> SEQUENCE: 136

Trp Gln Leu Val Arg Arg Leu Leu Gly Gln Leu Gly
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Antimicrobial peptide PL097

<400> SEQUENCE: 137

Trp Val Thr Ala Arg Asp Trp Val Lys Ser Trp Trp
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Antimicrobial peptide PL098

<400> SEQUENCE: 138

Trp Arg Arg Trp Lys Met Arg Gly Arg Ala Arg Val
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Antimicrobial peptide PL104

<400> SEQUENCE: 139

Met Gly Met Leu Arg Trp Leu Phe Ser Phe Trp Arg
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Antimicrobial peptide PL111

<400> SEQUENCE: 140

Leu Ser Arg Ala Lys Ala Leu Leu Lys Arg Ala Lys
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Antimicrobial peptide PL113

<400> SEQUENCE: 141

Cys Arg Tyr Leu Arg Leu Leu Trp Ser Asn Ile Arg
1 5 10

<210> SEQ ID NO 142
<211> LENGTH: 12
<212> TYPE: PRT
<213> ORGANISM: Artificial Sequence
<220> FEATURE:
<223> OTHER INFORMATION: Antimicrobial peptide PL118

<400> SEQUENCE: 142

Tyr Arg Arg Val Gly Gly Trp Leu Arg Arg Val Leu
1 5 10

<210> SEQ ID NO 143
<211> LENGTH: 12
<212> TYPE: PRT
<213> ORGANISM: Artificial Sequence
<220> FEATURE:
<223> OTHER INFORMATION: Antimicrobial peptide PL122

<400> SEQUENCE: 143

Val Asn Trp Trp Arg Arg Cys Trp Lys Gln Trp His
1 5 10

<210> SEQ ID NO 144
<211> LENGTH: 12
<212> TYPE: PRT
<213> ORGANISM: Artificial Sequence
<220> FEATURE:
<223> OTHER INFORMATION: Antimicrobial peptide PL123

<400> SEQUENCE: 144

Trp Thr Trp Ile Lys Arg Val Leu Gln Glu Met Gly
1 5 10

<210> SEQ ID NO 145
<211> LENGTH: 12
<212> TYPE: PRT
<213> ORGANISM: Artificial Sequence
<220> FEATURE:
<223> OTHER INFORMATION: Antimicrobial peptide PL126

<400> SEQUENCE: 145

Trp Thr Arg Phe Met Arg Ala Leu Gly Phe Thr Gln
1 5 10

<210> SEQ ID NO 146
<211> LENGTH: 12
<212> TYPE: PRT
<213> ORGANISM: Artificial Sequence
<220> FEATURE:
<223> OTHER INFORMATION: Antimicrobial peptide PL131

<400> SEQUENCE: 146

Tyr Ser Ala Ile Lys Arg Arg Leu Leu Gln Gly Arg
1 5 10

<210> SEQ ID NO 147
<211> LENGTH: 12
<212> TYPE: PRT
<213> ORGANISM: Artificial Sequence
<220> FEATURE:
<223> OTHER INFORMATION: Antimicrobial peptide PL137

<400> SEQUENCE: 147

Leu Ser Leu Ala Ile Glu Phe Ser Leu Ser Val Gln
1 5 10

<210> SEQ ID NO 148
<211> LENGTH: 12
<212> TYPE: PRT
<213> ORGANISM: Artificial Sequence
<220> FEATURE:
<223> OTHER INFORMATION: Antimicrobial peptide PL138

<400> SEQUENCE: 148

Trp Arg Trp Val Ser Arg Lys Trp Gln Thr Arg Gly
1 5 10

<210> SEQ ID NO 149
<211> LENGTH: 12
<212> TYPE: PRT
<213> ORGANISM: Artificial Sequence
<220> FEATURE:
<223> OTHER INFORMATION: Antimicrobial peptide PL139

<400> SEQUENCE: 149

Met Ala Trp Leu Ala Gln Trp Trp Gly Ala Arg Arg
1 5 10

<210> SEQ ID NO 150
<211> LENGTH: 12
<212> TYPE: PRT
<213> ORGANISM: Artificial Sequence
<220> FEATURE:
<223> OTHER INFORMATION: Antimicrobial peptide PL140

<400> SEQUENCE: 150

Val Asn Ala Trp Arg Lys Leu Ala Gln Ile Trp Arg
1 5 10

<210> SEQ ID NO 151
<211> LENGTH: 12
<212> TYPE: PRT
<213> ORGANISM: Artificial Sequence
<220> FEATURE:
<223> OTHER INFORMATION: Antimicrobial peptide PL142

<400> SEQUENCE: 151

Ile Gly Leu Leu Lys Arg Leu Val Thr Thr Arg Ser
1 5 10

<210> SEQ ID NO 152
<211> LENGTH: 12
<212> TYPE: PRT
<213> ORGANISM: Artificial Sequence
<220> FEATURE:
<223> OTHER INFORMATION: Antimicrobial peptide PL144

<400> SEQUENCE: 152

Trp Asp Arg Val Ile Lys Trp Leu Arg Cys Gly Lys
1 5 10

<210> SEQ ID NO 153
<211> LENGTH: 12
<212> TYPE: PRT
<213> ORGANISM: Artificial Sequence
<220> FEATURE:
<223> OTHER INFORMATION: Antimicrobial peptide PL145

<400> SEQUENCE: 153

Gly Arg Leu Val Ala Arg Val Trp Arg Lys Trp Lys
1 5 10

<210> SEQ ID NO 154
<211> LENGTH: 12
<212> TYPE: PRT
<213> ORGANISM: Artificial Sequence
<220> FEATURE:
<223> OTHER INFORMATION: Antimicrobial peptide PL146

<400> SEQUENCE: 154

Met Arg Phe Leu Arg Arg Leu Trp Trp Arg Ala Arg
1 5 10

<210> SEQ ID NO 155
<211> LENGTH: 12
<212> TYPE: PRT
<213> ORGANISM: Artificial Sequence
<220> FEATURE:
<223> OTHER INFORMATION: Antimicrobial peptide PL149

<400> SEQUENCE: 155

Trp Thr Trp Ile Lys Arg Val Leu Gln Glu Met Gly
1 5 10

<210> SEQ ID NO 156
<211> LENGTH: 12
<212> TYPE: PRT
<213> ORGANISM: Artificial Sequence
<220> FEATURE:
<223> OTHER INFORMATION: Antimicrobial peptide PL166

<400> SEQUENCE: 156

Ala Gly Ile Ile Lys Arg Trp Leu Phe Arg His Thr
1 5 10

<210> SEQ ID NO 157
<211> LENGTH: 12
<212> TYPE: PRT
<213> ORGANISM: Artificial Sequence
<220> FEATURE:
<223> OTHER INFORMATION: Antimicrobial peptide PL177

<400> SEQUENCE: 157

Trp Gly Tyr Leu Ile Arg Ala Ile Arg Arg Arg Val
1 5 10

<210> SEQ ID NO 158
<211> LENGTH: 12
<212> TYPE: PRT
<213> ORGANISM: Artificial Sequence
<220> FEATURE:
<223> OTHER INFORMATION: Antimicrobial peptide PL184

<400> SEQUENCE: 158

Val Ala Ala Val Gln Arg Trp Cys Arg Lys Trp Gln
1 5 10

<210> SEQ ID NO 159
<211> LENGTH: 12
<212> TYPE: PRT
<213> ORGANISM: Artificial Sequence
<220> FEATURE:
<223> OTHER INFORMATION: Antimicrobial peptide PL189

<400> SEQUENCE: 159

Trp Glu Trp Met Arg Arg Ala Ala Gly Ala Arg Arg
1 5 10

<210> SEQ ID NO 160
<211> LENGTH: 12
<212> TYPE: PRT
<213> ORGANISM: Artificial Sequence
<220> FEATURE:
<223> OTHER INFORMATION: Antimicrobial peptide PL200

<400> SEQUENCE: 160

Trp Arg Trp Leu Arg Arg Arg Gln Gly Pro Gly Arg
1 5 10

<210> SEQ ID NO 161
<211> LENGTH: 12
<212> TYPE: PRT
<213> ORGANISM: Artificial Sequence
<220> FEATURE:
<223> OTHER INFORMATION: Antimicrobial peptide PL202

<400> SEQUENCE: 161

Trp Ala Arg Val Lys Arg Gly Trp Gln Lys Lys Ala
1 5 10

<210> SEQ ID NO 162
<211> LENGTH: 12
<212> TYPE: PRT
<213> ORGANISM: Artificial Sequence
<220> FEATURE:
<223> OTHER INFORMATION: Antimicrobial peptide PL208

<400> SEQUENCE: 162

Phe Gln Leu Leu Leu Ser Trp Ala Arg Lys Cys Lys
1 5 10

<210> SEQ ID NO 163
<211> LENGTH: 12
<212> TYPE: PRT
<213> ORGANISM: Artificial Sequence
<220> FEATURE:
<223> OTHER INFORMATION: Antimicrobial peptide PL211

<400> SEQUENCE: 163

Ile Ser Leu Trp Arg Ser Val Ala Gln Arg Trp Gly
1 5 10

<210> SEQ ID NO 164
<211> LENGTH: 12
<212> TYPE: PRT
<213> ORGANISM: Artificial Sequence
<220> FEATURE:
<223> OTHER INFORMATION: Antimicrobial peptide PL212

<400> SEQUENCE: 164

Gly Arg Trp Leu Arg Asn Arg Trp Ala Gly Trp Arg
1 5 10

<210> SEQ ID NO 165
<211> LENGTH: 12
<212> TYPE: PRT
<213> ORGANISM: Artificial Sequence
<220> FEATURE:
<223> OTHER INFORMATION: Antimicrobial peptide PL213

<400> SEQUENCE: 165

Trp Gln Leu Val Thr Arg Leu Leu Arg Arg Gln Gly

-continued 1 5 10

<210> SEQ ID NO 166
<211> LENGTH: 12
<212> TYPE: PRT
<213> ORGANISM: Artificial Sequence
<220> FEATURE:
<223> OTHER INFORMATION: Antimicrobial peptide PL214

<400> SEQUENCE: 166

Ser Ala Met Leu Lys Arg Trp Trp Gln Gly Thr Gly
1 5 10

<210> SEQ ID NO 167
<211> LENGTH: 12
<212> TYPE: PRT
<213> ORGANISM: Artificial Sequence
<220> FEATURE:
<223> OTHER INFORMATION: Antimicrobial peptide PL215

<400> SEQUENCE: 167

Tyr Arg Ala Leu Arg Ala Trp Leu Trp Ala Pro Arg
1 5 10

<210> SEQ ID NO 168
<211> LENGTH: 12
<212> TYPE: PRT
<213> ORGANISM: Artificial Sequence
<220> FEATURE:
<223> OTHER INFORMATION: Antimicrobial peptide PL225

<400> SEQUENCE: 168

Ala Glu Arg Ser Arg Ala Trp Leu Arg Arg Ile Thr
1 5 10

<210> SEQ ID NO 169
<211> LENGTH: 12
<212> TYPE: PRT
<213> ORGANISM: Artificial Sequence
<220> FEATURE:
<223> OTHER INFORMATION: Antimicrobial peptide PL226

<400> SEQUENCE: 169

Met Arg Val Ile Arg Arg Leu Val Arg Trp Pro Arg
1 5 10

<210> SEQ ID NO 170
<211> LENGTH: 12
<212> TYPE: PRT
<213> ORGANISM: Artificial Sequence
<220> FEATURE:
<223> OTHER INFORMATION: Antimicrobial peptide PL239

<400> SEQUENCE: 170

Trp Ser Arg Val Val Arg Gly Phe Ala Ala Ala Arg
1 5 10

<210> SEQ ID NO 171
<211> LENGTH: 12
<212> TYPE: PRT
<213> ORGANISM: Artificial Sequence
<220> FEATURE:
<223> OTHER INFORMATION: Antimicrobial peptide PL240

<400> SEQUENCE: 171

Trp Ala Leu Leu Arg Arg Met Trp Arg Asp Gly Lys
1 5 10

<210> SEQ ID NO 172
<211> LENGTH: 12
<212> TYPE: PRT
<213> ORGANISM: Artificial Sequence
<220> FEATURE:
<223> OTHER INFORMATION: Antimicrobial peptide PL248

<400> SEQUENCE: 172

Phe Cys Arg Leu Arg Ser Trp Trp Arg Ser Trp Gln
1               5                   10

<210> SEQ ID NO 173
<211> LENGTH: 12
<212> TYPE: PRT
<213> ORGANISM: Artificial Sequence
<220> FEATURE:
<223> OTHER INFORMATION: Antimicrobial peptide PL251

<400> SEQUENCE: 173

Gly Asp Arg Val Ala Ala Ala Pro Gly Ala Leu Leu
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Antimicrobial peptide PL260

<400> SEQUENCE: 174

Val Gly Arg Val Arg Lys Ala Trp Arg Arg Val Arg
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Antimicrobial peptide PL261

<400> SEQUENCE: 175

Met Arg Arg Leu Lys Ala Leu Trp Ala Gly Lys Glu
1               5                   10

<210> SEQ ID NO 176
<211> LENGTH: 12
<212> TYPE: PRT
<213> ORGANISM: Artificial Sequence
<220> FEATURE:
<223> OTHER INFORMATION: Antimicrobial peptide PL268

<400> SEQUENCE: 176

Leu Glu Phe Thr Ala Arg Leu Phe Arg Arg Arg Ser
1               5                   10

<210> SEQ ID NO 177
<211> LENGTH: 12
<212> TYPE: PRT
<213> ORGANISM: Artificial Sequence
<220> FEATURE:
<223> OTHER INFORMATION: Antimicrobial peptide PL274

<400> SEQUENCE: 177

Ser Val Cys Glu Trp Ser Trp Arg Met Ala Val Trp
1               5                   10

<210> SEQ ID NO 178
<211> LENGTH: 12
<212> TYPE: PRT
<213> ORGANISM: Artificial Sequence
<220> FEATURE:
<223> OTHER INFORMATION: Antimicrobial peptide PL275

<400> SEQUENCE: 178

Val Arg Arg Phe Lys Arg Ala Val Phe Arg Arg Ser
1 5 10

<210> SEQ ID NO 179
<211> LENGTH: 12
<212> TYPE: PRT
<213> ORGANISM: Artificial Sequence
<220> FEATURE:
<223> OTHER INFORMATION: Antimicrobial peptide PL291

<400> SEQUENCE: 179

Ile Cys Leu Met Arg Arg Leu Thr Arg Arg Leu Thr
1 5 10

<210> SEQ ID NO 180
<211> LENGTH: 12
<212> TYPE: PRT
<213> ORGANISM: Artificial Sequence
<220> FEATURE:
<223> OTHER INFORMATION: Antimicrobial peptide PL293

<400> SEQUENCE: 180

Ala Ala Trp Leu Gly Gly Trp Trp Arg Gly Arg Gly
1 5 10

<210> SEQ ID NO 181
<211> LENGTH: 12
<212> TYPE: PRT
<213> ORGANISM: Artificial Sequence
<220> FEATURE:
<223> OTHER INFORMATION: Antimicrobial peptide PL294

<400> SEQUENCE: 181

Leu Ser Trp Leu Arg Arg Arg Ser Arg Glu Leu Gly
1 5 10

<210> SEQ ID NO 182
<211> LENGTH: 12
<212> TYPE: PRT
<213> ORGANISM: Artificial Sequence
<220> FEATURE:
<223> OTHER INFORMATION: Antimicrobial peptide PL297

<400> SEQUENCE: 182

Leu Thr Trp Ile Arg Asn Trp Val Gly Asp Arg Ser
1 5 10

<210> SEQ ID NO 183
<211> LENGTH: 12
<212> TYPE: PRT
<213> ORGANISM: Artificial Sequence
<220> FEATURE:
<223> OTHER INFORMATION: Antimicrobial peptide PL299

<400> SEQUENCE: 183

Leu Arg Leu Leu Gly Thr Val Cys Arg Lys Trp Arg
1 5 10

<210> SEQ ID NO 184
<211> LENGTH: 12
<212> TYPE: PRT
<213> ORGANISM: Artificial Sequence
<220> FEATURE:
<223> OTHER INFORMATION: Antimicrobial peptide PL308

<400> SEQUENCE: 184

Trp Arg Trp Leu Arg Asp Gly Val Ala Arg Ala Leu
1 5 10

<210> SEQ ID NO 185
<211> LENGTH: 12
<212> TYPE: PRT
<213> ORGANISM: Artificial Sequence
<220> FEATURE:
<223> OTHER INFORMATION: Antimicrobial peptide PL309

<400> SEQUENCE: 185

Tyr Ala Trp Trp Arg Arg Phe Cys Gly Arg Ser Glu
1 5 10

<210> SEQ ID NO 186
<211> LENGTH: 12
<212> TYPE: PRT
<213> ORGANISM: Artificial Sequence
<220> FEATURE:
<223> OTHER INFORMATION: Antimicrobial peptide PL311

<400> SEQUENCE: 186

Trp Ala Arg Ile Arg Ala Trp Trp Trp Arg Val Lys
1 5 10

<210> SEQ ID NO 187
<211> LENGTH: 12
<212> TYPE: PRT
<213> ORGANISM: Artificial Sequence
<220> FEATURE:
<223> OTHER INFORMATION: Antimicrobial peptide PL312

<400> SEQUENCE: 187

Trp Gly Trp Phe Lys Arg Trp Gly Val Arg Gly Ala
1 5 10

<210> SEQ ID NO 188
<211> LENGTH: 12
<212> TYPE: PRT
<213> ORGANISM: Artificial Sequence
<220> FEATURE:
<223> OTHER INFORMATION: Antimicrobial peptide PL325

<400> SEQUENCE: 188

Trp Ala Gln Ile Arg Gly Arg Leu Gly Arg Asn Met
1 5 10

<210> SEQ ID NO 189
<211> LENGTH: 12
<212> TYPE: PRT
<213> ORGANISM: Artificial Sequence
<220> FEATURE:
<223> OTHER INFORMATION: Antimicrobial peptide PL344

<400> SEQUENCE: 189

Leu His Asn Leu Trp Gly Trp Phe Ile Arg Arg Phe
1 5 10

<210> SEQ ID NO 190

<211> LENGTH: 12
<212> TYPE: PRT
<213> ORGANISM: Artificial Sequence
<220> FEATURE:
<223> OTHER INFORMATION: Antimicrobial peptide PL350

<400> SEQUENCE: 190

Trp Gly Trp Val Arg Lys Leu Met Arg Met Arg Ser
1 5 10

<210> SEQ ID NO 191
<211> LENGTH: 12
<212> TYPE: PRT
<213> ORGANISM: Artificial Sequence
<220> FEATURE:
<223> OTHER INFORMATION: Antimicrobial peptide PL353

<400> SEQUENCE: 191

Ile Arg Trp Cys Val Ser Arg Cys Ile Ser Leu Trp
1 5 10

<210> SEQ ID NO 192
<211> LENGTH: 12
<212> TYPE: PRT
<213> ORGANISM: Artificial Sequence
<220> FEATURE:
<223> OTHER INFORMATION: Antimicrobial peptide PL358

<400> SEQUENCE: 192

Tyr Ala Trp Cys Arg Ala Lys Val Arg Arg Ala Leu
1 5 10

<210> SEQ ID NO 193
<211> LENGTH: 12
<212> TYPE: PRT
<213> ORGANISM: Artificial Sequence
<220> FEATURE:
<223> OTHER INFORMATION: Antimicrobial peptide PL361

<400> SEQUENCE: 193

Val Ser Trp Ile Arg Arg Gln Trp Lys Ala Thr Ile
1 5 10

<210> SEQ ID NO 194
<211> LENGTH: 12
<212> TYPE: PRT
<213> ORGANISM: Artificial Sequence
<220> FEATURE:
<223> OTHER INFORMATION: Antimicrobial peptide PL376

<400> SEQUENCE: 194

Trp Gly Ala Phe Gly Arg Ala Trp Arg Arg Tyr Arg
1 5 10

<210> SEQ ID NO 195
<211> LENGTH: 12
<212> TYPE: PRT
<213> ORGANISM: Artificial Sequence
<220> FEATURE:
<223> OTHER INFORMATION: Antimicrobial peptide PL380

<400> SEQUENCE: 195

Leu Arg Arg Ala Arg Ala Trp Met Lys Gly Arg Arg
1 5 10

<210> SEQ ID NO 196
<211> LENGTH: 12

```
<212> TYPE: PRT
<213> ORGANISM: Artificial Sequence
<220> FEATURE:
<223> OTHER INFORMATION: Antimicrobial peptide PL403

<400> SEQUENCE: 196

Ala Gln Leu Leu Arg Arg Phe Arg Thr Arg Gly Arg
1               5                   10


<210> SEQ ID NO 197
<211> LENGTH: 12
<212> TYPE: PRT
<213> ORGANISM: Artificial Sequence
<220> FEATURE:
<223> OTHER INFORMATION: Antimicrobial peptide PL406

<400> SEQUENCE: 197

Trp Thr Phe Leu Lys Lys Leu Ala Ser Ser Lys Ala
1               5                   10


<210> SEQ ID NO 198
<211> LENGTH: 12
<212> TYPE: PRT
<213> ORGANISM: Artificial Sequence
<220> FEATURE:
<223> OTHER INFORMATION: Antimicrobial peptide PL421

<400> SEQUENCE: 198

Ala Gly Ala Val Arg Arg Leu Trp Arg Ser Trp Arg
1               5                   10


<210> SEQ ID NO 199
<211> LENGTH: 12
<212> TYPE: PRT
<213> ORGANISM: Artificial Sequence
<220> FEATURE:
<223> OTHER INFORMATION: Antimicrobial peptide PL431

<400> SEQUENCE: 199

Val Gln Trp Leu Arg Arg Leu Gly Gly Ser Gly Val
1               5                   10


<210> SEQ ID NO 200
<211> LENGTH: 12
<212> TYPE: PRT
<213> ORGANISM: Artificial Sequence
<220> FEATURE:
<223> OTHER INFORMATION: Antimicrobial peptide PL443

<400> SEQUENCE: 200

Phe Ser Phe Phe Arg Arg Lys Ser Ile Arg Leu Arg
1               5                   10


<210> SEQ ID NO 201
<211> LENGTH: 12
<212> TYPE: PRT
<213> ORGANISM: Artificial Sequence
<220> FEATURE:
<223> OTHER INFORMATION: Antimicrobial peptide PL444

<400> SEQUENCE: 201

Ala Ala Trp Leu Ala Arg Arg Trp Arg Ala Trp Val
1               5                   10


<210> SEQ ID NO 202
<211> LENGTH: 12
<212> TYPE: PRT
```

<213> ORGANISM: Artificial Sequence
<220> FEATURE:
<223> OTHER INFORMATION: Antimicrobial peptide PL459

<400> SEQUENCE: 202

Phe Glu Val Phe Trp Ser Ile Thr Tyr Ile Tyr Ala
1 5 10

<210> SEQ ID NO 203
<211> LENGTH: 12
<212> TYPE: PRT
<213> ORGANISM: Artificial Sequence
<220> FEATURE:
<223> OTHER INFORMATION: Antimicrobial peptide PL460

<400> SEQUENCE: 203

Phe Asn Ile Ile Arg Cys Trp Trp Lys Gly Thr Arg
1 5 10

<210> SEQ ID NO 204
<211> LENGTH: 12
<212> TYPE: PRT
<213> ORGANISM: Artificial Sequence
<220> FEATURE:
<223> OTHER INFORMATION: Antimicrobial peptide PL461

<400> SEQUENCE: 204

Trp Arg Trp Val Ala Arg Arg Thr Arg Gly Lys Lys
1 5 10

<210> SEQ ID NO 205
<211> LENGTH: 12
<212> TYPE: PRT
<213> ORGANISM: Artificial Sequence
<220> FEATURE:
<223> OTHER INFORMATION: Antimicrobial peptide PL466

<400> SEQUENCE: 205

Leu Ser Phe Phe Ala Arg Lys Lys Arg Val Arg Gln
1 5 10

<210> SEQ ID NO 206
<211> LENGTH: 12
<212> TYPE: PRT
<213> ORGANISM: Artificial Sequence
<220> FEATURE:
<223> OTHER INFORMATION: Antimicrobial peptide PL468

<400> SEQUENCE: 206

Lys Ala Trp Ala Gly Arg Trp Trp Lys Lys Trp Ser
1 5 10

<210> SEQ ID NO 207
<211> LENGTH: 12
<212> TYPE: PRT
<213> ORGANISM: Artificial Sequence
<220> FEATURE:
<223> OTHER INFORMATION: Antimicrobial peptide PL471

<400> SEQUENCE: 207

Trp Asn Val Leu Lys Lys Tyr Leu Trp Leu Thr Glu
1 5 10

<210> SEQ ID NO 208
<211> LENGTH: 12
<212> TYPE: PRT
<213> ORGANISM: Artificial Sequence
<220> FEATURE:
<223> OTHER INFORMATION: Antimicrobial peptide PL472

<400> SEQUENCE: 208

Trp Arg Arg Leu Thr Gly Arg Arg Arg Gly Ser Gly
1 5 10

<210> SEQ ID NO 209
<211> LENGTH: 12
<212> TYPE: PRT
<213> ORGANISM: Artificial Sequence
<220> FEATURE:
<223> OTHER INFORMATION: Antimicrobial peptide PL473

<400> SEQUENCE: 209

Leu Ser Trp Met Lys Ala Arg Trp Ala Gly Cys Gly
1 5 10

<210> SEQ ID NO 210
<211> LENGTH: 12
<212> TYPE: PRT
<213> ORGANISM: Artificial Sequence
<220> FEATURE:
<223> OTHER INFORMATION: Antimicrobial peptide PL481

<400> SEQUENCE: 210

Trp Lys Gly Leu Val Arg Leu Leu Lys Ala Ala Val
1 5 10

<210> SEQ ID NO 211
<211> LENGTH: 12
<212> TYPE: PRT
<213> ORGANISM: Artificial Sequence
<220> FEATURE:
<223> OTHER INFORMATION: Antimicrobial peptide PL491

<400> SEQUENCE: 211

Leu Lys Ala Val Ala Lys Leu Ala Gln Trp Val Arg
1 5 10

<210> SEQ ID NO 212
<211> LENGTH: 12
<212> TYPE: PRT
<213> ORGANISM: Artificial Sequence
<220> FEATURE:
<223> OTHER INFORMATION: Antimicrobial peptide PL497

<400> SEQUENCE: 212

Phe Arg Arg Ile Trp Thr Val Leu Phe Gly Arg Ala
1 5 10

<210> SEQ ID NO 213
<211> LENGTH: 12
<212> TYPE: PRT
<213> ORGANISM: Artificial Sequence
<220> FEATURE:
<223> OTHER INFORMATION: Antimicrobial peptide PL500

<400> SEQUENCE: 213

Trp Arg Ala Leu Thr Arg Arg Val Arg Leu Trp Arg
1 5 10

<210> SEQ ID NO 214
<211> LENGTH: 12
<212> TYPE: PRT
<213> ORGANISM: Artificial Sequence
<220> FEATURE:

<223> OTHER INFORMATION: Antimicrobial peptide PL014

<400> SEQUENCE: 214

Trp Thr Val Arg Val Asp Val Ile Glu Ser Arg Trp
1 5 10

<210> SEQ ID NO 215
<211> LENGTH: 12
<212> TYPE: PRT
<213> ORGANISM: Artificial Sequence
<220> FEATURE:
<223> OTHER INFORMATION: Antimicrobial peptide PL037

<400> SEQUENCE: 215

Phe Arg Trp Leu Tyr Arg Leu Phe Met Phe Arg Leu
1 5 10

<210> SEQ ID NO 216
<211> LENGTH: 12
<212> TYPE: PRT
<213> ORGANISM: Artificial Sequence
<220> FEATURE:
<223> OTHER INFORMATION: Antimicrobial peptide PL045

<400> SEQUENCE: 216

Cys Ile Leu Val Val Leu Val His Leu Phe Val Ala
1 5 10

<210> SEQ ID NO 217
<211> LENGTH: 12
<212> TYPE: PRT
<213> ORGANISM: Artificial Sequence
<220> FEATURE:
<223> OTHER INFORMATION: Antimicrobial peptide PL048

<400> SEQUENCE: 217

Val Thr Leu Gly Leu Val Met Leu Ala Val Ser Leu
1 5 10

<210> SEQ ID NO 218
<211> LENGTH: 12
<212> TYPE: PRT
<213> ORGANISM: Artificial Sequence
<220> FEATURE:
<223> OTHER INFORMATION: Antimicrobial peptide PL060

<400> SEQUENCE: 218

Leu Ser Trp Val Trp Arg Gln Leu Gly Gly Ala Trp
1 5 10

<210> SEQ ID NO 219
<211> LENGTH: 12
<212> TYPE: PRT
<213> ORGANISM: Artificial Sequence
<220> FEATURE:
<223> OTHER INFORMATION: Antimicrobial peptide PL069

<400> SEQUENCE: 219

Phe Phe Cys Leu Trp Val Leu Tyr Leu Gly Thr Pro
1 5 10

<210> SEQ ID NO 220
<211> LENGTH: 12
<212> TYPE: PRT
<213> ORGANISM: Artificial Sequence
<220> FEATURE:
<223> OTHER INFORMATION: Antimicrobial peptide PL073

<400> SEQUENCE: 220

Asn Val Arg Ile Ile Val Asp Met Thr Ile Ser Ala
1 5 10

<210> SEQ ID NO 221
<211> LENGTH: 12
<212> TYPE: PRT
<213> ORGANISM: Artificial Sequence
<220> FEATURE:
<223> OTHER INFORMATION: Antimicrobial peptide PL088

<400> SEQUENCE: 221

Ile Ile Val Leu Val Phe Val Thr Tyr Leu Thr Ala
1 5 10

<210> SEQ ID NO 222
<211> LENGTH: 12
<212> TYPE: PRT
<213> ORGANISM: Artificial Sequence
<220> FEATURE:
<223> OTHER INFORMATION: Antimicrobial peptide PL089

<400> SEQUENCE: 222

Phe Val Ile Ala Ser Phe Val Trp Val Ile Leu Val
1 5 10

<210> SEQ ID NO 223
<211> LENGTH: 12
<212> TYPE: PRT
<213> ORGANISM: Artificial Sequence
<220> FEATURE:
<223> OTHER INFORMATION: Antimicrobial peptide PL101

<400> SEQUENCE: 223

Ile Leu Tyr Leu Cys Val Leu Ser Val Ser Arg Asn
1 5 10

<210> SEQ ID NO 224
<211> LENGTH: 12
<212> TYPE: PRT
<213> ORGANISM: Artificial Sequence
<220> FEATURE:
<223> OTHER INFORMATION: Antimicrobial peptide PL112

<400> SEQUENCE: 224

Gly Leu Trp Gly Lys Trp Glu Pro Gly Gly Gln Gly
1 5 10

<210> SEQ ID NO 225
<211> LENGTH: 12
<212> TYPE: PRT
<213> ORGANISM: Artificial Sequence
<220> FEATURE:
<223> OTHER INFORMATION: Antimicrobial peptide PL117

<400> SEQUENCE: 225

Val Ile Gly Thr Val Met Cys Thr Leu Thr Trp Gly
1 5 10

<210> SEQ ID NO 226
<211> LENGTH: 12
<212> TYPE: PRT
<213> ORGANISM: Artificial Sequence
<220> FEATURE:
<223> OTHER INFORMATION: Antimicrobial peptide PL119

<400> SEQUENCE: 226

Thr Ser Asp Leu Glu Thr Gln Ser Gly Gly Arg Leu
1 5 10

<210> SEQ ID NO 227
<211> LENGTH: 12
<212> TYPE: PRT
<213> ORGANISM: Artificial Sequence
<220> FEATURE:
<223> OTHER INFORMATION: Antimicrobial peptide PL121

<400> SEQUENCE: 227

Asp Gly Met Phe Arg Met Thr Leu Leu Thr Ser Trp
1 5 10

<210> SEQ ID NO 228
<211> LENGTH: 12
<212> TYPE: PRT
<213> ORGANISM: Artificial Sequence
<220> FEATURE:
<223> OTHER INFORMATION: Antimicrobial peptide PL125

<400> SEQUENCE: 228

Leu Asn Trp Leu Arg Gly Trp Thr Gly Leu Val Gly
1 5 10

<210> SEQ ID NO 229
<211> LENGTH: 12
<212> TYPE: PRT
<213> ORGANISM: Artificial Sequence
<220> FEATURE:
<223> OTHER INFORMATION: Antimicrobial peptide PL126

<400> SEQUENCE: 229

Trp Thr Arg Phe Met Arg Ala Leu Gly Phe Thr Gln
1 5 10

<210> SEQ ID NO 230
<211> LENGTH: 12
<212> TYPE: PRT
<213> ORGANISM: Artificial Sequence
<220> FEATURE:
<223> OTHER INFORMATION: Antimicrobial peptide PL132

<400> SEQUENCE: 230

Ile Thr Phe Trp Ser Phe Val Phe Thr Met Arg Trp
1 5 10

<210> SEQ ID NO 231
<211> LENGTH: 12
<212> TYPE: PRT
<213> ORGANISM: Artificial Sequence
<220> FEATURE:
<223> OTHER INFORMATION: Antimicrobial peptide PL148

<400> SEQUENCE: 231

Gly Phe Trp Val Tyr Gly Gly Val Gly Trp Tyr Ala
1 5 10

<210> SEQ ID NO 232
<211> LENGTH: 12
<212> TYPE: PRT
<213> ORGANISM: Artificial Sequence
<220> FEATURE:
<223> OTHER INFORMATION: Antimicrobial peptide PL151

<400> SEQUENCE: 232

Ile Cys Trp Leu Lys Asp Phe Tyr Gly Arg Leu Gln
1 5 10

<210> SEQ ID NO 233
<211> LENGTH: 12
<212> TYPE: PRT
<213> ORGANISM: Artificial Sequence
<220> FEATURE:
<223> OTHER INFORMATION: Antimicrobial peptide PL164

<400> SEQUENCE: 233

Cys Thr Phe Val Ser Ile His Tyr Gly Cys Glu Cys
1 5 10

<210> SEQ ID NO 234
<211> LENGTH: 12
<212> TYPE: PRT
<213> ORGANISM: Artificial Sequence
<220> FEATURE:
<223> OTHER INFORMATION: Antimicrobial peptide PL165

<400> SEQUENCE: 234

Leu Ile Val Cys Cys Leu Val Val Val Trp Gly Glu
1 5 10

<210> SEQ ID NO 235
<211> LENGTH: 12
<212> TYPE: PRT
<213> ORGANISM: Artificial Sequence
<220> FEATURE:
<223> OTHER INFORMATION: Antimicrobial peptide PL176

<400> SEQUENCE: 235

Trp His Thr Leu Thr Lys Leu Leu Gly Arg Lys Asp
1 5 10

<210> SEQ ID NO 236
<211> LENGTH: 12
<212> TYPE: PRT
<213> ORGANISM: Artificial Sequence
<220> FEATURE:
<223> OTHER INFORMATION: Antimicrobial peptide PL181

<400> SEQUENCE: 236

Trp Gly Val Ser Val Gln Val Pro Trp Ala Gly Val
1 5 10

<210> SEQ ID NO 237
<211> LENGTH: 12
<212> TYPE: PRT
<213> ORGANISM: Artificial Sequence
<220> FEATURE:
<223> OTHER INFORMATION: Antimicrobial peptide PL187

<400> SEQUENCE: 237

Gly Ala Arg Trp Val Ala Glu Gly Trp Ser Glu Arg
1 5 10

<210> SEQ ID NO 238
<211> LENGTH: 12
<212> TYPE: PRT
<213> ORGANISM: Artificial Sequence
<220> FEATURE:
<223> OTHER INFORMATION: Antimicrobial peptide PL188

<400> SEQUENCE: 238

Val Asn Thr Cys Gln Val Thr Val Ala Ser Ala His
1 5 10

<210> SEQ ID NO 239
<211> LENGTH: 12
<212> TYPE: PRT
<213> ORGANISM: Artificial Sequence
<220> FEATURE:
<223> OTHER INFORMATION: Antimicrobial peptide PL218

<400> SEQUENCE: 239

Phe Leu Leu Ser Ile Ile Tyr Leu Trp Ser Trp Gly
1 5 10

<210> SEQ ID NO 240
<211> LENGTH: 12
<212> TYPE: PRT
<213> ORGANISM: Artificial Sequence
<220> FEATURE:
<223> OTHER INFORMATION: Antimicrobial peptide PL233

<400> SEQUENCE: 240

Ser Asp Thr Leu Glu Leu Leu Gly Cys Val Asn Trp
1 5 10

<210> SEQ ID NO 241
<211> LENGTH: 12
<212> TYPE: PRT
<213> ORGANISM: Artificial Sequence
<220> FEATURE:
<223> OTHER INFORMATION: Antimicrobial peptide PL235

<400> SEQUENCE: 241

Ala Ile Val Val Tyr Leu Ala Leu Phe Asn Tyr Gly
1 5 10

<210> SEQ ID NO 242
<211> LENGTH: 12
<212> TYPE: PRT
<213> ORGANISM: Artificial Sequence
<220> FEATURE:
<223> OTHER INFORMATION: Antimicrobial peptide PL242

<400> SEQUENCE: 242

Val Ser Glu Val Ser Val Ile Ser Pro Trp Gly Cys
1 5 10

<210> SEQ ID NO 243
<211> LENGTH: 12
<212> TYPE: PRT
<213> ORGANISM: Artificial Sequence
<220> FEATURE:
<223> OTHER INFORMATION: Antimicrobial peptide PL246

<400> SEQUENCE: 243

Asp Ile Ser Leu Ser Ala Val Met Val Tyr Val Asn
1 5 10

<210> SEQ ID NO 244
<211> LENGTH: 12
<212> TYPE: PRT
<213> ORGANISM: Artificial Sequence
<220> FEATURE:
<223> OTHER INFORMATION: Antimicrobial peptide PL247

<400> SEQUENCE: 244

Ile Ala Tyr Met Val Leu Val Ala Val Val Ala Gly 1 5 10

<210> SEQ ID NO 245
<211> LENGTH: 12
<212> TYPE: PRT
<213> ORGANISM: Artificial Sequence
<220> FEATURE:
<223> OTHER INFORMATION: Antimicrobial peptide PL250

<400> SEQUENCE: 245

Leu Lys Gly Leu Trp Gly Trp Trp Ile Gly Arg Ser
1 5 10

<210> SEQ ID NO 246
<211> LENGTH: 12
<212> TYPE: PRT
<213> ORGANISM: Artificial Sequence
<220> FEATURE:
<223> OTHER INFORMATION: Antimicrobial peptide PL254

<400> SEQUENCE: 246

Ile Ile His Ser Tyr Asn Phe Val Ser Ile Cys Lys
1 5 10

<210> SEQ ID NO 247
<211> LENGTH: 12
<212> TYPE: PRT
<213> ORGANISM: Artificial Sequence
<220> FEATURE:
<223> OTHER INFORMATION: Antimicrobial peptide PL276

<400> SEQUENCE: 247

Ser Asp Thr Leu Glu Ala Val Gly Cys Val Asn Trp
1 5 10

<210> SEQ ID NO 248
<211> LENGTH: 12
<212> TYPE: PRT
<213> ORGANISM: Artificial Sequence
<220> FEATURE:
<223> OTHER INFORMATION: Antimicrobial peptide PL280

<400> SEQUENCE: 248

Met Val Val Ala Met Val Gly Val Trp Trp Gly Gly
1 5 10

<210> SEQ ID NO 249
<211> LENGTH: 12
<212> TYPE: PRT
<213> ORGANISM: Artificial Sequence
<220> FEATURE:
<223> OTHER INFORMATION: Antimicrobial peptide PL281

<400> SEQUENCE: 249

Trp Ile Ile Ser Met Ser Ala Leu Ala Trp Gly Cys
1 5 10

<210> SEQ ID NO 250
<211> LENGTH: 12
<212> TYPE: PRT
<213> ORGANISM: Artificial Sequence
<220> FEATURE:
<223> OTHER INFORMATION: Antimicrobial peptide PL360

<400> SEQUENCE: 250

Gly Ser Trp Gln Ala His Thr Glu Ser Pro Arg Glu
1 5 10

<210> SEQ ID NO 251
<211> LENGTH: 12
<212> TYPE: PRT
<213> ORGANISM: Artificial Sequence
<220> FEATURE:
<223> OTHER INFORMATION: Antimicrobial peptide PL365

<400> SEQUENCE: 251

Gly Ser His Phe Tyr Leu His Ile His Val Asp Trp
1 5 10

<210> SEQ ID NO 252
<211> LENGTH: 12
<212> TYPE: PRT
<213> ORGANISM: Artificial Sequence
<220> FEATURE:
<223> OTHER INFORMATION: Antimicrobial peptide PL408

<400> SEQUENCE: 252

Val Leu Tyr Ile Thr Val Leu Val Gly Leu Val Val
1 5 10

<210> SEQ ID NO 253
<211> LENGTH: 12
<212> TYPE: PRT
<213> ORGANISM: Artificial Sequence
<220> FEATURE:
<223> OTHER INFORMATION: Antimicrobial peptide PL436

<400> SEQUENCE: 253

Val Ser Ile Met Ile Phe Ile Thr Gly Val Tyr Trp
1 5 10

<210> SEQ ID NO 254
<211> LENGTH: 12
<212> TYPE: PRT
<213> ORGANISM: Artificial Sequence
<220> FEATURE:
<223> OTHER INFORMATION: Antimicrobial peptide PL449

<400> SEQUENCE: 254

Ile Met Trp Ser Leu Leu Val Thr Ala Asn Tyr Pro
1 5 10

<210> SEQ ID NO 255
<211> LENGTH: 12
<212> TYPE: PRT
<213> ORGANISM: Artificial Sequence
<220> FEATURE:
<223> OTHER INFORMATION: Antimicrobial peptide PL467

<400> SEQUENCE: 255

Ile Arg Met Leu Gly Arg Val Arg Thr Trp Trp Arg
1 5 10

<210> SEQ ID NO 256
<211> LENGTH: 12
<212> TYPE: PRT
<213> ORGANISM: Artificial Sequence
<220> FEATURE:
<223> OTHER INFORMATION: Antimicrobial peptide PL477

<400> SEQUENCE: 256

Tyr Leu Thr Cys Leu Cys Met Phe Leu Ala Gly Pro
1 5 10

<210> SEQ ID NO 257
<211> LENGTH: 12
<212> TYPE: PRT
<213> ORGANISM: Artificial Sequence
<220> FEATURE:
<223> OTHER INFORMATION: Antimicrobial peptide PL482

<400> SEQUENCE: 257

Trp Glu Leu His Ala Tyr Ala Met Cys Trp Ser Met
1 5 10

<210> SEQ ID NO 258
<211> LENGTH: 12
<212> TYPE: PRT
<213> ORGANISM: Artificial Sequence
<220> FEATURE:
<223> OTHER INFORMATION: Antimicrobial peptide PL012

<400> SEQUENCE: 258

Gly Ile Gly Ala Ile Val Gly Val Leu Ile Leu Gly
1 5 10

<210> SEQ ID NO 259
<211> LENGTH: 12
<212> TYPE: PRT
<213> ORGANISM: Artificial Sequence
<220> FEATURE:
<223> OTHER INFORMATION: Antimicrobial peptide PL021

<400> SEQUENCE: 259

Ala Leu Leu Val Ala Met Trp Ala Gly Val Ala Gly
1 5 10

<210> SEQ ID NO 260
<211> LENGTH: 12
<212> TYPE: PRT
<213> ORGANISM: Artificial Sequence
<220> FEATURE:
<223> OTHER INFORMATION: Antimicrobial peptide PL023

<400> SEQUENCE: 260

Val Cys Glu Cys Gly Pro Arg Val Thr Leu Thr Gln
1 5 10

<210> SEQ ID NO 261
<211> LENGTH: 12
<212> TYPE: PRT
<213> ORGANISM: Artificial Sequence
<220> FEATURE:
<223> OTHER INFORMATION: Antimicrobial peptide PL027

<400> SEQUENCE: 261

Leu Thr Thr Ile Cys Arg Trp Met Arg Arg Arg Asp
1 5 10

<210> SEQ ID NO 262
<211> LENGTH: 12
<212> TYPE: PRT
<213> ORGANISM: Artificial Sequence
<220> FEATURE:
<223> OTHER INFORMATION: Antimicrobial peptide PL032

<400> SEQUENCE: 262

Phe Lys Trp Val Leu Ala Arg Leu Thr Gln Ser Ser
1 5 10

<210> SEQ ID NO 263
<211> LENGTH: 12
<212> TYPE: PRT
<213> ORGANISM: Artificial Sequence
<220> FEATURE:
<223> OTHER INFORMATION: Antimicrobial peptide PL039

<400> SEQUENCE: 263

Cys Glu Ser Gly Lys Ser Tyr Arg Ile Gly Lys Trp
1               5                   10

<210> SEQ ID NO 264
<211> LENGTH: 12
<212> TYPE: PRT
<213> ORGANISM: Artificial Sequence
<220> FEATURE:
<223> OTHER INFORMATION: Antimicrobial peptide PL115

<400> SEQUENCE: 264

Val Leu Ser Ala Asn Ile Trp Ala Gly Met Arg Phe
1               5                   10

<210> SEQ ID NO 265
<211> LENGTH: 12
<212> TYPE: PRT
<213> ORGANISM: Artificial Sequence
<220> FEATURE:
<223> OTHER INFORMATION: Antimicrobial peptide PL116

<400> SEQUENCE: 265

Ile Val Ile Cys Cys Val Gly Val Leu Thr His Pro
1               5                   10

<210> SEQ ID NO 266
<211> LENGTH: 12
<212> TYPE: PRT
<213> ORGANISM: Artificial Sequence
<220> FEATURE:
<223> OTHER INFORMATION: Antimicrobial peptide PL120

<400> SEQUENCE: 266

Ile Val Thr Thr Asn His Val Leu Val Cys Thr Tyr
1               5                   10

<210> SEQ ID NO 267
<211> LENGTH: 12
<212> TYPE: PRT
<213> ORGANISM: Artificial Sequence
<220> FEATURE:
<223> OTHER INFORMATION: Antimicrobial peptide PL124

<400> SEQUENCE: 267

Leu Leu Val Ser Leu Pro Val Leu Leu Ser Cys Gly
1               5                   10

<210> SEQ ID NO 268
<211> LENGTH: 12
<212> TYPE: PRT
<213> ORGANISM: Artificial Sequence
<220> FEATURE:
<223> OTHER INFORMATION: Antimicrobial peptide PL127

<400> SEQUENCE: 268

Tyr Cys Pro Gly Pro Ser Val Glu Ile Arg Arg Cys
1               5                   10

<210> SEQ ID NO 269

<211> LENGTH: 12
<212> TYPE: PRT
<213> ORGANISM: Artificial Sequence
<220> FEATURE:
<223> OTHER INFORMATION: Antimicrobial peptide PL128

<400> SEQUENCE: 269

Leu Tyr Ala Phe Gly Thr Cys Glu Phe Ser Val Met
1 5 10

<210> SEQ ID NO 270
<211> LENGTH: 12
<212> TYPE: PRT
<213> ORGANISM: Artificial Sequence
<220> FEATURE:
<223> OTHER INFORMATION: Antimicrobial peptide PL129

<400> SEQUENCE: 270

Tyr Tyr Thr Phe Ile Leu Pro Leu Ser Leu Ser Cys
1 5 10

<210> SEQ ID NO 271
<211> LENGTH: 12
<212> TYPE: PRT
<213> ORGANISM: Artificial Sequence
<220> FEATURE:
<223> OTHER INFORMATION: Antimicrobial peptide PL130

<400> SEQUENCE: 271

Met Glu Arg Val Arg Lys Trp Phe Asn Glu Gly Arg
1 5 10

<210> SEQ ID NO 272
<211> LENGTH: 12
<212> TYPE: PRT
<213> ORGANISM: Artificial Sequence
<220> FEATURE:
<223> OTHER INFORMATION: Antimicrobial peptide PL136

<400> SEQUENCE: 272

Phe Gln Leu Glu Phe Ser Val Ala Val Gly Ala Val
1 5 10

<210> SEQ ID NO 273
<211> LENGTH: 12
<212> TYPE: PRT
<213> ORGANISM: Artificial Sequence
<220> FEATURE:
<223> OTHER INFORMATION: Antimicrobial peptide PL141

<400> SEQUENCE: 273

Tyr Cys Ala His Leu Ser Cys Thr Val Cys Val Tyr
1 5 10

<210> SEQ ID NO 274
<211> LENGTH: 12
<212> TYPE: PRT
<213> ORGANISM: Artificial Sequence
<220> FEATURE:
<223> OTHER INFORMATION: Antimicrobial peptide PL147

<400> SEQUENCE: 274

Phe Phe Gly Tyr Thr Glu Ala Leu Val Val Thr Val
1 5 10

<210> SEQ ID NO 275
<211> LENGTH: 12

<212> TYPE: PRT
<213> ORGANISM: Artificial Sequence
<220> FEATURE:
<223> OTHER INFORMATION: Antimicrobial peptide PL150

<400> SEQUENCE: 275

Cys Ile Asp Cys Ala Pro Arg Ile Cys Cys Ser Leu
1 5 10

<210> SEQ ID NO 276
<211> LENGTH: 12
<212> TYPE: PRT
<213> ORGANISM: Artificial Sequence
<220> FEATURE:
<223> OTHER INFORMATION: Antimicrobial peptide PL154

<400> SEQUENCE: 276

Thr Glu His Ser Arg Val Ala Val Arg Ser Ala Arg
1 5 10

<210> SEQ ID NO 277
<211> LENGTH: 12
<212> TYPE: PRT
<213> ORGANISM: Artificial Sequence
<220> FEATURE:
<223> OTHER INFORMATION: Antimicrobial peptide PL169

<400> SEQUENCE: 277

Ile Phe Ser Cys Trp Val Gly Trp Val Val Leu Thr
1 5 10

<210> SEQ ID NO 278
<211> LENGTH: 12
<212> TYPE: PRT
<213> ORGANISM: Artificial Sequence
<220> FEATURE:
<223> OTHER INFORMATION: Antimicrobial peptide PL170

<400> SEQUENCE: 278

Val Glu Pro Val Leu Phe Ile Gly Ala Cys Ala Cys
1 5 10

<210> SEQ ID NO 279
<211> LENGTH: 12
<212> TYPE: PRT
<213> ORGANISM: Artificial Sequence
<220> FEATURE:
<223> OTHER INFORMATION: Antimicrobial peptide PL178

<400> SEQUENCE: 279

Trp Val Cys Glu Val Lys Gln Ser Val Trp Leu Ala
1 5 10

<210> SEQ ID NO 280
<211> LENGTH: 12
<212> TYPE: PRT
<213> ORGANISM: Artificial Sequence
<220> FEATURE:
<223> OTHER INFORMATION: Antimicrobial peptide PL179

<400> SEQUENCE: 280

Asn Ile His Leu Cys Thr Thr Asn Trp His Trp Val
1 5 10

<210> SEQ ID NO 281
<211> LENGTH: 12
<212> TYPE: PRT

<213> ORGANISM: Artificial Sequence
<220> FEATURE:
<223> OTHER INFORMATION: Antimicrobial peptide PL182

<400> SEQUENCE: 281

Gly Asp Leu Asn Leu Pro His Phe Gln Tyr Ala Met
1 5 10

<210> SEQ ID NO 282
<211> LENGTH: 12
<212> TYPE: PRT
<213> ORGANISM: Artificial Sequence
<220> FEATURE:
<223> OTHER INFORMATION: Antimicrobial peptide PL192

<400> SEQUENCE: 282

Val Val Thr Ala Val Leu Ala Leu Trp Gly Ser Gly
1 5 10

<210> SEQ ID NO 283
<211> LENGTH: 12
<212> TYPE: PRT
<213> ORGANISM: Artificial Sequence
<220> FEATURE:
<223> OTHER INFORMATION: Antimicrobial peptide PL195

<400> SEQUENCE: 283

Val Val Asn Tyr Gln Glu Leu Ala Val Val Val Gly
1 5 10

<210> SEQ ID NO 284
<211> LENGTH: 12
<212> TYPE: PRT
<213> ORGANISM: Artificial Sequence
<220> FEATURE:
<223> OTHER INFORMATION: Antimicrobial peptide PL204

<400> SEQUENCE: 284

Cys Val Ser Tyr Asp Tyr Leu Ala Ile Val Arg Phe
1 5 10

<210> SEQ ID NO 285
<211> LENGTH: 12
<212> TYPE: PRT
<213> ORGANISM: Artificial Sequence
<220> FEATURE:
<223> OTHER INFORMATION: Antimicrobial peptide PL229

<400> SEQUENCE: 285

Ser Met Ala Ala Ala Phe Phe Trp Cys Met Ala Tyr
1 5 10

<210> SEQ ID NO 286
<211> LENGTH: 12
<212> TYPE: PRT
<213> ORGANISM: Artificial Sequence
<220> FEATURE:
<223> OTHER INFORMATION: Antimicrobial peptide PL249

<400> SEQUENCE: 286

Asp Ala Met Asn Phe Trp Ala Val Arg Phe Ser Val
1 5 10

<210> SEQ ID NO 287
<211> LENGTH: 12
<212> TYPE: PRT
<213> ORGANISM: Artificial Sequence
<220> FEATURE:
<223> OTHER INFORMATION: Antimicrobial peptide PL253

<400> SEQUENCE: 287

Ile Leu Gln Glu Asp Val Phe Met Leu Leu Met Asn
1 5 10

<210> SEQ ID NO 288
<211> LENGTH: 12
<212> TYPE: PRT
<213> ORGANISM: Artificial Sequence
<220> FEATURE:
<223> OTHER INFORMATION: Antimicrobial peptide PL257

<400> SEQUENCE: 288

Leu Val Val Gln Asn Met Ala Val His Leu Val Gln
1 5 10

<210> SEQ ID NO 289
<211> LENGTH: 12
<212> TYPE: PRT
<213> ORGANISM: Artificial Sequence
<220> FEATURE:
<223> OTHER INFORMATION: Antimicrobial peptide PL270

<400> SEQUENCE: 289

Phe Val Leu Pro Ser Val Phe Val Cys Met Leu Val
1 5 10

<210> SEQ ID NO 290
<211> LENGTH: 12
<212> TYPE: PRT
<213> ORGANISM: Artificial Sequence
<220> FEATURE:
<223> OTHER INFORMATION: Antimicrobial peptide PL288

<400> SEQUENCE: 290

Asp His Leu Asn Ala Cys Leu Asn Met Gln Trp Ala
1 5 10

<210> SEQ ID NO 291
<211> LENGTH: 12
<212> TYPE: PRT
<213> ORGANISM: Artificial Sequence
<220> FEATURE:
<223> OTHER INFORMATION: Antimicrobial peptide PL332

<400> SEQUENCE: 291

Val Ser Cys Val Leu Asp Val His Leu Leu Trp Val
1 5 10

<210> SEQ ID NO 292
<211> LENGTH: 12
<212> TYPE: PRT
<213> ORGANISM: Artificial Sequence
<220> FEATURE:
<223> OTHER INFORMATION: Antimicrobial peptide PL381

<400> SEQUENCE: 292

Val Phe Ala Phe Val Val Gly Ala Leu Thr Asp Tyr
1 5 10

<210> SEQ ID NO 293
<211> LENGTH: 12
<212> TYPE: PRT
<213> ORGANISM: Artificial Sequence
<220> FEATURE:

<223> OTHER INFORMATION: Antimicrobial peptide PL388

<400> SEQUENCE: 293

Cys Gln Cys Thr Val Thr Ser Cys His Val Arg Trp
1 5 10

<210> SEQ ID NO 294
<211> LENGTH: 12
<212> TYPE: PRT
<213> ORGANISM: Artificial Sequence
<220> FEATURE:
<223> OTHER INFORMATION: Antimicrobial peptide PL426

<400> SEQUENCE: 294

Val Val Leu Asn Thr Val Thr Ile Thr Ala Ser Met
1 5 10

<210> SEQ ID NO 295
<211> LENGTH: 12
<212> TYPE: PRT
<213> ORGANISM: Artificial Sequence
<220> FEATURE:
<223> OTHER INFORMATION: Antimicrobial peptide PL456

<400> SEQUENCE: 295

Glu Tyr His Leu Phe Ile Gly Ala Val Glu Val Arg
1 5 10

<210> SEQ ID NO 296
<211> LENGTH: 12
<212> TYPE: PRT
<213> ORGANISM: Artificial Sequence
<220> FEATURE:
<223> OTHER INFORMATION: Antimicrobial peptide PL494

<400> SEQUENCE: 296

Glu Tyr His Leu Phe Ile Gly Ala Val Glu Val Arg
1 5 10

<210> SEQ ID NO 297
<211> LENGTH: 12
<212> TYPE: PRT
<213> ORGANISM: Artificial Sequence
<220> FEATURE:
<223> OTHER INFORMATION: Antimicrobial peptide PC001

<400> SEQUENCE: 297

Leu Val Val Val Val Arg Glu Ala Ile Ala Leu Trp
1 5 10

<210> SEQ ID NO 298
<211> LENGTH: 12
<212> TYPE: PRT
<213> ORGANISM: Artificial Sequence
<220> FEATURE:
<223> OTHER INFORMATION: Antimicrobial peptide PC006

<400> SEQUENCE: 298

Cys His Gly Ala Leu Cys Trp Arg Gly Gln Pro Ile
1 5 10

<210> SEQ ID NO 299
<211> LENGTH: 12
<212> TYPE: PRT
<213> ORGANISM: Artificial Sequence
<220> FEATURE:
<223> OTHER INFORMATION: Antimicrobial peptide PC013

<400> SEQUENCE: 299

Val Ser Phe Ser Leu Val Ala Ser Leu Leu Tyr Ala
1 5 10

<210> SEQ ID NO 300
<211> LENGTH: 12
<212> TYPE: PRT
<213> ORGANISM: Artificial Sequence
<220> FEATURE:
<223> OTHER INFORMATION: Antimicrobial peptide PC024

<400> SEQUENCE: 300

Ala Pro Pro Pro Pro Pro Pro Pro Trp Pro Pro Pro
1 5 10

<210> SEQ ID NO 301
<211> LENGTH: 12
<212> TYPE: PRT
<213> ORGANISM: Artificial Sequence
<220> FEATURE:
<223> OTHER INFORMATION: Antimicrobial peptide PC025

<400> SEQUENCE: 301

Val Ser Trp Ala Leu Leu Gly Met Val Leu Ile Ala
1 5 10

<210> SEQ ID NO 302
<211> LENGTH: 12
<212> TYPE: PRT
<213> ORGANISM: Artificial Sequence
<220> FEATURE:
<223> OTHER INFORMATION: Antimicrobial peptide PC034

<400> SEQUENCE: 302

Ile Leu Leu Tyr Leu Val Arg Ala Val Leu Asn Val
1 5 10

<210> SEQ ID NO 303
<211> LENGTH: 12
<212> TYPE: PRT
<213> ORGANISM: Artificial Sequence
<220> FEATURE:
<223> OTHER INFORMATION: Antimicrobial peptide PC035

<400> SEQUENCE: 303

Phe Leu Phe Leu Ile Ser His Phe Trp Cys Ser Ala
1 5 10

<210> SEQ ID NO 304
<211> LENGTH: 12
<212> TYPE: PRT
<213> ORGANISM: Artificial Sequence
<220> FEATURE:
<223> OTHER INFORMATION: Antimicrobial peptide PC036

<400> SEQUENCE: 304

Arg Arg Lys Gly Glu Glu Ala His Thr Arg Gln Gly
1 5 10

<210> SEQ ID NO 305
<211> LENGTH: 12
<212> TYPE: PRT
<213> ORGANISM: Artificial Sequence
<220> FEATURE:
<223> OTHER INFORMATION: Antimicrobial peptide PC042

<400> SEQUENCE: 305

Leu Gly Ala Trp Gly Leu Gly Leu Trp Leu Met Val
1 5 10

<210> SEQ ID NO 306
<211> LENGTH: 12
<212> TYPE: PRT
<213> ORGANISM: Artificial Sequence
<220> FEATURE:
<223> OTHER INFORMATION: Antimicrobial peptide PC016

<400> SEQUENCE: 306

Tyr Asn Phe Ile Lys Arg Arg Leu Cys Leu Ile Lys
1 5 10

<210> SEQ ID NO 307
<211> LENGTH: 12
<212> TYPE: PRT
<213> ORGANISM: Artificial Sequence
<220> FEATURE:
<223> OTHER INFORMATION: Antimicrobial peptide PC022

<400> SEQUENCE: 307

Ile Ile Met Ser Ala Leu Trp Val Pro Leu Gly Trp
1 5 10

<210> SEQ ID NO 308
<211> LENGTH: 12
<212> TYPE: PRT
<213> ORGANISM: Artificial Sequence
<220> FEATURE:
<223> OTHER INFORMATION: Antimicrobial peptide PC030

<400> SEQUENCE: 308

Ala Val Ser Thr Gln Val Val Val Asn Phe Glu Ala
1 5 10

<210> SEQ ID NO 309
<211> LENGTH: 12
<212> TYPE: PRT
<213> ORGANISM: Artificial Sequence
<220> FEATURE:
<223> OTHER INFORMATION: Antimicrobial peptide PC041

<400> SEQUENCE: 309

Ile Leu Ile Ala Phe Gly Tyr Val Val Cys Ala Thr
1 5 10

<210> SEQ ID NO 310
<211> LENGTH: 12
<212> TYPE: PRT
<213> ORGANISM: Artificial Sequence
<220> FEATURE:
<223> OTHER INFORMATION: Antimicrobial peptide EO1

<400> SEQUENCE: 310

Phe Ala Trp Leu Trp Ser Trp Trp Arg Ala Arg Arg
1 5 10

<210> SEQ ID NO 311
<211> LENGTH: 12
<212> TYPE: PRT
<213> ORGANISM: Artificial Sequence
<220> FEATURE:
<223> OTHER INFORMATION: Antimicrobial peptide EO2

<400> SEQUENCE: 311

Phe Ala Arg Leu Arg Arg Trp Trp Arg Arg Trp Arg
1 5 10

<210> SEQ ID NO 312
<211> LENGTH: 12
<212> TYPE: PRT
<213> ORGANISM: Artificial Sequence
<220> FEATURE:
<223> OTHER INFORMATION: Antimicrobial peptide RR1

<400> SEQUENCE: 312

Trp Arg Trp Leu Ala Arg Arg Trp Arg Arg Trp Arg
1 5 10

<210> SEQ ID NO 313
<211> LENGTH: 12
<212> TYPE: PRT
<213> ORGANISM: Artificial Sequence
<220> FEATURE:
<223> OTHER INFORMATION: Antimicrobial peptide RR2

<400> SEQUENCE: 313

Trp Ala Arg Leu Ala Arg Trp Trp Arg Arg Ala Arg
1 5 10

<210> SEQ ID NO 314
<211> LENGTH: 12
<212> TYPE: PRT
<213> ORGANISM: Artificial Sequence
<220> FEATURE:
<223> OTHER INFORMATION: Antimicrobial peptide GD1

<400> SEQUENCE: 314

Trp Arg Trp Leu Arg Arg Trp Trp Arg Arg Ala Arg
1 5 10

<210> SEQ ID NO 315
<211> LENGTH: 12
<212> TYPE: PRT
<213> ORGANISM: Artificial Sequence
<220> FEATURE:
<223> OTHER INFORMATION: Antimicrobial peptide GD2

<400> SEQUENCE: 315

Ala Ala Arg Leu Arg Arg Leu Trp Arg Ala Ala Arg
1 5 10

<210> SEQ ID NO 316
<211> LENGTH: 12
<212> TYPE: PRT
<213> ORGANISM: Artificial Sequence
<220> FEATURE:
<223> OTHER INFORMATION: Antimicrobial peptide EOD001

<400> SEQUENCE: 316

Ile Lys Leu Leu Ala Arg Trp Trp Arg Arg Pro Tyr
1 5 10

<210> SEQ ID NO 317
<211> LENGTH: 12
<212> TYPE: PRT
<213> ORGANISM: Artificial Sequence
<220> FEATURE:
<223> OTHER INFORMATION: Antimicrobial peptide EOD007

<400> SEQUENCE: 317

```
Phe Arg Leu Leu Met Arg Arg Trp Arg Arg Tyr Val
1               5                   10


<210> SEQ ID NO 318
<211> LENGTH: 12
<212> TYPE: PRT
<213> ORGANISM: Artificial Sequence
<220> FEATURE:
<223> OTHER INFORMATION: Antimicrobial peptide EOD022

<400> SEQUENCE: 318

Ile Lys Leu Leu Ala Arg Trp Trp Arg Arg Pro Tyr
1               5                   10


<210> SEQ ID NO 319
<211> LENGTH: 12
<212> TYPE: PRT
<213> ORGANISM: Artificial Sequence
<220> FEATURE:
<223> OTHER INFORMATION: Antimicrobial peptide EOD032

<400> SEQUENCE: 319

Phe Trp Arg Leu Leu Arg Arg Trp Arg Gly Ser Gly
1               5                   10


<210> SEQ ID NO 320
<211> LENGTH: 12
<212> TYPE: PRT
<213> ORGANISM: Artificial Sequence
<220> FEATURE:
<223> OTHER INFORMATION: Antimicrobial peptide EOD061

<400> SEQUENCE: 320

Met Met Arg Leu Leu Arg Arg Trp Arg Arg Pro Ala
1               5                   10


<210> SEQ ID NO 321
<211> LENGTH: 12
<212> TYPE: PRT
<213> ORGANISM: Artificial Sequence
<220> FEATURE:
<223> OTHER INFORMATION: Antimicrobial peptide EOD096

<400> SEQUENCE: 321

Met Thr Trp Leu Asp Arg Trp Trp Arg Gly Arg Thr
1               5                   10


<210> SEQ ID NO 322
<211> LENGTH: 12
<212> TYPE: PRT
<213> ORGANISM: Artificial Sequence
<220> FEATURE:
<223> OTHER INFORMATION: Antimicrobial peptide EOD107

<400> SEQUENCE: 322

Phe Val Arg Leu Arg Arg Trp Trp Arg Arg His Asn
1               5                   10


<210> SEQ ID NO 323
<211> LENGTH: 12
<212> TYPE: PRT
<213> ORGANISM: Artificial Sequence
<220> FEATURE:
<223> OTHER INFORMATION: Antimicrobial peptide EOD122

<400> SEQUENCE: 323

Ile Ser Leu Leu Asp Ser Trp Trp Arg Gly Ser Arg
```

1 5 10

<210> SEQ ID NO 324
<211> LENGTH: 12
<212> TYPE: PRT
<213> ORGANISM: Artificial Sequence
<220> FEATURE:
<223> OTHER INFORMATION: Antimicrobial peptide EOD003

<400> SEQUENCE: 324

Ile Asp Trp Leu Pro Arg Trp Trp Arg Arg Gly Trp
1 5 10

<210> SEQ ID NO 325
<211> LENGTH: 12
<212> TYPE: PRT
<213> ORGANISM: Artificial Sequence
<220> FEATURE:
<223> OTHER INFORMATION: Antimicrobial peptide EOD025

<400> SEQUENCE: 325

Phe Arg Leu Leu Met Arg Arg Trp Arg Arg Tyr Val
1 5 10

<210> SEQ ID NO 326
<211> LENGTH: 12
<212> TYPE: PRT
<213> ORGANISM: Artificial Sequence
<220> FEATURE:
<223> OTHER INFORMATION: Antimicrobial peptide EOD042

<400> SEQUENCE: 326

Met Asn Leu Leu Val Arg Arg Trp Arg Gly Asn Ser
1 5 10

<210> SEQ ID NO 327
<211> LENGTH: 12
<212> TYPE: PRT
<213> ORGANISM: Artificial Sequence
<220> FEATURE:
<223> OTHER INFORMATION: Antimicrobial peptide EOD093

<400> SEQUENCE: 327

Phe Thr Trp Leu Ala Ser Arg Trp Arg Gly Gln Leu
1 5 10

<210> SEQ ID NO 328
<211> LENGTH: 12
<212> TYPE: PRT
<213> ORGANISM: Artificial Sequence
<220> FEATURE:
<223> OTHER INFORMATION: Antimicrobial peptide EOD004

<400> SEQUENCE: 328

Leu Asn Leu Leu Lys Arg Trp Trp Arg Arg Pro Asn
1 5 10

<210> SEQ ID NO 329
<211> LENGTH: 12
<212> TYPE: PRT
<213> ORGANISM: Artificial Sequence
<220> FEATURE:
<223> OTHER INFORMATION: Antimicrobial peptide EOD006

<400> SEQUENCE: 329

Ile Lys Leu Leu Ala Arg Trp Trp Arg Arg Pro Tyr
1 5 10

<210> SEQ ID NO 330
<211> LENGTH: 12
<212> TYPE: PRT
<213> ORGANISM: Artificial Sequence
<220> FEATURE:
<223> OTHER INFORMATION: Antimicrobial peptide EOD008

<400> SEQUENCE: 330

Leu Val Trp Leu Leu Arg Trp Trp Arg Arg Tyr Tyr
1               5                   10

<210> SEQ ID NO 331
<211> LENGTH: 12
<212> TYPE: PRT
<213> ORGANISM: Artificial Sequence
<220> FEATURE:
<223> OTHER INFORMATION: Antimicrobial peptide EOD010

<400> SEQUENCE: 331

Phe Trp Leu Leu Ala Arg Trp Trp Arg Arg Cys Leu
1               5                   10

<210> SEQ ID NO 332
<211> LENGTH: 12
<212> TYPE: PRT
<213> ORGANISM: Artificial Sequence
<220> FEATURE:
<223> OTHER INFORMATION: Antimicrobial peptide EOD012

<400> SEQUENCE: 332

Met Arg Arg Leu Arg Ser Arg Trp Arg Arg Gly Ser
1               5                   10

<210> SEQ ID NO 333
<211> LENGTH: 12
<212> TYPE: PRT
<213> ORGANISM: Artificial Sequence
<220> FEATURE:
<223> OTHER INFORMATION: Antimicrobial peptide EOD013

<400> SEQUENCE: 333

Leu Asn Leu Leu Lys Arg Trp Trp Arg Arg Pro Asn
1               5                   10

<210> SEQ ID NO 334
<211> LENGTH: 12
<212> TYPE: PRT
<213> ORGANISM: Artificial Sequence
<220> FEATURE:
<223> OTHER INFORMATION: Antimicrobial peptide EOD016

<400> SEQUENCE: 334

Leu Arg Arg Leu Ser Ser Trp Trp Arg Gly Trp Ser
1               5                   10

<210> SEQ ID NO 335
<211> LENGTH: 12
<212> TYPE: PRT
<213> ORGANISM: Artificial Sequence
<220> FEATURE:
<223> OTHER INFORMATION: Antimicrobial peptide EOD017

<400> SEQUENCE: 335

Ile Asp Leu Leu Cys Arg Trp Trp Arg Gly Trp Thr
1               5                   10

<210> SEQ ID NO 336
<211> LENGTH: 12
<212> TYPE: PRT
<213> ORGANISM: Artificial Sequence
<220> FEATURE:
<223> OTHER INFORMATION: Antimicrobial peptide EOD018

<400> SEQUENCE: 336

Met Asn Leu Leu Trp Ser Trp Trp Arg Arg Val Thr
1 5 10

<210> SEQ ID NO 337
<211> LENGTH: 12
<212> TYPE: PRT
<213> ORGANISM: Artificial Sequence
<220> FEATURE:
<223> OTHER INFORMATION: Antimicrobial peptide EOD019

<400> SEQUENCE: 337

Ile Ala Arg Leu Arg Ser Trp Trp Arg Gly Ser Leu
1 5 10

<210> SEQ ID NO 338
<211> LENGTH: 12
<212> TYPE: PRT
<213> ORGANISM: Artificial Sequence
<220> FEATURE:
<223> OTHER INFORMATION: Antimicrobial peptide EOD020

<400> SEQUENCE: 338

Leu Leu Trp Leu Arg Arg Arg Trp Arg Arg Ala Val
1 5 10

<210> SEQ ID NO 339
<211> LENGTH: 12
<212> TYPE: PRT
<213> ORGANISM: Artificial Sequence
<220> FEATURE:
<223> OTHER INFORMATION: Antimicrobial peptide EOD021

<400> SEQUENCE: 339

Phe Arg Leu Leu Lys Ser Trp Trp Arg Gly Arg Ser
1 5 10

<210> SEQ ID NO 340
<211> LENGTH: 12
<212> TYPE: PRT
<213> ORGANISM: Artificial Sequence
<220> FEATURE:
<223> OTHER INFORMATION: Antimicrobial peptide EOD023

<400> SEQUENCE: 340

Met Glu Leu Leu Gly Arg Trp Trp Arg Gly His Lys
1 5 10

<210> SEQ ID NO 341
<211> LENGTH: 12
<212> TYPE: PRT
<213> ORGANISM: Artificial Sequence
<220> FEATURE:
<223> OTHER INFORMATION: Antimicrobial peptide EOD024

<400> SEQUENCE: 341

Ile Ile Leu Leu Arg Arg Trp Trp Arg Arg Ser Ser
1 5 10

<210> SEQ ID NO 342
<211> LENGTH: 12
<212> TYPE: PRT
<213> ORGANISM: Artificial Sequence
<220> FEATURE:
<223> OTHER INFORMATION: Antimicrobial peptide EOD027

<400> SEQUENCE: 342

Ile Leu Leu Leu Met Ser Trp Trp Arg Gly Leu Phe
1 5 10

<210> SEQ ID NO 343
<211> LENGTH: 12
<212> TYPE: PRT
<213> ORGANISM: Artificial Sequence
<220> FEATURE:
<223> OTHER INFORMATION: Antimicrobial peptide EOD028

<400> SEQUENCE: 343

Phe Ile Trp Leu Cys Ser Trp Trp Arg Arg Val Arg
1 5 10

<210> SEQ ID NO 344
<211> LENGTH: 12
<212> TYPE: PRT
<213> ORGANISM: Artificial Sequence
<220> FEATURE:
<223> OTHER INFORMATION: Antimicrobial peptide EOD029

<400> SEQUENCE: 344

Phe Ile Trp Leu Asn Arg Trp Trp Arg Arg Thr His
1 5 10

<210> SEQ ID NO 345
<211> LENGTH: 12
<212> TYPE: PRT
<213> ORGANISM: Artificial Sequence
<220> FEATURE:
<223> OTHER INFORMATION: Antimicrobial peptide EOD030

<400> SEQUENCE: 345

Ile Ala Trp Leu Phe Ser Trp Trp Arg Gly Tyr Thr
1 5 10

<210> SEQ ID NO 346
<211> LENGTH: 12
<212> TYPE: PRT
<213> ORGANISM: Artificial Sequence
<220> FEATURE:
<223> OTHER INFORMATION: Antimicrobial peptide EOD035

<400> SEQUENCE: 346

Phe Arg Leu Leu Asp Arg Trp Trp Arg Arg Met Ser
1 5 10

<210> SEQ ID NO 347
<211> LENGTH: 12
<212> TYPE: PRT
<213> ORGANISM: Artificial Sequence
<220> FEATURE:
<223> OTHER INFORMATION: Antimicrobial peptide EOD037

<400> SEQUENCE: 347

Ile Arg Trp Leu Ala Arg Arg Trp Arg Arg Thr Phe
1 5 10

<210> SEQ ID NO 348

<211> LENGTH: 12
<212> TYPE: PRT
<213> ORGANISM: Artificial Sequence
<220> FEATURE:
<223> OTHER INFORMATION: Antimicrobial peptide EOD038

<400> SEQUENCE: 348

Phe Lys Leu Leu Val Ser Trp Trp Arg Gly His Gly
1 5 10

<210> SEQ ID NO 349
<211> LENGTH: 12
<212> TYPE: PRT
<213> ORGANISM: Artificial Sequence
<220> FEATURE:
<223> OTHER INFORMATION: Antimicrobial peptide EOD039

<400> SEQUENCE: 349

Ile Arg Leu Leu Thr Ser Trp Trp Arg Arg Gly Gln
1 5 10

<210> SEQ ID NO 350
<211> LENGTH: 12
<212> TYPE: PRT
<213> ORGANISM: Artificial Sequence
<220> FEATURE:
<223> OTHER INFORMATION: Antimicrobial peptide EOD040

<400> SEQUENCE: 350

Leu Ser Trp Leu Arg Arg Arg Trp Arg Arg Trp Pro
1 5 10

<210> SEQ ID NO 351
<211> LENGTH: 12
<212> TYPE: PRT
<213> ORGANISM: Artificial Sequence
<220> FEATURE:
<223> OTHER INFORMATION: Antimicrobial peptide EOD041

<400> SEQUENCE: 351

Ile Arg Leu Leu Thr Ser Trp Trp Arg Arg Gly Gln
1 5 10

<210> SEQ ID NO 352
<211> LENGTH: 12
<212> TYPE: PRT
<213> ORGANISM: Artificial Sequence
<220> FEATURE:
<223> OTHER INFORMATION: Antimicrobial peptide EOD043

<400> SEQUENCE: 352

Ile His Trp Leu Arg Ser Arg Trp Arg Arg Asp Glu
1 5 10

<210> SEQ ID NO 353
<211> LENGTH: 12
<212> TYPE: PRT
<213> ORGANISM: Artificial Sequence
<220> FEATURE:
<223> OTHER INFORMATION: Antimicrobial peptide EOD044

<400> SEQUENCE: 353

Leu Gln Leu Leu Lys Ser Trp Trp Arg Arg Ile Gln
1 5 10

<210> SEQ ID NO 354
<211> LENGTH: 12

<212> TYPE: PRT
<213> ORGANISM: Artificial Sequence
<220> FEATURE:
<223> OTHER INFORMATION: Antimicrobial peptide EOD045

<400> SEQUENCE: 354

Phe Ile Trp Leu Leu Arg Trp Trp Arg Gly Ser Leu
1 5 10

<210> SEQ ID NO 355
<211> LENGTH: 12
<212> TYPE: PRT
<213> ORGANISM: Artificial Sequence
<220> FEATURE:
<223> OTHER INFORMATION: Antimicrobial peptide EOD046

<400> SEQUENCE: 355

Leu Ser Trp Leu Arg Arg Arg Trp Arg Arg Trp Pro
1 5 10

<210> SEQ ID NO 356
<211> LENGTH: 12
<212> TYPE: PRT
<213> ORGANISM: Artificial Sequence
<220> FEATURE:
<223> OTHER INFORMATION: Antimicrobial peptide EOD047

<400> SEQUENCE: 356

Phe Ala Trp Leu His Arg Trp Trp Arg Gly Val Thr
1 5 10

<210> SEQ ID NO 357
<211> LENGTH: 12
<212> TYPE: PRT
<213> ORGANISM: Artificial Sequence
<220> FEATURE:
<223> OTHER INFORMATION: Antimicrobial peptide EOD048

<400> SEQUENCE: 357

Met Cys Trp Leu Ala Arg Arg Trp Arg Arg Asp Gln
1 5 10

<210> SEQ ID NO 358
<211> LENGTH: 12
<212> TYPE: PRT
<213> ORGANISM: Artificial Sequence
<220> FEATURE:
<223> OTHER INFORMATION: Antimicrobial peptide EOD049

<400> SEQUENCE: 358

Ile His Leu Leu Thr Arg Trp Trp Arg Gly Ser Thr
1 5 10

<210> SEQ ID NO 359
<211> LENGTH: 12
<212> TYPE: PRT
<213> ORGANISM: Artificial Sequence
<220> FEATURE:
<223> OTHER INFORMATION: Antimicrobial peptide EOD052

<400> SEQUENCE: 359

Leu Arg Trp Leu Cys Ser Trp Trp Arg Arg Thr Ile
1 5 10

<210> SEQ ID NO 360
<211> LENGTH: 12
<212> TYPE: PRT

<213> ORGANISM: Artificial Sequence
<220> FEATURE:
<223> OTHER INFORMATION: Antimicrobial peptide EOD053

<400> SEQUENCE: 360

Leu Met Arg Leu Leu Arg Trp Trp Arg Gly Thr Ser
1 5 10

<210> SEQ ID NO 361
<211> LENGTH: 12
<212> TYPE: PRT
<213> ORGANISM: Artificial Sequence
<220> FEATURE:
<223> OTHER INFORMATION: Antimicrobial peptide EOD056

<400> SEQUENCE: 361

Phe Lys Leu Leu Phe Arg Trp Trp Arg Arg Arg Leu
1 5 10

<210> SEQ ID NO 362
<211> LENGTH: 12
<212> TYPE: PRT
<213> ORGANISM: Artificial Sequence
<220> FEATURE:
<223> OTHER INFORMATION: Antimicrobial peptide EOD057

<400> SEQUENCE: 362

Phe Ser Leu Leu Val Arg Trp Trp Arg Arg Gln Thr
1 5 10

<210> SEQ ID NO 363
<211> LENGTH: 12
<212> TYPE: PRT
<213> ORGANISM: Artificial Sequence
<220> FEATURE:
<223> OTHER INFORMATION: Antimicrobial peptide EOD058

<400> SEQUENCE: 363

Ile Arg Leu Leu Arg Arg Trp Trp Arg Arg Val Glu
1 5 10

<210> SEQ ID NO 364
<211> LENGTH: 12
<212> TYPE: PRT
<213> ORGANISM: Artificial Sequence
<220> FEATURE:
<223> OTHER INFORMATION: Antimicrobial peptide EOD059

<400> SEQUENCE: 364

Phe Arg Leu Leu Ser Arg Trp Trp Arg Arg Leu Lys
1 5 10

<210> SEQ ID NO 365
<211> LENGTH: 12
<212> TYPE: PRT
<213> ORGANISM: Artificial Sequence
<220> FEATURE:
<223> OTHER INFORMATION: Antimicrobial peptide EOD060

<400> SEQUENCE: 365

Ile Gln Leu Leu Leu Ser Trp Trp Arg Arg Thr Leu
1 5 10

<210> SEQ ID NO 366
<211> LENGTH: 12
<212> TYPE: PRT
<213> ORGANISM: Artificial Sequence
<220> FEATURE:
<223> OTHER INFORMATION: Antimicrobial peptide EOD062

<400> SEQUENCE: 366

Ile Ser Arg Leu Arg Ser Arg Trp Arg Arg Ala Ser
1 5 10

<210> SEQ ID NO 367
<211> LENGTH: 12
<212> TYPE: PRT
<213> ORGANISM: Artificial Sequence
<220> FEATURE:
<223> OTHER INFORMATION: Antimicrobial peptide EOD064

<400> SEQUENCE: 367

Met Glu Leu Leu Ser Arg Arg Trp Arg Arg Ser Arg
1 5 10

<210> SEQ ID NO 368
<211> LENGTH: 12
<212> TYPE: PRT
<213> ORGANISM: Artificial Sequence
<220> FEATURE:
<223> OTHER INFORMATION: Antimicrobial peptide EOD065

<400> SEQUENCE: 368

Phe Asp Trp Leu Cys Arg Arg Trp Arg Gly Val Lys
1 5 10

<210> SEQ ID NO 369
<211> LENGTH: 12
<212> TYPE: PRT
<213> ORGANISM: Artificial Sequence
<220> FEATURE:
<223> OTHER INFORMATION: Antimicrobial peptide EOD070

<400> SEQUENCE: 369

Ile Thr Trp Leu Leu Ser Arg Trp Arg Arg Ile Gln
1 5 10

<210> SEQ ID NO 370
<211> LENGTH: 12
<212> TYPE: PRT
<213> ORGANISM: Artificial Sequence
<220> FEATURE:
<223> OTHER INFORMATION: Antimicrobial peptide EOD071

<400> SEQUENCE: 370

Phe Leu Trp Leu Ser Arg Arg Trp Arg Arg Ser Glu
1 5 10

<210> SEQ ID NO 371
<211> LENGTH: 12
<212> TYPE: PRT
<213> ORGANISM: Artificial Sequence
<220> FEATURE:
<223> OTHER INFORMATION: Antimicrobial peptide EOD073

<400> SEQUENCE: 371

Phe His Leu Leu Gln Ser Trp Trp Arg Arg His Leu
1 5 10

<210> SEQ ID NO 372
<211> LENGTH: 12
<212> TYPE: PRT
<213> ORGANISM: Artificial Sequence
<220> FEATURE:

<223> OTHER INFORMATION: Antimicrobial peptide EOD075

<400> SEQUENCE: 372

Ile Tyr Leu Leu Phe Ser Trp Trp Arg Arg Cys Leu
1 5 10

<210> SEQ ID NO 373
<211> LENGTH: 12
<212> TYPE: PRT
<213> ORGANISM: Artificial Sequence
<220> FEATURE:
<223> OTHER INFORMATION: Antimicrobial peptide EOD076

<400> SEQUENCE: 373

Met Thr Leu Leu His Arg Trp Trp Arg Gly Lys Thr
1 5 10

<210> SEQ ID NO 374
<211> LENGTH: 12
<212> TYPE: PRT
<213> ORGANISM: Artificial Sequence
<220> FEATURE:
<223> OTHER INFORMATION: Antimicrobial peptide EOD077

<400> SEQUENCE: 374

Ile Arg Leu Leu Thr Ser Trp Trp Arg Arg Pro Arg
1 5 10

<210> SEQ ID NO 375
<211> LENGTH: 12
<212> TYPE: PRT
<213> ORGANISM: Artificial Sequence
<220> FEATURE:
<223> OTHER INFORMATION: Antimicrobial peptide EOD078

<400> SEQUENCE: 375

Ile Lys Trp Leu Met Arg Trp Trp Arg Gly Ser Asp
1 5 10

<210> SEQ ID NO 376
<211> LENGTH: 12
<212> TYPE: PRT
<213> ORGANISM: Artificial Sequence
<220> FEATURE:
<223> OTHER INFORMATION: Antimicrobial peptide EOD082

<400> SEQUENCE: 376

Ile Gly Leu Leu Arg Arg Trp Trp Arg Gly Pro Gly
1 5 10

<210> SEQ ID NO 377
<211> LENGTH: 12
<212> TYPE: PRT
<213> ORGANISM: Artificial Sequence
<220> FEATURE:
<223> OTHER INFORMATION: Antimicrobial peptide EOD083

<400> SEQUENCE: 377

Ile Ser Trp Leu Lys Arg Trp Trp Arg Arg Ile Asn
1 5 10

<210> SEQ ID NO 378
<211> LENGTH: 12
<212> TYPE: PRT
<213> ORGANISM: Artificial Sequence
<220> FEATURE:
<223> OTHER INFORMATION: Antimicrobial peptide EOD089

<400> SEQUENCE: 378

Ile Ile Trp Leu Met Ser Arg Trp Arg Arg Leu Lys
1               5                   10

<210> SEQ ID NO 379
<211> LENGTH: 12
<212> TYPE: PRT
<213> ORGANISM: Artificial Sequence
<220> FEATURE:
<223> OTHER INFORMATION: Antimicrobial peptide EOD091

<400> SEQUENCE: 379

Ile Asn Trp Leu Leu Ser Trp Trp Arg Gly Thr Ser
1               5                   10

<210> SEQ ID NO 380
<211> LENGTH: 12
<212> TYPE: PRT
<213> ORGANISM: Artificial Sequence
<220> FEATURE:
<223> OTHER INFORMATION: Antimicrobial peptide EOD094

<400> SEQUENCE: 380

Phe Arg Trp Leu Leu Ser Trp Trp Arg Gly Arg Gly
1               5                   10

<210> SEQ ID NO 381
<211> LENGTH: 12
<212> TYPE: PRT
<213> ORGANISM: Artificial Sequence
<220> FEATURE:
<223> OTHER INFORMATION: Antimicrobial peptide EOD099

<400> SEQUENCE: 381

Ile Asn Trp Leu Leu Ser Trp Trp Arg Gly Thr Ser
1               5                   10

<210> SEQ ID NO 382
<211> LENGTH: 12
<212> TYPE: PRT
<213> ORGANISM: Artificial Sequence
<220> FEATURE:
<223> OTHER INFORMATION: Antimicrobial peptide EOD103

<400> SEQUENCE: 382

Met Phe Leu Leu Lys Arg Trp Trp Arg Arg Trp Leu
1               5                   10

<210> SEQ ID NO 383
<211> LENGTH: 12
<212> TYPE: PRT
<213> ORGANISM: Artificial Sequence
<220> FEATURE:
<223> OTHER INFORMATION: Antimicrobial peptide EOD106

<400> SEQUENCE: 383

Leu Cys Trp Leu Thr Ser Trp Trp Arg Arg His Leu
1               5                   10

<210> SEQ ID NO 384
<211> LENGTH: 12
<212> TYPE: PRT
<213> ORGANISM: Artificial Sequence
<220> FEATURE:
<223> OTHER INFORMATION: Antimicrobial peptide EOD110

<400> SEQUENCE: 384

Met Val Arg Leu Arg Arg Trp Trp Arg Arg Thr Leu
1 5 10

<210> SEQ ID NO 385
<211> LENGTH: 12
<212> TYPE: PRT
<213> ORGANISM: Artificial Sequence
<220> FEATURE:
<223> OTHER INFORMATION: Antimicrobial peptide EOD112

<400> SEQUENCE: 385

Ile Asn Leu Leu Arg Arg Arg Trp Arg Arg Asp Arg
1 5 10

<210> SEQ ID NO 386
<211> LENGTH: 12
<212> TYPE: PRT
<213> ORGANISM: Artificial Sequence
<220> FEATURE:
<223> OTHER INFORMATION: Antimicrobial peptide EOD113

<400> SEQUENCE: 386

Phe Ser Leu Leu Arg Arg Trp Trp Arg Gly Asp Asp
1 5 10

<210> SEQ ID NO 387
<211> LENGTH: 12
<212> TYPE: PRT
<213> ORGANISM: Artificial Sequence
<220> FEATURE:
<223> OTHER INFORMATION: Antimicrobial peptide EOD116

<400> SEQUENCE: 387

Phe Ser Leu Leu Ser Arg Trp Trp Arg Gly Arg Leu
1 5 10

<210> SEQ ID NO 388
<211> LENGTH: 12
<212> TYPE: PRT
<213> ORGANISM: Artificial Sequence
<220> FEATURE:
<223> OTHER INFORMATION: Antimicrobial peptide EOD121

<400> SEQUENCE: 388

Phe His Trp Leu Val Arg Trp Trp Arg Gly His Ser
1 5 10

<210> SEQ ID NO 389
<211> LENGTH: 12
<212> TYPE: PRT
<213> ORGANISM: Artificial Sequence
<220> FEATURE:
<223> OTHER INFORMATION: Antimicrobial peptide EOD123

<400> SEQUENCE: 389

Ile Ala Leu Leu Leu Ser Arg Trp Arg Arg Arg Gly
1 5 10

<210> SEQ ID NO 390
<211> LENGTH: 12
<212> TYPE: PRT
<213> ORGANISM: Artificial Sequence
<220> FEATURE:
<223> OTHER INFORMATION: Antimicrobial peptide EOD126

<400> SEQUENCE: 390

Ile Ala Leu Leu Leu Ser Arg Trp Arg Arg Arg Gly
1 5 10

<210> SEQ ID NO 391
<211> LENGTH: 12
<212> TYPE: PRT
<213> ORGANISM: Artificial Sequence
<220> FEATURE:
<223> OTHER INFORMATION: Antimicrobial peptide EOD128

<400> SEQUENCE: 391

Phe His Trp Leu Ala Ser Arg Trp Arg Arg Ser Tyr
1 5 10

<210> SEQ ID NO 392
<211> LENGTH: 12
<212> TYPE: PRT
<213> ORGANISM: Artificial Sequence
<220> FEATURE:
<223> OTHER INFORMATION: Antimicrobial peptide EOD133

<400> SEQUENCE: 392

Ile Ala Leu Leu Arg Arg Trp Trp Arg Gly Ser Arg
1 5 10

<210> SEQ ID NO 393
<211> LENGTH: 12
<212> TYPE: PRT
<213> ORGANISM: Artificial Sequence
<220> FEATURE:
<223> OTHER INFORMATION: Antimicrobial peptide EOD136

<400> SEQUENCE: 393

Ile Gln Arg Leu Met Ser Trp Trp Arg Gly Leu Thr
1 5 10

<210> SEQ ID NO 394
<211> LENGTH: 12
<212> TYPE: PRT
<213> ORGANISM: Artificial Sequence
<220> FEATURE:
<223> OTHER INFORMATION: Antimicrobial peptide EOD002

<400> SEQUENCE: 394

Ile Gln Leu Leu Gly Arg Arg Trp Arg Arg Ile Pro
1 5 10

<210> SEQ ID NO 395
<211> LENGTH: 12
<212> TYPE: PRT
<213> ORGANISM: Artificial Sequence
<220> FEATURE:
<223> OTHER INFORMATION: Antimicrobial peptide EOD005

<400> SEQUENCE: 395

Ile Cys Leu Leu Gln Arg Arg Trp Arg Arg Met His
1 5 10

<210> SEQ ID NO 396
<211> LENGTH: 12
<212> TYPE: PRT
<213> ORGANISM: Artificial Sequence
<220> FEATURE:
<223> OTHER INFORMATION: Antimicrobial peptide EOD009

<400> SEQUENCE: 396

Met Asn Leu Leu Glu Arg Arg Trp Arg Arg Trp Trp
1 5 10

<210> SEQ ID NO 397
<211> LENGTH: 12
<212> TYPE: PRT
<213> ORGANISM: Artificial Sequence
<220> FEATURE:
<223> OTHER INFORMATION: Antimicrobial peptide EOD011

<400> SEQUENCE: 397

Met Asn Leu Leu Glu Arg Arg Trp Arg Arg Trp Asn
1 5 10

<210> SEQ ID NO 398
<211> LENGTH: 12
<212> TYPE: PRT
<213> ORGANISM: Artificial Sequence
<220> FEATURE:
<223> OTHER INFORMATION: Antimicrobial peptide EOD014

<400> SEQUENCE: 398

Ile Ala Leu Leu Ala Ser Arg Trp Arg Arg Arg Pro
1 5 10

<210> SEQ ID NO 399
<211> LENGTH: 12
<212> TYPE: PRT
<213> ORGANISM: Artificial Sequence
<220> FEATURE:
<223> OTHER INFORMATION: Antimicrobial peptide EOD015

<400> SEQUENCE: 399

Leu Pro Arg Leu Leu Ser Arg Trp Arg Arg Arg Pro
1 5 10

<210> SEQ ID NO 400
<211> LENGTH: 12
<212> TYPE: PRT
<213> ORGANISM: Artificial Sequence
<220> FEATURE:
<223> OTHER INFORMATION: Antimicrobial peptide EOD026

<400> SEQUENCE: 400

Phe Ala Arg Leu Thr Arg Arg Trp Arg Arg Thr Ser
1 5 10

<210> SEQ ID NO 401
<211> LENGTH: 12
<212> TYPE: PRT
<213> ORGANISM: Artificial Sequence
<220> FEATURE:
<223> OTHER INFORMATION: Antimicrobial peptide EOD031

<400> SEQUENCE: 401

Phe Thr Leu Leu Leu Ser Trp Trp Arg Gly Tyr His
1 5 10

<210> SEQ ID NO 402
<211> LENGTH: 12
<212> TYPE: PRT
<213> ORGANISM: Artificial Sequence
<220> FEATURE:
<223> OTHER INFORMATION: Antimicrobial peptide EOD036

<400> SEQUENCE: 402

Phe Thr Leu Leu Ile Ser Arg Trp Arg Arg His Val 1 5 10

<210> SEQ ID NO 403
<211> LENGTH: 12
<212> TYPE: PRT
<213> ORGANISM: Artificial Sequence
<220> FEATURE:
<223> OTHER INFORMATION: Antimicrobial peptide EOD051

<400> SEQUENCE: 403

Ile Gly Arg Leu Arg Ser Arg Trp Arg Gly Tyr Ser
1 5 10

<210> SEQ ID NO 404
<211> LENGTH: 12
<212> TYPE: PRT
<213> ORGANISM: Artificial Sequence
<220> FEATURE:
<223> OTHER INFORMATION: Antimicrobial peptide EOD054

<400> SEQUENCE: 404

Ile Leu Leu Leu Ile Ser Arg Trp Arg Gly Val Leu
1 5 10

<210> SEQ ID NO 405
<211> LENGTH: 12
<212> TYPE: PRT
<213> ORGANISM: Artificial Sequence
<220> FEATURE:
<223> OTHER INFORMATION: Antimicrobial peptide EOD055

<400> SEQUENCE: 405

Leu Asp Trp Leu Pro Arg Arg Trp Arg Arg Arg Ala
1 5 10

<210> SEQ ID NO 406
<211> LENGTH: 12
<212> TYPE: PRT
<213> ORGANISM: Artificial Sequence
<220> FEATURE:
<223> OTHER INFORMATION: Antimicrobial peptide EOD063

<400> SEQUENCE: 406

Phe Val Leu Leu Ala Ser Arg Trp Arg Arg Leu Arg
1 5 10

<210> SEQ ID NO 407
<211> LENGTH: 12
<212> TYPE: PRT
<213> ORGANISM: Artificial Sequence
<220> FEATURE:
<223> OTHER INFORMATION: Antimicrobial peptide EOD067

<400> SEQUENCE: 407

Met Met Leu Leu Arg Ser Arg Trp Arg Arg Thr Gln
1 5 10

<210> SEQ ID NO 408
<211> LENGTH: 12
<212> TYPE: PRT
<213> ORGANISM: Artificial Sequence
<220> FEATURE:
<223> OTHER INFORMATION: Antimicrobial peptide EOD069

<400> SEQUENCE: 408

Met Asp Arg Leu Ser Arg Arg Trp Arg Gly Leu Lys
1 5 10

<210> SEQ ID NO 409
<211> LENGTH: 12
<212> TYPE: PRT
<213> ORGANISM: Artificial Sequence
<220> FEATURE:
<223> OTHER INFORMATION: Antimicrobial peptide EOD079

<400> SEQUENCE: 409

Met Val Leu Leu Lys Arg Arg Trp Arg Gly Ala Arg
1 5 10

<210> SEQ ID NO 410
<211> LENGTH: 12
<212> TYPE: PRT
<213> ORGANISM: Artificial Sequence
<220> FEATURE:
<223> OTHER INFORMATION: Antimicrobial peptide EOD081

<400> SEQUENCE: 410

Phe Asp Leu Leu Ala Arg Arg Trp Arg Arg Pro Val
1 5 10

<210> SEQ ID NO 411
<211> LENGTH: 12
<212> TYPE: PRT
<213> ORGANISM: Artificial Sequence
<220> FEATURE:
<223> OTHER INFORMATION: Antimicrobial peptide EOD084

<400> SEQUENCE: 411

Phe Met Arg Leu Pro Arg Trp Trp Arg Arg Met Gln
1 5 10

<210> SEQ ID NO 412
<211> LENGTH: 12
<212> TYPE: PRT
<213> ORGANISM: Artificial Sequence
<220> FEATURE:
<223> OTHER INFORMATION: Antimicrobial peptide EOD085

<400> SEQUENCE: 412

Ile Thr Leu Leu Cys Ser Arg Trp Arg Arg Thr Leu
1 5 10

<210> SEQ ID NO 413
<211> LENGTH: 12
<212> TYPE: PRT
<213> ORGANISM: Artificial Sequence
<220> FEATURE:
<223> OTHER INFORMATION: Antimicrobial peptide EOD086

<400> SEQUENCE: 413

Met Arg Leu Leu Leu Ser Arg Trp Arg Arg Ser Pro
1 5 10

<210> SEQ ID NO 414
<211> LENGTH: 12
<212> TYPE: PRT
<213> ORGANISM: Artificial Sequence
<220> FEATURE:
<223> OTHER INFORMATION: Antimicrobial peptide EOD087

<400> SEQUENCE: 414

Ile Ser Leu Leu Cys Ser Arg Trp Arg Arg Cys Thr
1 5 10

<210> SEQ ID NO 415
<211> LENGTH: 12
<212> TYPE: PRT
<213> ORGANISM: Artificial Sequence
<220> FEATURE:
<223> OTHER INFORMATION: Antimicrobial peptide EOD088

<400> SEQUENCE: 415

Met Trp Leu Leu Val Arg Arg Trp Arg Gly Leu Ser
1 5 10

<210> SEQ ID NO 416
<211> LENGTH: 12
<212> TYPE: PRT
<213> ORGANISM: Artificial Sequence
<220> FEATURE:
<223> OTHER INFORMATION: Antimicrobial peptide EOD090

<400> SEQUENCE: 416

Phe Cys Trp Leu Val Ser Trp Trp Arg Gly Ser Asp
1 5 10

<210> SEQ ID NO 417
<211> LENGTH: 12
<212> TYPE: PRT
<213> ORGANISM: Artificial Sequence
<220> FEATURE:
<223> OTHER INFORMATION: Antimicrobial peptide EOD097

<400> SEQUENCE: 417

Ile Phe Leu Leu Ser Arg Trp Trp Arg Arg Asn Glu
1 5 10

<210> SEQ ID NO 418
<211> LENGTH: 12
<212> TYPE: PRT
<213> ORGANISM: Artificial Sequence
<220> FEATURE:
<223> OTHER INFORMATION: Antimicrobial peptide EOD100

<400> SEQUENCE: 418

Ile Gly Leu Leu His Ser Trp Trp Arg Gly Phe Ala
1 5 10

<210> SEQ ID NO 419
<211> LENGTH: 12
<212> TYPE: PRT
<213> ORGANISM: Artificial Sequence
<220> FEATURE:
<223> OTHER INFORMATION: Antimicrobial peptide EOD101

<400> SEQUENCE: 419

Met His Leu Leu Leu Ser Trp Trp Arg Gly Thr Val
1 5 10

<210> SEQ ID NO 420
<211> LENGTH: 12
<212> TYPE: PRT
<213> ORGANISM: Artificial Sequence
<220> FEATURE:
<223> OTHER INFORMATION: Antimicrobial peptide EOD102

<400> SEQUENCE: 420

Phe Thr Trp Leu Ala Ser Arg Trp Arg Gly Gln Leu
1 5 10

<210> SEQ ID NO 421
<211> LENGTH: 12
<212> TYPE: PRT
<213> ORGANISM: Artificial Sequence
<220> FEATURE:
<223> OTHER INFORMATION: Antimicrobial peptide EOD104

<400> SEQUENCE: 421

Leu Trp Arg Leu Gly Ser Trp Trp Arg Gly Ser Pro
1 5 10

<210> SEQ ID NO 422
<211> LENGTH: 12
<212> TYPE: PRT
<213> ORGANISM: Artificial Sequence
<220> FEATURE:
<223> OTHER INFORMATION: Antimicrobial peptide EOD109

<400> SEQUENCE: 422

Met Arg Arg Leu Gly Arg Arg Trp Arg Arg Pro Arg
1 5 10

<210> SEQ ID NO 423
<211> LENGTH: 12
<212> TYPE: PRT
<213> ORGANISM: Artificial Sequence
<220> FEATURE:
<223> OTHER INFORMATION: Antimicrobial peptide EOD111

<400> SEQUENCE: 423

Ile Leu Leu Leu Asn Ser Trp Trp Arg Gly His Cys
1 5 10

<210> SEQ ID NO 424
<211> LENGTH: 12
<212> TYPE: PRT
<213> ORGANISM: Artificial Sequence
<220> FEATURE:
<223> OTHER INFORMATION: Antimicrobial peptide EOD114

<400> SEQUENCE: 424

Met Val Leu Leu Trp Arg Arg Trp Arg Gly Leu Leu
1 5 10

<210> SEQ ID NO 425
<211> LENGTH: 12
<212> TYPE: PRT
<213> ORGANISM: Artificial Sequence
<220> FEATURE:
<223> OTHER INFORMATION: Antimicrobial peptide EOD115

<400> SEQUENCE: 425

Ile Leu Leu Leu Val Arg Arg Trp Arg Arg Thr Asn
1 5 10

<210> SEQ ID NO 426
<211> LENGTH: 12
<212> TYPE: PRT
<213> ORGANISM: Artificial Sequence
<220> FEATURE:
<223> OTHER INFORMATION: Antimicrobial peptide EOD117

<400> SEQUENCE: 426

Met Ser Leu Leu Pro Ser Arg Trp Arg Arg Arg Pro
1 5 10

<210> SEQ ID NO 427

-continued

<211> LENGTH: 12
<212> TYPE: PRT
<213> ORGANISM: Artificial Sequence
<220> FEATURE:
<223> OTHER INFORMATION: Antimicrobial peptide EOD119

<400> SEQUENCE: 427

Ile Tyr Leu Leu Ser Arg Arg Trp Arg Arg Ser Asp
1 5 10

<210> SEQ ID NO 428
<211> LENGTH: 12
<212> TYPE: PRT
<213> ORGANISM: Artificial Sequence
<220> FEATURE:
<223> OTHER INFORMATION: Antimicrobial peptide EOD120

<400> SEQUENCE: 428

Phe Trp Leu Leu Trp Ser Arg Trp Arg Arg Lys Leu
1 5 10

<210> SEQ ID NO 429
<211> LENGTH: 12
<212> TYPE: PRT
<213> ORGANISM: Artificial Sequence
<220> FEATURE:
<223> OTHER INFORMATION: Antimicrobial peptide EOD125

<400> SEQUENCE: 429

Phe Tyr Leu Leu Arg Arg Arg Trp Arg Arg Pro Ser
1 5 10

<210> SEQ ID NO 430
<211> LENGTH: 12
<212> TYPE: PRT
<213> ORGANISM: Artificial Sequence
<220> FEATURE:
<223> OTHER INFORMATION: Antimicrobial peptide EOD127

<400> SEQUENCE: 430

Phe His Leu Leu Tyr Arg Arg Trp Arg Arg Leu Cys
1 5 10

<210> SEQ ID NO 431
<211> LENGTH: 12
<212> TYPE: PRT
<213> ORGANISM: Artificial Sequence
<220> FEATURE:
<223> OTHER INFORMATION: Antimicrobial peptide EOD129

<400> SEQUENCE: 431

Leu Pro Arg Leu Leu Ser Arg Trp Arg Arg Glu Leu
1 5 10

<210> SEQ ID NO 432
<211> LENGTH: 12
<212> TYPE: PRT
<213> ORGANISM: Artificial Sequence
<220> FEATURE:
<223> OTHER INFORMATION: Antimicrobial peptide EOD130

<400> SEQUENCE: 432

Ile Leu Trp Leu His Ser Arg Trp Arg Arg Glu Gln
1 5 10

<210> SEQ ID NO 433
<211> LENGTH: 12

<212> TYPE: PRT
<213> ORGANISM: Artificial Sequence
<220> FEATURE:
<223> OTHER INFORMATION: Antimicrobial peptide EOD131

<400> SEQUENCE: 433

Ile His Leu Leu Val Ser Trp Trp Arg Gly Thr Ser
1 5 10

<210> SEQ ID NO 434
<211> LENGTH: 12
<212> TYPE: PRT
<213> ORGANISM: Artificial Sequence
<220> FEATURE:
<223> OTHER INFORMATION: Antimicrobial peptide EOD134

<400> SEQUENCE: 434

Ile Ser Leu Leu Ala Ser Arg Trp Arg Gly Ser Arg
1 5 10

<210> SEQ ID NO 435
<211> LENGTH: 12
<212> TYPE: PRT
<213> ORGANISM: Artificial Sequence
<220> FEATURE:
<223> OTHER INFORMATION: Antimicrobial peptide EOD135

<400> SEQUENCE: 435

Phe Met Leu Leu His Arg Arg Trp Arg Gly Leu Thr
1 5 10

<210> SEQ ID NO 436
<211> LENGTH: 12
<212> TYPE: PRT
<213> ORGANISM: Artificial Sequence
<220> FEATURE:
<223> OTHER INFORMATION: Antimicrobial peptide EOD137

<400> SEQUENCE: 436

Phe His Leu Leu His Ser Arg Trp Arg Arg Ser Ala
1 5 10

<210> SEQ ID NO 437
<211> LENGTH: 12
<212> TYPE: PRT
<213> ORGANISM: Artificial Sequence
<220> FEATURE:
<223> OTHER INFORMATION: Antimicrobial peptide EOD037Pro+

<400> SEQUENCE: 437

Ile Arg Trp Leu Pro Arg Arg Trp Arg Arg Thr Phe
1 5 10

<210> SEQ ID NO 438
<211> LENGTH: 12
<212> TYPE: PRT
<213> ORGANISM: Artificial Sequence
<220> FEATURE:
<223> OTHER INFORMATION: Antimicrobial peptide EODPro-

<400> SEQUENCE: 438

Phe Met Arg Leu Leu Arg Trp Trp Arg Arg Met Gln
1 5 10

<210> SEQ ID NO 439
<211> LENGTH: 12
<212> TYPE: PRT

<213> ORGANISM: Artificial Sequence
<220> FEATURE:
<223> OTHER INFORMATION: Antimicrobial peptide EO1 A1

<400> SEQUENCE: 439

Ala Ala Trp Leu Trp Ser Trp Trp Arg Ala Arg Arg
1 5 10

<210> SEQ ID NO 440
<211> LENGTH: 12
<212> TYPE: PRT
<213> ORGANISM: Artificial Sequence
<220> FEATURE:
<223> OTHER INFORMATION: Antimicrobial peptide EO1 A3

<400> SEQUENCE: 440

Phe Ala Ala Leu Trp Ser Trp Trp Arg Ala Arg Arg
1 5 10

<210> SEQ ID NO 441
<211> LENGTH: 12
<212> TYPE: PRT
<213> ORGANISM: Artificial Sequence
<220> FEATURE:
<223> OTHER INFORMATION: Antimicrobial peptide EO1 A4

<400> SEQUENCE: 441

Phe Ala Trp Ala Trp Ser Trp Trp Arg Ala Arg Arg
1 5 10

<210> SEQ ID NO 442
<211> LENGTH: 12
<212> TYPE: PRT
<213> ORGANISM: Artificial Sequence
<220> FEATURE:
<223> OTHER INFORMATION: Antimicrobial peptide EO1 A5

<400> SEQUENCE: 442

Phe Ala Trp Leu Ala Ser Trp Trp Arg Ala Arg Arg
1 5 10

<210> SEQ ID NO 443
<211> LENGTH: 12
<212> TYPE: PRT
<213> ORGANISM: Artificial Sequence
<220> FEATURE:
<223> OTHER INFORMATION: Antimicrobial peptide EO1 A6

<400> SEQUENCE: 443

Phe Ala Trp Leu Trp Ala Trp Trp Arg Ala Arg Arg
1 5 10

<210> SEQ ID NO 444
<211> LENGTH: 12
<212> TYPE: PRT
<213> ORGANISM: Artificial Sequence
<220> FEATURE:
<223> OTHER INFORMATION: Antimicrobial peptide EO1 A7

<400> SEQUENCE: 444

Phe Ala Trp Leu Trp Ser Ala Trp Arg Ala Arg Arg
1 5 10

<210> SEQ ID NO 445
<211> LENGTH: 12
<212> TYPE: PRT
<213> ORGANISM: Artificial Sequence
<220> FEATURE:
<223> OTHER INFORMATION: Antimicrobial peptide EO1 A8

<400> SEQUENCE: 445

Phe Ala Trp Leu Trp Ser Trp Ala Arg Ala Arg Arg
1 5 10

<210> SEQ ID NO 446
<211> LENGTH: 12
<212> TYPE: PRT
<213> ORGANISM: Artificial Sequence
<220> FEATURE:
<223> OTHER INFORMATION: Antimicrobial peptide EO1 A9

<400> SEQUENCE: 446

Phe Ala Trp Leu Trp Ser Trp Trp Ala Ala Arg Arg
1 5 10

<210> SEQ ID NO 447
<211> LENGTH: 12
<212> TYPE: PRT
<213> ORGANISM: Artificial Sequence
<220> FEATURE:
<223> OTHER INFORMATION: Antimicrobial peptide EO1 A11

<400> SEQUENCE: 447

Phe Ala Trp Leu Trp Ser Trp Trp Arg Ala Ala Arg
1 5 10

<210> SEQ ID NO 448
<211> LENGTH: 12
<212> TYPE: PRT
<213> ORGANISM: Artificial Sequence
<220> FEATURE:
<223> OTHER INFORMATION: Antimicrobial peptide EO1 A12

<400> SEQUENCE: 448

Phe Ala Trp Leu Trp Ser Trp Trp Arg Ala Arg Ala
1 5 10

<210> SEQ ID NO 449
<211> LENGTH: 12
<212> TYPE: PRT
<213> ORGANISM: Artificial Sequence
<220> FEATURE:
<223> OTHER INFORMATION: Antimicrobial peptide EO1 I

<400> SEQUENCE: 449

Phe Ala Trp Ile Trp Ser Glu Glu Arg Ala Arg Arg
1 5 10

<210> SEQ ID NO 450
<211> LENGTH: 12
<212> TYPE: PRT
<213> ORGANISM: Artificial Sequence
<220> FEATURE:
<223> OTHER INFORMATION: Antimicrobial peptide EO1 V

<400> SEQUENCE: 450

Phe Ala Trp Val Trp Ser Trp Trp Arg Ala Arg Arg
1 5 10

<210> SEQ ID NO 451
<211> LENGTH: 12
<212> TYPE: PRT
<213> ORGANISM: Artificial Sequence
<220> FEATURE:

-continued

<223> OTHER INFORMATION: Antimicrobial peptide EO1 F

<400> SEQUENCE: 451

Phe Ala Trp Phe Trp Ser Trp Trp Arg Ala Arg Arg
1 5 10

<210> SEQ ID NO 452
<211> LENGTH: 12
<212> TYPE: PRT
<213> ORGANISM: Artificial Sequence
<220> FEATURE:
<223> OTHER INFORMATION: Antimicrobial peptide EO1 Y

<400> SEQUENCE: 452

Phe Ala Trp Tyr Trp Ser Trp Trp Arg Ala Arg Arg
1 5 10

<210> SEQ ID NO 453
<211> LENGTH: 12
<212> TYPE: PRT
<213> ORGANISM: Artificial Sequence
<220> FEATURE:
<223> OTHER INFORMATION: Antimicrobial peptide EO1 N

<400> SEQUENCE: 453

Phe Ala Trp Asn Trp Ser Trp Trp Arg Ala Arg Arg
1 5 10

<210> SEQ ID NO 454
<211> LENGTH: 12
<212> TYPE: PRT
<213> ORGANISM: Artificial Sequence
<220> FEATURE:
<223> OTHER INFORMATION: Antimicrobial peptide EO1 D

<400> SEQUENCE: 454

Phe Ala Trp Asp Trp Ser Trp Trp Arg Ala Arg Arg
1 5 10

<210> SEQ ID NO 455
<211> LENGTH: 12
<212> TYPE: PRT
<213> ORGANISM: Artificial Sequence
<220> FEATURE:
<223> OTHER INFORMATION: Antimicrobial peptide EO1 K

<400> SEQUENCE: 455

Phe Ala Trp Lys Trp Ser Trp Trp Arg Ala Arg Arg
1 5 10

<210> SEQ ID NO 456
<211> LENGTH: 12
<212> TYPE: PRT
<213> ORGANISM: Artificial Sequence
<220> FEATURE:
<223> OTHER INFORMATION: Antimicrobial peptide EO1 1

<400> SEQUENCE: 456

Ala Ala Trp Ile Trp Ser Trp Ala Arg Ala Arg Arg
1 5 10

<210> SEQ ID NO 457
<211> LENGTH: 11
<212> TYPE: PRT
<213> ORGANISM: Artificial Sequence
<220> FEATURE:
<223> OTHER INFORMATION: Antimicrobial peptide EO1 2

```
<400> SEQUENCE: 457

Ala Trp Val Trp Ser Trp Trp Arg Ala Arg Arg
1               5                   10

<210> SEQ ID NO 458
<211> LENGTH: 12
<212> TYPE: PRT
<213> ORGANISM: Artificial Sequence
<220> FEATURE:
<223> OTHER INFORMATION: Antimicrobial peptide EO1 3

<400> SEQUENCE: 458

Ser Ala Trp Phe Trp Ser Trp Ala Arg Ala Arg Arg
1               5                   10

<210> SEQ ID NO 459
<211> LENGTH: 12
<212> TYPE: PRT
<213> ORGANISM: Artificial Sequence
<220> FEATURE:
<223> OTHER INFORMATION: Antimicrobial peptide EO1 4

<400> SEQUENCE: 459

Ser Ala Trp Tyr Trp Ser Trp Ser Arg Ala Arg Arg
1               5                   10

<210> SEQ ID NO 460
<211> LENGTH: 12
<212> TYPE: PRT
<213> ORGANISM: Artificial Sequence
<220> FEATURE:
<223> OTHER INFORMATION: Antimicrobial peptide EO1 5

<400> SEQUENCE: 460

Phe Ala Trp Asn Trp Ser Trp Trp Arg Ala Arg Glu
1               5                   10

<210> SEQ ID NO 461
<211> LENGTH: 12
<212> TYPE: PRT
<213> ORGANISM: Artificial Sequence
<220> FEATURE:
<223> OTHER INFORMATION: Antimicrobial peptide EO1 6

<400> SEQUENCE: 461

Phe Ala Trp Asp Trp Ser Trp Trp Arg Glu Arg Glu
1               5                   10

<210> SEQ ID NO 462
<211> LENGTH: 36
<212> TYPE: DNA
<213> ORGANISM: Artificial Sequence
<220> FEATURE:
<223> OTHER INFORMATION: Degenerate nucleotide sequence coding for
      peptide antimicrobial
<220> FEATURE:
<221> NAME/KEY: misc_feature
<222> LOCATION: (1)..(36)
<223> OTHER INFORMATION: n=g, a, t or c
<220> FEATURE:
<221> NAME/KEY: misc_feature
<222> LOCATION: (1)..(36)
<223> OTHER INFORMATION: k=t or g

<400> SEQUENCE: 462

nnknnknnkn nknnknnknn knnknnknnk nnknnk                          36
```

<210> SEQ ID NO 463
<211> LENGTH: 36
<212> TYPE: DNA
<213> ORGANISM: Artificial Sequence
<220> FEATURE:
<223> OTHER INFORMATION: Consensus nucleotide sequence for peptide antimicrobial
<220> FEATURE:
<221> NAME/KEY: misc_feature
<222> LOCATION: (1)..(1)
<223> OTHER INFORMATION: d=a, g or t
<220> FEATURE:
<221> NAME/KEY: misc_feature
<222> LOCATION: (2)..(35)
<223> OTHER INFORMATION: n=g, a, t or c
<220> FEATURE:
<221> NAME/KEY: misc_feature
<222> LOCATION: (3)..(36)
<223> OTHER INFORMATION: k=g or t

<400> SEQUENCE: 463
dnknnknnkn nknnknnknn knnknnknnk nnknnk 36

<210> SEQ ID NO 464
<211> LENGTH: 36
<212> TYPE: DNA
<213> ORGANISM: Artificial Sequence
<220> FEATURE:
<223> OTHER INFORMATION: Degenerate nucleotide sequence coding for peptide antimicrobial
<220> FEATURE:
<221> NAME/KEY: misc_feature
<222> LOCATION: (1)..(1)
<223> OTHER INFORMATION: w = a or t
<220> FEATURE:
<221> NAME/KEY: misc_feature
<222> LOCATION: (3)..(3)
<223> OTHER INFORMATION: b=c, g or t
<220> FEATURE:
<221> NAME/KEY: misc_feature
<222> LOCATION: (4)..(5)
<223> OTHER INFORMATION: n=a, c, g or t
<220> FEATURE:
<221> NAME/KEY: misc_feature
<222> LOCATION: (6)..(6)
<223> OTHER INFORMATION: k=g or t
<220> FEATURE:
<221> NAME/KEY: misc_feature
<222> LOCATION: (6)..(6)
<223> OTHER INFORMATION: k=g or t
<220> FEATURE:
<221> NAME/KEY: misc_feature
<222> LOCATION: (7)..(7)
<223> OTHER INFORMATION: y=c or t
<220> FEATURE:
<221> NAME/KEY: misc_feature
<222> LOCATION: (8)..(8)
<223> OTHER INFORMATION: k=g or t
<220> FEATURE:
<221> NAME/KEY: misc_feature
<222> LOCATION: (13)..(14)
<223> OTHER INFORMATION: n=g, a, t or c
<220> FEATURE:
<221> NAME/KEY: misc_feature
<222> LOCATION: (15)..(15)
<223> OTHER INFORMATION: y=t or c
<220> FEATURE:
<221> NAME/KEY: misc_feature
<222> LOCATION: (18)..(18)
<223> OTHER INFORMATION: n=g, a, t or c
<220> FEATURE:
<221> NAME/KEY: misc_feature
<222> LOCATION: (19)..(19)
<223> OTHER INFORMATION: y=t or c
<220> FEATURE:
<221> NAME/KEY: misc_feature
<222> LOCATION: (28)..(28)
<223> OTHER INFORMATION: s=c or g
<220> FEATURE:
<221> NAME/KEY: misc_feature
<222> LOCATION: (31)..(32)
<223> OTHER INFORMATION: n=g, a, t or c
<220> FEATURE:
<221> NAME/KEY: misc_feature
<222> LOCATION: (33)..(33)
<223> OTHER INFORMATION: k=g or t
<220> FEATURE:
<221> NAME/KEY: misc_feature
<222> LOCATION: (34)..(35)
<223> OTHER INFORMATION: n=g, a, t or c
<220> FEATURE:
<221> NAME/KEY: misc_feature
<222> LOCATION: (36)..(36)
<223> OTHER INFORMATION: k=g or t

<400> SEQUENCE: 464
wtbnnkykgc tgnnkagnyg gtggcgtsgt nnknnk 36

<210> SEQ ID NO 465
<211> LENGTH: 12
<212> TYPE: PRT
<213> ORGANISM: Artificial Sequence
<220> FEATURE:
<223> OTHER INFORMATION: Antimicrobial peptide consensus sequence
<220> FEATURE:
<221> NAME/KEY: MISC_FEATURE
<222> LOCATION: (1)..(1)
<223> OTHER INFORMATION: hydrophobic amino acid
<220> FEATURE:
<221> NAME/KEY: MISC_FEATURE
<222> LOCATION: (2)..(2)
<223> OTHER INFORMATION: basic amino acid or small amino acid
<220> FEATURE:
<221> NAME/KEY: MISC_FEATURE
<222> LOCATION: (3)..(3)
<223> OTHER INFORMATION: hydrophobic amino acid or basic amino acid
<220> FEATURE:
<221> NAME/KEY: MISC_FEATURE
<222> LOCATION: (4)..(4)
<223> OTHER INFORMATION: hydrophobic amino acid
<220> FEATURE:
<221> NAME/KEY: MISC_FEATURE
<222> LOCATION: (5)..(5)
<223> OTHER INFORMATION: basic amino acid
<220> FEATURE:
<221> NAME/KEY: MISC_FEATURE
<222> LOCATION: (6)..(6)
<223> OTHER INFORMATION: basic amino acid or small amino acid
<220> FEATURE:
<221> NAME/KEY: MISC_FEATURE
<222> LOCATION: (7)..(7)
<223> OTHER INFORMATION: hydrophobic  amino acid or basic amino acid
<220> FEATURE:
<221> NAME/KEY: MISC_FEATURE
<222> LOCATION: (8)..(8)
<223> OTHER INFORMATION: hydrophobic amino acid or small amino acid
<220> FEATURE:
<221> NAME/KEY: MISC_FEATURE
<222> LOCATION: (9)..(10)
<223> OTHER INFORMATION: basic amino acid or small amino acid
<220> FEATURE:
<221> NAME/KEY: MISC_FEATURE
<222> LOCATION: (11)..(11)
<223> OTHER INFORMATION: tryptophan or arginine
<220> FEATURE:
<221> NAME/KEY: MISC_FEATURE
<222> LOCATION: (12)..(12)
<223> OTHER INFORMATION: basic amino acid or small amino acid -continued

```
<400> SEQUENCE: 465

Xaa Xaa Xaa Xaa Xaa Xaa Xaa Xaa Xaa Xaa Xaa Xaa
1               5                   10
```